US007384750B2

(12) United States Patent
Nakagawara

(10) Patent No.: US 7,384,750 B2
(45) Date of Patent: Jun. 10, 2008

(54) NUCLEIC ACID SEQUENCES HAVING CHARACTERISTICS OF ENHANCED EXPRESSION IN HUMAN NEUROBLASTOMA WITH FAVORABLE PROGNOSIS BASED ON COMPARISON BETWEEN HUMAN NEUROBLASTOMA WITH FAVORABLE PROGNOSIS AND HUMAN NEUROBLASTOMA WITH UNFAVORABLE PROGNOSIS

(75) Inventor: Akira Nakagawara, Chiba (JP)

(73) Assignees: Eisamitsu Pharmaceutical Co., Ltd., Tosu-shi (JP); Chiba-Prefecture, Chiba-shi (JP)

( * ) Notice: Subject to any disclaimer, the term of this patent is extended or adjusted under 35 U.S.C. 154(b) by 14 days.

(21) Appl. No.: 11/405,549

(22) Filed: Apr. 18, 2006

(65) Prior Publication Data

US 2006/0188919 A1 Aug. 24, 2006

Related U.S. Application Data

(62) Division of application No. 10/220,891, filed as application No. PCT/JP01/01631 on Mar. 2, 2001, now Pat. No. 7,087,383.

(30) Foreign Application Priority Data

Mar. 7, 2000 (JP) ............................ 2000-159195
May 12, 2000 (JP) ............................ 2000-140387

(51) Int. Cl.
*C12Q 1/68* (2006.01)
*C07H 21/04* (2006.01)

(52) U.S. Cl. ...................... 435/6; 536/23.5; 536/24.31; 536/24.33

(58) Field of Classification Search .................... 435/6; 536/23.5, 24.31, 24.33
See application file for complete search history.

(56) References Cited

U.S. PATENT DOCUMENTS

| | | | | |
|---|---|---|---|---|
| 4,683,202 | A | 7/1987 | Mullis | |
| 5,333,675 | A | 8/1994 | Mullis et al. | |
| 5,424,186 | A | 6/1995 | Fodor et al. | |
| 5,807,522 | A | 9/1998 | Brown et al. | |
| 6,255,468 | B1 | 7/2001 | Southan et al. | |
| 6,426,186 | B1 | 7/2002 | Jones et al. | |
| 6,756,212 | B1 | 6/2004 | Curtis et al. | |
| 7,205,146 | B1 * | 4/2007 | Keith et al. | 435/325 |

FOREIGN PATENT DOCUMENTS

WO 98/21366 5/1998

OTHER PUBLICATIONS

EST Accession No. AA678190 (1997).*

Osoegawa, Kazutoyo, et al., "An Improved Approach for construction of Bacterial Artificial Chromosome Libraries", Genomics 52, 1-8 (1998).

Accession BD100555, 2002.

Accession AC096556, 2002.

Ohira, Miki, et al., "Hunting the subset-Specific Genes of Neuroblastoma: Expression Profiling and Differential Screening of the Full-Length-Enriched Oligo-Capping cDNA Libraries", Med. Pediatr. Oncol. (Dec. 2000) vol. 35, No. 6, pp. 547-549.

Kawomoto, Takemasa, et al., "Multistep carcinogenesis of neurogenic tumors", Molecular Medicine vol. 36, No. 4, pp. 367-373 1999.

Neto, Emmanuel Dias, et al., "Shotgun sequencing of the human transcriptome with ORF expressed sequence tags", PNAS, Mar. 28, 2000, vol. 97, No. 7, 3491-3496.

Horii, Akira, et al., "Genomic Analysis of 1p36 Kaiseki", Genome Science: Hito Genome Kaiseki ni motozuku Bio Science no Shintenkai (1999) pp. 116-118.

Takada, Naoyuki, et al., "Shuyou Maker no Sentaku to Yomikata; Gan Shindan ni Okeru Shuyou Maker no Yuyousei to Genkai; Shouni Gan", Rinshou to Kenkyu (1998) vol. 75, No. 3, pp. 546-552.

1996 SIGMA Catalog, p. 1513.

Holmes et al., J. Biol. Chem. 274(33), 23491-23498 (1999).

Accession No. AA046951 (1997).

Accession No. AI802048 (1999).

Accession No. AI056359 (1998).

Database EMBL Online, "mRNA for KIAA0327", Database Accession No. AB002325—Document No. XP002283249 (Jul. 1, 1997).

Database EMBL Online ,"EST", Database Accession No. AA578755—Document No. XP002283250 (Sep. 11, 1997).

Database EMBL Online, "EST", Database Accession No. AA999664—Document No. XP002283251 (Jun. 8, 1998).

Tang et al., "High-Level Expression of *EPHB6, EFNB2*, and *EFNB3* is Associated with Low Tumor Stage and High *TrkA* Expression in Human Neuroblastomas", Clinical Cancer Research, vol. 5, pp. 1491-1496—Document No. XP-002283248 (Jun. 1999).

(Continued)

*Primary Examiner*—Kenneth R. Horlick
(74) *Attorney, Agent, or Firm*—Fitch, Even, Tabin & Flannery

(57) ABSTRACT

There are disclosed a nucleic acid which is derived from the gene expressed in human neuroblastoma, and which comprises any sequence selected from the group consisting of the nucleic acid sequences set forth SEQ ID NO:1 to NO:104 in the Sequence Listing, or its complementary nucleic acid; a fragment of the nucleic acid; their use as probes or primers; and the diagnosis of neuroblastoma prognosis using any of the foregoings.

3 Claims, 4 Drawing Sheets

OTHER PUBLICATIONS

Database EMBL Online, "Microsatellite Sequence From Clon TGLA357", Database Accession No. AA033965—Document No. XP002283252 (Feb. 2, 1993).

Database EMBL Online, "Sequence 415," Database Accession No. 131503—Document No. XP002283253 (Feb. 13, 1997).

Database EM_HUM, EMBL, "*Homo sapiens* Clone 25048", Database Accession No. AF131776—Document No. XP002296850 (Mar. 15, 1999).

Database EM_EST, EMBL, "*Homo sapiens* mRNA", Database Accession No. HSM016129, Document No. XP002296851 (Feb. 20, 2000).

Database EM_EST, EMBL, "*Homo sapiens* mRNA", Database Accession No. HSM018419, Document No. XP002296852 (Feb. 20, 2000).

Database EM_EST, EMBL, "*Homo sapiens* cDNA", Database Accession No. HSAA45741, Document No. XP002296853 (Mar. 3, 2000).

Database EM_EST, EMBL, "IB 467 Infant Brain", Database Accession No. HST03555, Document No. XP002296854 (Mar. 4, 2000).

Database GSN, EMBL, "Human Nervous System Related Polynucleotide SEQ ID No. 1205", Database Accession No. ABA12198, Document No. XP002296855 (Jan. 17, 2001).

Database EM_PAT, EMBL, "Sequence 3 From Patent WO9720068", Database Accession No. A62991, Document No. XP002297150 (Mar. 12, 1998).

Takahiro et al., "Prediction of the Coding Sequences of Unidentified Human Genes. VII. The Complete Sequences of 100 New cDNA Clones from Brain Which Can Code for Large Proteins in vitro," DNA Res. (1997), vol. 4, No. 2, pp. 141-150.

Takemasa et al., "Multistep Carcinogenesis of Neurogenic Tumors," Molecular Medicine (1999), vol. 36, No. 4, pp. 366-372.

* cited by examiner nbla-00106 nbla-00219 nbla-03145

SEQUENCE LISTING

```
<160> NUMBER OF SEQ ID NOS: 108

<210> SEQ ID NO 1
<211> LENGTH: 2187
<212> TYPE: DNA
<213> ORGANISM: Homo sapiens

<400> SEQUENCE: 1

tgttggccta ctggtaatgc tcactgccta cccatttctc catattcaca agaaaatata     60

catatttgca ggaaaatata taatttttag atgtcatgga tcattttagg aaagttgtag    120

tcagttaaaa agctgtcata tcattctaca aaggaggagt aaagtaggag caattgtgtg    180

gcccaacatt tgtttgtttt ttagccaagc ttagatttat aaagcaatga gggtgtggtt    240

ttaaccacaa agtgaaagtg ttagacagtt gttggctctc tcctaaaaag tgaatgagat    300

ttttcctata cattttcctt cttgttgact aatatatgat gaatactttt ttcagcttgg    360

atataccata aatataaaaa taataaagcc aaagaattta agctaaaatt caacactttt    420

cttaactaat ttaactggta tggtctccat agtagtccac tgttttgttt cctgtgttaa    480

cttccctttt gtttcgaaag ctcttagaat aaggagtcaa ctggattttt atgtccatgg    540

accccttgtg attatatgca gtgtacgctg tgtgtgcgtg tgtgtgtgtg tgtgtgtgag    600

agagatcctt ttacttagaa aaaggtctac tatgctcatt agaagatcaa aagcagattc    660

tccttacttg taacatagga gtttcaggat taatctgtat tcaagctcat tctatatcct    720

tcatcaaaga aaagacaatg ttttgtgtct gttgtccctc tcacacacag ccctaatata    780

taatgtgtaa ctgccttatc tgcagcccta aactaatata gctagaggtc ttctaatcat    840

tctcctacct ctaggaaaga aatatagtct tgaaaactgc caatctggtg tgcatacaaa    900

atatatacaa aataccaagg aacattatat gagccttttg ctaggtatat ctaagcaact    960

gcttcagtta atggccactt tacaaattgc tgaaagaagg aaacgtcttt cgattctttt   1020

tttttctttt tttttttttg agacagagtc tctgtctgtt actcaggctg tagtgcagtg   1080
```

-continued

```
gcacaatgat agctccctcc agcctcaaac tcctgggctc aagcattcct tctgcatcag   1140
cctcctgact agctggaact caggctcatg ccaccagacc tggctaattt ttctgttttc   1200
agtagagaaa atattttctt tcactaattt aactggtatg gtttccattg tctacccagt   1260
tttccatatg cataagaaaa tatattcaca ggaaaatata aagttttcag atttcatgag   1320
tggttttaag aaagttttag tcagtgaaaa aactatcata ccagtcttca aaggaagggt   1380
gaaataagtt catctgctac gttgcccagg ctggtcttga agggaaacag actttttttgc   1440
agtcatactt atcctttggc ttcttagtaa gtattatata gtcattactt tttgcagttt   1500
tttagatcaa agtgttaatg taggtaaagt taattttaga atatatgtaa aagtcaagtc   1560
tgctttaaat ttaatcatct ctttggtgaa agggatggga tggagctttg ctttttatca   1620
tatattcatc tgtacctttc aagtattcaa atagaaaaat ataaacaatg taaataaaat   1680
agcaaaacaa tgtaatatct cataaaactg caatggtaaa agcatttatc ctattgaaat   1740
tccacaattt ttatttgaaa atattatcga catgtaattc aagtggcatt tagaagaata   1800
atttaaaagc aacaactcta tagaaagctt gtaaaatgat taagtagttt aaaccaaata   1860
aaacaatttc tgagtcagtc atctccagta ggtctatttt agtctcaaga taaattcatt   1920
tctggtgaca actgaagttc ttagttattt gttagtatat attggagaca tttacaataa   1980
agcttagagc acaatgggaa atgaaagtat catgtttttt ttaagaccaa atgtattgca   2040
gaaatgtgag taatttaatc cgatgctaca atctgatcat tctgatctaa tctgatcatt   2100
taataacact aaataaaacc ttcatctcaa aaaaaaaaaa aaaaggccac atgtgctcga   2160
gctgcaggtc gcggccgcta gactagt                                        2187
```

<210> SEQ ID NO 2
<211> LENGTH: 2238
<212> TYPE: DNA
<213> ORGANISM: Homo sapiens

<400> SEQUENCE: 2

```
gaattcctcg agcactgttg gcctactggc tgaccattta gatgcttaca agatgctttt     60
ctctgacttc ttcagctcca actgctcctt tccattaccc taaagctgtg gatcataaag    120
agtgttctcc agaccagcag tatctgcacc acctggatct tgttagaaat gcagattttc    180
aaaccccacc catgagctac tgaaacagaa ctctgaaggt gaggcctaga aaccggtttt    240
aaccaatgtg ccaagtgatt ctaatgcctg ctatcaatca tttgggaacc attgtcctaa    300
actcagctgc tgcttctgct tcatctccag ttgattcagt ttccttaatt gttaccatta    360
taaaaacaaa ataaagcaaa acaagacatt tacctatatt attaatcaca aataagttcc    420
ctaccctgtg gggtcacaat ttgggctttg gatatctaat tctgcatcaa gtacatatct    480
ctgtctttac aatctcaaca aattattaga tatatcagta acttccatat atgctctcat    540
tttgtagttg cagtgtcact atctccattt aatggatagg gaaatagggg ctcaggaaag    600
agaagtgtat tatccatgac ggaggtaaca tgggctgcat tcaattaggg tttctcattt    660
ccagctaaga cactttgcac catattgaag cagcttgtaa ctaaatttgc cataaaaata    720
tatctaaaat cctaattaag tttgaatagc ttgatcttag ttgaaagtta ttcctaattc    780
attcacaagt agcttttaaa agggatatgt ttatgttaaa caatagaagg tctccaaatc    840
ctatcagata actgtatcct gtctttaaaa atgtaatttt ttatatctac tgcctgaatt    900
aaattgctta gttgtacttt ccagagaaat agaatggacc aaagcagttc aaatatttta    960
atattcttct ggagtttgac tgctgagatg taaagaacta ttgatatcac tagtaaataa   1020
```

-continued

```
ataatgtata tttattgagg tttagtcaat agagcgatta cttataagag gcatgtagta   1080
cttaattatc atcctcttca cgaaactcca acttaacctt ggacaataca attaagagtt   1140
gtgttcagat ggctttaaaa acaggtgcat ggtacaacat gctcttgttg ttaaccattt   1200
tgcttaatgg ccaaacttct cttgggtcag ttttgataac tcctctgcaa tttcatcaac   1260
aatgagggaa atgtaatttc aaggtgagca ttgagactga gtatattagg caagagtggg   1320
gcttgcttat ttttggcctt gcagctccca gaaatagaat gtttacaagg tgtaatcata   1380
tttcagtacc ttgtttttcc agaattgttt tcttttccca gaaatttttt actctctatt   1440
tatttgtatt tagctcttct ttactaaagt ataactctat cagagcagaa gactgtgtct   1500
tcttcttcat ctttatatct tacattctta gcatggtaga tgtttaattg gaatgtgatt   1560
tcagagagtg gctgtgttcc agtcttgatc caatattgat gaactgaatg tgttagtcta   1620
ttataagcaa agattttcag gtcaaacttg gtttgaaata cagactgtat gttcctcaca   1680
gaaaatgtga ctttgagcaa ccaagtctgc ttaaagtcag ctattaaaag tatgtatttc   1740
atgcatctag ttttttctta atatatttta taaagtcttt aaagtgatat gtggaagaat   1800
gtggtaaagc acttagttag agcaaaaagg gttgttttcc ctatcagccc aaaataccat   1860
atgtctagaa tcattaggaa ttaactgtaa catagtggac aagcattatt actatgtgct   1920
agtgtttcat gacttcctca gattattcaa atggtatcca atctacttgg tccaatccaa   1980
ctcttctttt cttccacaaa cctttcactt attttacatg gatgactttt gtttctcaac   2040
ttttatacaa ttacagtttc ataatagaat ttgacattga ttttatactg cctacaatat   2100
tgtttattta atgtaattct tagcataaaa ataataaaaa tgagcaagtc aaaaaaaaaa   2160
aaaaaaaaaa aaaaaaaaaa aaaaaaaaaa aaaaaggcca catgtgctcg agctgcaggt   2220
cgcggccgct agactagt                                                 2238
```

<210> SEQ ID NO 3
<211> LENGTH: 1861
<212> TYPE: DNA
<213> ORGANISM: Homo sapiens

<400> SEQUENCE: 3

```
cactgttggc ctactggatg cgaccgatcc ccttctcccg gaccccagga gccggcgccc     60
ccgccctgta gggttacgac tcactgatta aaaagaggga ctttttcaaa tactttgcac    120
ttttgattgt gtattatgga taccaaggaa gagaagaagg aacggaaaca aagttatttt    180
gctcgatgac aatcaaaaca aaacacatga taaaaaagag aagaagatgg tggttcagaa    240
gccccatggg actatggaat acactgctgg aaaccaggac accctaaact ccatagcact    300
gaaatttgac atcactccca ataaattggt ggaactgaat aaacttttca cacatactat    360
tgttccaggc caggtccttt ttgtgccaga tgccaactct ccttccagta ccttaaggct    420
atcatcatcc agtcctggtg ctactgtctc tccttcatca tcagatgcag aatatgataa    480
attgcctgat gctgacttag cgcgaaaggc cttgaaaccc attgaaagag tcttatcgtc    540
tacttctgaa gaagatgagc caggtgtggt gaaattttta aaaatgaatt gtcgatactt    600
caccgatgga aagggtgtgg ttggcggtgt tatgatagtg actcctaaca acatcatgtt    660
tgaccctcat aaatctgatc ctctggttat tgaaaatggg tgtgaggagt atggtctcat    720
ctgccccatg gaagaggttg tttccattgc gctctacaat gacatttctc acatgaagat    780
caaagatgcc ttgccatcgc ctggagaatg ggaagacctg gcttcagaaa aggatatcaa    840
```

-continued cccattcagt aagttcaaat ctatcaacaa ggaaaaacga cagcagaatg gagagaaaat 900
tatgacttcg gattccagac caatagtacc tttggagaag tccacaggac atacacctac 960
aaagccctca ggcagctctg tgtcagagaa attaaagaaa ctggactcct ctagggagac 1020
atcccatggt tctcccacag tgactaagct cagcaaggaa ccttccgaca cttcttctgc 1080
atttgaatct acagccaaag aaaactttct aggggaagat gatgattttg ttgacttgga 1140
agaactttct tctcaaactg gtggtggaat gcacaaaaaa gacaccttga aggagtgcct 1200
ttctcttgac ccagaggaac gaaagaaagc tgagtcacaa ataaacaatt ctgccgtgga 1260
aatgcaggtg cagtcagccc tagccttttt gggaacagag aatgatgttg aactgaaggg 1320
ggcgctagat ttagaaacct gtgagaagca agatataatg ccagaagtgg acaagcagtc 1380
tggttcgcca gaaagccgag tagaaaacac actgaacata catgaagatt tagataaagt 1440
taaactcatt gaatattacc tgactaagaa caaagaaggg ccacaggtat ctgaaaattt 1500
gcagaaaaca gaattaagtg atggaaaaag tattgaacca gggggaatag acattaccct 1560
tagtagttct ctttcccagg cgggtgatcc cataactgag ggcaataaag agccagataa 1620
gacctgggtg aaaaagggag agcccctccc ggtaaaactg aactcttcta cagaagcaaa 1680
tgtgattaaa gaggctctag actcctcttt ggaatctact ctggacaacg gctgtcaagg 1740
tgcacaaatg gataataaat ctgaagttca gttgtggctg ttaaagagaa ttcaggtacc 1800
cattgaagat atacttcctt caaaaaaaaa aaaaaaaagg ccacatgtgc tcgagctgca 1860
g 1861

<210> SEQ ID NO 4
<211> LENGTH: 2481
<212> TYPE: DNA
<213> ORGANISM: Homo sapiens

<400> SEQUENCE: 4
gaattcctcg agcactgttg gcctactggt tcagcagctt tttaactggc gttgttttta 60
tgctgatgta ttatgccttc tttcatccca atggacccag attcgggcag tcaccaagtt 120
gtgcttgtga ggacccagcc gctgccttca ctttgccccc agacgtggcc acaagcaccc 180
tacggtccat ctccaacaac cgcagtgttg tcagcgaccg cgatcagaaa ttcgcagagc 240
gggatgggtg tgtacctgtc tttcaagtga ggcccactgc cccatccacc ccatcatctc 300
gcccaccacg gattgaagaa tcagtcatta aaattgactt gttcaggaat aggtacccag 360
catgggagag acatgttttg gaccgaagcc tccgaaaggc tattttagct tttgaatgtt 420
ccccatctcc tccaaggctg cagtacaaag atgatgccct tattcaggag cggttggagt 480
acgaaaccac tttataaagc aaaaggagtt gcaggaccca caacatccag atgaaggggt 540
gacagcaggg ctgtggccat aatgacactt catcctagag cagggcagtg agccgtgaag 600
ttcctagtgg gaccgtcatc accattatca tttgatcctg tcggctgggg gcggctggtc 660
tccttccaaa gcagctgcac ccgagagtct ctgactccac ctgaaagaat gacgctggct 720
taataggact ctccattgct accaaactcc tcctgcacgg tcttgggtgc acccaccaga 780
gggtactact attatggaaa aattttgcct ccaatcatta gggtgtcttg atggcgttaa 840
ctgatctttc cataaaaata gattcagtca tacacacata cacacactaa cacacataag 900
ttacaccagt cctctgtcaa aaaagcttag gtgacttttc ttgatgcaaa gctctgattc 960
ccacaggaat ataaaaacaa agaaagaggg aaacatccct cgagaaaaaa aatagtattg 1020
cttagaaaag aaaccatttt ctcatttgga aatccatacc atgtgtgaaa atcctatcca 1080

-continued

```
acggacagca aacccaaatg ttgtctacac atgtgttagc attgatggag tggttcattt   1140
tctacacatt tcaggatttg ttttatattt taaattttca gttgcgaaca tcctttttga   1200
cagaaatcct atgcagccca tgtacggctt tcaacaagac caaggagctc aataacttca   1260
tgatgtaaat taaatagtaa tcatgattca gtattcaatt gcaaaaatgt aacaggtaca   1320
caaagaggaa gtggggaaaa aggcaaaatg agagtctgat tcccaggcat gtgcagcgcc   1380
cattgggaca taacggcagt gcggcgcgag ccagaggaat gggctggaac cggatctgtt   1440
tccagacgca gaatgagtgg ctctgtgtga ccataggcag atgctgactc tggaagactc   1500
cgtgccactc ctttctagtg ccaaacacca tccaaccaca ggactgacgt ggaagcccca   1560
aacaactgag aatgagtggc atgagccccc taaaagcagg cgagagaacg agcaatcaag   1620
ttctccactg tgtacagact tttcctcccc ccaatccaag gtcaaagtga tgtgtctttt   1680
agaggctttg ggacactttt tagtaagtat gagcagacaa atgcaatgaa tatgctatga   1740
aaaaaccctt ctgaactgag agagggctta tcactatatc cagctaagat ttgtatttga   1800
atcatctgta aagtcgcact cttacaacaa gcttctgggt tttaaatacc tccgtacagc   1860
aagtaaacgt tccccgcttt ctgttctcag tgtcctcggt catggtgctt ttcgttgcat   1920
taaaagtgcc ggtcaaactt tgatagtatt tttttatagt tggtgcagag tggaataact   1980
catggattat ttcaatattt ctgtaataaa aaatataggg tatacacata ggcatcatca   2040
catttttat agacctggaa tcgtttaaaa tactttaagc atcataatta cttgggatgt    2100
cagaaactgg tccacaaatt ccatcagcct gcctcagcag attgaaaaca tttgtctctt   2160
gcaagatcac cctactttgc aagttggtgc ccccaggaac ctggccaggg gtgctatcag   2220
aatatcaggt gaagagagaa tcagcttaaa tagaaagggc ttgtcaagac tggccaatgt   2280
ttcccaggaa atcaaagatg taaatgatta ctttcatcca tccattgtaa caaacctgac   2340
cacagtggaa gctgtcttaa acttccttcc ctggttttat attaacccaa ctgatagatt   2400
aagtattagt caaaccacta aaaaagaaaa aaaaaaaggc cacatgtgct cgagctgcag   2460
gtcgcggccg ctagactagt c                                             2481
```

<210> SEQ ID NO 5
<211> LENGTH: 3208
<212> TYPE: DNA
<213> ORGANISM: Homo sapiens

<400> SEQUENCE: 5

```
gaattcctcg agcactgttg gcctactggt actgggttgc gagggctgtg acgcgtcctg     60
ctgcagcccc tcgtgctaca gctcctcgtg ctacagcacg tcctgctaca gcagctcgtg    120
ctacagcgcc tcgtgctaca gcccctcctg ctacaacggc aacaggttcg ccagccacac    180
gcgcttctcc tccgtggaca gcgccaagat ctccgagagc acggtcttct cctcgcaaga    240
cgacgaggag gaggagaaca gcgcgttcga gtcggtaccc gactccatgc agagccctga    300
gctggacccg gagtccacga acggcgctgg gccgtggcaa gacgagctgg ccgcccctag    360
cgggcacgtg gaaagaagcc cggaaggtct ggaatccccc gtggcaggtc caagcaatcg    420
gagagaaggt gaatgtccta tactccataa ttcccagcca gtaagccagc ttccttccct    480
gaggcctgaa catcatcact acccaacaat cgatgagcct cttccaccaa actgggaagc    540
tcgaattgac agccacgggc gggtctttta tgtggaccac gtgaaccgca caaccacctg    600
gcagcgtccg acggcagcag ccaccccgga tggcatgcgg agatcggggt ccatccagca    660
```

-continued

```
gatggagcaa ctcaacaggc ggtatcaaaa cattcagcga accattgcaa cagagaggtc    720
cgaagaagat tctggcagcc aaagctgcga gcaagcccca gcaggaggag gcggaggtgg    780
agggagtgac tcagaagccg aatcttccca gtccagctta gatctaagga gagaggggtc    840
actttctcca gtgaactcac aaaaaatcac cttgctgctg cagtccccag cggtcaagtt    900
catcaccaac cccgagttct tcactgtgct acacgccaat tatagtgcct accgagtctt    960
caccagtagc acctgcttaa agcacatgat tctgaaagtc cgacgggatg ctcgcaattt   1020
tgaacgctac cagcacaacc gggacttggt gaatttcatc aacatgttcg cagacactcg   1080
gctggaactg ccccggggct gggagatcaa aacggaccag cagggaaagt ctttttttcgt   1140
ggaccacaac agtcgagcta ccactttcat tgacccccga atccctcttc agaacggtcg   1200
tcttcccaat catctaactc accgacagca cctccagagg ctccgaagtt acagcgctgg   1260
agaggcctca gaagtttcta gaaacagagg agcctcttta ctggccaggc caggacacag   1320
cttagtagct gctattcgaa gccaacatca acatgagtca ttgccactgg catataatga   1380
caagattgtg gcatttcttc gccagccaaa catttttgaa atgctgcaag agcgtcagcc   1440
aagcttagca agaaaccaca cactcaggga gaaaatccat tacattcgga ctgagggtaa   1500
tcacgggctt gagaagttgt cctgtgatgc ggatctggtc attttgctga gtctctttga   1560
agaagagatt atgtcctacg tccccctgca ggctgccttc caccctgggt atagcttctc   1620
tccccgatgt tcaccctgtt cttcacctca gaactcccca ggtttacaga gagccagtgc   1680
aagagcccct tccccctacc gaagagactt tgaggccaag ctccgcaatt tctacagaaa   1740
actggaagcc aaaggatttg gtcagggtcc ggggaaaatt aagctcatta ttcgccggga   1800
tcatttgttg gagggaacct tcaatcaggt gatggcctat tcgcggaaag agctccagcg   1860
aaacaagctc tacgtcacct ttgttggaga ggagggcctg gactacagtg gcccctcgcg   1920
ggagttcttc ttccttctgt ctcaggagct cttcaaccct tactatggac tctttgagta   1980
ctcggcaaat gatacttaca cggtgcagat cagccccatg tccgcatttg tagaaaacca   2040
tcttgagtgg ttcaggttta gcggtcgcat cctgggtctg gctctgatcc atcagtacct   2100
tcttgacgct ttcttcacga ggcccttcta caaggcactc ctgagactgc cctgtgattt   2160
gagtgacctg gaatatttgg atgaggaatt ccaccagagt ttgcagtgga tgaaggacaa   2220
caacatcaca gacatcttag acctcacttt cactgttaat gaagaggttt ttggacaggt   2280
cacggaaagg gagttgaagt ctggaggagc caacacacag gtgacggaga aaaacaagaa   2340
ggagtacatc gagcgcatgg tgaagtggcg ggtggagcgc ggcgtggtac agcagaccga   2400
ggcgctggtg cgcggcttct acgaggttgt agactcgagg ctggtgtccg tgtttgatgc   2460
cagggagctg gagctggtga tagctggcac cgcggaaatc gacctaaatg actggcggaa   2520
taacactgag taccggggag gttaccacga tgggcatctt gtgatccgct ggttctgggc   2580
tgcggtggag cgcttcaata atgagcagag gctgagatta ctgcagtttg tcacgggaac   2640
atccagcgtg ccctacgaag gcttcgcagc cctccgtggg agcaatgggc ttcggcgctt   2700
ctgcatagag aaatggggga aaattacttc tctccccagg gcacacacat gcttcaaccg   2760
actggatctt ccaccgtatc cctcgtactc catgttgtat gaaaagctgt taacagcagt   2820
agaggaaacc agcacctttg gacttgagtg aggacatgga acctcgcctg acattttcct   2880
ggccagtgac atcacccttc ctgggatgat ccccttttcc ctttccctta atcaactctc   2940
ttttgatttt ggtattccat gatttttatt ttcaaaccaa atcaggattg acaaaagctg   3000
tgcatgaaga actgccttct tctaagatct aaccttcagg cttctctcct ctgttttcaa   3060
```

```
tgaactgcta gcctgtatgc aatattaaaa aacagctgtc tcaaggtctg tgtatatctc   3120

cacatacctc cattactaac aatgaaatat gaatgcaagt taagctacac ttgaccaaat   3180

ggtaataaat gtttacttcc atttctat                                      3208


<210> SEQ ID NO 6
<211> LENGTH: 818
<212> TYPE: DNA
<213> ORGANISM: Homo sapiens
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (742)..(742)
<223> OTHER INFORMATION: a, t, c, g, unknown or other
<220> FEATURE:
<221> NAME/KEY: modified_base
<222> LOCATION: (749)..(749)
<223> OTHER INFORMATION: a, t, c, g, unknown or other
<220> FEATURE:
<221> NAME/KEY: modified_base
<222> LOCATION: (779)..(779)
<223> OTHER INFORMATION: a, t, c, g, unknown or other
<220> FEATURE:
<221> NAME/KEY: modified_base
<222> LOCATION: (789)..(789)
<223> OTHER INFORMATION: a, t, c, g, unknown or other
<220> FEATURE:
<221> NAME/KEY: modified_base
<222> LOCATION: (791)..(791)
<223> OTHER INFORMATION: a, t, c, g, unknown or other
<220> FEATURE:
<221> NAME/KEY: modified_base
<222> LOCATION: (815)..(815)
<223> OTHER INFORMATION: a, t, c, g, unknown or other
<220> FEATURE:
<221> NAME/KEY: modified_base
<222> LOCATION: (817)..(817)
<223> OTHER INFORMATION: a, t, c, g, unknown or other

<400> SEQUENCE: 6

cctcgagcac tgttggccta ctgggtcgac gtgtggcgtc ggctctaccc ggaatggaga     60

atatccagga gaaaagcaaa gaagggatga tcgacatcaa gctgggcaaa ccccaggagc    120

ccccggccag cgagggcggc tgctcctgct aatgcagagc cgacctgtgg cttcccatga    180

cactccttgc ttgttgtgtt gcttcctatt ggctagcttc ctaagggggg agggaaccga    240

gttatcaaga tgggaggatt tttcttttct ctctgtcttt aggagtaggg tgggatgggg    300

agggaggctg ggcatcaggg atcacatcac tcttaacggc tgttacttaa acaactattt    360

tttggtttgg ttgtaatata ttgtacttta ttaagattgc caaaaactgt taaaatttaa    420

aaaaaattta aatcatgtgt atacaatttt ttgccagata aaaatgtagt catttttatt    480

tgaaagatgt gctttttgtt tttgtatatt tgtaaactta tagagaacct tttccacaca    540

cctcctcctt cctgttctct ttgaaccgtt catcacctct gccttcctcc tatccccaac    600

ccaataaatt aaaacaatta actgagcaaa ttaattaggc ttcaatctgg ggccatctgg    660

cccactctct anggcctact ccagttaaat caaacattgg gttgacacat caacctctga    720
```

-continued

```
aaaggtactc cgantcctgn cnttccaang gcaaaatggg tcgtcaacct cctgttganc    780

tgaaacaang nccgttggct ccaaggaacc ccggnana                            818


<210> SEQ ID NO 7
<211> LENGTH: 821
<212> TYPE: DNA
<213> ORGANISM: Homo sapiens
<220> FEATURE:
<221> NAME/KEY: modified_base
<222> LOCATION: (504)..(504)
<223> OTHER INFORMATION: a, t, c, g, unknown or other
<220> FEATURE:
<221> NAME/KEY: modified_base
<222> LOCATION: (577)..(577)
<223> OTHER INFORMATION: a, t, c, g, unknown or other
<220> FEATURE:
<221> NAME/KEY: modified_base
<222> LOCATION: (610)..(610)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (711)..(711)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (751)..(751)
<223> OTHER INFORMATION: a, t, c, g, unknown or other
<220> FEATURE:
<221> NAME/KEY: modified_base
<222> LOCATION: (766)..(766)
<223> OTHER INFORMATION: a, t, c, g, unknown or other
<220> FEATURE:
<221> NAME/KEY: modified_base
<222> LOCATION: (774)..(774)
<223> OTHER INFORMATION: a, t, c, g, unknown or other
<220> FEATURE:
<221> NAME/KEY: modified_base
<222> LOCATION: (783)..(783)
<223> OTHER INFORMATION: a, t, c, g, unknown or other
<220> FEATURE:
<221> NAME/KEY: modified_base
<222> LOCATION: (793)..(793)
<223> OTHER INFORMATION: a, t, c, g, unknown or other
<220> FEATURE:
<221> NAME/KEY: modified_base
<222> LOCATION: (797)..(797)
<223> OTHER INFORMATION: a, t, c, g, unknown or other
<220> FEATURE:
<221> NAME/KEY: modified_base
<222> LOCATION: (800)..(800)
<223> OTHER INFORMATION: a, t, c, g, unknown or other
<220> FEATURE:
<221> NAME/KEY: modified_base
<222> LOCATION: (815)..(815)
<223> OTHER INFORMATION: a, t, c, g, unknown or other

<400> SEQUENCE: 7

ggcttttttt tttttttttt tttttttttt gagaattagg acagtttatt gtttgaccaa     60

catgctgagt cttttccaca ttttacacag tttaatgtga aatcaacatg gcggctatgt    120

cttctgagcc cataacagat ggaattgcca ccctctgtgc tcctcacagc caatcacttt    180

aaagggatgg gtgaggggaa agtgagggga gaagtggaca cacaccgcga gatgcaggct    240
```

```
ggccttcaat gctatggagg cttcccacct cctgaaggaa ccatctaaac ccctgctgca    300

aggatttcct gatgaaacca cacactgctg ggagtgccaa ccagacaggg gtctggagtc    360

caaggagttt gcacattgag atcccaaggt tttggaacac ctaaatagtt catgtcaaac    420

aaaaattcaa agggtgtcct gatctgtgtg ggtgcccatg acaatcaatc agagtagact    480

tggggactgg cccttgtgca gtanaggagc ccaaaatacc accaatattc tcactcatat    540

gctgggaaaa acctagtgtc ctaaccaaaa agagtanaga tggtctgagg aacacaccct    600

cacacagcan tccttgctgt gtaataaata tggagtcaca tttgttcaca cacanggcaa    660

caatgggntg aaaaatggga acttcactct gtgccaaatt ctacctgcaa ncaaggggac    720

aaggatggtg cctgctcaan acaaaaatca nggaaccaac aaattntgaa aaanaggcct    780

ggntgccttg gantttnttn ccccgaaaaa ggaantgatt t                          821
```

<210> SEQ ID NO 8
<211> LENGTH: 3591
<212> TYPE: DNA
<213> ORGANISM: Homo sapiens

<400> SEQUENCE: 8

```
aattcctcga gcactgttgg cctactgggg tagaggccga cctgacattc tttaacacgc     60

tggtgagaaa gaagagcaag ctgggagacc tggagggggc caaggcgctg ttgccggtcc    120

tggcaaagag ggcctcgtc cccaacctgc agacattctg caacctggcc atcgggtgcc    180

acaggccgaa ggacggtcta cagcttctca cagacatgaa gaagtcccag gtgaccccca    240

acactcacat ctacagtgcc ctcatcaacg cggccatcag gaagctgaac tacacctatc    300

tcatcagcat cttgaaggac atgaagcaga acagggtccc ggtgaacgaa gtggtcatcc    360

gccagctgga gtttgcagcc cagtaccctc ccacctttga ccggtaccaa gggaagaaca    420

cctacctgga gaagattgac ggcttccgag cctattacaa gcagtggctg acagtgatgc    480

ccgcagagga aaccccgcac ccctggcaga agttccggac caagccccag ggggaccagg    540

acaccggcaa ggaggctgat gacggatgtg ccccttgggg caggtgatgg gagcacagct    600

ggaacaatgt gctcggcccc cagtgctctg tgggagcccc aggacaagtg agctggtgtc    660

acctcctgcc tgggggaaga gccaggccct gaggaacagc cgcagcgtgt cacaggtgtt    720

ggtgaggaca cacactaggc ccaaggtgcc tgtgctccca gcaggtccaa gtgcagctcc    780

agccaccttt gcgtgtcacc ttcacgggac ttccagctcc agctaccttt gtgcgtcacc    840

tcacacacca caagggggct ggggcatctg gtccctgggg cctgggccgc cccgccgggt    900

tccataggcc gatgctctga aagaagagac gtggggctcg agagatttaa agattttatt    960

tttacaaatc acagctgata gacagcgaag ccttccccat agagaccgtg ctccaactcg   1020

ggcctggggc actgctcgct gctcccagga agggggtggc gtgacaggca ggaacctgcg   1080

aagtccagag tccagggtgg agcgcgccag cctcagccag agcagccacg acagccacag   1140

tgtgtgcact cgatgatgcg gccctgcaac ggaggaggac agtgagacga tgccactgcg   1200

ccacgctcgc ccctgcacac tcacatatgt ggcaaccctc ccacgaagga cctgccacca   1260

tgccatatag ggacacacct cagaaaccct tccttgacag ctctggacag ggaaaatttg   1320

gctccctcat gaaggtagga ccagctgctg ttgacaccga ggttacatct gtatgtctat   1380

ttataaatatg ttctgcaaat ccaacacacg tttgccaatc aagaaaaaga aatcggtgtg   1440

aatgagtctc gttattctgc taagtgagca tgacagaccc tgcgatgagc agaggtggct   1500
```

-continued

```
ctgctactgt ttggggactt caggggggcc tctgggctgg tacactctgg tgggggaaga   1560

gggcaggaga ctatgcactt gagtcacacc cttctggccc agagcccccc cagaaagaag   1620

ggtcttgtcc cccaggcctg gtgcggccca acacttggcc agccagaaag ccctagaaca   1680

gtggcttgtg tttattttac tttttcaagt tcttttttttg gaagaacaag accatagttt   1740

aagtaaacag gatcctctgg tgaaacccag gtaagtctac agcgggctgt tttggccaca   1800

gggctgaagc agcaccccag cccaccagcc cctgacctgg actccttgtg gaatctgggc   1860

actcagagga agggggcttc tgccactctg ccacctgtcc ctgcctccat cagaaagcca   1920

acaccccagt cttccgtcgg ggaggcggcc cttgctcgcc cccactgctc agtacccaag   1980

tcctcagcat ccagccacag ctctccattg tcagtctcac tgcagcataa aggggactca   2040

tgtgaagagg cccctgtgtg gagctgggga aaagaaggcc aggctggcag atgggcggtg   2100

gggccaacaa ctgtgctgag ggctgcact gagcggccac tgctgtgact ctgcctcggg   2160

ccacagctgc ctttcagagg ggcttggaac cggatggagc tcagctcctg tccctcagca   2220

ccactcctga ggcgcctggc ctaggagtgg tacttggaac agaaagttct gaaagaagaa   2280

acacagtggg ctgggtgcag tagctcatgc ctgtaatccc ggcactttgg gaggctgagg   2340

caggtggatc acctgaggtc gggagttcga gaccagcctg agcaacattg agaaaccccg   2400

tctctactaa aaatacaaaa ttagccaggc gtggtggtgc atgcctgtag tcccagctac   2460

tcaggaggat gaggcaggag aaccgcttga acccgggagg tggaggttgc agtgagccaa   2520

gatggcatca ctgcactcca gcctgggcga caaagcaaga ctccgtcttg gggggggcggg   2580

aaagatagtg atggtaatgt taaagtatca ctgtgaggac tgaaagggac aggaactcac   2640

tggttgtcct tccctgatgt caccctgcca ccaccttggg attagggctc cccaccacca   2700

tttcctaagt gaggaaaggg gttcagtaat ttgcccaaaa gtggagttga gattgacccc   2760

agacctaaca aacacacagc cacacgctgc ctcacatgga ttcctgaata cagggaccca   2820

ctcccacgag ggagagccag caggacatcc agggacaaaa cgacattcca gcccaaccaa   2880

ataacataag atcccttgca gtcgactaag gcagaatttt gagctgaaaa caacaccaag   2940

cttgagtgtc agacattacc acttccagct tgcttttggg cacgcggcag atgcagttcg   3000

tcccgaagtt ggtgtcccgt gtctgaatgc accgcaggca gcacaagttc tcatatcctt   3060

gctttttcca ttttgcaatc aggtttttgt ctgcatagcc ttctttaata caatattcat   3120

agagttctgt caaaaagatg ggaaaagagc atcaggccat ggtctaaaaa ccttccccac   3180

ccttgatcaa aaaaagcatt caggccgggt gcagtggctc acacctgtaa tcccagcact   3240

ttgggaggcc gaggcaggcg gatcacctga ggtcaggagt tcaggaccag cccggccaac   3300

atggtaaaac cccgtctcta ctaaaaatac aaaaattact cgggcgtggt agcagctgta   3360

atcccagcta cttaggaggc tgaggcagga gaatcacttg aacccaggag gcggaggttg   3420

tagtgacctg aggtcgtgcc actggactcc agcctgggtg acagcgaaac tccatctcaa   3480

aaaaaaaaag gcattcagta ttgcaacggg acagtccttg gaggaggaac aaaaaaaaaa   3540

aaaaaaaggc cacatgtgct cgagctgcag gtcgcggccg ctagactagt c            3591
```

```
<210> SEQ ID NO 9
<211> LENGTH: 2954
<212> TYPE: DNA
<213> ORGANISM: Homo sapiens

<400> SEQUENCE: 9

gaattcctcg agcactgttg gcctactggg aagctcttct agttcatctg ctggccggct     60
```

-continued

```
ctcagtcccc gtggcgcccc ctttcctctt gtcccagagc gctctcgact ccaccatgcc    120
aaggggattc ctggtgaagc gaactaaacg gacaggcggc ttgtaccgag ttcgccttgc    180
ggagcgtgtc ttccctctgc tggggcccca gggggcgccg cccttcttgg aggaggctcc    240
cagcgcctcc ttgcccggcg cggagcgggc gacacccccc acccgagagg aaccaggaaa    300
ggggttgacg gcggaggcgg cccgggaaca gtcggggtcg ccatgtcggg cggctggggt    360
gagcccgggg acgggcgggc gggaaggcgc ggagtggcgg gcgggtggca gggaaggtcc    420
cgggcccagc cccagcccca gccccagtcc agcgaagccg gcaggcgcag agctgcgtcg    480
ggcgttcctg gagcgctgcc tcagctcgcc cgtctccgcc gagtctttcc ccgggggcgc    540
cgccgccgtg gccgctttct cctgctccgt ggcgccagca gccgcaccga ccccggggga    600
gcagtttctg ctgccgcttc gggcgccgtt cccagagccc gcgcttcagc cggaccctgc    660
gcccctctcg gccgcccttc agagtctgaa gcgggcggcc ggcggcgggc gccgcggcaa    720
ggcacccacg ggctgcgcgt ctggacccgc ggccgcggga atcaagaagc caaaggccat    780
gaggaagttg agctttgccg atgaggtgac cacatcccct gtcctgggcc tgaagatcaa    840
ggaggaggag cccggagcgc cgtcccgggg cttgggggc agccgcacgc cactggggga    900
gttcatctgc cagctgtgca aggagcagta cgcagacccc ttcgcgctgg cccagcaccg    960
ctgctcccgc atcgtgcgcg tagagtaccg ctgccctgag tgcgacaagg tgttcagctg   1020
tcctgcgaac ctggcctccc atcgccgctg gcataagccg cgtcctgcgg ctgcaaacgc   1080
cgccacagtc tcctccgccg acgggaagcc gccttcttcg tcgtcttcgt cctcccggga   1140
ctccggggcc attgcatctt ttctggcgga gggaaaggag aacagccgaa tagagcggac   1200
tgcggatcag cacccgcagg ccagggacag ctccggggcg gatcagcacc cggacagcgc   1260
cccgaggcag ggcctccagg tgctgacgca tccagagcca ccgctgcctc agggcccta    1320
cacggagggg gtgttggggc gccgggtacc tgtgccgggc agtaccagtg gtggcagggg   1380
atccgagatt ttcgtgtgcc catattgcca caaaaagttt cgtcgccaag cctatctgcg   1440
caagcacctg agcactcacg aggcgggctc ggcccgtgcg ctagcgccgg gctttggctc   1500
cgaacgcggt gccccacttg ccttcgcttg cccattgtgc ggagcgcact tccctacagc   1560
agatatcagg gagaagcacc ggctgtggca tgctgtccgc gaggagctgc tcctgcccgc   1620
tctggcgggg gctcctcccg aaacgtcggg ccctagcggg ccatctgacg ggagtgccca   1680
gcaaattttc tcgtgcaagc actgcccgtc cacttttttt agctctccag ggctgacccg   1740
gcacatcaat aagtgccacc cctcagaaag ccggcaagtg ctgctgctgc agatgccact   1800
gcggcctggc tgctgaggga cgagagacca ggatgatttc gaggttggcc ttagaggaaa   1860
cagatcatgg gaatttctgt ggggctttct tcaacttgca agtttacttt cattccttcc   1920
tatgttttaa tcccctaaaa ttctccctgt agtcaatgtt ccaccagagg agcggacagt   1980
gaaatgtaat atccctctct agagcaggta tgtatatggt ataaaccttg agatcaaaga   2040
ctgtcagctt taaatccttc tcactttccc cactaaaata ggatttttcc ccttaaaact   2100
ctggagaccc taacgaatcc tatatgattt gtaattccta tggaaagtcg cggtgaatgc   2160
gtgcatgtct caatgtccac aaaggattct ggctaccctt tggtagccaa tgtttttttt   2220
gtcttgtcat cacaggcgcc tatacagctt ctgtctcaat agggtcagat attttgcaca   2280
tattctgtga attaaaagtt atgtgattgg tgccaaactt aaggagattc aagacctggc   2340
agaaaatgta agaggatttt tgctgctttt ggggtgcatg ggatctcccc ctgtaaactt   2400
```

-continued

```
tcctttgccc aattatatgt acatgtccat tcttaagttg gtgtttggag gtggggagga   2460
tgctacttta ctggagttga gacacccccct aaaattctca ccctcagcta ttttgtgggc   2520
agtattcagg aagagctact tcaaaccttt ctttaaatgg ctttttggaa atacagaagt   2580
cgtttcctca agtttgactg ttttaatggg gtttcaccca aattgtttaa tgcttctgct   2640
gtaaatgtca tactgtgtat tcattatgaa aatatgtaca gcttaaggaa gatgttaaca   2700
cctgtaatcc actaaggaac tgaatggcaa tttgctcaat attcagtatt ttcttttcag   2760
cggcaacttg tttttgattt ttttaaaaaa ccatttcagt gtacattgtg tactaattcc   2820
ctactagcca gtttgggaca ttggctgagc actgcctgac agaaagcccg tatttgtaag   2880
atgcttacca ccaaataaat gtacatagac tgtgaaaaaa aaaaaaaaaa aggccacatg   2940
tgctcgagct gcag                                                       2954
```

<210> SEQ ID NO 10
<211> LENGTH: 2269
<212> TYPE: DNA
<213> ORGANISM: Homo sapiens

<400> SEQUENCE: 10

```
tgttggccta ctggtaagcc tgggaacatt aaaagctaat ttataaaagc aatacttttt     60
aatatgaaaa cttactgcaa agtttgttta tacttttgcc taaaaaggaa attggatggg    120
atactgtggc aaatcataaa aaaccagata attgaacttt gaagttatag aaaatcagag    180
aggggtaagt ttatagggca ttttgttctg atggttcaac cagaggtctg ggaaatagca    240
ctgttggccc aaacagaaca ggcttttaga agataaaagc gacaagaagg aatctggtga    300
attttagtca tcccagcttt ttagtcttaa ccacagttct cactctctta aatggtacct    360
caaaaagctg gagcctctct gccatgatta tgcttctaca aatttctttt ataaagagac    420
tcaaagctaa tgatagctta aaagaaaagt taatgccttc tcattggaaa tgtataatca    480
aataagtagt taagggcttt tggtattaaa gatattctga agctctgaaa tgctagaaaa    540
aaatttggaa tggagtatat gcctgaaaag gttttggatt cagaaagaaa aaggatggtt    600
agtttaatca gtgattcttt ttaaactctt caaatatcat gaacaagata ctaaattgta    660
cctaaggatt tgtatttctt tacaatttgt tctaaatatc tgtttaatga ctagttgata    720
tttgtgcatg ttatttaata aagagttata tttttataga aaaaaagagt gaaatgtgtg    780
ctaactgttt ttttacttaa ttttacttgg gcagctagca aaattgcaga aatatgcatc    840
ctgggaaaag aaacagcctt tgaagaatta gcctttcaag ttcaaatcta tttaataatg    900
agaagtctca caagtgaatt tttaagtaca ggcatacctc agacgtactt taggttccag    960
accatctcag taaagcaaat accacaacaa agcgagtcag gaggaatttt ttggtttccc   1020
agtgcatata aaagttttgt ttatactata ttaagtgtgc aatagcatta tgtctaaaaa   1080
tatgtacata agtttaaaaa tattttattg ctaaaaatgg taacaaagtg agcacatgct   1140
gttggaaaaa gagcaccaat agacttgctt gaagcagggt tgccacaaac cttcaatttg   1200
taaaaaacgc caatatgtac aaagcacaat aaagcaaagc acaatagaac aggattgcct   1260
gtattagaca tgctacaaac ttcataactg gaaacatctc aaagacccca tgaagctcat   1320
ttgaatggga cttaacaatt agacagttat tttagaaatt gagtgcagac ctaaatacat   1380
agttttccaa aaagaaaatt attgtctctg atatcttaaa acataaaaac ccaaaatttt   1440
atatagaaga aattgactct gtaaaacgca atgaaatagt cctcttttta aacagtttaa   1500
aggaagcatt ttcaccgttt gtaaaaatta tttttaaata tttagggcaa aatttttgtt   1560
```

-continued

```
agataataat ggaaaagctt gtgtgagttt agtggttaaa atatcttgta attcatcatt   1620

atttaagtga cttcttggga gccgtctttg tacctaaaat ggagtttttt ttttaagcct   1680

ccacagagat agtcacccaa agtatttcca gtcagtaaaa gtagaattca tagaaaaaac   1740

tgaggcaaat taaaacaatt ccattaatca aaatggcttt aaacaaatta agtattagca   1800

taaaaatagc aaaaagtaca actaaaaaaa tggttgggtt ttcccagtgg ttaaatgcta   1860

tataataact gcaaataaaa gttttttgt acatggacag cgtcctcata aaagaaaata    1920

ggccaggcca ggcgcagtgg ctcgcgcctg taatcccagc actttgggag gccaaggcgg   1980

gcggatcacg aggtcaggag atcgagacca tcctggctaa cacggtgaaa ccccgtctct   2040

actaaacaaa atgcaaaaaa tcagccgggt gtggccgcgg gcgcctgtag ttccagctac   2100

tcgggaggct gaggcaggag aatggcgtga gcctgggagg cggagcttgc agtgagccga   2160

gatcgtgcca ctgcactcca gcctgggcga cagagcgaga ctccgtctca aaaaaaaaaa   2220

aaaaaaggcc acatgtgctc gagctgcagg tcgcggccgc tagactagt               2269
```

<210> SEQ ID NO 11
<211> LENGTH: 2260
<212> TYPE: DNA
<213> ORGANISM: Homo sapiens

<400> SEQUENCE: 11

```
aattcctcga gcactgttgg cctactggtt tcagcacatg atgatgtttt caggtttgcg     60

aggagcgatc gcatttgcct tagctattcg gaacacagaa tctcagccca aacaaatgat    120

gtttaccact acgctgctcc tcgtgttctt cactgtctgg gtatttggag gaggaacaac    180

ccccatgttg acttggcttc agatcagagt tggcgtggac ctggatgaaa atctgaagga    240

ggacccctcc tcacaacacc aggaagcaaa taacttggat aaaaacatga cgaaagcaga    300

gagtgctcgg ctcttcagaa tgtggtatag ctttgaccac aagtatctga aaccaatttt    360

aacccactct ggtcctccgc tgactacaac attacctgaa tggtgtggtc cgatttccag    420

gctgcttacc agtcctcaag cctatgggga acagctaaaa gaggatgatg tggaatgcat    480

tgtaaaccag gatgaactag ccataaatta ccaggagcaa gcctcctcac cctgcagtcc    540

tcctgcaagg ctaggtctgg accagaaagc ttcaccccag acgccaggca aggaaaacat    600

ttatgaggga gacctcggcc tgggaggcta tgaactcaag cttgagcaaa ctttgggtca    660

atcccagttg aattaattgg catgaagagt acagatgtaa tcacaagtaa tgcaagactc    720

actgaggaat acaagccaag ctgatgaggc agtacagggg agaggctgga aaacatatta    780

agagcataaa ttggagagaa tcaaagcctt gtcacatgga tcctctggtg cctgaagaaa    840

tgagatttta ttatccctct ctattatgca aatgaattta gtttttgac agcagccatt     900

ctgattactg gattggctgg ggtggggatg gaggtatcag gagtctagct gctggaggat    960

gggacagctg tgctgggtct tcagggcatt tctgctgcga atgcggctct ccaggccctt   1020

cacttctatt ctggatttta ttccctccat taaggagagt ttaaaaataa aagaaagctt   1080

ctgagagtaa acattttgct cctaagctga agggaatgcc cagctattta gtaagtgata   1140

agtttcttat tttgaggact tgactcccat ttgctctcag tgaccccagg gcagagccca   1200

gagaagtgtt ccgtacccac tgctgatggt ttcccagagc ccacactgag ttgaagaacc   1260

tattgttctt cttggcatcc ttcttatgct acttctccca tcgctcaaag ggttgcctaa   1320

tggctgggtg tgccctgccc taaatgcagc accactttca agcttagtag gaccattcca   1380
```

-continued

```
agaaaaccag gtttcttctc cccataccac gttgtgcctg aagaacaagc cttcccgtcc   1440

ttgcctgcat gtgagtcact tcttggctgt gcagcaggtc ccccccctccc cgcgatatgc   1500

tggagggtag gattctgcag cctgtgttgc tctctacctg gcagcagact gtgcaggagc   1560

cccaacctgt cctccaattc cagcattcac agctgatgag cagtgcagga gcagggcgag   1620

aggaacagag ccaatgatgt gtgggttaca ctgaggagcc aaggacaggg cctcaggtct   1680

ccccccttaca aggcgtggct catggcctgc attccagaga ccaacatgat agcttttaat   1740

tcagctgcat gacctgtgcc ttttaagcca taaagatacc tcaagcctag cacctcttga   1800

aatccagatg ttcatattag actcgaaaaa ataggctcca ggcctaggtg cccaggctat   1860

gatgagtctg cttttgaagg aggtagggaa tgacatcttc cttggaccca aagcttaaaa   1920

gtaatgtatg ctttgctgac cactgtttgt taggccttaa acaacattca ctgtggtggt   1980

atcaggcaca ctgctatgtg catcaattat tttttgctt tccaaacaga atctctgggg   2040

cacaagtttt acacttaagc taagtataac tttgtcattt caggtaaata tgacaagtgg   2100

tggagcatga agttttctaa tttgacttaa tcctaataaa tttttgttac aaagtaaaaa   2160

aaaaaaaaaa aaaaaaaaaa aaaaaaaaaa aaaaaaaaaa aaaaaaaaaa aaaaaaaaaa   2220

aaaaaaaaaa aaaaaaaaaa aaaaaaaaaa aaaaaaaaaa                         2260
```

<210> SEQ ID NO 12
<211> LENGTH: 2561
<212> TYPE: DNA
<213> ORGANISM: Homo sapiens

<400> SEQUENCE: 12

```
cactgttggc ctactggtta gacaaaccaa cagcagcttc ttctgacata tacacacgca     60

cactcacccc ggacacacac tcagcacact tttcctccat tcgattaaca gtgctgcaca    120

cacaatgatt acgggaaagc gcaaataaat acggaaaggg gtgcttattt tgactactgg    180

aagagctttg ctgggtctca gcgcaacttt tgttttttat tcctgagaag gtgatctctc    240

catgcggttc tctcacacaa ggattcttta aaagaggaag agagacaagc agaggggggga    300

ggacagtctt tcactttaag aacggctggg ctcaaagata aaaggaaggg aaaagcagca    360

gcagcagcag cagcagcagc agcagcagca gcagcagcag cagcagggaa accaacgctg    420

cagcacttcc gaaaggcatt tttgatccat ttctgagtgt tgcggcccgt ttctccaccg    480

aagttggctc cagctctagc agccgcattg gatcccacag cttactgcga gactccggtg    540

tacaatccgg atctctgccc caacatgatt gcggcccagg ccaagctggt ctaccatctg    600

aataaatact acaacgaaaa atgccaagcc aggaaagctg ccattgccaa aactatccgg    660

gaagtctgca aagtagtttc cgacgtactg aaggaagtgg aagtgcagga gccgcggttc    720

atcagctctc tcaacgagat ggacaatcgc tacgagggcc tcgaggtcat ctccccccacc    780

gaatttgaag tggtgcttta tctcaaccaa atgggggtgt tcaacttcgt ggacgatggc    840

tcactgcccg gctgcgcggt gctgaagttg agcgacgggc gcaagaggag catgtccctc    900

tgggtggaat tcattaccgc ctccggctac ctctcggcgc gcaaaatccg gtccaggttt    960

cagacgctgg tggctcaagc ggtagacaaa tgtagctacc gggatgtggt aaagatggtg   1020

gcagacacca gcgaagtgaa actgagaatc cgagataggt acgtggtgca gatcacgccg   1080

gcctttaaat gcaccgggat ctggccgagg agtgctgccc actggccact tccccacatc   1140

ccctggccgg gacccaaccg ggtggcggag gtcaaggcgg aaggtttcaa tctcttgtcc   1200

aaggagtgcc actccttggc cggcaagcag agctcggcgg agagcgacgc ctgggtgctg   1260
```

```
cagttcgcgg aggcagagaa cagactgcag atggggggct gcagaaagaa gtgcctctcc   1320

atcctcaaaa ccttaaggga tcgtcacctt gaactgccgg gccagccctt gaacaattac   1380

catatgaaga ctctggtttc ctacgagtgt gaaaagcatc cccgagagtc ggactgggac   1440

gagtcttgcc tgggtgatcg gctgaacggg attttgctgc aacttatctc ctgcctgcag   1500

tgccggcggt gtccccacta ctttctaccg aacttagatc tgtttcaagg caaacctcac   1560

tcagctctgg aaaacgctgc caaacaaacg tggcgactgg caagagagat cctgaccaac   1620

ccgaaaagtt tggaaaaact ttagaggatg atttaatcaa gagccgaaat tattaccctt   1680

ctcaaagtcc ttattaagtg taaacttctg ctcaattcct aatattccac tccgcagtgc   1740

aaacaatctc ttcctttaaa aaggaataat aatacaatat ttaaacatca tctcacccac   1800

ccccacaagg ggagaaaaag taggggaagc ggatggagaa aaacccaaag ccactagtat   1860

tagaagactt ctttccacac gatttcctat ctcccttgaa aagtacaccg taacactccg   1920

taaacagccc agctgtaacg ccagaccgag acgaacactc tgcctaacta tcaaaggatt   1980

atagcaatcc tggtgattta ggtgcatctg tctgtgagta aacacgattt ggatatgcca   2040

tctgaaagaa actgtaatgt atattttgat ttgtaacaaa tattgtgatc tcacattgtc   2100

tttgaaagtg tggatgttgg tgttttgtga tttggtgaac agaacttaaa ttgccattct   2160

ggatacttcc agacattttc cactaacaaa gatatcattt aaaggtagat ttcttcctgg   2220

tacttttatc tgtctttgaa agtgtctgaa ctttaaaaag tttacatttt gtttcaaata   2280

ttgcttgttc tatttctaac attccataaa tatacttgaa atgttattta aatatattca   2340

aagaaatttg aattcagctt atataataac gcttgaatat ctgaattata tatttgaaaa   2400

atgcacttga aatacactgg ataattactt ttgtgattta gattttaatt tgttgctggt   2460

ttttatttaa ttagatggta ataaatgaag taaaataaaa gttaaaaaaa aaaaaaaaaa   2520

aaaaggccac atgtgctcga gctgcaggtc gcggccgcta g                        2561
```

<210> SEQ ID NO 13
<211> LENGTH: 2952
<212> TYPE: DNA
<213> ORGANISM: Homo sapiens

<400> SEQUENCE: 13

```
gaattcctcg agcactgttg gcctactggt gtttcattaa gaggcagtct gttctgtgga     60

cctgggaggg agagacaggg agcgtttttc accaacaact tacaactcca cagtaagttg    120

agaggagtcc cgactccatg ctgtatgaag tccagcactg acacaccatg gccagcgacc    180

aacttgctaa gtcaaaaaaa tctaactcag aacccctttga ctgaggaaca gttttcacac    240

tccagaaaat tctaaatgac tttcatttgc tgttggttca catgccctcg tggaagactt    300

tgcttgctgc tttgttttca taagcagctt gaaggaaact caggcaggaa ctatggaact    360

ccagctgctg ctgtaactgc atcttgacga tgcaaaatga cgatggaaat atagaagcat    420

gtacatcata tctatcatga attgagcatg tgggtctgtt ccctcgaatg aaaaatacat    480

gcaaataaaa atatttggct ataggtggtg caacttttaa cagttgttct agaacttaca    540

catccaaata tgtgttttca ctttgcacag ggtggcctat ggagttttat gcttgctcta    600

gtaatgttgt agtggaaaac attttggaag tattttaatg tattaaccac attgtttaat    660

atctttaacc tcattaaatc acagtccttt aaggaatgat atgtgtgcac tcttgtatgt    720

gtatgagtgt atgtatgtgt gtgtgcagtt gcatgtgtgg gagtggggat gcacgtgtgt    780
```

-continued

```
gttcggtgtg tgtatatgag catgtgtgag tatgtgtgta tatgtgtgtg caattgcatg    840

tgtatgtatg tgtatgtatg tgtgtttgtt gtgtggtatg tatatgggca tgtgtgtgta    900

tatatgtgtg tgtgcagttg atgtgtttgg gggatacctg tgcttgttgt gtggtatgtg    960

tatgtatggg catgtgtgtg tatatatgtg tgtgtgcagc tgatgtgtgt gtggggatgc   1020

atgtgtgtgc attgtgtata tgtgtctggg catgtgtgtg tatctatgtg tgtgtgcagt   1080

ttggggatgc atgtgtggtg tgcatatgta tatggacatg tgtgagtatg tgagtatatg   1140

gtgtatgcac acatacttat atatgcatgt acatatttat cccttataaa cacatataca   1200

cacatgtaca cacacatatg tgcacataca tatatatgtg catgtatata tcccttacat   1260

atacacacat atacatgcac acatatatgc acacatacat atatatgtgt gtgtatatat   1320

ttatccctta taaacacata tacacacgta tatgcacaca tacatatata tgtgtgtgta   1380

tatatttatc ccttataaac acatatacac acgtatatgc acacatacat atatatgtgt   1440

gtgtatatat ttatccctta taaacacata tacacacgta tatgcacaca tacatatata   1500

tgtgtgtgta tatatttatc ccttataaac acatatacac acgtatatgc acacgtacat   1560

atttatgtgt gtgtatatat ttatccctta taaacacgta tacacacgta tatgcacaca   1620

tacatattta tgtgcatgta tatatttatc ccttatgaac aaaagctctt tggggtcctc   1680

aatagcttct aaaggtgcaa agggtttctg agaccaacat gtctgaaagc cactgaatta   1740

ccttaacagc tcctaggtct gaaagtttat ggttctaaaa aatgcccagc acttgctgtt   1800

tctatgagga ataaaagtga ttgtctcacc gtcaacactg tctacaacac tgttagggag   1860

acaaagctta tctacatcaa gatgatggat tagctacttt tcttagttct ttctagctcc   1920

cacaacaaaa taccgtaaac tgggtggctt ataaacaaga gaaatgtatt gctcacggtt   1980

ctggaacttg gaagtccaag atcaaagtgg aaacagattc agcatctggt gagggcccgt   2040

tcctcattga cagtcatctt gctgtattct catatggtgg atgggactag aggtctccct   2100

ctgggatttc ctttataagg gcattaatcc tattcaggag gtaacattca tgacctaacc   2160

ccttccggag gccttgcctc ctaacaccat cacactgaag gttaggattc tgacataggg   2220

attttggatg gatgcatgca ttcagaccac agtgacagcc tacaatcaag ttctaaattg   2280

tgtagttcaa actaggagaa ctgtgaggag atggttttgg ggaaagtgac ttctgcattt   2340

gcctcaatga ttttccctgc gatgacacgt ggcctgctct gaacagtgtt tgttccacaa   2400

aatgctgctg tcctttattc agaaactttc tattgaaacc aatttttatc tcaataacct   2460

gatttttaat ctcacaaaac tggacctggt gactttgagt tactatatta gaaccttgta   2520

aattgccttg tttactgatt gttttaacac aagatcctgt catctcacta gactatgtaa   2580

atttgcagat aaaaatgccc atctggccgg gcgcggtggc tcacgcctgt aatcccagca   2640

ctttgggagg ccgaggcggg cggatcacga ggccaggaga tcgagaccat tctggctaac   2700

acggtgaaac cccgtctcta ctaaaaatac aaaaaaattag ccgggcgtgg tagcgggcgc   2760

ctgtagtccc agctactcgg gaggctgagg caggagaatg gcgtgaaccc gggaggcgga   2820

gcttgcagtg agccgagatc gagccactgc actccagcct gggcgacaga gcgagactcc   2880

gtctcaaaaa aaaaaaaaaa aaaaaaaaag gccacatgtg ctcgagctgc aggtcgcggc   2940

cgctagacta gt                                                       2952
```

<210> SEQ ID NO 14
<211> LENGTH: 1403
<212> TYPE: DNA
<213> ORGANISM: Homo sapiens

<400> SEQUENCE: 14

```
cctactgggt ttccccctgt gtggataaga gcaaaaaccc cgattttaag gtgttcaggt      60
acagcacttc cctagagaaa cacaagctgt tcatctcagg cctgcctttc tcctgtacta     120
aagaggaact agaagaaatc tgtaaggctc atggcaccgt gaaggacctc aggctggtca     180
ccaaccgggc tggcaaacca aagggcctgg cctacgtgga gtatgaaaat gagtcccagg     240
cgtcgcaggc tgtgatgaag atggacggca tgactatcaa agagaacatc atcaaagtgg     300
caatcagcaa ccctcctcag aggaaagttc cagagaagcc agagaccagg aaggcaccag     360
gtggccccat gcttttgccg cagacataca gagcgagggg gaagggaagg acgcagctgt     420
ctctactgcc tcgtgccctg cagcgcccaa gtgctgcagc tcctcaggct gagaacggcc     480
ctgccgcggc tcctgcagtt gccgccccag cagccaccga ggcacccaag atgtccaatg     540
ccgattttgc caagctgttt ctgagaaagt gaacgggacg ctgggagaca ggaaatgcct     600
tacttcactc tggcccggcg gacctcccac cacccagcag tgcactgggg atggacaggc     660
ctggtgtgct gcgtgctcgc aaccacagat ggctcctcgg ctttagacag aaaggggaag     720
gggttctaag tcaagagcct ttcagtgctc cctcatattg agggcagtgg cagaaaagtg     780
accactcagc aggctgggcc caggatgtgg tgtcctgaga tagttttgta tcttaaagac     840
tgaggcacag aagcgaaacg agaacacact gtttttgaga cacagttgtc caaatgtttc     900
tggccagctc cggccccttt ttgtatgaca cttctcttcc accctgcaca gcacatgtgc     960
ccgtcattct tttaatttta aaagatgaaa tggcagatgc tagtaattca cagaatggcc    1020
tcttgtgggg gtgggtctga gggaagtcag ctataaaaca tttgctggag ttttgttcaa    1080
tggggctgtg catttttata ttatgtgttt gtaaatgaca tgtcagccct tgtttcatgt    1140
ttcctaaaag cagaatattt gcaacatttg ttttgtatag gaattatttg tgccacctgc    1200
tgtggactgt ttctttgcc tagtgactag tgacctgtgt tgtctaaaca tgagtttcag    1260
ccctttggtt ttgtttaata ccatgtcaaa tgcaaacttc aattctcccc atttagcttt    1320
attaaactga cgttctcttc aaaaaaaaaa aaaaaaaaaa aaaaaaaaaa aaaaaaaaaa    1380
ggccacatgt gctcgagctg cag                                            1403
```

<210> SEQ ID NO 15
<211> LENGTH: 2144
<212> TYPE: DNA
<213> ORGANISM: Homo sapiens

<400> SEQUENCE: 15

```
cactgttggc ctactggtgt gtcaatttta tctcttagaa ttgtggattt tattgtcaag      60
acagaatggc tgttcattta ttttataaaa gcatctcctt ctataactca aaatggtctt     120
taagtgtcat ataaaagtgt acattttact tttaagcaac taatttagat acctaagaaa     180
aactatgtgc attaggaaaa gtcatgtttt tcttctcaga aaggttgatc acatgatatg     240
tctactaaga attttcacct ctgtacttgt atgtatattt tattgttact caatcttgta     300
ttttatttac aaattcaaca ctgtcaaccc tgggaattct aaaataccaa tgtattttta     360
ggttgtagct aatgttgtat tcactttcaa ttctcagttg tccacactgg tgatataaga     420
ggaacaaatc agaatcatta aatactttgt aatgccatca taaactcata tattcatcct     480
caaactccct tgtttaatgc taattggtgg cctggaactt cactgagatg caaaatcaag     540
aactgaagcc tagttgctag ataacaaaaa gctataaatg tttatgtatg tgaattttaa     600
```

-continued

```
attagaataa ccgtcttaaa ctcctacttg ccatttctaa ggcaaagcat tcattttaat    660

attgtacttt gccttttcat tcagttagtg gagtaagtca tgaaaccctt aggaagaaaa    720

acaagttatg acttattcac taaaattgat gcaagacagt tggttctaga tgaccatggc    780

catgtgttca tcatataaaa ccttcagttc tctctatggt gcttggctgg agattgacat    840

gtgaggatgt gccaatcata ttaaatggat ttggtctatg tgggtgatat gtggcctgaa    900

tgtaactgtg atagactgaa atttgttctt agctctcaaa atccactgaa gaagtcaagt    960

gaaggtgggt aaaataggga gattagtgac aactttgtgc caaatttttt aaaaaatgga   1020

agcaggtagc caatattaga atgataattt aagggtgtgg ttgaatttta gttagttgtc   1080

acatagttat tgaacctcat atgctcagtg ctgtgggaat caaacatgga agaggtatgg   1140

ctcctgcccc taatgagaac aagggggaaa aatccagata taatctaaat gctaggttat   1200

gtcagggtat aggaacacag agaatggggg acctgtaaga actggaagag tcagagaggg   1260

ctccattgaa gaggtcaaac ataattccgg aaagaattag gtagtgagga gattgtgcca   1320

ggaaaataag tgggaaaggc cacagttatg cttcctttga atggaagaga gacaaagcta   1380

tcagctatag atcattgttt tcttaagaca gccaaactgg ccctttgaaa ccattcaaat   1440

taccccagtt tagctcccta ccttttagtc tccgtgagga agacaagctg ttgcattatc   1500

atattcctct gtgctgagca gctcaagact cagccacaat atgcaaattg ctttaatgcc   1560

atattacggc agttgattta gacatttgcc agtgcaccaa accatgagag attgtccgac   1620

ctaatgccac ctggcagatg tgtacccaga gatttttctg tagctccatg tttcccataa   1680

agggcattgg aaatgcacag atgaagatct tcctttggaa ccaggcacat ttggcccctt   1740

ctcagtgact gcactgtgga actcttctta agaaaatatt gaaaacagct taatgctttc   1800

atatagtgac cgacatttag ttgaaaacta ctgctgcata gcaaatattg tgactcttcg   1860

tgtgtccaca ggagctcttg tgtgggttta aagctatgaa gtgtattcac attgtgaagt   1920

tttaattatc tttattgaaa ttaattgtgt aaaaatggta tgtgctctat taggtattca   1980

gtttgtatgt gaattctata aagaaagtgg tttttgttct ttgagtttgt tttgtttctt   2040

gaagattaca ataaatatct aagagactat attcctgaaa aaaaaaaaaa aaaaaaaaaa   2100

ggccacatgt gctcgagctg caggtcgcgg ccgctagact agtc                    2144
```

<210> SEQ ID NO 16
<211> LENGTH: 2995
<212> TYPE: DNA
<213> ORGANISM: Homo sapiens

<400> SEQUENCE: 16

```
gaattcctcg agcactgttg gcctactggc accccaagtt tgtcttgtga acttttgagt     60

taagttatta atcctcttac attcagctgg catagtggtt tctttaaagg gttgctacaa    120

agactacagt tgagaagtcc ttttataacc atgtccaaat acatagtatt ctctatactt    180

gtgtttaatt gtcttatttt tgctaggaaa taaaatttct gaatgagatc tgaaaatgga    240

ccttagaacc tgaatactca cacttttgat acctatgcag tgttatatga atttccttaa    300

acccactgtt gtttgcaata agttgattca tgacagtgtt ccttggaagg taatggtcag    360

aagctatgta gtttttcata aaatattcca tcttgagtaa aactgtaaag gttcttcacg    420

gttcaacctt acatttggca gatctaacat atttctgttc tattcaacat tttaaataga    480

tatagctaat ctccccatat gctctaatgc tgcttcttat gaactatcaa atgccttggc    540

ttttgggaaa acccggaagc atgcatttgg tttgcctata aataaataag acatgtacag    600
```

-continued

```
agtattttcc tggaaaagta ttacttatcc tcgtgacaag tcttaacacc tggtaagact    660
tgttcactta acatttttta agtttggttg ctttttttccc ctgctggctg ttgaatttga    720
atcctgaaac agttgtagta tatcttgctt gcctgcttgc acgcttcctc tctttccacc    780
ttttgttcca tcttaaagct aatttaggaa aagtctggtt ataaactagt ctttatataa    840
aaattatctt ttatcactaa tgtagttttt tttccagaac catcagctaa taggaatata    900
agaccattgc tctccataat tactggatta cttctacatc tttcattagt atttaaagag    960
ccaaagagct aacaatatat tccagatttt ttacgtggac atgccttcct tttggactca   1020
tcataaattc ataggactgt aaggacagtt gagtatgatg gttctgggca cctttaggta   1080
ataacatctt cttcctactt ttctctctat ctgtgctttg ctccttttcc tgaacctgct   1140
tttggctttc ttcaactgct cctctggcac tcttgtgtgt aaaaccaatc acctgcaccc   1200
tagttatccc catttgtcct cgttcagcat cttgcagccc catcatcatg ccctacaaag   1260
ctgcacactc tagaaattcg atggatcgac caaaactctt tgtaacacca cctgagggct   1320
cttctcgcag gaggatcatt catggcacag cggtgagtag ctgttgggag cagctgggca   1380
agtctgggag ccagtgctgt tcctgtgcag actgtacatg accctgagct gtggtgtggg   1440
cgtaagaggg ggagaccgtg acatccacca tcccatcttt cccattgatc atgaatctgg   1500
ctagctgggc agtagtgtcc cctcacttcc tcttcacttg ggattttgc tctccctaaa    1560
catttgaatt tgaagatgaa agctgttctt tgttcaagca tgtatgagtg gacgccctac   1620
cctcctggag cgtccataca cataagtaca atgccagaat actttcattt ttgaaagtag   1680
gaaaaccaaa tggcctttga aggggaagtg ggcttggact gctgccttgg catttttattt   1740
caaccatatc cagaagctgg ctgaactcta aatgtggttc actcaaaagc aagataaaga   1800
atttttatcc tgcttggcta atccctgtca aggccctgtc aagggatctt aaaatttagt   1860
caaaaaagta ttttgaaaac attagtcatt tgctatatca ctaattcgta aaaggctgtt   1920
aggctgtgct ataaattctg attttgtaag tgaaaaatat aatttgtact tattattacg   1980
ggctgaggta atgttaattt tcaccatgct ataaatgcaa tgaggtaatt tgtatgtctc   2040
caggaatctt cttctttgtt ttaaatcttg tgtttatttg gtgtcagttg aaagatataa   2100
accttgttct gtggtcttta gacattgtac tttagtctta aaggactcac cagtgaacta   2160
gaagatctca ttgcctctct ccaggataac agtatgaccc ttttgatgaa aggctgaaac   2220
agtttcttaa aatcgtaact tcccagagca attcagattt ataaacctga tgaacactta   2280
aaaggatttt gcttaaagga taattcaggg ttgtgagagc ttgatggctt tgcctacagc   2340
ctgtttttct ttcaagctcc atcggccttt ctggaatcag tgtttgattc atgattgagt   2400
caggcctcca accctctaag ccacaggtga aacaatcttt gatgtctgga aagttttaat   2460
ttattagagt gttggtgttt cagagatcct ccttagctgt agacagaaag ccgtagttaa   2520
acagaacagc ttggccccaa agttgggtac tcactgggca ggggaaaaga gcatttacca   2580
tggaaaaact atcttgttct gggtaaaaac aaaaattaac actccttgag agaaggttga   2640
gggccacctg tggctgacag gttaaatgag agatttgtca tcacatgatc cagagccttg   2700
ttttgttttg tttttattac cttcctcttt ctctatttaa tcacatagct gtctttttac   2760
ctctttacaa ccaagtattt aggcaaatac taacagaaaa cgactcagag tcatttatac   2820
cctggagctg cactgtggaa ttcagtagtg actggccaca gtgagcactt ggaaagtggc   2880
tactgaaact gacaagctaa attttaagtt tttaaaaaat atttagttgt gttaaaaaaa   2940
```

-continued aaaaaaaaaa aggccacatg tgctcgagct gcaggtcgcg gccgctagac tagtc 2995

<210> SEQ ID NO 17
<211> LENGTH: 1877
<212> TYPE: DNA
<213> ORGANISM: Homo sapiens

<400> SEQUENCE: 17
gaattcctcg agcactgttg gcctactggt aagattttta tagttaagtg aggcatttgt 60
tgattacaca aaacatgtta ttgatatttg tatcacatat gcacattttt ttccttttaa 120
gtatggtata ccgtgttctc agcaattatt tcattatcgt ttctctgcaa cctttcttca 180
atggtactaa gcaagacaca tctggggagg cctactttct atgttgtggc ataaaagtat 240
gtattgaagc tttagtagag atctcaaaaa tggttggatg gtagcaaatt actaagaact 300
ctcaaagttt ctaaagcctt agtttcagct tgctagaaaa cctatgttga gtattatggc 360
tagttccata gttgagttgg gaaatgtctt tgaggagaca ctttttcact ttgtattcat 420
ctgtacattt tctgttactt gcattctgtc atgctcaggc tattagagca ggtacatttt 480
tataactgga atgtttatgt gtagtgaagc tctgagagga ctttgcatta gatctcagca 540
gcataatcag aaggttgtcc tttgtctcag caatttttaa gctaatagta gcagaaattg 600
cagtggaaat agactgcttt gccacaacat tcagaaaatc atttatcttt ttattgcagt 660
tcttgtcacc aaacaataca ttttagtact tctcaaattg cagaactctc atagggctgg 720
gaaaatgcct gtagacacat acatactatg aatgtgctaa tgtttttttgt attttcatag 780 cccatcaaag ctcctgagtc agtttccact ataatcactg cagaatcaat cttctacaag 840
ggagtatatt accaaattgg tgatgttgtt tctgtgattg atgaacaaga tggaaagccc 900
tactatgctc aaatcagagg ttttatccag gaccagtatt gcgagaagag tgcagcactg 960
acgtggctca ttcctaccct ctctagcccc agagaccaat ttgatcccgc ctcctatatc 1020
atagggccag aggaagatct tccaaggaag atggaatact tggaatttgt ttgtcatgca 1080
ccttctgagt atttcaagtc acggtcatca ccatttccca cagttcccac cagaccagag 1140
aagggctaca tatggactca tgttgggcct actcctgcaa taacaattaa ggaatcagtt 1200
gccaaccatt tgtagttcac aaattaaaac tgggtttcca ggcctggtgt ggtggctcac 1260
gcctgtagcc ccagctattg caccactgct ctccaagctg ggcaatggag tcagattctc 1320
tttcttaaaa aaccacaaaa aaactggatt tccagttctc taatattctt agtaccacaa 1380
gatatgtcat aggtatcttt aaatgaaatt cttagctgga aaagtgacta aaaagttttt 1440
ctcctgctac ctagtaataa acaaatcatt gtttattact ggtcacttag aaaattaaaa 1500
gggatagggc caggcacagt ggcttatgcc tgtaattgca gcacttttag aggccgaggc 1560
aggcggatca cctgaggtcg ggaagtggat cgcctgaggt caggagttcg agaccagcct 1620
ggccaacatg gcgaaacccc gtcgctacta aaaatacaaa aattagccag gtgtggtggc 1680
atgtgcctgt aatcccagct atttgggagg ctgaggcagg agaatcgcct aaacccagga 1740
ggtggaggtt gtagtgagcc aagattgcac cgctgtgctc cagcctgggc aacagagtga 1800
gactcttgtc tcggaaaaaa aaaaaaaaaa aaaaggccac atgtgctcga gctgcaggtc 1860
gcggccgcta gactagt 1877

<210> SEQ ID NO 18
<211> LENGTH: 2290
<212> TYPE: DNA
<213> ORGANISM: Homo sapiens -continued

<400> SEQUENCE: 18

```
gaattcctcg agcactgttg gcctactgga gttcccaccg ctggggctgg cggcgaccaa     60
ctgtaagaga aactcactgg gaggcgaggc agggggggtgc ggaggatggg aaggcgactc    120
tgaagggtgg gaagtgaatg ctggacttga tcgtctttct ctttctttca gcgcagacct    180
gtcgcagcca gagagctgtc atttcagtac cgggattcag aattgatcca gtccgcagcg    240
gagggggcac atcccagcta ccgagctgct gagtgtctct ggctgggaca atagtatttt    300
tttctctgcg aggctgcaat taacatctta tttgttctgg ctccatacag gctttgtcag    360
gatcgcggtg cggcgaccga cgttgggctc ttgcattgct ttgtgcttgg caatggaatc    420
atggtttcgg ggtctaaact tttgtttcgt tttgtagtct taatgtatct gattcttttt    480
caagtttccc tagtaacagg tttggggacg gggtgggaag aagcgagaaa aggggtgaag    540
agaaaaaacc agattatata gaaaggaaaa agggaaaagg gatgtttccc caccttttaa    600
tctaactatc tatctgtctg tctatctatc atcatagata gtcattttgc ctcctggaca    660
gttggctgac gaagtgtctg ataaaccagc ttcagataca tgctacaaaa ggtcattcgc    720
ctcctgatta tgtttctact tgtaaacgca gttggtggtt tgcaaaacaa gtgctaaaat    780
agtgcagtga tgtggtggga ggaaaccata atgggtaatt catataaagt gctggaatct    840
tcgtaagggt gagtttctcg agcggcaggt gaagttgaat aaagcaattt tccatcattt    900
gttcccctca ctcttgcatt tttttcctcc gcttgtttct ctcccctggg gcgattatgg    960
atagccaaga acaccatttt aaaagagatt gatagtgaaa acaggaagtt tatggtctgt   1020
tatccactgg agttgtttga aatattaaaa ttggtccttt acttcttaat gcatattaat   1080
agagtgaccc tcttcaaggc tttcccgtct taaacgaatg cctgggataa acactgtaag   1140
gggaaacagt taataattcc ccagcaggct ttaactattt tcccagtaac aaatcaccgg   1200
caagagagca gcctgggtgg cattttggtt ttgtgtcatt ttggttcttt acaatatttt   1260
ttattcattt aaggaaatgt taaaaggaaa taattagggt ttatgtccag aacaaatttt   1320
gaaacaccgt ttaagcaaca cattttcttt taaaaacaaa gaacattgag caacacaaag   1380
gagaaaaaca ttttatttat ttcaacttcc ctagagatcg taattatgat tttcgcaagg   1440
caatttggtc agttctgtta ctttatccag aggaaaaaaa agcatgacag atgtggaata   1500
aaaacggagg aaaaaatgct ttggatggtt tatacataaa aaggaaagaa tgtaatgtga   1560
ggttcagtta tacctctatt ttgcatctag tgatttctca tattatcttg taacactgat   1620
tttgatgttt cttagaaatt cttaaagtca tgacacagtg gcataagaat aacagctgaa   1680
agggacaatt taaaagccta aatcctaaat ggaaaggttc acttactccc aggatcattt   1740
atattcaagt agaagtcagg gcagggtcag aaaagaaagc cacccttaat aaagcgcttc   1800
acccttcaca ttgtttctca taaccttcat aaattgcagg ctactgagct ggcctgatga   1860
tgatccttct gagatatatt tatagcagat gatttgtgga tgataactac gccaagcaag   1920
acactgtctc cagtaacccc aggctcgtct gacttcctca ggggattata ataaagaatc   1980
acaaaaagaa ccctatatga acagtctggt ctctggacac taacaacagc acaatccaaa   2040
ggcaaagaaa ggaggaacca ccttgtttca tgtctgcaag ctgctccata tgaaagcatt   2100
gctgacatgt tgacccaaca gcaaaaagag agcagcagtt tacgcaccct cagctctctg   2160
tcctttcctt tctattgatg ttggtccact tttatgactg aatacatatt aaaatcacca   2220
tttcaaatta taaaaaaaaa aaaaaaaggc cacatgtgct cgagctgcag gtcgcggccg   2280
```

-continued

```
ctagactagt                                                          2290


<210> SEQ ID NO 19
<211> LENGTH: 2347
<212> TYPE: DNA
<213> ORGANISM: Homo sapiens

<400> SEQUENCE: 19

ttcctcgagc actgttggcc tactggcaga atacaaggaa gaaagatgca cagagaagaa     60

tgaagatcgt catgcactac acatggatta catacttgta aaccgtgaag aaaattcaca    120

ctcaaagcca gagacctgtg aagaaagaga aagcatagct gaattagaat tgtatgtagg    180

ttccaaagaa acagggctgc agggaactca gttagcaagc ttcccagaca catgtcagcc    240

agcctcctta aatgaaagaa aaggtctctc tgcagagaaa atgtcttcta aaggcgatac    300

gagatcatct tttgaaagcc ctggcaagac tgtggagccg ttctctgaac tcggcttggg    360

tgagggtccc cagctgcaga ttctggaaga aatgaagcct ctagaatctt tagcactaga    420

ggaagcctct ggtccagtca gccaatcaca gaagagtaag agccgaggca gggctggccc    480

ggatgcagtt acccatgata atgaatggga aatgctttca ccacagcctg ttcagaaaaa    540

catgatccct gacacggaaa tggaggagga gacagagttc cttgagctcg gaaccaggat    600

atcaagacca aatggactac tgtcagagga tgtaggaatg gacatcccct ttgaagaggg    660

cgtgctgagt cccagtgctg cagacatgag gcctgaacct cctaattctc tggatcttaa    720

tgacactcat cctcggagaa tcaagctcac agccccaaat atcaatcttt ctctggacca    780

aagtgaagga tctattctct ctgatgataa cttggacagt ccagatgaaa ttgacatcaa    840

tgtggatgaa cttgataccc ccgatgaagc agattctttt gagtacactg gccatgatcc    900

cacagccaac aaagattctg gccaagagtc agagtctatt ccagaatata cggccgaaga    960

ggaacgggag gacaaccggc tttggaggac agtggtcatt ggagaacaag agcagcgcat   1020

tgacatgaag gtcatcgagc cctacaggag agtcatttct cacggaggag attcaggata   1080

ctatggggac ggtctaaatg ccatcattgt gtttgccgcc tgttttctgc cagacagcag   1140

tcgggcggat taccactatg tcatggaaaa tcttttccta tatgtaataa gtactttaga   1200

gttgatggta gctgaagact atatgattgt gtacttgaat ggtgcaaccc caagaaggag   1260

gatgccaggg ctaggctgga tgaagaaatg ctaccagatg attgacggac ggttgaggaa   1320

gaatttgaaa tcattcatca ttgttcatcc atcttggttc atcagaacaa tccttgctgt   1380

gacacgacct tttataagtt caaaattcag cagtaaaatt aaatatgtca atagcttatc   1440

agaactcagt gggctgatcc caatggattg catccacatt ccagagagca tcatcaagta   1500

cgatgaagag agatcttata agagaagtgt gaggtaaaat ctcctgatct cctattcatg   1560

ctggaccctg tgtgtgtaca ccagtgtttt acttgtgggt gacctcaaca agctaccaga   1620

gcaagaggtc actgtatcag tcttttgtat gccattttca gtctttgtcc tgtgtgtaaa   1680

gctgttgagg tcaacctaat ttgcaactga aacctactaa accagataca tccctgactt   1740

ggcccaggct gcaagctaac ttgaactgta cccaccagac tgacgtggat gttttcagct   1800

ttattcagcc agcatgtttc tgatcccttt gcaacttatg tctacatttt atgaaggaat   1860

ttgcaaagta aatgtacata aacactgaat gggaggcaat gacaacatat ttaatggaag   1920

gagtacgtct cagggctcca gaagacagtt tcgaaaagca catatgcacc actttcattt   1980

ggccctgctt tgctgagtga ctgtctcatg ctgtgcttgc ttctcttttg tttcttttcc   2040

acaccaataa tttttgctcc tgcagactgg atgaagaact gagggaagca tcagaggcag   2100
```

-continued

```
ctaagtaaga cttggttttc gtttagcggc tggcatgatg ttggcttgca tttcagaact   2160

gaattgggaa aatctgcatg cctggtgttt tattcctgct tcctgataat aatgcacttt   2220

agaaattctc tttctcctat gatagatgta atctctatta ttcttactac aatctatttt   2280

tccccatgaa aaaaaaaaaa aaaggccaca tgtgctcgag ctgcaggtcg cggccgctag   2340

actagtc                                                              2347
```

<210> SEQ ID NO 20
<211> LENGTH: 2267
<212> TYPE: DNA
<213> ORGANISM: Homo sapiens

<400> SEQUENCE: 20

```
gaattcctcg agcactgttg gcctactggt tccagatgtc cagcacattt ttaataggaa     60

agtattggga acagatgtca ttattttcag cctaggtttt aaaacatttt agtatgtcat    120

gaattatctt caaaaggatc ataaatcttt tttaaaggtc cattttattt aaaatatata    180

aaaataatca ctgcactgca gcctgggtga cagagagtct gtttccaaaa aaaaaaaaaa    240

aaaaaaacta tagcatcagt cttttctagg ttattttcag aaatttcaaa caatgggaaa    300

agaatggaag aacttttgag gggagttgag gaacacgaaa aaagatcagt tcacagtcat    360

ataaataaaa agtcatgtta cttgtttttt ctcttttgac ggaaatatgt aatacattta    420

tccagtttta aaatcaaagt atgtgcttag aatgtaaaga caaggaatgc taaaagtaca    480

tttatcactt aatggcaggg ataagttatg gtaagtgcaa tgttaagtga ttttgttgtg    540

cgaacatcat aaagtatact tatacaaacc tagatggtct agccttctcc acacctacgc    600

tacaaagctg tacagtatgt tactgtacta aacactgtag ggaattgtaa cacagtggta    660

agtatttgtg tatctaaaca tcgaaaaagt aaaaacagag tataaaagat ttttagccca    720

ggcacagtgg ctcacgcctg taatcccagc actttgggag gccaaggtgg gtggatcact    780

tgaggttagg agtttgtgac cagcctggcc aacatgttaa aacccggtct ctactgaaaa    840

tacaaaaatt ggctgagcgc agtggctcac acctataatc ccagcacttt aggaggccaa    900

ggcaggcaga tcacctgagg tcaggagttc gagatcagcc tgaccaacgt ggagaaaccc    960

cgtctttact aaaaatacaa aattagccag gcctggtggc aggtgcctat aatcccagct   1020

actcaggagg ctgaggcagg agaattgctt gaactcaggc agcagaggtt gcggtgagcc   1080

aaaatcgcac cattgtcatg ccatcgcact ccagcctgag caacaagagt gaaactcatc   1140

tcaaaaaaaa aaaaaaaaaa aaaaaagtac acctgtatgg aacacttaac catgactgga   1200

gcttgcagga ccggaagttg ctctggatga gtcagtgagt gagtggtgag tgaatgtgaa   1260

agcctaggac actactctac catagactgt agaaacactg tacacttagg ctacactaaa   1320

tttatcttta aaatttttgt ttcttcaata ataaatcagc caggcatggt ggctcatggc   1380

ttaatcccag cacttcggga gtccaaggtg ggcggattac ttgaggccag gagtctcaga   1440

ctggtttggc caacatagtg aaacactgtc tctacaaaat aaaaaaatta gccaggcgtg   1500

gtggtgcatg cctgtaattc cagttactca ggaggctgag gcacaagaat tgcttgaacc   1560

tgtaggcaga ggttgtggtg agccaagatt gcaccactgc actccagcct gggtgacaga   1620

gtgagactct gtctcagaaa aaaaaaataa ataaataaat acaaataata aattagctta   1680

ctgtaacttt tttactttat gaactttttg attttttaa ctttttgact gttgtaataa    1740

cataactcaa aaggcaaaca tgttgcacag ctatacaaaa acattttta tccccctatt    1800
```

-continued

```
ctataggggt ttttctagtt aaaaaaattt ttattttata ctttttaagc tttttttgtt   1860

aaaaattcat acaccctcca agctaggcaa cagagcaaaa ctccatctca aaaaaaaaaa   1920

aaaggccagg cgcagtggcc cacgcctcta atcctggcac tttgggaggc gaaggtgggc   1980

aaatcacttg aggtcaggag ttcaagacca gcctggccaa catggcgaaa cgccgtctgt   2040

actaaaaata caaaaattag ttggttgtgg tggtgtacac ctgtaatcgc agctactcag   2100

gaggctgaga cacaagaacg cttgaacccg ggaggtggag gttgcagcaa accaagatgg   2160

ctcctctgca ctccagcctg ggcgacagag caacactcat ctcaaaaaaa aaaaaaaaaa   2220

aaaaggccac atgtgctcga gctgcaggtc gcggccgcta gactagt                 2267
```

```
<210> SEQ ID NO 21
<211> LENGTH: 2475
<212> TYPE: DNA
<213> ORGANISM: Homo sapiens

<400> SEQUENCE: 21

gaattcctcg agcactgtgg cctttttttt tttttttttt tggaaagcaa ggatcacact     60

tccccctccc tgttccttaa tcccttttct aaaaaggggg gaaaatccgg atggatttta    120

gggattggtc tggtgtcagc tgtgttttat tgcacaccta aatcctgatt ataggctttt    180

catttctccg caaagccttt attttggcag ttaagccaaa tgtgttttcc agaaagttag    240

ttattttctc ctctttcttt cctttctttc ctcccttttt cccgtctgac cccaaacgtt    300

attgtccaaa catgactgga cagcagcttt tgtttcttga ccctgtaata tgacagtctg    360

ctaatattga cagaaggtgc agtttttggg ttatagtcgt gattttcgct aatcaatcat    420

attagcagga aaaaaaatga cttgtttctg ttgtacttga gtcttaagaa aaagtgccca    480

tagtttagtg acaatttcca aaggctttag taccacctgt atttcaaaat gggggaccca    540

aactcccgga agaaacaagc tctgaacaga ctacgtgctc agcttagaaa gaaaaaaagaa   600

tctctagctg accagtttga cttcaagatg tatattgcct ttgtattcaa ggagaagaag    660

aaaaagtcag cactttttga agtgtctgag gttataccag tcatgacaaa taattatgaa    720

gaaaatatcc tgaaaggtgt gcgagattcc agctattcct tggaaagttc cctagagctt    780

ttacagaagg atgtggtaca gctccatgct cctcgatatc agtctatgag aagggatgta    840

attggctgta ctcaggagat ggatttcatt ctttggcctc ggaatgatat tgaaaaaatc    900

gtctgtctcc tgttttctag gtggaaagaa tctgatgagc cttttaggcc tgttcaggcc    960

aaatttgagt ttcatcatgg tgactatgaa aaacagtttc tgcatgtact gagccgcaag   1020

gacaagactg gaatcgttgt caacaatcct aaccagtcag tgtttctctt cattgacaga   1080

cagcacttgc agactccaaa aaacaaagct acaatcttca agttatgcag catctgcctc   1140

tacctgccac aggaacagct cacccactgg gcagttggca ccatagagga tcacctccgt   1200

ccttatatgc cagagtaggg tactgaccag caaaatggag aagatcagag aatgcagcag   1260

cagttttttt tcttgttttc ttaccacttt attctttcag agtttaaaga aaatggactc   1320

atgcacagaa cactatgcat tttgaaactt gttcatcctg gattttttta aatcattttt   1380

atctcagaac ttaaacaaaa attagatgtc gtgcacggac tgtgtgaaag aagatgcttt   1440

gcatatttgc tgcactgcat cagtatctta ctaaaaatgt gaaatgaaag gactattgta   1500

cactgaaatg cttaaatgta tctgaaagca caaggtgata ctcattttta tggtcttccc   1560

atttgtgctg gtttttgcct ctttgacatc tgtcatcagt atttagaggg tgagaagtga   1620

atgtaacagg tataaataac atttttaaaa acaataactt tgctataatc acagttgttc   1680
```

-continued

```
cagagcactg tcagatacat tctaatgacc agaactggtt taaaaaaaga aaatataacc   1740
atgggaaaga aatcttaaat gaaaaacgca tctcattgta ggcatttttg cctcatattt   1800
tactgggcca tgtttgtttc ctggtactca tgtatttttt ttttccagat ctctttcccc   1860
aagttgctat tgtaagagta ttctgctgcg tgtggatgca gttatacaca ttaaagcaga   1920
tctggagtct gaagtagcta taaagcagct ataaaacaga aatacatgca tagctgcaga   1980
aaccatgata ggtagaggac ttttcttttg gttttgtttt gttttgtttt gttttgtttt   2040
tggttttaca gagaagagat ttttattaca aagaaaaaaa ttccagtgaa ttgtgcagaa   2100
atgctggttt ttacaccatc ctaaagaaaa actttacaag ggtgttttgg agtagaaaaa   2160
aggttataaa gttggaatct taaattgtaa aattaaccat tgagtgtcaa agttctaaaa   2220
gcagaactca ttttgtgcaa tgaacataag gaaagactac tgtataggtt ttttttttt    2280
ctccttttaa atgaagaaaa gctttgctta agggttgcat acttttattg gagtaaatct   2340
gaatgatcct actcctttgg agtaaaacta gtgcttacca gtttccaatt gtatttagct   2400
tctggttgga atttgaaaaa aaaaaaaaaa aaggccacat gtgctcgagc tgcaggtcgc   2460
ggccgctaga ctagt                                                     2475
```

<210> SEQ ID NO 22
<211> LENGTH: 1980
<212> TYPE: DNA
<213> ORGANISM: Homo sapiens

<400> SEQUENCE: 22

```
ttcctcgagc actgttggcc tactggtaaa gagcctgaaa atattaatgc agctcttcaa     60
gaaacagaag ctccttatat atctattgca tgtgatttaa ttaaagaaac aaagctttct    120
gctgaaccag ctccggattt ctctgattat tcagaaatgg caaaagttga acagccagtg    180
cctgatcatt ctgagctagt tgaagattcc tcacctgatt ctgaaccagt tgacttattt    240
agtgatgatt caatacctga cgttccacaa aaacaaggtg aaactgtgat gcttgtgaaa    300
gaaagtctca ctgagacttc atttgagtca atgatagaat atgaaaataa ggaaaaactc    360
agtgctttgc cacctgaggg aggaaagcca tatttggaat cttttaagct cagtttagat    420
aacacaaaag ataccctgtt acctgatgaa gtttcaacat tgagcaaaaa ggagaaaatt    480
cctttgcaga tggaggagct cagtactgca gtttattcaa atgatgactt atttatttct    540
aaggaagcac agataagaga aactgaaacg ttttcagatt catctccaat tgaaattata    600
gatgagttcc ctacattgat cagtcctaaa actgattcat tttctaaatt agccagggaa    660
tatactgacc tagaagtatc ccacaaaagt gaaattgcta atgccccgga tggagctggg    720
tcattgcctt gcacagaatt gccccatgac ctttctttga agaacataca acccaaagtt    780
gaagagaaaa tcagtttctc agatgacttt tctaaaaatg ggtctgctac atcaaaggtg    840
ctcttattgc ctccagatgt ttctgctttg gccactcagg cagagataga gagcatagtt    900
aaacccaaag ttcttgtgaa agaagctgag aaaaaacttc cttccgatac agaaaaagag    960
gacagatcac catctgctat attttcagca gagctgagta aaacttcagt tgttgacctc   1020
ctgtactgga gagacattaa gaagactgga gtggtgtttg gtgccagcct attccagctg   1080
ctttcattga cagtattcag cattgtgagc gtaacagcct acattgcctt ggccctgctc   1140
tctgtgacca tcagctttag gatatacaag ggtgtgatcc aagctatcca gaaatcagat   1200
gaaggccacc cattcagggc atatctggaa tctgaagttg ctatatctga ggagttggtt   1260
```

-continued

```
cagaagtaca gtaattctgc tcttggtcat gtgaactgca cgataaagga actcaggcgc   1320
ctcttcttag ttgatgattt agttgattct ctggagtttg cagtgttgat gtgggtattt   1380
acctatgttg gtgccttgtt taatggtctg acactactga ttttggctct catttcactc   1440
ttcagtgttc ctgttattta tgaacggcat caggcacaga tagatcatta tctaggactt   1500
gcaaataaga atgttaaaga tgctatggct aaaatccaag caaaaatccc tggattgaag   1560
cgcaaagctg aatgaaaacg cccaaaataa ttagtaggag ttcatcttta aaggggatat   1620
tcatttgatt atacgggggga gggtcaggga agaacgaacc ttgacgttgc agtgcagttt   1680
cacagatcgt tgttagatct ttatttttag ccatgcactg ttgtgaggaa aaattacctg   1740
tcttgactgc catgtgttca tcatcttaag tattgtaagc tgctatgtat gggtttaaac   1800
cgtaatcata tctttttcct atctatctga ggcactggtg gaataaaaaa cctgtatatt   1860
ttactttgtt gcagatagtc ttgccgcatc ttggcaagtt gcagagatgg tggagctaga   1920
aaaaaaaaaa aaaaaaaggc cacatgtgct cgagctgcag gtcgcggccg ctagactagt   1980
```

<210> SEQ ID NO 23
<211> LENGTH: 3305
<212> TYPE: DNA
<213> ORGANISM: Homo sapiens

<400> SEQUENCE: 23

```
gaattcctcg agcactgttg gcctactgga ttttgtaaaa actgggacca tatcctgtgt     60
gccatagaaa ggatgataat accaagatga agccactggt tcctgccttc aagttctttc    120
aagtttttat tttaaagaaa actctgtgca tactaccaaa ttttacagtg aatgattgtg    180
cggactcgtg tgtaagaaaa actaggactg tgtggtgtaa ataactacaa ttctcttaac    240
tccgtagcag ttgccaactc agtccttgta cttcgttaac acgaatctgt ttcagagctc    300
tcctaccttg ctcactgcct taatcagacc gatttcctgc ccacctgacc agcccagcgt    360
ggtaaacctc tgtatattga gaccttggca taattggtga tcctgaagaa agaggtctct    420
ctcctaagtc tctgtcagaa ttgagcttca caattgctaa tggttgtttt ctgtgagtcc    480
tataaaaagc aaggatatgc atgattcagg gaatgaagaa tcacaggctt gggcagtgtt    540
aaacactgtg gcctatggtc cccgtgtgat ccaccctgct tctctccagg ggaccatagg    600
tcccgtcatg tactcagtgt ccacagcagt cagtcgtgta tgaccctgta acgtggaaat    660
cttatcacac acctgttatc caacaagtct acctgagggg ttttgttaca ctttaaatgg    720
gaaggcatag ggatttatga atggggcttt caccttctca tacccaggca accaacacct    780
gattttgtct caactggcta gcaaatgccc agccttcaga gtgtgcagga atgttttcaa    840
atccctcatc agactgtgac tttaacatta atttggaatc ctgtgagcac tactctgaag    900
gtttgtgttt tggcaaatct tttttctttt ttgagacagg gctctgctaa atattgctca    960
ggctggttgc aaactccttg cttcaaggga tcctcccacc tcagcctccc aagcagccgg   1020
gactgcaggc acaagccacc atgcctggct gtttttttggc aaatcttgat tgtgataagc   1080
ccccctggag gatatgattc actttatgtg attcatctta ttcacaggtc tgtgagggac   1140
tgcaaagctt actcaggaaa tgaaaacaaa tgatggtcat gttgcagttt tttccttgaa   1200
ggacaaccga accatagcct ctaaagttca agtgcactga ggtgtcggaa cgctgaaagc   1260
atgaggaaac gaggacgtag ggtgtgactg aatggtggct agattagtgg gagcagttca   1320
cctggatgaa gattgagagc atcgtctttg agaagtgaaa gactagcaag aataaaataa   1380
attaagtcca gtgtttgagc caaggttgcc acctgtctct taacatctca ctgaacataa   1440
```

-continued

```
gtcctgaggt attaggacga ccatactgcc tctgagctga aaacattcaa aagttcacat   1500
ccctgtttgg gggataccat tcaccgcctt cagcccagat gatactttcc tttaaatctg   1560
tgtctctgtg tgtataacaa agaggaagat ggaaacaatg ttcatggaaa ctgctgttga   1620
gcccccttgtc ccaccactcc cgccatctgc tgcaggcagg aaggcatgtg agtgtacgtt   1680
ttcttccagg agacatcagg tccccctgga ttcaaattaa gtgcaatatt ttgcaaacag   1740
ctcttcttag ggaaatctcc tgaaggaaaa aaatgtgaca gaatgttcca tagtctgaga   1800
gaatggaatc gttgagcatt tagtacaagt ccagtgtgtg tgagcgggac ttaggcagct   1860
caagcttgct ttttttttta agcgtacaat tgagtggttt tagtaaattc acaaacttgt   1920
tcaaccatca ccactatcta attccagact cacgcatttt taaacaataa atgtcatttc   1980
atgaaatctt tggtgataaa gtattttgga ttcagagaag agctcccttta ccagtcccac   2040
cctgatctca tggctgtctc tcctttcatt gtcagactcc ccctggtcta ccgcgttgat   2100
gtgtatacac tgatctttca agtctgggag acagataagg aggccaggtg caaggcaggg   2160
aggcagagag aatgttgtgc ttcctttagc ttttgtattt cgatggccag cattaccctt   2220
tacctgtggg catcagactc agcgtgggct gagtgctgag tgtaacttac actcctaaat   2280
caagctgggg cctgggtggg cccctcttgg tatctgtgaa tctttccaag caccacttcg   2340
gacacaccag ggattgagtg ctgctgttag tttagagaag gagagatgtc taacccttga   2400
ggtgaagggc tctgggaggg tccaagaaga cgtaggcttc attttcacac cagcccacac   2460
cattccagtg ctcagcctag caaatgtgct ttaatgcaca cttctcagac ctgtgatccg   2520
tgtatcttct ccccagtgac agaagtagag aagagaatgg aaagcagcac actccgtccc   2580
ctctagtctg gagctgttaa cagaatctgc tagaaactag ctttattcta acataccgta   2640
ggatctaaat cctcctacct ggatcatgaa ttcctttgaa ataattcata ttttcattga   2700
ctctcactaa atgtcaaata accttgtttt cacttggata ggctcagcct acctggcata   2760
tttattttgc agtcttgttg aaagttcatg aaactttgta ctttttaata agatgataca   2820
ctcgaaggaa acttttaatc tctgcagttt attctctctt aaggaataaa cactcccact   2880
gtttgttctc ttcaatgtgt aaggagatta aatgacattt tagaaatatt acaattaaaa   2940
atagtgatgt agctgtaaca tatgctggaa ttggatattt aatttatgtt tgtgtcaact   3000
ataatccttt ccccacccct ttcatttatg gtaaacatct tgggcaaacc caaagatgga   3060
aagtgcttgt tgggtgggta agcaccacct ggtctctcag caaacactcc tgagtggttg   3120
aagatgctgg acattggatt ctagcactgg gtttatctgg tgacatagtc tcctgtgggt   3180
cttgagttgg ttatttcaag ctcaaactct gaatatgatt aaaccagaac accccacccc   3240
caactgccaa aaaaaaaaaa aaggccacat gtgctcgagc tgcaggtcgc ggccgctaga   3300
ctagt                                                               3305
```

<210> SEQ ID NO 24
<211> LENGTH: 2254
<212> TYPE: DNA
<213> ORGANISM: Homo sapiens

<400> SEQUENCE: 24

```
atattatagt gggaatcaga tctaaattaa tatgaaacgt atgcttcttt ttatttacca     60
ctcctccaaa tggttttact atgattttgc tggtcatgtt cactgagcgg actgcccagt    120
tcatttaagt atttcttatt tgataaacaa tgacagggga cacctaattt gataccaaaa    180
```

-continued

```
atcttaaatt tcttggtact ttgttttgat atctgtaacc ttaaacatct cgagagagcg    240
aattcaaata ctccaccggt cctaatattg taatatcacc ctcctctttc tctgttctgc    300
tatatcccat atcagtaaaa caagcgtaag cagggacccc cgagggactc ctgctgtcct    360
ccctggcctt ttcctccttt tgctatttca taatttacat cagcccccat taagtcactg    420
aagacttcta acaccccatc gtgttttaaa gcgtgtgctg ttcttgctat agcccagcat    480
ctcggtatct gaaaccttaa atcctgtacc ttcctatgtc aaaagcaagc catcacgtgg    540
cgtactaagg tacgggagat aatccagagg agtgtgcaaa cacgagtgga tgtctcactg    600
attggggcac agagaaaact gggaggggat cgattttggt gttttctgcc tttcagccta    660
ttcccattct gtctggacat taggcctcca ggtagttact gtttggccgc aaacagagaa    720
atggtgggaa atgaggcgta ggagagaagc agagatcaaa ttatggaggg actgaggagg    780
gaaaggtcaa ggtgaaattt ttttagagaa agttattctg taaagggttt tgatggtaca    840
cttttgaagg gggatgggag tgggtccagg aggctgggaa acatgctata tggaaccctc    900
caggcaggaa acatggcctg aaatacgtca gtaccagggg aaggcagact caagatgatc    960
ttatccagcg ttctgactgc cagtcagagg gacagagaat gtcgtccggg ggagccttcg   1020
attctgacct aggtgatggg tgcccttgag aacgcaagga taagaacaac gttgaatgga   1080
aaacctggct tagaaactct tgagcttgag gggtgtgaac aggacctctg agcctctcca   1140
aacagaacgg aacttaggcc aaagcagtat tcacaccgcg agcagctccc gtcgtcactt   1200
tggacgcagt agcacgcagt ggtagaggca tcagacatgg ggaagggagt gacatggtac   1260
atgtgcgttc tgacgtggat tttactaggg ctgtgtgtgt tcagcccaaa agaacaagag   1320
caataaccag tgcaggcagt tccacccaca ttctactcag ccagagcagg ggctggcctg   1380
gaggcctggc tctacaggag cctctgcagg ctggggtaca cacgcctctt gtggtgtgag   1440
catgacacca gcggagatgt gtgcataaca ttgtgtgtgt tcacagaaca cactccccaa   1500
atataagcca actactccat ctggtgctca gccagaggaa gaatcttttc taaggctggc   1560
agagaaatct ggctgttgga cctaatgagg ggggacttga ctggttataa cttttgagtg   1620
tcttcgtatt tagatgttat taaaaaccct cgataggaag aaatcgccag gggcacatgc   1680
acagtaaaaa ggataggtgg cctagaaata gtctgtaatg tcaacagaga aaaataagct   1740
aataatggag ccggtgagag aaggcccagg gcagtcacag gtaaataaga gtaggacctt   1800
caaggtccaa gcagaagagt ggggcggggc agggcagtga gtgtgcacct ggcagcgttg   1860
ctgaacagga agatgcagga agtatgtggg gctgcctctt ccaattaatt tttgtgataa   1920
aatctacata aaatttatct aaaattggcc aggtatagtg cctcagcctg taatcccagc   1980
actttggaag gctgaggcgg gtggatcacc tgaggtcagg agttcgagac cagcttggcc   2040
aacacggcga gaccctgtct ctactaaaaa tacaaaaatt agccgggcat ggtggcatct   2100
gcctgtaatt ccagctactt gggaggctga ggtgggagaa ttgcttgaac ccgggaggtg   2160
gaggtggcag tgagccgaga tcacgctact gcacttcagc ctgggtgaca gagcgagact   2220
ctgtctcaat ttaaaaaaaa aaaaaaaaaa aaaa                                2254
```

<210> SEQ ID NO 25
<211> LENGTH: 2393
<212> TYPE: DNA
<213> ORGANISM: Homo sapiens

<400> SEQUENCE: 25

-continued

```
cctactggtc aatttgagat gagatttggg ttgggacaga gccaagccat atcacccagc     60
attgtagtaa cagtctcact ggtgacagta acggaggtaa tggtagtggt aataaaatat    120
atatttttta ctgtgcttgt tttttgagac agggtttcac cctgttgccc aggctggagt    180
gcagtggcat gatcatagct cactgcagct ttgaactcct ggcttcaagc aatcctcctg    240
ccagcctggg attacaggta taataacagt aattactgag agcctgacag tcattatgct    300
aagtactttt aatttacatt atttctaatc ttcaaaacaa cagtggcagg tgggaattat    360
tttcctgagt taataggtga ggggggccat aaaagactga cttcacaaat aaatagtatt    420
tcaactaggc atactgattt aaaagggcac taatattctg ctcaatgctt cttttttttt    480
tttttagata agcaaaagaa cttatatgag aaaaatggct tacttaaaaa ttacggggct    540
gggcatggtg gctcatatct gtaattccca gtactttgga aggccaagat gggaagatta    600
cctgagccta ggagttggag aacagcctag gcaatatggc aagccctcat ctctaaaata    660
aataaacaaa caattttttt aaattgtggt cccagaaaca ccattttgag gaaattttcc    720
aagagccagg ggatctttga aaggaggcta ctgaggtagc taaacacaac cccaacaaag    780
ataaaaggtt taagtaatac tggaagacag gcaaacagta cctacaatct tttaacttcc    840
catcagccta gagatcctca gctctacact agatccccca tcacaggcct tgagaccaac    900
tcaagttctc cacattcctc tcaagacact ttagggatgc ttggaacttc ctgttatacc    960
ttgttggcag accatcttca ggcaatacag aggctaatgt ctgcatcata actatgattc   1020
caccttggga aagtgggaat cacaatttgc agactatcca aatgtgaagg ggggaagggg   1080
tgctcagaag attctgggga gctgcaaatg acagatgtcc acctagcatc cctctgacaa   1140
atagggcccc tctacatatt aatccatgtg actttggaaa tgcatagttt tactgagtaa   1200
gaggtgatct tcctggaaat gaaagaaaga accaaacaac agaaggccag atgagttggt   1260
gttacactgt aacatcttca attagcaatt tattaagtcc tgattactct gccatggaca   1320
gctaaggaag tagagtagat tttcttaaaa aaggaactct aaagaaatta aaacagaaaa   1380
tttaaaacta tttgtcaact tatttaaaaa tagtaataaa cgattacagc cgggcacagt   1440
ggctcacgcc tgtaatccca gcactttgga aggccgaggt gggcaaacac gaggtcaaga   1500
gagcgagacc atcctggcca acatggtgaa accccgactc tactaaaaat acaaaaatta   1560
gctgggcgtg gtggcgtgtg cctgtagtcc cagctactgg ggaggctgag gcaggagaat   1620
cgcttgaacc cagaaggcgg agagtgcagt gagccaagat cacgccactg tactccagcc   1680
tggtgacaga gcgagactcc gtttcaaaat aaataaataa ataataaaca attacatgtt   1740
aacataacat tttaataaac aactgggccg ggcacggtgg cttacacctg taaaactagc   1800
accttgggag gcctaggtgg gaggatcagt tgagcccagg agttcaagac cagcctgggc   1860
aacgtagtga gattctatat aacaaaaaga aaaaagttat ttaaaaaata aataaatagt   1920
ttccaaaaac ataagagggg tattgtttta tattttggca ttaagagaag acaactggat   1980
tctcatattt gcttctgcat tcaggcttgt ggtatcacac attgcacggc ctactccatg   2040
cactccactc tacattcatg aaagaatgag taaaaaaagg cctggtgcag tagctcatgc   2100
ctgtaatctc agcacttttg gaggtccagg tgggcagatc acttgaggcc aggagtttgc   2160
gaccagcttg gccaacatgg tgaaaccctg cctctactaa aaatgcaaaa attagtcagg   2220
tgtggtggca catgcctgta gtctcagcta ctcgggaggc gaggcatatg agaattgctt   2280
ggacccagga ggtggaggtt gcagtgagcc aagactgtac cactgcactc tagtctgcgc   2340
gatagtatga gactctcaaa aaaaaaaaaa aaaaaaaagg ccacatgtgc tcg           2393
```

<210> SEQ ID NO 26
<211> LENGTH: 718
<212> TYPE: DNA
<213> ORGANISM: Homo sapiens

<400> SEQUENCE: 26

```
cactgttggc ctactggcaa aaaataaaat aaaatatata ctatcttgct cctcagaacc     60
agtggggaag aagagggaag gcaaagaaag aaactgagca tagtaaacac agcatttttt    120
tgtaggctct tatttaaaat gtgtgtgtgt gtgtgtatgt gtgtgtttct gagtaagtat    180
tgactgggaa aaagagagaa gtcaatcaaa agtatactgt gcaattgaga gaggctggcc    240
caagatttaa aacttcctgt gggtaatcta actgtgagta gataggaatc ggccatatga    300
cgaaatgaga tcaataggaa atgtgctttt tgaggaaatt ttattttagt accaaatgtt    360
gccagtgaca atcttcagtt aagaagtaag ttattctgac ctaaaattct tatctctgcc    420
actttggttt aaaaacaaaa acccttatat acatggaata gttatatttt aattaagcat    480
ttattttagt tgttttcatc cattcaagca aaatgaataa gcagcatttt tcattgcact    540
taaaaatgta aaatacctgc atgccactaa tctgtaacat tttaccagtt cagatgcctg    600
taatgtgtga ctttatgtgt gtctgtgttg ttttgaagag aataaaggaa ataatacttt    660
gcaaaaaaaa aaaaaaaaaa aaggccacat gtgctcgagc tgcaggtcgc ggccgcta      718
```

<210> SEQ ID NO 27
<211> LENGTH: 2214
<212> TYPE: DNA
<213> ORGANISM: Homo sapiens

<400> SEQUENCE: 27

```
gagcatccag taagaagacc tgcctcaaga ggtgcactgc ggtgaccagt ggaggtgact     60
ggttggagcc tggaattgga aacagattcc aagctctggt ggacaaactc tccaggcctg    120
gtgggaatca cagctggggc agacctcatc ctggctgcct ggccacaggc ccccactctc    180
tgccactggt ggtaggacga tgcctgtgtg gagagctggc ttctctgctc ccgcctggtc    240
caccacttgg ctagagttca gagacaggaa gtgattggtc taagctaaca cagcaagttg    300
gtggcagacc tggttctaga ggcaaaacct tcttccagat gtgaatgaaa cctgcaggct    360
tcattttcct ttctgagcag tgcttcttag ctctttggag acacgaagcc cttggaaaat    420
ctgatgaagg ttacggacct tccctaggaa aacagataac tgacgtagac tcaaaaaccc    480
caagcaattt caggagccac tggactccct gaatgaaacc catccctgga ctccaggcta    540
agaacctcag ccctggggac ttcacctgct gccctttcct tacctgtcac acattgagcc    600
ccgagtcaag gccactgtac aagtagtgcc cctccctccc cctggccaag cctccttccc    660
ttgttcagga ataaagaatt ccgaggagcc ctttttagtc attcccttct cccagaccta    720
acgaatggtg cgtcaggttt ctggagcctc atttcccttc cccagacatt ggcagaggtc    780
ccttgggcta gattttctct tctggttttg tttcttgttc tgcctgactg gccgctggct    840
tccacaaagg agccctttgc tcctggcctg ggctctgatt tcactgtgtg gtctcagggg    900
aagctggact gctgtggacg ctggtgggag cttgagtctg gtctgagtct gccccaggaa    960
gaaagaatcc tgcttccacc aaccaagccc agtcagcggt tcctcccaac tggccaagtg   1020
ttcagcccag tgggctgggg aggaagagga tgagggcctc gctcctggtg cctgtggctc   1080
tgggcagggt gagaggtcgg tggaggatct ttctgtgtgt tctctgagta tgcagcagtg   1140
```

-continued

```
cagttgaagg gaacagggcc caggcaggca gcaggacgag gactcctccc atcttcacac   1200

ctgaaccagt cagcctggaa gctacaagtt ctcacctgcc tccccagaat gaacatcaga   1260

aaaggcaaaa ctgaccaggg ctgggatggg tttgggtcag cgtggttgga gggcagcctg   1320

tggatccctg cactggagtc ctgctgtctt cgatgcaggt tggatcatac attgttacct   1380

cctactgtat gcctcaccct ggaatagcag aatgctcagg gggagatccg agaacgagaa   1440

ggtgctccca gccccaggag cttccagtct ggctctgatc cttggccgac ctagaggaaa   1500

cctccacaca cgcccctttt gtgctaatgg tgcagtttgt gtccccctct gcccatcact   1560

gtgctgtgct tgttcctgcc tctgtgcctt cccctatact gctcggacat gtcccctttc   1620

ctctcctcta cccagctaag cccttctgat ccacggggcc cggcttccca aaccacccag   1680

cccacattcc tccttcctgc tccgaacagg tcccgtgtga gcccctgccc ccgaattgca   1740

tgctgtccca tggacgctcc agtctcttcc gtgtgtgtct tgagtcccta actagacagt   1800

tagctccctg agggcaaggg actgtcattt cctcttgagt cctaccaggg tctagcacag   1860

gactgggctc ctaactctca ggaaacactt gtcggctgac tggtgcctca agcgctggag   1920

cttgtcggtg gccggtaatg ggcagtgcac gtggggagag ggtatgtgag ttaactcaag   1980

ggtgcctttt cttgggctgt gggctggctc ccctgggtca aaagtggatg tcggaggcct   2040

caggctctta cctccttggg gcagtgggag catcagggac cccccacccccc accccggctc 2100

tgcaggagtg cacggaagtg gtcgtccagc ctggatattt ctacaggttg ctgactcctg   2160

cgggagctga ctgagtggaa taaatgttct ctcaacaaaa aaaaaaaaaa aaaa         2214
```

<210> SEQ ID NO 28
<211> LENGTH: 2016
<212> TYPE: DNA
<213> ORGANISM: Homo sapiens

<400> SEQUENCE: 28

```
aacacatcta gacataggga aataaggttc caaagaaaac cttacacttt tattcagatt     60

ttatgttggc ctcagttgta ctagaaaagc gtttcagtat gtgtctcttg gggaatctgc    120

accttcttgg tcactgcact tcatagcccg gcatatcact gagaattcag aaatctgact    180

ctttacccag ggacgaatac atcgttatga gttcaggtgc actaaataca taggaacacc    240

cagagaaaat gagcccgaaa caatggttct ttttattttg gaagtttcag acaaactctt    300

tggaaaattg aagaaatcta tggatccttt tcctgggaag actgtacaga catacgtatt    360

cgtgtggttt ctgtgggtgt agggactggc cctggtcatg tgtcaggaag ccccaatcca    420

gaagatcgtc ttcattttac cttggccggt gatctgactc tgttctcgcg cccatctgtg    480

gttgattctc tgtcgccttg gaatggagca tcagatcttg aaggtcgctc attgcttttc    540

cacgcataga actgagccac atggcaagag cttcctaatg aaatggacgg aaactctctg    600

caaagggctg ccccagaagc acgggtgata gaaatagagt ccaaggcact aaggccgctg    660

agccacagtc ctcctaggca atgcctcctg ctggcttagt gggtttattt cataagttga    720

gtactaatgt cctgtttttt aaatgaacat atttcttcta acatttctaa caattatgaa    780

gattttctcc ctaagtgtga ctttttctta tgtcttgggg tatcagattt acagcgtaac    840

atgtgtactt caaattgtag tagtgactgg aaatttagga ttctgttgtt tcataacact    900

taaatctgca gcagattttc aggaaaatgg tcaagattca cagataattc cttccttatt    960

ccttacagat tttacaattg tatggttatt tctgaatttg gttaatttgt ttataagtgt   1020

agtggacatt taacagaaca gatgcacccg attatctgat tagaaatgtg tttcaacaca   1080
```

```
cgggtccctt tgcgtgtttc caatctctgt tttcggatct gggattctcc acctgttaca   1140

tcgttcactg gaactttcct acaaaataca gcctcgctga gaggcgcatc gtggaaaaat   1200

gaagcagcct gaagaaactc taatattggg accgagtgga gagatggaag agcatcatca   1260

gagtggtgcc gccgcacatg cgggaggcgt cccaggcagc attgctcttt gtacatgaga   1320

caggatacca ctgtctttta tgcattagac tggtaaccag ataaaataac cttgtaaaac   1380

agatctttta tgtaagaaaa atacaactct cacctcgcaa acattcctgt ctgttgcgga   1440

tgaacctagc agcaggagag gagccagggt cagtccactt ggcctgaaag ttaacgtcat   1500

atattcagat gtcaaggggt ttctgtgcat gcttttgaag tattgtgttt gggcttttac   1560

aacatgtgcc tcactgtttc gcatctacag agagagtgcc gctgagagag gagcctgagt   1620

ggatccgtgc ccagatctgc attctctgtc ctcaccactt ctccctgctg gttgatataa   1680

atgtggggat aacgtcgagc acaaaggagt caaaaattga tcagggctgg gtgtggtggc   1740

tcacgcctaa aatcctagca ctctgggagg ccgaggcagg aggactgccc aaggccagga   1800

gttaacatag caggaccctg tctctacaaa aaaataaaaa aaatcagctg ggcatggtgg   1860

tgtgcacttg tagtctcagc tgtttgagag gctgaggcag gaggatctct tgagcccagg   1920

agtttgagca tgcagtgagc tgtgatcgtg ccactgcact tcatcccggg cgatggagtg   1980

agaccccatc tcttatttaa aaaaaaaaaa aaaaaa                             2016


<210> SEQ ID NO 29
<211> LENGTH: 2730
<212> TYPE: DNA
<213> ORGANISM: Homo sapiens

<400> SEQUENCE: 29

cactgttggc ctactggtga aaaccactgc cccagacagc aatatgtttg acctgaatgg     60

cattccaatc ttttctgtac ctccactcag cacagttcat gttcagtaga tgctgaacat    120

tcttagaaat actgtgtgtg aacttagaaa agtgcaagaa gacaggcatg tctttgaccc    180

caggaatgat catttgctga agatggtgtc aagtgaacct agattaacag ccctccactc    240

cagatggata tccagtgatt cctagaatgg gatatagcca gagaacaatt ctatgcaccc    300

tacactgaca gactccctta agcaacacca gatgctctac tggtacttga agtacatgac    360

tttgaagtct tgaccctcca tgaatacctg aattatcagc aagcgggttt tgaagctggt    420

gcctcattga ggccatatta gagcaacttg tacatttgac ctcttgttat cagccatggt    480

actctacttc gtgtgcaaga gataactatg aaagccaaat tcaaatactg gcaacatttc    540

ctaaaggggc tcaatatcta tcattcgtct tcttttccaa actacacatc actgtatgac    600

tcaaccagta gcagttatat tgccccttgg tttttattca gtttaactac tgtttccaag    660

ataaatgagc taataagctt taaaaaaaaa aaaaaaaaaa ggctgaattc ttttttcttc    720

atcactggca tatctgccta ttctccagaa ttattatgac tattcagctc actttaacag    780

ttgaacttca agcgacaatc tttgaacacc ccttctcatg tgatttaaaa tgaaaccatt    840

tggaaaagtt tcttctagcc agtaatagat ttttttttta attgctctgc cttgtgccga    900

gagatgttct tttaagatga atcttttgat gtctgatacc accaaatata ggtggtaggg    960

agagttggag gctggccctt tgagcaggcc attagcttac ttgctgggca tttccgatag   1020

cttattgcct accttttttgc tggaaacaaa ctgatttgaa aaacaaaatc tatgaagact   1080

gcagctaagg attttatcgg tagacttaag agcttttgtc cttgtggata ttttagtgga   1140
```

-continued

```
accacatcag tctcaatact gtcattttac actgactcag agcagctgac ttcattcctt   1200
gccatgatat atatttaagg caggcattgt aacagacata aagacaactt atctgtttca   1260
gcaggaagga ttcagtttat gaactctcag accagatcat gttgaacaag gagactttga   1320
tgtgtgtcat gagaaaactc attctttact tcccagtcaa tttaaaggcc agctatcctg   1380
agctactcga atgaatgcac tggttaaaca ttggaaatag tttgtttata tccttgtctc   1440
tctctaggcc aattgtgatt acatgactcg actctacatc tcgtcaaaca aggcctaggt   1500
ctggttgctg tagactgctc gccctcaaca aataaaatct ggttgactag cctccttgta   1560
tatacaacta ttatttgtta agaagaaatt atcgtcaatt ttctactacc ttccaattgt   1620
cagctctttt tttcctctct ggtttttcct atactttaca gaaaaagaca ttgatctata   1680
ctgccattcc ctctaatcct gccatactca gtcaaaagga atgacttaag atgaagatga   1740
tcatctgctc gagtctaaaa tatacattgt atataagaat tggtgattag aaaagcaaaa   1800
aacctaaaac ttaaatctag gagtctgtat actgtctcca tgtctccatg cctcaggtct   1860
catctaaatc tttgaacagc accattcaac caatctgagg ccttgacttg cttgtaagat   1920
gattctcaga gatcggctga gttaaaaaag atgacgactt gattaccaaa gaaagtaggg   1980
ccaactttga caaatctggc tctgctgacc ctgtcactcc cagatgtagc atagactcct   2040
aaacagaacc tcaagtctga ttgaggataa ggccttctcc tgagctgaaa gttctttggc   2100
agatgagcaa gaaactgaaa gctgatgtac ctgactggct ctgtaagatc agaaaactgt   2160
atccagaata agccctatgg attaacccct gagtacccag agtaaaaact aatttacaga   2220
acttccttat tgatctgctg gttcttccag atcatattct ggctattggt atggctggcc   2280
tttctgaagg taccctgctt gtctattttc ctgactcagc tcttgcctgc ctttttcaca   2340
tgttgctgca attagactca ccgtgaggac tacagtcaat ttcagtctat cttgtgccca   2400
atacaacaag gatttttaat agtaacaacc cacacctcac ccactaggac tcaatgttca   2460
caacaggaag gaccattgct gcatactcct tgaccagcaa ctttttttgaa gatattttta   2520
agtgcagagt aggcctctat tcctgtatgt aattgttcat tttcagcacc tggaacctca   2580
tctatcgggt ctggaaggaa tacagcagtt cgaaagccgc gtccatttct ctccttcagt   2640
agtgcagaaa tgagtccgat tcaccagtac acacagaact gtaccagttc aacctagcaa   2700
aaaaaaaaaa aaaaggccac atgtgctcga                                   2730
```

```
<210> SEQ ID NO 30
<211> LENGTH: 865
<212> TYPE: DNA
<213> ORGANISM: Homo sapiens
<220> FEATURE:
<221> NAME/KEY: modified_base
<222> LOCATION: (1)..(2)
<223> OTHER INFORMATION: a, t, c, g, unknown or other
<220> FEATURE:
<221> NAME/KEY: modified_base
<222> LOCATION: (4)..(9)
<223> OTHER INFORMATION: a, t, c, g, unknown or other
<220> FEATURE:
<221> NAME/KEY: modified_base
<222> LOCATION: (11)..(16)
<223> OTHER INFORMATION: a, t, c, g, unknown or other
<220> FEATURE:
<221> NAME/KEY: modified_base
<222> LOCATION: (21)..(22)
<223> OTHER INFORMATION: a, t, c, g, unknown or other
<220> FEATURE:
<221> NAME/KEY: modified_base
<222> LOCATION: (24)..(24)
<223> OTHER INFORMATION: a, t, c, g, unknown or other
```

<220> FEATURE:
<221> NAME/KEY: modified_base
<222> LOCATION: (41)..(42)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (674)..(674)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (745)..(745)
<223> OTHER INFORMATION: a, t, c, g, unknown or other
<220> FEATURE:
<221> NAME/KEY: modified_base
<222> LOCATION: (756)..(756)
<223> OTHER INFORMATION: a, t, c, g, unknown or other
<220> FEATURE:
<221> NAME/KEY: modified_base
<222> LOCATION: (770)..(770)
<223> OTHER INFORMATION: a, t, c, g, unknown or other
<220> FEATURE:
<221> NAME/KEY: modified_base
<222> LOCATION: (773)..(773)
<223> OTHER INFORMATION: a, t, c, g, unknown or other
<220> FEATURE:
<221> NAME/KEY: modified_base
<222> LOCATION: (798)..(798)
<223> OTHER INFORMATION: a, t, c, g, unknown or other
<220> FEATURE:
<221> NAME/KEY: modified_base
<222> LOCATION: (819)..(819)
<223> OTHER INFORMATION: a, t, c, g, unknown or other
<220> FEATURE:
<221> NAME/KEY: modified_base
<222> LOCATION: (834)..(834)
<223> OTHER INFORMATION: a, t, c, g, unknown or other
<220> FEATURE:
<221> NAME/KEY: modified_base
<222> LOCATION: (843)..(843)
<223> OTHER INFORMATION: a, t, c, g, unknown or other
<220> FEATURE:
<221> NAME/KEY: modified_base
<222> LOCATION: (845)..(845)
<223> OTHER INFORMATION: a, t, c, g, unknown or other
<220> FEATURE:
<221> NAME/KEY: modified_base
<222> LOCATION: (853)..(853)
<223> OTHER INFORMATION: a, t, c, g, unknown or other
<220> FEATURE:
<221> NAME/KEY: modified_base
<222> LOCATION: (857)..(857)
<223> OTHER INFORMATION: a, t, c, g, unknown or other
<220> FEATURE:
<221> NAME/KEY: modified_base
<222> LOCATION: (860)..(860)
<223> OTHER INFORMATION: a, t, c, g, unknown or other
<220> FEATURE:
<221> NAME/KEY: modified_base
<222> LOCATION: (864)..(864)
<223> OTHER INFORMATION: a, t, c, g, unknown or other

<400> SEQUENCE: 30
nngnnnnnnt nnnnnnggcc nngnatcctc gagcacggtg nngcctactg ctagcaaaac 60
ttgtttagct tagcaaaaac aaacacacaa aaaaactgag aactctgctg tttcagatat 120
gccataacat acatctgaaa cacatgtgta acaatcaaaa tggtgggctc tagaatggtt 180
ttggagctcg agatcttcat gggttagact tgctggtcag acccaggagc acctgtggct 240

-continued

```
cacaccttct gttcccctcc tggcctgtgc agaatgtaaa cagcagactc atactcaatg    300

ggcactacag gccttatcag acgttttata caagcctgga ttgcttagta ggggaataag    360

gcattctctg agggggcttt ccacttagat tgagaatttt atttgaaaag aatctggttt    420

aaatggcatt gtggtccgag gtagctgctc tccccactga gagctgagcc gaaatataag    480

aataatatat ttgtgcttcg agttggtgtt tctttcagtg taatgcatgc agtggtcaca    540

acccagttac tcataatatt tggattgtat ttgttcgtaa gatatgccca agaagactag    600

agaattagtg ttatatacca tatagaactt actgtcagtc aactataaac anggccaatt    660

aaaaactgtt ccantactac gcaaacacat attaaaggcc nttgctgatg acacattaac    720

tggatctaac caacccaaaa agggnttgat ttgaanctga ttgttgccan tangcatatt    780

ggatcccacc taccaaantt cctccgaagg ggattttgna atttgaaaag ggtntaggaa    840

atntncctaa aancaanttn tggng                                          865
```

```
<210> SEQ ID NO 31
<211> LENGTH: 876
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(4)
<223> OTHER INFORMATION: a, t, c, g, unknown or other
<220> FEATURE:
<221> NAME/KEY: modified_base
<222> LOCATION: (7)..(12)
<223> OTHER INFORMATION: a, t, c, g, unknown or other
<220> FEATURE:
<221> NAME/KEY: modified_base
<222> LOCATION: (27)..(27)
<223> OTHER INFORMATION: a, t, c, g, unknown or other
<220> FEATURE:
<221> NAME/KEY: modified_base
<222> LOCATION: (35)..(35)
<223> OTHER INFORMATION: a, t, c, g, unknown or other
<220> FEATURE:
<221> NAME/KEY: modified_base
<222> LOCATION: (383)..(383)
<223> OTHER INFORMATION: a, t, c, g, unknown or other
<220> FEATURE:
<221> NAME/KEY: modified_base
<222> LOCATION: (597)..(597)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (650)..(650)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (717)..(717)
<223> OTHER INFORMATION: a, t, c, g, unknown or other
```

<220> FEATURE:
<221> NAME/KEY: modified_base
<222> LOCATION: (767)..(767)
<223> OTHER INFORMATION: a, t, c, g, unknown or other
<220> FEATURE:
<221> NAME/KEY: modified_base
<222> LOCATION: (769)..(769)
<223> OTHER INFORMATION: a, t, c, g, unknown or other
<220> FEATURE:
<221> NAME/KEY: modified_base
<222> LOCATION: (775)..(775)
<223> OTHER INFORMATION: a, t, c, g, unknown or other
<220> FEATURE:
<221> NAME/KEY: modified_base
<222> LOCATION: (786)..(786)
<223> OTHER INFORMATION: a, t, c, g, unknown or other
<220> FEATURE:
<221> NAME/KEY: modified_base
<222> LOCATION: (795)..(795)
<223> OTHER INFORMATION: a, t, c, g, unknown or other
<220> FEATURE:
<221> NAME/KEY: modified_base
<222> LOCATION: (809)..(809)
<223> OTHER INFORMATION: a, t, c, g, unknown or other
<220> FEATURE:
<221> NAME/KEY: modified_base
<222> LOCATION: (815)..(815)
<223> OTHER INFORMATION: a, t, c, g, unknown or other
<220> FEATURE:
<221> NAME/KEY: modified_base
<222> LOCATION: (827)..(828)
<223> OTHER INFORMATION: a, t, c, g, unknown or other
<220> FEATURE:
<221> NAME/KEY: modified_base
<222> LOCATION: (834)..(834)
<223> OTHER INFORMATION: a, t, c, g, unknown or other
<220> FEATURE:
<221> NAME/KEY: modified_base
<222> LOCATION: (843)..(843)
<223> OTHER INFORMATION: a, t, c, g, unknown or other
<220> FEATURE:
<221> NAME/KEY: modified_base
<222> LOCATION: (862)..(862)
<223> OTHER INFORMATION: a, t, c, g, unknown or other
<220> FEATURE:
<221> NAME/KEY: modified_base
<222> LOCATION: (871)..(871)
<223> OTHER INFORMATION: a, t, c, g, unknown or other

<400> SEQUENCE: 31
gngntgnnnn nntgtggctt ttttttnggc ttttnaaaga aaaatgttaa gacttattca 60
agatgtgtat caggcattat aacaaaacag cagaacttca acctttggga atactgtaat 120
tttacatccc tttgatgcac aagtccaagt atactatttt attacagatc attctatagg 180
ggactacaag acatgaacta agaggaaatg tgcacagtca caatccaaga atatcagctc 240
tgggagtgta cactgtttgt tagaggatga agcacatcct ttgccatttc aaatactgtg 300
ccaggtggag gactaggaag gctcaaagat ggtcatggtt gacaagcact cttatcacaa 360
acacatggat agcttatcac ggngaacaca tttcaaaggg cagcaaagtg agcaagctat 420
tcacacaaag ccaggaggga ttatgactaa actctccagt ttataagcac aagtccacat 480
ctcaactcct caagaacagg tgctcaatgg caattaacta aaagttatga catgaacatt 540
acaagacttt ccagctagca ttttgttaac agcctgtgtc tgtaagtcag caaattnaaa 600
acattcagtt gtatcctcca gacagaacac cacaccacta catgtncacn tacanggctt 660
cacattttat gtcaagttca tacacaaaat gtncaacntg tcaagtactt aacacanttt 720
gccaaaaata tggcaactgc ttcaattgtc aattgagtgt ccttaanana gaaancggct 780
ccctantcaa cactngaggg aaaatagtnc cattncatta agacaanntt gggnacctta 840

-continued

```
aantttcaac ctgaagggaa antataatca ncaagt                              876


<210> SEQ ID NO 32
<211> LENGTH: 2274
<212> TYPE: DNA
<213> ORGANISM: Homo sapiens

<400> SEQUENCE: 32

cactgttggc ctactggtag ttggttttag ataatatctt ctactgccaa acttctggca      60

aatttacctg tgaatttcaa aatgttataa aatctcttga tatgcttttg tttttccttt     120

tagccatttt ctcttcaatt tcttagtccc tctgccctct gtaaatgtgt tgagtgatat     180

agctatcaga tgtattgaag gcaaagttct cgcagaggtc tctgttccag ctctgtaaag     240

gtcacaggaa tcgtgaagga gctgagaaat cttcctctcc ggcccactgt ctgtggccca     300

ttgtcattgt ttcctcatga aacattgcag agtttgaatc ctcagtaact ctcattgact     360

ggattagagg tgatggccac agcaaatggg agagcaaaat gttggcctac agagaatgac     420

acaattttat tcgcctttgg tgttagttgc catagtgctg tatttgaaaa tcgatgcttt     480

agccaaaagc tgaatgacca ccgtttccgt agtttccact gttttgtctg catagaattt     540

tcctgaacta caagcaaaaa tgtattttgt ccaatgtcac aaaagtgaaa atgttactaa     600

tcttagatgt gttgcatatt ttgtgttttt acgttccaaa ctctttcaaa agctgccgtt     660

acaaagctgt ttggctgtat tgacagcatg tggtgttttt acaaaagcaa ttctaggaga     720

gccagtgtct accatgaact cctgacatcc ccactccagg gtcattcatg acattgaaat     780

ggcaacttgt acactgtaat tcttcgaaaa gtaacagggg atggaaatca gacctggccg     840

ttagtcacta gtgtgtagta ccgtgatctg aagtaggaaa tttaactgac atagaataat     900

tgtggttttt gaagcagcta ctcattgctt tttccttttg ctgtggagat catggattgg     960

gaatgtcctc gtgaggtgga cctaaggcag taacatttaa acttcatgtc ctagcacccg    1020

ccctccatct gacccaaaga taaaaaaggc atcaagcttc atggttatgc ctaagcttaa    1080

aaattccctt ccccactact aatattgagt tcagcagggc cccatcttac ttatttttca    1140

aaaaagttat agctttgaat tatagactat attactaaat ttggtaaggt agttctttgc    1200

atgaatggga atgtgtgtca aaatactttc acaaaaggca tgattacaat ggaaatgccc    1260

ctttgcctcc agttttgcta accctaaaaa gtatttcact aatttcaagc actgtttaca    1320

ctcaaatccc aaaattggcc aaattatata attctcttaa attttcattt ctgtaggtgg    1380

agatttaact atggttctgg tgaatcatag aagggagaga caatatttga ggggagttta    1440

tcagcagaat atcatgcctt atgaccccat tactgaaaca cagacattac aatcagaaat    1500

agacctaata attccaatat ccctccatta actagttcca gtgatgctga gagacacagc    1560

accctgtgcc aggtatcaga aatataagcc tcagcagagg gtaactgaaa actttcaatc    1620

agaaacactc tccaaggctt atggctagat tatgtaggtc actaccattc aaaacttttc    1680

tatacaaagg tggaaaagca ctcagaatct gggaattttc tggttggaag aacaatgttc    1740

tccttttcca aattggaata aagactcaga attacccatt cttcataatc atgtctgatt    1800

ggtacataca ctccaggaag tctcaaccta gaaacatttc caacctaagc atttaaagga    1860

aaactggctc attcttctga cccaaactca aaaaatatga gtacttgcgt acctccattt    1920

ctgcatgaag attttaaaac agatttcatt tttttctgtt tattttggga aggtgcgtgg    1980

gggtgttctt tcaagtgatt cacatctcaa acccatacca ctctcaactt ttatttgatg    2040

tgttcaaagc caaaaaataa aataaaataa agcagggctg aacacttaat ttgacatgaa    2100
```

```
gctgaaggac tgagcaagcc agaggagaga ggttgaatga agcatagcct tggcttcata   2160

ccacactttt tgtgccttgt attatcaatg taaattctga atgttgtaca gtaaacctgg   2220

atggacttct tagaaaaaaa aaaaaaaaaa aggccacatg tgctcgagct gcag         2274


<210> SEQ ID NO 33
<211> LENGTH: 2465
<212> TYPE: DNA
<213> ORGANISM: Homo sapiens

<400> SEQUENCE: 33

cactgttggc ctactggcaa atggatcaac atcggctatg agggtgagga gttgaagcca     60

tacacagagc ccgaggagga cttcggggac accaagagaa ttgaggtgat ggtgggtatg    120

ggctacacac gggaagaaat caaagagtcc ttgaccagcc agaagtacaa cgaagtgacc    180

gccacctacc tcctgctggg caggaagact gaggagggtg gggaccgggg cgccccaggg    240

ctggccctgg cacgggtgcg ggcgcccagc gacaccacca acggaacaag ttccagcaaa    300

ggcaccagcc acagcaaagg gcagcggagt tcctcttcca cctaccaccg ccagcgcagg    360

catagcgatt tctgtggccc atcccctgca cccctgcacc ccaaacgcag cccgacgagc    420

acgggggagg cggagctgaa ggaggagcgg ctgccaggcc ggaaggcgag ctgcagcacc    480

gcggggagtg ggagtcgagg gctgcccccc tccagcccca tggtcagcag cgcccacaac    540

cccaacaagg cagagatccc agagcggcgg aaggacagca cgagcacccc caacaacctc    600

cctcctagca tgatgacccg cagaaacacc tacgtttgca cagaacgccc gggggctgag    660

cgcccgtcac tgttgccaaa tgggaaagaa aacagctcag gcaccccacg ggtgcccccct    720

gcctccccct ccagtcacag cctggcaccc ccatcagggg agcggagccg cctggcacgc    780

ggttccacca tccgcagcac cttccatggt ggccaggtcc gggaccggcg ggcagggggt    840

gggggtggtg ggggtgtgca gaatgggccc cctgcctctc ccacactggc ccatgaggct    900

gcacccctgc ccgccgggcg gccccgcccc accaccaacc tcttcaccaa gctgacctcc    960

aaactgaccc gaagggttac cctcgatccc tctaaacggc agaactctaa tcgctgtgtt   1020

tcgggcgcct ctctgcccca gggatccaag atcaggtcgc agacgaacct gagagaatcg   1080

ggggacctga ggtcacaagt tgccatctac cttgggatca aacggaaacc gccccccggc   1140

tgctccgatt cccctggagt gtgaagctga ccagctcgcg ccctcctgag gccctgatgg   1200

cagctctgcg ccaggccaca gcagccgccc gctgccgctg ccgccagcca cagccgttcc   1260

tgctggcctg cctgcacggg ggtgcgggcg ggcccgagcc cctgtcccac ttcgaagtgg   1320

aggtctgcca gctgccccgg ccaggcttgc ggggagttct cttccgccgt gtggcgggca   1380

ccgccctggc cttccgcacc ctcgtcaccc gcatctccaa cgacctcgag ctctgagcca   1440

ccacggtccc agggccctta ctcttcctct cccttgtcgc cttcacttct acaggagggg   1500

aaggggccag ggaggggatt ctccctttat catcacctca gtttccctga attatatttg   1560

ggggcaaaga ttgtcccctc tgctgttctc tgaggccgct cagcacagaa gaaggatgag   1620

ggggctcagc ggggggagct ggcaccttcc tggagcctcc agccagtcct gtcctccctc   1680

gccctaccaa gagggcacct gaggagactt tggggacagg gcaggggcag ggagggaaac   1740

tgaggaaatc ttccattcct cccaacagct caaaattagg ccttgggcag ggcagggag    1800

agctgctgag cctaaagact ggagaatctg gggggactggg agtgggggtc agagaggcag   1860

attccttccc ctcccgtccc ctcacgctca aacccccact tcctgcccca ggctggcgcg   1920
```

-continued

```
gggcactttg tacaaatcct tgtaaatacc ccacaccctc ccctctgcaa aggtctcttg   1980

aggagctgcc gctgtcacct acggttttta agttattaca ccccgaccct cctcctgtca   2040

gccccctcac ctgcagcctg ttgcccaata aatttaagag agtccccccc tccccaatgc   2100

tgaccctagg attttccttc cctgccctca cctgcaaatg agttaaagaa gaggcgtggg   2160

aatccaggca gtggtttttc ctttcggagc ctcggttttc tcatctgcag aatgggagcg   2220

gtgggggtgg gaaggtaagg atggtcgtgg aagaaggcag gatggaactc ggcctcatcc   2280

ccgaggcccc agttcctata tcgggccccc cattcatcca ctcacactcc cagccaccat   2340

gttacactgg actctaagcc acttcttact ccagtagtaa atttattcaa taaacaatca   2400

ttgacccaaa aaaaaaaaaa aaaaaaaggc cacatgtgct cgagctgcag gtcgcggccg   2460

ctaga                                                               2465
```

<210> SEQ ID NO 34
<211> LENGTH: 2280
<212> TYPE: DNA
<213> ORGANISM: Homo sapiens

<400> SEQUENCE: 34

```
cactgttggc ctactggcac ttttttaaat gccactgggg gttatttttg ctttccttgg     60

cccccaccaa tttatacatc tccattttct gacctctgga ctaactggtt gctcagcaag    120

gttctgaagg agagtttctt gcattggaca ggcccagtct tctcccatca ttgccctgct    180

gtgactccaa agaaaggagc ttcttgctga cagtgccctg tggagcaagg ctgtgtttcc    240

taccccacac ggtgctcagt gggtgccagc cctcagtgtg gctttgtgat tgctgcccta    300

aaggagaatg ctctttcctt cctcactggt actgcctgct gttttctaag cattgctcct    360

gcacagacat ggagtcccag ccccagcaag gctcttctgt tcccatctgt tgacaatgtc    420

ttgtggagca tttttgctga ggaaaaggtc acttgtaaac agaggagaaa gggaaagagt    480

acaaagccct aagtttattg taagtgaaaa ctgagggaat tcctgtcttc tttaggagta    540

atgattcata gatctagata ggtggaaata tcattcaaaa tagtcacttg agctcacaaa    600

aaaagcaagg aagaattctc atgtcctttg tcttccttct gtagccatta actgctgaat    660

ccatgtgagg aagacaggct tcccttcctt ccccctcctt agtgattttt tctttaacag    720

cataagtaaa gaggactttc tggttcattt ttgtttgttt tgttttgttt tgttttgttt    780

acaggtgagg tcttgctgtg ttgcccaggc tggagtgcgg tggccattca cagatgctat    840

catagcacac tacagcctcc aactcttggg ctcaagcatc acgcctagca gtttctggtt    900

cctttaacag caaaaggaaa gagaggttct gattcttacc tcagggtttt ttggttgttc    960

attgtttttg tttttgtttt tgttttgaca ctgcagagca caaggctaaa ggttacagct   1020

gagatctttg gaaccaaagg cagagcaagc agagcccgtt gtctgggccc cacaccactg   1080

caggcaggtg gatagaagtg cggcccctct catagtatgc ccataagtca gggcataggg   1140

cagaactacc tgtcatgttg ctacaccatc ctgtcttctc agcatctcct tgcctgtttt   1200

ctttatcagt ccaaaggaaa acaacagcag caaaatctgt ttttaaaatg tcttatatga   1260

acatatatca aatatccatg cgctgaaacc cacataccat cacttggcaa ttttttagaa   1320

taagacccca ttattatcta ttgctataaa cctagccagt tctcttgctc ttctgtattt   1380

tcctatttcc ctgccatcat ctgctatttc tgccacttct cttagactcc ttgtctgcaa   1440

agcccaagct agaactcact gtctatggca gaaggacatc cagagcccat tctggagttt   1500

tgttttttcc ttctgccaga tgctttgtgt cctgtcttcc ttcctcctca tatttctgtt   1560
```

-continued

```
tctcatttgt gttcagtttt gtgcagcatt gctagcactg cttttgtgac cagaaaaggc   1620

cataacatgg tccaggatca tcattcttct gactctagat gggacacttg acagtgactt   1680

gaaacatttg catattcagg aatgcatgag atttcaagag agcctacagt atgaaatcat   1740

tttcacaaaa taagcagctt gcttctgaaa tgctgtcttt cccagtagct actcacctgc   1800

ctctggtggc tgggattcag atgccacaaa actgtcagta tctatagacc aggtctgtgc   1860

cacctcctct ctcctctgtg ctcagtgagg aggcagtaaa tgaagttaca ggctagcaca   1920

atacctaact catgtttccc agtacacctg tagatattac tgtactttta tgttctcaag   1980

aaataagttg ttgcctattc agtgttacag atttctttgt ttctttttaa ttaaaataca   2040

agaagcagct gaggaaaggg agacaaggta ttttatttct gactgatttt agaaaaaact   2100

tgtgtacatg tgtttggaac tgttgaaatg ccaagttttc tgtataagtg tttttgtaat   2160

taaactttca gattttcttt gtttttttaag aagttgatgt gcttgtttga catttgtctc   2220

attaaaactt ttctacgttg aaaaaaaaaa aaaaaaaggc cacatgtgct cgagctgcag   2280
```

<210> SEQ ID NO 35
<211> LENGTH: 2404
<212> TYPE: DNA
<213> ORGANISM: Homo sapiens

<400> SEQUENCE: 35

```
cactgttggc ctactgggca catgcgcaaa ctgcggacgg ggaactgggc tccctagccc     60

tggcgttttt ggtgttgctg tcccagccag aatcgcgtct ggccggtggg aagccgggaa    120

ctccagcccc ctgtaggaga ggagaaagga gcgagatcat gatacatggt gatggcttgc    180

agagtcgtaa acaaaagaag acacatggga cttcaacaac tttcatcatt cgcggaaaca    240

ggaagaactt tcctaggccc actaaaatca tccaaattta ttatagatga agaatgtcat    300

gaaagtgtat taatcagttc aacagtaagg cttcttgaaa gtttggattt aaccagtgca    360

gtgggacaac ttctcaatga agcagttcaa gcacaaaaca acacatatag aactggaatc    420

agtactcttt tgtttcttgt tggtgcttgg agcagtgcag ttgaagaatg tcttcatctt    480

ggtgtcccca tttccataat agtatcagta atgtcagaag gcttaaactt ttgtagtgaa    540

gaggtagttt ctcttcatgt acctgttcac aatatatttg actgtatgga cagcacaaaa    600

acattttctc aacttgaaac atttagtgta agtttgtgtc cttttctaca ggtcccttca    660

gatactgatt tgatagagga attgcatggt ctcaaagatg ttgcctctca aacactgacc    720

atttccaacc tttctgggag acctcttaaa tcatatgaat tatttaaacc tcagacaaag    780

gttgaagcag ataacaacac atcacgaact ctgaaaaaca gcctgcttgc agatacctgc    840

tgcagacagt caatactaat ccacagtagg cattttaata ggacagataa tactgaaggg    900

gtaagcaaac cagatggatt tcaagaacat gttacagcta ctcacaaaac ttacagatgt    960

aatgatttgg tagagttggc agtaggcttg agtcatggag atcacagcag catgaagtta   1020

gtagaagaag cagtacagct gcaatatcag aatgcttgtg tgcaacaagg caactgtaca   1080

aaaccattta tgtttgacat ttcaagaatt ttcacttgct gtctaccagg cttacctgaa   1140

acttcttctt gtgtttgtcc aggatatatc actgttgtgt cagtatctaa taatcctgtg   1200

atcaaggaat tgcagaatca gcctgtgcga atagttctca ttgagggtga cctcacagag   1260

aattaccgcc acctgggatt taataagtct gcaaatatta aaacagtatt agatagcatg   1320

cagcttcaag aagacagctc agaagaactg tggcaaatc acgtgttaca ggtgttaatc    1380
```

-continued

```
cagttcaagg tgaaccttgt cctggtacaa ggaaatgtgt ccgaacgctt aattgaaaaa   1440

tgtataaaca gtaagcggtt ggtaatcggc tcagtgaatg gcagtgtgat gcaggctttt   1500

gcagaggctg caggagcagt acaggtggcc tacattacac aagtgaatga agattgtgtg   1560

ggtgacgggg tctgcgtgac cttctggaga agcagcccctt tggatgttgt agataggaac   1620

aacagaatcg caatcttatt aaaaacagaa ggaattaatt tggttacggc cgtgctcact   1680

aacccagtta ctgcacagat gcaaatcaaa gaagataggt tctggacatg tgcctatcgt   1740

ttgtattatg ctctaaaaga ggaaaaggtc ttccttggag gtggtgcagt tgaatttttg   1800

tgtcttagct gtcttcatat tcttgcagag caatctctga aaaaaagaaa accatgcctg   1860

ctcagggtgg ctgcataata cttcctcttg gctggcttca tctctggcaa tatacagacc   1920

aactgtgctt aaattcctgg caaatggatg gcagaaatac ctttcaactc tcctatataa   1980

cactgccaat tactcatcag aatttgaagc cagcacatac attcaacatc atctgcaaaa   2040

tgccacagac tctggccctc cttcatctta catcttgaat gaatatagta aactaaatag   2100

tagaattttt aattcagaca tttcaaataa actggagcag attccgagag tttatgacgt   2160

tgttacacca aagattgagg cgtggcgccg agcattggat ttagtattgt tagtacttca   2220

gacagacagt gaaataatta ctggacatgg acacacacag ataaattcac aggaattaac   2280

gggctttcta tttttgtagt gttactggct aagtctttgg aaaataattt ttcataatat   2340

gtcatgctaa taataaatat attgatagcc aaaaaaaaaa aaaaaaaagg ccacatgtgc   2400

tcga                                                                 2404
```

<210> SEQ ID NO 36
<211> LENGTH: 1690
<212> TYPE: DNA
<213> ORGANISM: Homo sapiens

<400> SEQUENCE: 36

```
cactgttggc ctactgggac tcaaagataa ggcttaggcc cctctagcca aagggccctg     60

cccagatgcc ttccttgtac tggaaactgg cccaagtggg gcagaaggcg ttgtcagtgg    120

ggttaagaag ggacggtccc agggtccatg ctagaccagt tggaaagttt tgaagtcagg    180

aaaagacgtt tttgtatcaa gggatttta gcagttaatg gtggtggatt tttaaaggtc    240

aggggaataa agtctggggc atggggagtg cagaccaagt tactgaactg cacaggcaaa    300

attaggaagg ttattttatg agtcaaaaca tactacagac aagctaccaa aaattatttg    360

ttaaaaaatg caacaagaca aataaaaaga gaaataatca tctgtttata tttctaataa    420

aggagcaaaa tataaaaata ggacctgcta agagacattt tccattctaa ttcacgattc    480

acttttccaa ggacagcctt caactgtcac cacacagctg ggggggagtc atttcttaac    540

aagggatgcc tcttgggata gaactaggga gttttaaatc tttacttgat catcttttat    600

tttcttttcc actttttcct tttttctctc tctctgtgtc ctagacttcc attgcattta    660

tatttaatgt ttatttctga gaatcaagca gtatattttt cctaaatgaa acataaatta    720

tattcctatt cattagatag gttcctagga acaatgccaa ttaatccatt gtttaagtag    780

taacttgaat gtttttctat atccctccag ctttgttgat agtggcgggt tttgtacaat    840

tggagggagc cctcagagcc ttctgggga ggagaggaac tgtccttaat ccatcaccac    900

taccataggg caaagccagc aggtgtggcc ctgtgagggg ctgtacagat gggatgtggc    960

caggagaaca gagccccacc tggaccacct gacccctcgg gattccaccc ctgtcatcgt   1020

ggggatgttc ctatatggga gaaagttggg ttaaatcaaa aaagaggcca cgcccaggtg   1080
```

```
taatcagagc caacctggtg ggctgggtct atcacaagac ataactgatg ctgaacatga   1140

acaaagataa aaactgtttg gagggttttt gagttgtttt tcttatgttg ttgggtgggg   1200

tataccagca taaactctaa agataaaatc tatgttagat tgtcaatcaa ctgtgttttt   1260

gaacagcata attgtgtagc agcacattgc aaaaatgcat tcatccaaag cgacacatgt   1320

ggcaacgtag accacgccag tgaaataagc cccttcgtga tcacctgact ccagttctcc   1380

gtgtgctcca ttggctgcgg ctgcaggagg aagatgcctg acagccctca tgctctccgc   1440

agggggcgc tcacaaagat gccaggggtg tttattgtgt ttattttttt aattactaaa   1500

atcagtagct aagaaagggt ccttgaagcc tcctaacctg ggttggacct ttgaaaaata   1560

tatttgtagc acatattata gatggaaaga agaagatatt tatttatacc tgtgatgcca   1620

attgtcatta aaaggctttt catggcttga caagtcaaaa aaaaaaaaaa aaaggccaca   1680

tgtgctcgag                                                          1690
```

<210> SEQ ID NO 37
<211> LENGTH: 2963
<212> TYPE: DNA
<213> ORGANISM: Homo sapiens

<400> SEQUENCE: 37

```
cactgttggc ctactggaag taattgtccg tgtcaggaag gtaggcgtgc caagccgcgg     60

ctctgcggag aaaccacgac caccgcggcc gccggaaacc caaagcgctc cagagcgtcc    120

ccgggtggcc gggcagcacc agggacagcg cccgggactc cactggggac cggctcctgg    180

gcttcccagc gtcgcgggta gaggtacagc tgctccgtgt gccgcaggct ccagattctc    240

gccaccccac ccctccctca gaaactcgga ctgctctcgt ctgccgtgtg gttctctttt    300

cttccgaaag gccagtgtct tatctctcca cttcaagtcc agaggacttg ctcagtctcc    360

tcccettaag tcatttccac catcctcagg cagctgtggg aagccgagag tcctggactg    420

ttcgtccggg tgccagcgct ggcagtccca gtccgtccgg tgcagcagcc cggcgcattc    480

ccctctctcc ctccctcttg ctctccctcc ctttctgtct tcctctcttt cctcctctac    540

tgctccctcc ctctcttgcc tcttaagttt cctgcaccgt gaatccaact gtgccaagcc    600

ttggctcccg cgaaccaatc ctgagcgcga cccgggcact gggacggcga ctccgccaaa    660

gctggacgag gcagccggac ccgtctgcgc tcgagcatgg agacggagcg cctgggaggg    720

cacgtccggg gcgctggaga cgccaggccc gagtagcttc tccatggagc ctgcccagag    780

cggtcccttc tcgcaggatt cgccccaagt cctgtgcggc tgctgagagc gctccttgct    840

ctgtaaagtg gatgtcaggt ggatctatgt ttctgaagga acaaagactc aaagaaggca    900

ccgccaagga agtttgagac gcgggagaat gcaggctgcg tgctggtacg tgcttttcct    960

cctgcagccc accgtctact tggtcacatg tgccaattta acgaacggtg gaaagtcaga   1020

acttctgaaa tcaggaagca gcaaatccac actaaagcac atatggacag aaagcagcaa   1080

agacttgtct atcagccgac tcctgtcaca gacttttcgt ggcaaagaga atgatacaga   1140

tttggacctg agatatgaca ccccagaacc ttattctgag caagacctct gggactggct   1200

gaggaactcc acagaccttc aagagcctcg gcccagggcc aagagaaggc ccattgttaa   1260

aacgggcaag tttaagaaaa tgtttggatg gggcgatttt cattccaaca tcaaaacagt   1320

gaagctgaac ctgttgataa ctgggaaaat tgtagatcat ggcaatggga catttagtgt   1380

ttatttcagg cataattcaa ctggtcaagg gaatgtatct gtcagcttgg taccccctac   1440
```

-continued

```
aaaaatcgtg gaatttgact tggcacaaca aaccgtgatt gatgccaaag attccaagtc   1500

ttttaattgt cgcattgaat atgaaaaggt tgacaaggct accaagaaca cactctgcaa   1560

ctatgaccct tcaaaaacct gttaccagga gcaaacccaa agtcatgtat cctggctctg   1620

ctccaagccc tttaaggtga tctgtattta catttccttt tatagtacag attataaact   1680

ggtacagaaa gtgtgccctg actacaacta ccacagtgac acaccttact ttccctcggg   1740

atgaaggtga acatgggggt gagactgaag cctgaggaat taaaggtcat atgacagggc   1800

tgttacctca aagaagaagg tcacatctgt tgcctggaat gtgtctacac tgctgctctt   1860

gtcaactggc tgcaaaatac actagtggaa aacactctga tgtaatttct gcccagtcag   1920

cttcatccct cagtataatt gtaaatcatc acagattttg aagtcacacc tgaagacatg   1980

ctctcacata tagaggtaca caaacacacc gtcatgcaca tttcagcttg cgtctatcat   2040

gattcctgtt gagagggctt tcattgtctg actcataatg gttcaggatc aactatcatc   2100

aaacggaagg attaactaga cagagaatgt ttctaacagt tgctgttatg gaaatctctt   2160

ttaaagtctt gagtacatgc taatcaataa tctccactca tgcattccta ctgcttggag   2220

tagctgtact ggtaaatact actgtaggag tatctgcttg ttaaaatgga aaaatgtgtc   2280

tttagagctc agtattcttt attttacaaa cacaacaaaa tgtagtaact tttttccagc   2340

atacagtagg cacattcaaa gtggtccaag atggctcttt tttctttgaa aggggcctgt   2400

tctcagtaaa gatgagcaaa catttggaat ttacatgtgg gcagacattg ggataacaac   2460

tttcatcacc aatcattgga cttttgtgaa gtcgacacca gctaaggctg cttaaaataa   2520

gttctgatca ttatataaga agggaaatgc ctggcagaca ccatgtaagt tataagtgtc   2580

tgtcttatct ttactacaca tattgtaaca aattcaatat cctagtcttc atttgtatga   2640

atggtttgta ttgtacatag tttaaccaag tgttatttga gctgcttatt aatattaact   2700

tgtacttgtc tctctgcttg ttattggtta agaaaaaagg atatgaggaa ttcattttat   2760

caatgtagct gtgaaggcca ttaaaaagac aaacttaatg tacagagcat ttattcagat   2820

caagtattgt tgaaagctat acatatacaa cattacagtc tgtctgtatt tagatatttt   2880

atttctggaa aaaatgaaat gtacataaaa ataaaacact taaagttgag tttcaaaaaa   2940

aaaaaaaaaa ggccacatgt gct                                           2963
```

<210> SEQ ID NO 38
<211> LENGTH: 2262
<212> TYPE: DNA
<213> ORGANISM: Homo sapiens

<400> SEQUENCE: 38

```
ctactgggga aaaaaaaaaa aaacaagatg acgacgacaa ccacaaaaaa aattgacatc     60

agatgaaatg aaaaaaaaaa aaaacaaaaa aaactaaagg aaggagaaag ctgtaaaaat    120

cactggcatt cgtggggcca ctccccaccc aagctccacg tgtgtccgtc tgtgctcctg    180

gcctctgggg gaccagctgg gacatgaact tgtctgccag gccccccgtcg cgtgctgaac    240

ggtgttagtt tgtaggtaac gcacacaccc cacacctaag gtgtctgcat cctcctgcca    300

acgcatgggc tccacgtggt gtgctcgctg gctgtcgtga ctgtcagctg tctcttggga    360

ggggctgtgg gggcccgctg ggctgcctcc tttcccgcta gttgtgcctg agagttgctg    420

ttgttcctgc tttcccttcc cttcctttca tcccctgaag ggctaggtgt gggttttccg    480

tgcccggtat ccccacacac ccagcacgga caacccttcg gcagagccca ggccggcccc    540

tcacccccctg gagtattgaa actggagtcc cgtccccaag gccttcagag atgcccctac    600
```

```
acacccaggg ctccagctct ggtccttctg ggggagtaaa gtgcaaagag gggcacagct    660

tagttttggg cctctcgccg agcaagagac agcactgctg gctacagctc caacacagcc    720

agctgtggca agaggactct gcctgggctg gcccccctcc tgtgtgaggt gtctgtccct    780

tctctgctgg ccagcagcag atgcactggc agctcccaac cctgtttccg cccctcggcc    840

ctcccccagc ctgttcggct tctctgcagc ccgcaagggg gagcagactt ttgacaaagg    900

actgcgggcc tcgctcaagt ccctgagccc ccagctgaag ctgggagggg aggccaggct    960

ttgtgtctgg gcatattcgt ctgctgatgg ggtttgggga agcctggggc ttggggtttg   1020

gtcgggtggt gcagctagtg gcagagcggg atcagaggtg gtggctgccc agcttctggg   1080

ctgagacaag ggtctgtgca ggggtttact gaagtgggag tgcctttgga atctgggccg   1140

ggagcagaag ggagcaaaag ctacagtggg agccagccta gggcacatgg gaggcgtgag   1200

ggcagtgctg cccgtgcagt gtcaggtgtg ccagtgcctt ggcgggctgc agtgcgtgtg   1260

agggcacctt ctaggtgggc cagggatgca gctatggaga taaggcgggc tggggacaga   1320

aacaggtggg cacagggccc aggacaccag cggatggagg gcagggtcta gccctgtgct   1380

cctgagcgtc ggctgcctgg gttcgaggcg gtgggtcccc ggccccttgt gatggtgtgt   1440

accatggggg agctcgggga cagggcaagc ccgagcatgg tggggctgca gggtgggtct   1500

gaagccaggt tgggtggggg tggtcacaag ccctgactgc agagggtcag ggctcctgc    1560

cccagtgcct gcccactttc aattcacatt gctttcaaca aggattttct ttatcttccc   1620

ctacaaatca agccaaggga ggggcacaga atggggaaca ggacacagga tcctaaactc   1680

caaggggact gtccaccgat gaacactcag agtggacacc atcttccgtc cacgctgtgc   1740

ccaggacagc tgtccccatc catgaacaca gggtaaacat ctgccgggct ccgcaccagt   1800

ggctccctgg gccatgggac agcggcaggg ctcaccacgg acagcacgtg gcccagcagc   1860

cggccaccct ggcgtcctgg ggcctcctcc cctcctctcc ctctcacctt gtcacctcca   1920

cggagctgcc tgtctgggat aatttgggga tttttttct gggggataat tcttttgcat    1980

gacccctaaa gagcaagcca caccggtctg ctagctaggt gtccgcggtg tggtggtggc   2040

ggccgctggc cagcgctgca aggggtcggc tgcccacggt gctggctggc ctcccctcct   2100

ctctcttttt gctgagtttc attgtctttt ctttctgagc cttgtaagtg tacaaaaatt   2160

attcttattt tgttctgtct cgggaaactg caaataaaag aaaaacagga caaaaaaaaa   2220

aaaaaaaaaa aaaaaaaaaa aaaaaaaaag gccacatgtg ct                      2262
```

<210> SEQ ID NO 39
<211> LENGTH: 3250
<212> TYPE: DNA
<213> ORGANISM: Homo sapiens

<400> SEQUENCE: 39

```
cactgttggc ctactgggaa atggcatttt tttggaactc agcttacaca caaattctgc     60

tagcaggagg aaagggtatt gtggctttcc gttgttaaaa tgcggaggta gagttggaaa    120

acaatcaaaa gaaatgttcc tctcattttt tggaccaaat gaacaaatct agcatttgtt    180

tttgagagaa taaatactct tcaaaaagaa cagaaactgt tctcaaaatc tttgaagtat    240

gtcactgatc ctttaaccag tagttggaga agcaagtatc ctactgacaa acacaggctt    300

tgtggggttg aaagccgatc ataagtttac aaagactgat tgggcctttg gcttgtgact    360

aatgcctggc actgacacag aggaggctct taatcgacac agccacatat attttaagta    420
```

-continued

```
aaaatgcttg ttctcaaaga aattaatttt tttgcctagt accctctttc gggttaaaag    480

aatgcattgc tcaggatgta aataacatta ataattctgt caaagtgaca tcattttctg    540

taatggtata gggaaacgga ttatttgggg agaaggattc tcgttatttg tttcttagag    600

atttttcttt taataattaa tttaatttgc cagttgtaaa agcacaagag atcatatgaa    660

taagaacaat gttcctaatg gccttctaat tacagggtct gtgttttgta gtactaacat    720

taaagccaac atgtttctta ttcatacagt aaaaaatatc tattctcaag acctgatcca    780

gaccctgcat tcatatttga tatcagggta tgaagacccc ctacaatccc cctccctcca    840

aaaaccatcc tgacctgctg gctaatgcct gaacttctcc tcctaggctt ggtttcctta    900

attcagttct atatttattg agttgctact gcttcagtca catatcagac atggcattag    960

cgctctgagt cacctgtata ttcttccatg tgccagggac tttctgctct gatccttgct   1020

gaaatgaaac ctctgaggtt tcatccataa gtaatacttt agtggctcta cttcagttct   1080

ttctaggcaa agatattagg atattaatag ctgaggagag ggtaaaggc cagtacctgt    1140

gtaagaaaat gtgcacgatt ggaagagacc acagagaagt tttcctagct tcacaattac   1200

agaggcccca ctttgtccac tagttgtagg gataaaagga taccattgct tgaacccctg   1260

tggttctctg agtagttggc atgctttctc catccttctt aagactgtgg agtgtgtgaa   1320

agtacttcag gcagaagtgt ctgacttcca tctataactg agtgaaacaa agaatagcct   1380

ttgcttcttc cagacaccct ctgggaactc tccgctagct caagtgcact ccttcagcaa   1440

gcgcagtgaa gccctttca aatgcagtca tgtgcagaac cccccatata caaagcagag    1500

ggaagtgggg ttgctccaga gcccctgttc ctcaccactc ctctgtgccc tgcagaggct   1560

ctggtccatg atgctgtgcc ctggttgagg acactgacca cagaggtact ttggtggttg   1620

tcacaaatgc tgttctccac tcatgaagat ggactgttta gcactgtttt cacatctgcg   1680

gactcaaaag tcaaataact tagacaatgt gagtcttggc tttgccaata acaagaaaca   1740

atgaatgcta tgaggtgaat gtttgtgtcc ccccaaaatt catatgttga agcctaaatc   1800

tctgatgtga tggcattagg atgtggtgtc tttgaaagtt gattaagtca tgaggttaag   1860

ccctattgga tgggattagt gcctttagga agaggccccg gggagctgtc ttgccctatt   1920

ctactgtggg tggacatagc aagaaattat ctgtgaacca aaaagtaggt cttcatcaga   1980

catggaatct gccagcacct tggcctttga tttcccagcc tccagaattg tgacaagtaa   2040

atttctgtta tgttaccctg tttatggtac tttgttataa cagcctgaat agactaagag   2100

aatggagaag taacttagct gctgtagacc ccactttact catctataga acatttgatt   2160

ttagagaggt gtaaaaaagt taacatatga aaagtgccta gtacagagcg agccctctgt   2220

aaagagtagt tgtcatttta aaattaaata aaacttaatc ccaaatgaca cagaattctt   2280

ccattttagg ggaaaaatac aaaatcaaca gatttaatga gggctgcaaa atacttgaca   2340

atctcttcat catttaatca ctttttcacc cattcttaac ccctgttgtt attagtagtt   2400

ctgtaccaaa tcatatatgt catcactgtg cccctttttg ctatagacaa aacgtttttc   2460

atgtgtggtg atgcaaatgt ggactttagg gatactaatg taataatgag ccagaagtta   2520

atgaacagga aactgaacaa gaatggggca gacaacttgg caccagagat ggctgcgggg   2580

caggaagtat aaactaagca tgtccaaaaa aggggaagtg attcggaaga ccgtaagggt   2640

gagctagaca aggggctgct tctggatcca ctgagaacag actagactgc atgccgaagg   2700

caaaacataa atgcaagtcc ctctcctcac agcacacaaa tagagtttgt gatgaagtgc   2760

ccattttcct tcccattgca caagtagtct gtgtacaatt tacctaagcc cttggatatg   2820
```

-continued

```
tctattttgt ttattcttgg ttcaaatgca ttcgttctat catctagaaa attacacatt   2880

ccttcaaggc agggacagtg tcatttgctt tatatccctt ttaatatcct tgacttccat   2940

ctgggtgcaa agcaacattc agcaggaaaa tggaagccac tttaggaatt ttgaacaagg   3000

aaatatactg gaaaagctgg aactgcaaca gggagaaaga ggggtgttgg aggaacataa   3060

aggaagaaga ggtgatcccc agattcgaag cagttagccc ttctgggcag gagcccatga   3120

gcttgttcct gaaagtccaa gtgggttggt gacacttgag tttgactgtg agttcactca   3180

agagctgctg tctcaaaaaa ggaaaaaaaa aaaaaaaaaa aaaaaaaggc cacatgtgct   3240

cgagctgcag                                                          3250
```

<210> SEQ ID NO 40
<211> LENGTH: 6638
<212> TYPE: DNA
<213> ORGANISM: Homo sapiens

<400> SEQUENCE: 40

```
ctctcccgcc gcgcctccgc ctgcccgccc ccgccggccg aggctgggct gcgggaggcg     60

gccgggcggc ccgagcttcg ctagggcgac caaaacaaag gcagcatccg gggctgggtg    120

gatgcaaaca accatgaaag actgggttct cgctctcccc ggctctgctg ctgctgctgc    180

tgccgccgcc gccgctgctc ctcctcctgc cgccgccgct agggctccgc tgtgaggggg    240

aagcaggggc gcagctgctg ggcgtgcatc cgaaaggtga gagccagaga gcgagcagag    300

ggggcgggca ggccacgaaa atgtcctcgg ccgtggggcc ccgcggtcct cgcccaccca    360

cggtgcctcc ccccatgcaa gagctgcccg acctgagcca cctgaccgaa gaggagagga    420

acattatcat ggcagtgatg gaccggcaga aggaagagga ggaaaaagaa gaagccatgc    480

tcaagtgtgt tgtcagggac atggcgaagc ctgctgcctg caaaacacca agaaatgctg    540

aaaaccagcc ccaccaacct tcaccgagat tgcatcaaca gtttgaaagc tataaggaac    600

aagtgagaaa aatagggggaa gaagcgcggc gttaccaggg cgagcacaaa gacgatgctc    660

cgacttgtgg aatctgtcat aaaacaaagt ttgctgatgg gtgcggtcat ctctgctcct    720

attgtcgcac taagttctgt gcgcgctgcg gaggccgcgt gtctctacgg tcaaacaacg    780

aggacaaagt ggttatgtgg gtatgcaatt tatgtcgaaa gcaacaagaa atcttaacca    840

aatctggggc atggttcttt ggaagtggcc ctcagcagac aagtcaggat ggaaccctga    900

gtgatacagc tacaggtgct ggctctgagg taccaagaga aaagaaagca cgactccaag    960

agcgatcgcg gtctcagaca cccctgagca cagcagctgc ctcctcccag gatgctgctc   1020

ctcccagcgc accaccagac aggagcaaag ggctgagcc ctcgcagcaa gccttggggc   1080

ctgaacagaa gcaggcttca tccaggtcta gaagtgaacc tcctagagag agaaagaaga   1140

ccccagggct ttccgagcag aatggcaaag gagccctgaa gagcgagcgg aaacgcgtgc   1200

caaagacctc agcgcagccc gtggaggggg ccgtcgaaga acgggagcgc aaagaaaggc   1260

gggaaagccg aaggcttgag aaagggcgat cacaggatta cccagacacg ccggaaaaac   1320

gggatgaggg caaagcggcg gatgaggaaa agcaaagaaa agaggaggat tatcagacca   1380

ggtaccgcag cgacccgaac ctggctcggt acccggtgaa accgccgcct gaggagcagc   1440

agatgcgcat gcacgcccgg gtgtcccgcg ccaggcacga gcggcgccac agcgacgtgg   1500

cgctcccgcg caccgaggcg ggcgcggcgc tgccggaggg caaggccggc aaacgcgcgc   1560

cggcggcagc cagggcctcg ccgccggact cgccgcgggc ttactcggct gagagaactg   1620
```

-continued

```
cggagaccag ggcgccgggc gccaagcagc taacgaacca cagcccgccg gcgcccagac   1680
atgggccggt tcccgcagaa gccccggagc tcaaagccca ggagcccctc aggaagcaga   1740
gccgcctgga ccccagctcg gcggtcctca tgctgcggaa cgactctttg agctcagacc   1800
agtccgagtc ggtgcggccg tccccgccca agccgcaccg gtccaagaga ggcggcaaga   1860
agcggcagat gtcggtgagc agctctgagg aggagggcgt gtcgacgccc gagtacacca   1920
gctgcgagga cgtggagctg gagagcgaga gcgtcagcga gaaaggtgat ttggattatt   1980
actggttgga tcctgccacg tggcacagcc gggagacatc acctattagt tcgcatcctg   2040
taacgtggca accatctaaa gagggggacc gattaattgg acgtgttatt cttaacaaga   2100
gaacaaccat gcccaaagac tcaggtgcat tgctgggtct gaaagttgtt ggaggaaaaa   2160
tgactgactt aggacgactt ggtgctttca tcaccaaagt aaagaagggt agcctagcag   2220
atgtagttgg acacctaaga gcaggggatg aagttctaga atggaatggt aaacccctgc   2280
cgggagctac aaatgaagaa gtttacaaca ttattttaga atcaaaatca gaacctcaag   2340
ttgaaattat tgtttcaagg cctattggtg acattccccg gattcctgag agctcccacc   2400
ctccactgga gtccagttca agttcctttg aatctcagaa gatggaaagg ccttccattt   2460
ctgttatttc tccaacaagt cctggagctc taaaagatgc cccacaagtc ttaccagggc   2520
aactttctgt gaagttgtgg tatgataaag tgggacacca gctgattgta aatgttctgc   2580
aagcaacaga tctacctgct agagtagatg gacgtcctcg aaatccctat gtaaaaatgt   2640
attttcttcc agatagaagt gataaaagta aaaggaggac caaaacagta aagaaaatac   2700
tagaaccaaa atggaatcaa acttttgtct attcacatgt acatcgtaga gattttagag   2760
aacgaatgtt agaaataact gtgtgggacc aaccaagagt gcaagaagaa gaaagtgaat   2820
ttcttggaga gatcctcata gaattggaga cagcgctttt agatgatgaa ccgcattggt   2880
ataaacttca gacacatgat gagtcttcac tacctctgcc tcagccatca cctttcatgc   2940
caaggcgaca tattcatgga gaaagctcta gcaaaaagct acaaagatct cagcgaatca   3000
gtgatagtga catctcagat tatgaggttg atgatggtat tggcgtagtt cctccagtag   3060
gctataggtc tagtgctaga gaaagtaaat ctacaacatt aactgtgcca gaacagcaaa   3120
gaacaactca tcaccgctca cgttcagtat ctcctcatcg cggcaatgat cagggaaagc   3180
cgcgttcacg tttaccaaat gtgccattac agaggagttt agatgaaatt catccaacaa   3240
gaaggtcacg ttctccaacc agacaccatg atgcctcccg aagtccagtt gatcatagaa   3300
ccagagatgt ggatagtcag tatttatcag aacaagacag tgagcttctt atgctgccca   3360
gagcaaaacg aggacgaagt gcagaatgcc tacatactac caggtaaata cagggatttg   3420
gtaatggtga ctgtgtgtga tgactctctt tccattctat tattcttccg tctctccctt   3480
agtggtatta ttacaagcaa gtcaaataaa tttcccaagt atttgaaatt tgttttgttt   3540
tatattgagg ttatggaaaa ggttccaaat atatttcagt tccgattcag gctgactgct   3600
ttgccatctg tagattcaaa aatccagaga ctagtgggcc tctctgggac tgtttgcgtt   3660
cctaaaactg aggaaccagt ttctgcaatt aaaattctaa atgctcactg tgagtgcccc   3720
caactttccc acacatattc ctgtctagtc acaagaggtc taatctgtgt atggcagtgt   3780
cattgtttca taattgtaag tttgctctgt tttagccttt tttaatttcc ttttagaatt   3840
tattgttgtt tatattctgt ttgcttttga taaaatcttt aacagttcac ttttaatggc   3900
tgagcttcag cttctttctt gatgaaaagt gaagatattc aacctgatct taactatcct   3960
agcccaccag ttgtcagaaa tgctgcagta caaactttcc cacaaaggca tataacagta   4020
```

-continued

```
tgaatgcctc tttagaagcg acaaaagata taatttttgc ttctaaattg gagcttagag   4080
cctgatgctt tatgttaatc tcattacatc tttaatttca tatccaagta aaacttctta   4140
cagattactc atggaacata ttctataaat acttaatgta tatttgaaat gaatatagaa   4200
gttaaggaag tagtaagtca gtgaaacaaa ctaacacaaa ataatcgaac tcaaatattt   4260
tagccaataa aaagcaagag gaaagagaaa gaaagaggta ttaccgcagt acttgggatg   4320
caaagacaaa tgcatgattt attatgtctg tgtgtaatat gtagttctgc ccaataatgc   4380
aaacaaaatt gggctaataa aaattgtttg aactttttac agtctgaagt tatactactc   4440
ataactactg ccatgtttgc ttggagtgcc acaggaaaaa atcgaggaaa tattagttct   4500
gcttgctgag aaaaaaatgt aaaatcatgc atattgtaaa aacctactga aggtcaaagc   4560
atgaactatc caggtttatt attacttgtt cttgacaaac agtttcttaa aataatggtt   4620
tatttactaa ttctgaaagt tttctcacac tcctcttgat gtgactaaag cttcaaaaga   4680
aataaaaaac atgcacacaa aacaaacaca aaaaaaatcc ttatatttta agctacttag   4740
tgtgtgcctg gcactcagtg tgtgaatatt tctaggatac tcacaccagt ggtctaaata   4800
taataactaa aaatattttt ctttccctta ttttgtactt gtaaaatatt atatacttat   4860
ataatattat ataatagttg catcatttta tataatctta tacttaagat tggtgctttg   4920
ctaataattc tgagctccac aagtcctatt taatagtctc tgtatgttga ctttgcattt   4980
cctgatttaa gcaaataatc atatttgtat gtatacaatt taaaaataaa tgagtattca   5040
gcgaggcaga taacatcctg tggacaggta ctacgacaat aagataggga gtggaaggaa   5100
gctgagctag ccaaatgtgt cagtgcgaaa catatgtcac cagtgtcttt tctccttcct   5160
gtctttcatt ctctaatgtg taatgctaaa agtatggaga tagagacaac atgagttcaa   5220
aaatacgtgc atgtatgtat atataatctc ttctgtgttt atattcatgt atttataaaa   5280
acattaattt atatctgtat aaaaatgaat gtcaaaatgt gtacatataa ataaccacaa   5340
ctttatatgg atatatcaat aatatagttt ggtttcatat aaactatgga cacttattat   5400
ttctataact atccatggct aaaatctaaa gctttcaaaa tacatcatac catgttcact   5460
taggacttat aaaaataaaa tctgaggatt tactagtctc tagtaaacat aaggaaaata   5520
acatttattt aataacaagc acagtgttaa atatttaatg tactttgtca atttcctgac   5580
aataattata tgttatgaat attattatcc tgattttaga gatgaggaaa aaagctacga   5640
aagtttattt tacgactaat agagtaagga ttcaaaatca gatctatttg atatcttctg   5700
tttaactagt ttttccaaaa atatgaaaac ttgtcctatg agatgtttca ccaataagag   5760
tttttgtgag tcaaatacat tttggaaact ttgcaactga aagtgtctac cttgaaattt   5820
aatacacaca gcatattaaa gtcatgttct aaagaaatct gtatgtttag tttcttttct   5880
cccaaattgt ttaatttccc aaccttttt tagtaaaacg tgtctcgagg aagtggtagt    5940
atagagaaaa tgctatagtt gccttactgt atcctactgt gtcctaaata ttgtgtacat   6000
gttaccacac acccctgtta agtggaagtt atttcccaca ttttgtggat gtagaaacag   6060
gcttggagac ttaatcgaat tacccaggtc acagccaata agtggcaaag ccaaggcagg   6120
aacttgaaca ttcagactat aaattttgtg ctattttcta gctgtttccc attctatgtt   6180
gatcccattc ttgaaaaaaa aatcactttt gaagcaatgc ttagaaaagt tttatagcaa   6240
cctattacta aagatatttg cctgaggtta ggagttgaaa agaagagtcg actgtctaga   6300
aaggaggcta aatccttagt ttcagtaaaa tttgtcctca acttgtactt aataaggagg   6360
```

-continued

```
aagctgaagc gggcagatca cttgaggtca ggagtttgag accagtgtgg ccaacatggt   6420

gaaaccccgt ctctactaaa acacacacac acacacacac acacacacac acacacacaa   6480

attaggtggg catggtggca ggtgcttgta atcccagcta cttgggaggc tgagagagga   6540

gatttgcttg aacccaggag gcagaggttg cagtgagcca agatcacacc attgcactcc   6600

agcctagata acaagagtga gactctgtct caaaaaag                           6638
```

<210> SEQ ID NO 41
<211> LENGTH: 782
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, t, c, g, unknown or other
<220> FEATURE:
<221> NAME/KEY: modified_base
<222> LOCATION: (8)..(9)
<223> OTHER INFORMATION: a, t, c, g, unknown or other
<220> FEATURE:
<221> NAME/KEY: modified_base
<222> LOCATION: (11)..(11)
<223> OTHER INFORMATION: a, t, c, g, unknown or other
<220> FEATURE:
<221> NAME/KEY: modified_base
<222> LOCATION: (39)..(39)
<223> OTHER INFORMATION: a, t, c, g, unknown or other
<220> FEATURE:
<221> NAME/KEY: modified_base
<222> LOCATION: (42)..(42)
<223> OTHER INFORMATION: a, t, c, g, unknown or other
<220> FEATURE:
<221> NAME/KEY: modified_base
<222> LOCATION: (48)..(48)
<223> OTHER INFORMATION: a, t, c, g, unknown or other
<220> FEATURE:
<221> NAME/KEY: modified_base
<222> LOCATION: (102)..(102)
<223> OTHER INFORMATION: a, t, c, g, unknown or other
<220> FEATURE:
<221> NAME/KEY: modified_base
<222> LOCATION: (312)..(312)
<223> OTHER INFORMATION: a, t, c, g, unknown or other
<220> FEATURE:
<221> NAME/KEY: modified_base
<222> LOCATION: (376)..(376)
<223> OTHER INFORMATION: a, t, c, g, unknown or other
<220> FEATURE:
<221> NAME/KEY: modified_base
<222> LOCATION: (430)..(430)
<223> OTHER INFORMATION: a, t, c, g, unknown or other
<220> FEATURE:
<221> NAME/KEY: modified_base
<222> LOCATION: (461)..(461)
<223> OTHER INFORMATION: a, t, c, g, unknown or other
<220> FEATURE:
<221> NAME/KEY: modified_base
<222> LOCATION: (473)..(473)
<223> OTHER INFORMATION: a, t, c, g, unknown or other
<220> FEATURE:
<221> NAME/KEY: modified_base
<222> LOCATION: (500)..(500)
<223> OTHER INFORMATION: a, t, c, g, unknown or other
<220> FEATURE:
<221> NAME/KEY: modified_base
<222> LOCATION: (529)..(529)
<223> OTHER INFORMATION: a, t, c, g, unknown or other
<220> FEATURE:
<221> NAME/KEY: modified_base
<222> LOCATION: (531)..(531)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other

```
<220> FEATURE:
<221> NAME/KEY: modified_base
<222> LOCATION: (600)..(600)
<223> OTHER INFORMATION: a, t, c, g, unknown or other
<220> FEATURE:
<221> NAME/KEY: modified_base
<222> LOCATION: (610)..(610)
<223> OTHER INFORMATION: a, t, c, g, unknown or other
<220> FEATURE:
<221> NAME/KEY: modified_base
<222> LOCATION: (619)..(619)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (631)..(631)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (636)..(636)
<223> OTHER INFORMATION: a, t, c, g, unknown or other
<220> FEATURE:
<221> NAME/KEY: modified_base
<222> LOCATION: (639)..(640)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (669)..(670)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (699)..(699)
<223> OTHER INFORMATION: a, t, c, g, unknown or other
<220> FEATURE:
<221> NAME/KEY: modified_base
<222> LOCATION: (716)..(717)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (723)..(723)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (744)..(744)
```

```
<223> OTHER INFORMATION: a, t, c, g, unknown or other
<220> FEATURE:
<221> NAME/KEY: modified_base
<222> LOCATION: (749)..(750)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other
<220> FEATURE:
<221> NAME/KEY: modified_base
<222> LOCATION: (762)..(762)
<223> OTHER INFORMATION: a, t, c, g, unknown or other
<220> FEATURE:
<221> NAME/KEY: modified_base
<222> LOCATION: (765)..(765)
<223> OTHER INFORMATION: a, t, c, g, unknown or other
<220> FEATURE:
<221> NAME/KEY: modified_base
<222> LOCATION: (767)..(767)
<223> OTHER INFORMATION: a, t, c, g, unknown or other
<220> FEATURE:
<221> NAME/KEY: modified_base
<222> LOCATION: (780)..(780)
<223> OTHER INFORMATION: a, t, c, g, unknown or other

<400> SEQUENCE: 41

ggngcttnng ngtggctttc atggcgccat tttttcttna antagcangg ggcccggtga     60

gacaatacaa acaggtaagg tttcgtttac ctgtgagggt antatatgct ccccactcca    120

gaacactaca aaacggccag acaagtctat accaaattgc gtcttttgaa gaggccattt    180

ttctctttct cagaaaaggc attggacacc attcgccact ttgtttagaa ataaattagt    240

ctggtatgga ttggttaata ggtccaacaa ctgaacaaag ctgacagagg gtatattcta    300

attgccaagc anaattatat ctaaattttt tggaaatatt ttctatgact gttcttttgc    360

tgagactcaa gggaancatc aacaaaacaa ctccctgtcc cactcccatc atgtgtgaga    420

tttcctcaan gattttctgg agttgcgata ttagactata ngcgtctgct tanacttatt    480

tattctgtcc atccattggn tttactaatc gtaaaaagtc tagggcaanc nttactcatt    540

taacctcatc atgctccaag ttgagtnaaa aagaactggc aacttttttta tccaaatttn    600

ccagtaaagn aacctaaant ctgnaatagg ngnganttnn aaaagtcana atccttgcat    660

ccaattnann tactggttca atcttcctnc gtctttaant aattcaggga ttatcnntnc    720

ccnccaanaa tgccngtcac nttnaaaann attgagtncc tnaangnaaa ggtttcccan    780

tt                                                                   782


<210> SEQ ID NO 42
<211> LENGTH: 772
<212> TYPE: DNA
<213> ORGANISM: Homo sapiens
<220> FEATURE:
<221> NAME/KEY: modified_base
<222> LOCATION: (3)..(5)
<223> OTHER INFORMATION: a, t, c, g, unknown or other
<220> FEATURE:
<221> NAME/KEY: modified_base
<222> LOCATION: (7)..(9)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (25)..(25)
<223> OTHER INFORMATION: a, t, c, g, unknown or other
<220> FEATURE:
<221> NAME/KEY: modified_base
```

<222> LOCATION: (39)..(40)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (622)..(622)
<223> OTHER INFORMATION: a, t, c, g, unknown or other
<220> FEATURE:
<221> NAME/KEY: modified_base
<222> LOCATION: (645)..(645)
<223> OTHER INFORMATION: a, t, c, g, unknown or other
<220> FEATURE:
<221> NAME/KEY: modified_base
<222> LOCATION: (647)..(647)
<223> OTHER INFORMATION: a, t, c, g, unknown or other
<220> FEATURE:
<221> NAME/KEY: modified_base
<222> LOCATION: (656)..(656)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base
<222> LOCATION: (747)..(747)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other

<400> SEQUENCE: 42

```
ggnnntnnng tgtggctttt ttngnccttt tttttctcnn gtagcaggan gacccggtga     60

gacaatacat acaggtaagg tttcgtttac ctgtgagggt agtatatgct ccccactcca    120

gaacactaca aaacggccag acaagtctat accaaattgc gtcttttgaa gaggccattt    180

ttctctttct cagaaaaggc attggacacc attcgccact ttgtttagaa ataaattagt    240

ctggtatgga ttggttaata ggtccaacaa ctgaacaaag ctgacagagg gtatattcta    300

attgccaagc aaaattatat ctaaattttt tggaaatatt ttctatgact gttcttttgc    360

tgagactcaa gggaagcaaa aacaaaacaa ctccctgtcc cactcccatc atgtgtgaga    420

tttcctcaaa gattttctgg agttgcgata ttagactata ggcgtctgct tatacttatt    480

tattctgtcc atccattggt tttactaatc gtaaaagtct aagggcaacc gtaactcatt    540

tatcctcatc atgctccaat gagtaaaaag aactggcaac tttttatcca atttaccaat    600

taagaaccta aatctgaaat angaggattt tgcacagtca taaancntgc atccanttca    660

atactggtca atcctcctcc ntccttaaat taattccngg gtnatccttc ccctcccaaa    720

aatgccngta actttcaaaa gattgantcc cttaaagtta aanattccca aa            772
```

<210> SEQ ID NO 43
<211> LENGTH: 782
<212> TYPE: DNA

-continued

<213> ORGANISM: Homo sapiens
<220> FEATURE:
<221> NAME/KEY: modified_base
<222> LOCATION: (5)..(5)
<223> OTHER INFORMATION: a, t, c, g, unknown or other
<220> FEATURE:
<221> NAME/KEY: modified_base
<222> LOCATION: (7)..(8)
<223> OTHER INFORMATION: a, t, c, g, unknown or other
<220> FEATURE:
<221> NAME/KEY: modified_base
<222> LOCATION: (21)..(21)
<223> OTHER INFORMATION: a, t, c, g, unknown or other
<220> FEATURE:
<221> NAME/KEY: modified_base
<222> LOCATION: (35)..(35)
<223> OTHER INFORMATION: a, t, c, g, unknown or other
<220> FEATURE:
<221> NAME/KEY: modified_base
<222> LOCATION: (39)..(39)
<223> OTHER INFORMATION: a, t, c, g, unknown or other
<220> FEATURE:
<221> NAME/KEY: modified_base
<222> LOCATION: (67)..(67)
<223> OTHER INFORMATION: a, t, c, g, unknown or other
<220> FEATURE:
<221> NAME/KEY: modified_base
<222> LOCATION: (71)..(71)
<223> OTHER INFORMATION: a, t, c, g, unknown or other
<220> FEATURE:
<221> NAME/KEY: modified_base
<222> LOCATION: (76)..(76)
<223> OTHER INFORMATION: a, t, c, g, unknown or other
<220> FEATURE:
<221> NAME/KEY: modified_base
<222> LOCATION: (94)..(94)
<223> OTHER INFORMATION: a, t, c, g, unknown or other
<220> FEATURE:
<221> NAME/KEY: modified_base
<222> LOCATION: (104)..(104)
<223> OTHER INFORMATION: a, t, c, g, unknown or other
<220> FEATURE:
<221> NAME/KEY: modified_base
<222> LOCATION: (107)..(107)
<223> OTHER INFORMATION: a, t, c, g, unknown or other
<220> FEATURE:
<221> NAME/KEY: modified_base
<222> LOCATION: (170)..(170)
<223> OTHER INFORMATION: a, t, c, g, unknown or other
<220> FEATURE:
<221> NAME/KEY: modified_base
<222> LOCATION: (178)..(178)
<223> OTHER INFORMATION: a, t, c, g, unknown or other
<220> FEATURE:
<221> NAME/KEY: modified_base
<222> LOCATION: (184)..(184)
<223> OTHER INFORMATION: a, t, c, g, unknown or other
<220> FEATURE:
<221> NAME/KEY: modified_base
<222> LOCATION: (195)..(195)
<223> OTHER INFORMATION: a, t, c, g, unknown or other
<220> FEATURE:
<221> NAME/KEY: modified_base
<222> LOCATION: (258)..(258)
<223> OTHER INFORMATION: a, t, c, g, unknown or other
<220> FEATURE:
<221> NAME/KEY: modified_base
<222> LOCATION: (316)..(316)
<223> OTHER INFORMATION: a, t, c, g, unknown or other
<220> FEATURE:
<221> NAME/KEY: modified_base
<222> LOCATION: (332)..(332)
<223> OTHER INFORMATION: a, t, c, g, unknown or other
<220> FEATURE:
<221> NAME/KEY: modified_base
<222> LOCATION: (339)..(340)
<223> OTHER INFORMATION: a, t, c, g, unknown or other
<220> FEATURE:
<221> NAME/KEY: modified_base
<222> LOCATION: (344)..(344)
<223> OTHER INFORMATION: a, t, c, g, unknown or other
<220> FEATURE:
<221> NAME/KEY: modified_base
<222> LOCATION: (346)..(346)
<223> OTHER INFORMATION: a, t, c, g, unknown or other
<220> FEATURE:
<221> NAME/KEY: modified_base
<222> LOCATION: (352)..(352)
<223> OTHER INFORMATION: a, t, c, g, unknown or other
<220> FEATURE:
<221> NAME/KEY: modified_base
<222> LOCATION: (368)..(368)
<223> OTHER INFORMATION: a, t, c, g, unknown or other
<220> FEATURE:
<221> NAME/KEY: modified_base
<222> LOCATION: (389)..(389)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (405)..(405)
<223> OTHER INFORMATION: a, t, c, g, unknown or other
<220> FEATURE:
<221> NAME/KEY: modified_base
<222> LOCATION: (422)..(422)
<223> OTHER INFORMATION: a, t, c, g, unknown or other
<220> FEATURE:
<221> NAME/KEY: modified_base
<222> LOCATION: (432)..(432)
<223> OTHER INFORMATION: a, t, c, g, unknown or other
<220> FEATURE:
<221> NAME/KEY: modified_base
<222> LOCATION: (435)..(435)
<223> OTHER INFORMATION: a, t, c, g, unknown or other
<220> FEATURE:
<221> NAME/KEY: modified_base
<222> LOCATION: (443)..(443)
<223> OTHER INFORMATION: a, t, c, g, unknown or other
<220> FEATURE:
<221> NAME/KEY: modified_base
<222> LOCATION: (463)..(463)
<223> OTHER INFORMATION: a, t, c, g, unknown or other
<220> FEATURE:
<221> NAME/KEY: modified_base
<222> LOCATION: (478)..(478)
<223> OTHER INFORMATION: a, t, c, g, unknown or other
<220> FEATURE:
<221> NAME/KEY: modified_base
<222> LOCATION: (493)..(493)
<223> OTHER INFORMATION: a, t, c, g, unknown or other
<220> FEATURE:
<221> NAME/KEY: modified_base
<222> LOCATION: (498)..(498)
<223> OTHER INFORMATION: a, t, c, g, unknown or other
<220> FEATURE:
<221> NAME/KEY: modified_base
<222> LOCATION: (504)..(505)
<223> OTHER INFORMATION: a, t, c, g, unknown or other
<220> FEATURE:
<221> NAME/KEY: modified_base
<222> LOCATION: (510)..(510)
<223> OTHER INFORMATION: a, t, c, g, unknown or other
<220> FEATURE:
<221> NAME/KEY: modified_base
<222> LOCATION: (516)..(517)
<223> OTHER INFORMATION: a, t, c, g, unknown or other
<220> FEATURE:
<221> NAME/KEY: modified_base
<222> LOCATION: (546)..(546)
<223> OTHER INFORMATION: a, t, c, g, unknown or other
<220> FEATURE:
<221> NAME/KEY: modified_base
<222> LOCATION: (549)..(549)
<223> OTHER INFORMATION: a, t, c, g, unknown or other
<220> FEATURE:

<221> NAME/KEY: modified_base
<222> LOCATION: (554)..(554)
<223> OTHER INFORMATION: a, t, c, g, unknown or other
<220> FEATURE:
<221> NAME/KEY: modified_base
<222> LOCATION: (560)..(560)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (573)..(573)
<223> OTHER INFORMATION: a, t, c, g, unknown or other
<220> FEATURE:
<221> NAME/KEY: modified_base
<222> LOCATION: (577)..(577)
<223> OTHER INFORMATION: a, t, c, g, unknown or other
<220> FEATURE:
<221> NAME/KEY: modified_base
<222> LOCATION: (584)..(584)
<223> OTHER INFORMATION: a, t, c, g, unknown or other
<220> FEATURE:
<221> NAME/KEY: modified_base
<222> LOCATION: (599)..(599)
<223> OTHER INFORMATION: a, t, c, g, unknown or other
<220> FEATURE:
<221> NAME/KEY: modified_base
<222> LOCATION: (601)..(601)
<223> OTHER INFORMATION: a, t, c, g, unknown or other
<220> FEATURE:
<221> NAME/KEY: modified_base
<222> LOCATION: (608)..(608)
<223> OTHER INFORMATION: a, t, c, g, unknown or other
<220> FEATURE:
<221> NAME/KEY: modified_base
<222> LOCATION: (626)..(626)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (659)..(660)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (743)..(743)
<223> OTHER INFORMATION: a, t, c, g, unknown or other
<220> FEATURE:
<221> NAME/KEY: modified_base
<222> LOCATION: (745)..(746)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other
<220> FEATURE:
<221> NAME/KEY: modified_base
<222> LOCATION: (760)..(761)
<223> OTHER INFORMATION: a, t, c, g, unknown or other
<220> FEATURE:
<221> NAME/KEY: modified_base
<222> LOCATION: (768)..(768)
<223> OTHER INFORMATION: a, t, c, g, unknown or other

<400> SEQUENCE: 43

```
ggggntnngt gtggctttta naggcctttt ttgtnatant ctcaaggggc ctccattata     60

ttccaangcc ngcctncccc aacttgtgct gatnttttaa ggangtnccc aagagtatga    120

agcagggtgc ttttgtccct ttctctcctc cctagtaatt ccctcctccn tatcccanag    180

ccangtaacc acccntcaaa tgaaccattc ctttttgctt tcatcaatgg tctctgtgaa    240

gttggggtcg ttgttcanga tggcggcgtc cgcgctctct gccgactccg ccccctttgc    300

ttcgttggta tggtangtgc ccttgtggcg gnacatgtnn cggntnagga anaccagggt    360

gcacaggntg gtgaaaatca ccacagcant gncgcctcca atganagccg agtttctgtt    420

gnctccattt cntanagctt ggncttgtcc tggattatat ggnaaatccg cactgggntg    480

aatccaagtg atncaggntg ccanngtcn agtggnngac gacatggggg agagggtcaa    540

cgggcnaang cccncagttn ggnctccaac aangtcnccc tggnatgtgg accttcagnc    600

ngaagggntt tgtccgcctc aaaggncggc ctttnaaggg ggccattttg ggttgaacnn    660

ggactcctgg atagggtaac cagtgaaanc ctggggtgtt ngatttgggg aaaccctttg    720

gncaaatttt ccccggtttc aananngttt tnccaagnan ngagcgantt tgggagaatt    780

gt                                                                   782
```

<210> SEQ ID NO 44
<211> LENGTH: 762
<212> TYPE: DNA
<213> ORGANISM: Homo sapiens
<220> FEATURE:
<221> NAME/KEY: modified_base
<222> LOCATION: (3)..(11)
<223> OTHER INFORMATION: a, t, c, g, unknown or other
<220> FEATURE:
<221> NAME/KEY: modified_base
<222> LOCATION: (29)..(29)
<223> OTHER INFORMATION: a, t, c, g, unknown or other
<220> FEATURE:
<221> NAME/KEY: modified_base
<222> LOCATION: (41)..(41)
<223> OTHER INFORMATION: a, t, c, g, unknown or other
<220> FEATURE:
<221> NAME/KEY: modified_base
<222> LOCATION: (70)..(70)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (595)..(595)
<223> OTHER INFORMATION: a, t, c, g, unknown or other
<220> FEATURE:
<221> NAME/KEY: modified_base
<222> LOCATION: (600)..(600)
<223> OTHER INFORMATION: a, t, c, g, unknown or other
<220> FEATURE:
<221> NAME/KEY: modified_base
<222> LOCATION: (620)..(620)
<223> OTHER INFORMATION: a, t, c, g, unknown or other
<220> FEATURE:
<221> NAME/KEY: modified_base
<222> LOCATION: (627)..(627)

-continued

<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (645)..(645)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (660)..(660)
<223> OTHER INFORMATION: a, t, c, g, unknown or other
<220> FEATURE:
<221> NAME/KEY: modified_base
<222> LOCATION: (664)..(664)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (671)..(671)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (702)..(702)
<223> OTHER INFORMATION: a, t, c, g, unknown or other
<220> FEATURE:
<221> NAME/KEY: modified_base
<222> LOCATION: (712)..(712)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other

<400> SEQUENCE: 44

```
ggnnnnnnnn ntgtggcctt tttttgccnt tttttgtgat nagtctcaag aatattccat     60

tatattccan cgcctgcctc ccccaacttg tgctgatatt ttaaggatgt gctcaagagt    120

atgaagcagg gtgcttttgt ccctttctct cctccctagt aattccctcc tccctatccc    180

atagccaagt agccacccct caaatgagcc attccttttt gctttcatca atggtctctg    240

tgaagttggg gtcgttgttc atgatggcgg cgtccgcgct ctctgccgac tccgcccccct   300

ttgcttcgtt ggtatggtag gtgcccttgt ggcggaacat gtaccggatc aggaagacca    360

gggtgcacag gatggtgaaa atcaccacag caatgacgcc tccaatgata gccgagtttc    420

tgttgactcc atttcttata gcttggcctt gtcctggatt atatggaaaa tccgcactgg    480

gctgaatcca ggtgatccaa gtgccaaggg tcggtggcgg acgacatggg ggaaagggtc    540

agcggcgaag gcccgcaatt ggnctccaac aactcgccct ggatgtggac gtnanccgan    600

gggtttgtcc gcctcaaggn ggccttnana agggcgatnt gggtnaactg gnctctggan    660

aagnaancaa ntgaatccct ggggtgttgn atttggnaat cncctgggca antttccccg    720
```

gttccaanaa cttttcccaa aaagagcgac ttgggaaaat tt 762

<210> SEQ ID NO 45
<211> LENGTH: 793
<212> TYPE: DNA
<213> ORGANISM: Homo sapiens
<220> FEATURE:
<221> NAME/KEY: modified_base
<222> LOCATION: (3)..(6)
<223> OTHER INFORMATION: a, t, c, g, unknown or other
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (11)..(11)
<223> OTHER INFORMATION: a, t, c, g, unknown or other
<220> FEATURE:
<221> NAME/KEY: modified_base
<222> LOCATION: (22)..(22)
<223> OTHER INFORMATION: a, t, c, g, unknown or other
<220> FEATURE:
<221> NAME/KEY: modified_base
<222> LOCATION: (38)..(38)
<223> OTHER INFORMATION: a, t, c, g, unknown or other
<220> FEATURE:
<221> NAME/KEY: modified_base
<222> LOCATION: (44)..(44)
<223> OTHER INFORMATION: a, t, c, g, unknown or other
<220> FEATURE:
<221> NAME/KEY: modified_base
<222> LOCATION: (51)..(51)
<223> OTHER INFORMATION: a, t, c, g, unknown or other
<220> FEATURE:
<221> NAME/KEY: modified_base
<222> LOCATION: (56)..(56)
<223> OTHER INFORMATION: a, t, c, g, unknown or other
<220> FEATURE:
<221> NAME/KEY: modified_base
<222> LOCATION: (64)..(64)
<223> OTHER INFORMATION: a, t, c, g, unknown or other
<220> FEATURE:
<221> NAME/KEY: modified_base
<222> LOCATION: (68)..(68)
<223> OTHER INFORMATION: a, t, c, g, unknown or other
<220> FEATURE:
<221> NAME/KEY: modified_base
<222> LOCATION: (72)..(72)
<223> OTHER INFORMATION: a, t, c, g, unknown or other
<220> FEATURE:
<221> NAME/KEY: modified_base
<222> LOCATION: (78)..(79)
<223> OTHER INFORMATION: a, t, c, g, unknown or other
<220> FEATURE:
<221> NAME/KEY: modified_base
<222> LOCATION: (83)..(83)
<223> OTHER INFORMATION: a, t, c, g, unknown or other
<220> FEATURE:
<221> NAME/KEY: modified_base
<222> LOCATION: (88)..(89)
<223> OTHER INFORMATION: a, t, c, g, unknown or other
<220> FEATURE:
<221> NAME/KEY: modified_base
<222> LOCATION: (93)..(93)
<223> OTHER INFORMATION: a, t, c, g, unknown or other
<220> FEATURE:
<221> NAME/KEY: modified_base
<222> LOCATION: (96)..(96)
<223> OTHER INFORMATION: a, t, c, g, unknown or other
<220> FEATURE:
<221> NAME/KEY: modified_base
<222> LOCATION: (133)..(133)
<223> OTHER INFORMATION: a, t, c, g, unknown or other
<220> FEATURE:
<221> NAME/KEY: modified_base
<222> LOCATION: (145)..(145)

<223> OTHER INFORMATION: a, t, c, g, unknown or other
<220> FEATURE:
<221> NAME/KEY: modified_base
<222> LOCATION: (147)..(147)
<223> OTHER INFORMATION: a, t, c, g, unknown or other
<220> FEATURE:
<221> NAME/KEY: modified_base
<222> LOCATION: (150)..(150)
<223> OTHER INFORMATION: a, t, c, g, unknown or other
<220> FEATURE:
<221> NAME/KEY: modified_base
<222> LOCATION: (152)..(152)
<223> OTHER INFORMATION: a, t, c, g, unknown or other
<220> FEATURE:
<221> NAME/KEY: modified_base
<222> LOCATION: (154)..(154)
<223> OTHER INFORMATION: a, t, c, g, unknown or other
<220> FEATURE:
<221> NAME/KEY: modified_base
<222> LOCATION: (158)..(158)
<223> OTHER INFORMATION: a, t, c, g, unknown or other
<220> FEATURE:
<221> NAME/KEY: modified_base
<222> LOCATION: (170)..(170)
<223> OTHER INFORMATION: a, t, c, g, unknown or other
<220> FEATURE:
<221> NAME/KEY: modified_base
<222> LOCATION: (172)..(173)
<223> OTHER INFORMATION: a, t, c, g, unknown or other
<220> FEATURE:
<221> NAME/KEY: modified_base
<222> LOCATION: (180)..(180)
<223> OTHER INFORMATION: a, t, c, g, unknown or other
<220> FEATURE:
<221> NAME/KEY: modified_base
<222> LOCATION: (205)..(205)
<223> OTHER INFORMATION: a, t, c, g, unknown or other
<220> FEATURE:
<221> NAME/KEY: modified_base
<222> LOCATION: (210)..(210)
<223> OTHER INFORMATION: a, t, c, g, unknown or other
<220> FEATURE:
<221> NAME/KEY: modified_base
<222> LOCATION: (212)..(212)
<223> OTHER INFORMATION: a, t, c, g, unknown or other
<220> FEATURE:
<221> NAME/KEY: modified_base
<222> LOCATION: (217)..(217)
<223> OTHER INFORMATION: a, t, c, g, unknown or other
<220> FEATURE:
<221> NAME/KEY: modified_base
<222> LOCATION: (222)..(223)
<223> OTHER INFORMATION: a, t, c, g, unknown or other
<220> FEATURE:
<221> NAME/KEY: modified_base
<222> LOCATION: (226)..(226)
<223> OTHER INFORMATION: a, t, c, g, unknown or other
<220> FEATURE:
<221> NAME/KEY: modified_base
<222> LOCATION: (230)..(230)
<223> OTHER INFORMATION: a, t, c, g, unknown or other
<220> FEATURE:
<221> NAME/KEY: modified_base
<222> LOCATION: (233)..(234)
<223> OTHER INFORMATION: a, t, c, g, unknown or other
<220> FEATURE:
<221> NAME/KEY: modified_base
<222> LOCATION: (244)..(245)
<223> OTHER INFORMATION: a, t, c, g, unknown or other
<220> FEATURE:
<221> NAME/KEY: modified_base
<222> LOCATION: (265)..(265)
<223> OTHER INFORMATION: a, t, c, g, unknown or other
<220> FEATURE:
<221> NAME/KEY: modified_base
<222> LOCATION: (273)..(273)
<223> OTHER INFORMATION: a, t, c, g, unknown or other
<220> FEATURE:
<221> NAME/KEY: modified_base
<222> LOCATION: (279)..(279)
<223> OTHER INFORMATION: a, t, c, g, unknown or other
<220> FEATURE:
<221> NAME/KEY: modified_base
<222> LOCATION: (284)..(284)
<223> OTHER INFORMATION: a, t, c, g, unknown or other
<220> FEATURE:
<221> NAME/KEY: modified_base
<222> LOCATION: (288)..(288)
<223> OTHER INFORMATION: a, t, c, g, unknown or other
<220> FEATURE:
<221> NAME/KEY: modified_base
<222> LOCATION: (290)..(291)
<223> OTHER INFORMATION: a, t, c, g, unknown or other
<220> FEATURE:
<221> NAME/KEY: modified_base
<222> LOCATION: (306)..(309)
<223> OTHER INFORMATION: a, t, c, g, unknown or other
<220> FEATURE:
<221> NAME/KEY: modified_base
<222> LOCATION: (323)..(323)
<223> OTHER INFORMATION: a, t, c, g, unknown or other
<220> FEATURE:
<221> NAME/KEY: modified_base
<222> LOCATION: (325)..(325)
<223> OTHER INFORMATION: a, t, c, g, unknown or other
<220> FEATURE:
<221> NAME/KEY: modified_base
<222> LOCATION: (341)..(341)
<223> OTHER INFORMATION: a, t, c, g, unknown or other
<220> FEATURE:
<221> NAME/KEY: modified_base
<222> LOCATION: (382)..(383)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (401)..(401)
<223> OTHER INFORMATION: a, t, c, g, unknown or other
<220> FEATURE:
<221> NAME/KEY: modified_base
<222> LOCATION: (413)..(413)
<223> OTHER INFORMATION: a, t, c, g, unknown or other
<220> FEATURE:
<221> NAME/KEY: modified_base
<222> LOCATION: (425)..(425)
<223> OTHER INFORMATION: a, t, c, g, unknown or other
<220> FEATURE:
<221> NAME/KEY: modified_base
<222> LOCATION: (430)..(430)
<223> OTHER INFORMATION: a, t, c, g, unknown or other
<220> FEATURE:
<221> NAME/KEY: modified_base
<222> LOCATION: (443)..(444)
<223> OTHER INFORMATION: a, t, c, g, unknown or other
<220> FEATURE:
<221> NAME/KEY: modified_base
<222> LOCATION: (448)..(448)
<223> OTHER INFORMATION: a, t, c, g, unknown or other
<220> FEATURE:
<221> NAME/KEY: modified_base
<222> LOCATION: (451)..(452)
<223> OTHER INFORMATION: a, t, c, g, unknown or other
<220> FEATURE:
<221> NAME/KEY: modified_base
<222> LOCATION: (454)..(455)
<223> OTHER INFORMATION: a, t, c, g, unknown or other
<220> FEATURE:
<221> NAME/KEY: modified_base
<222> LOCATION: (458)..(458)
<223> OTHER INFORMATION: a, t, c, g, unknown or other
<220> FEATURE:
<221> NAME/KEY: modified_base
<222> LOCATION: (467)..(467)
<223> OTHER INFORMATION: a, t, c, g, unknown or other
<220> FEATURE:

<221> NAME/KEY: modified_base
<222> LOCATION: (471)..(471)
<223> OTHER INFORMATION: a, t, c, g, unknown or other
<220> FEATURE:
<221> NAME/KEY: modified_base
<222> LOCATION: (478)..(478)
<223> OTHER INFORMATION: a, t, c, g, unknown or other
<220> FEATURE:
<221> NAME/KEY: modified_base
<222> LOCATION: (488)..(488)
<223> OTHER INFORMATION: a, t, c, g, unknown or other
<220> FEATURE:
<221> NAME/KEY: modified_base
<222> LOCATION: (519)..(519)
<223> OTHER INFORMATION: a, t, c, g, unknown or other
<220> FEATURE:
<221> NAME/KEY: modified_base
<222> LOCATION: (541)..(541)
<223> OTHER INFORMATION: a, t, c, g, unknown or other
<220> FEATURE:
<221> NAME/KEY: modified_base
<222> LOCATION: (545)..(546)
<223> OTHER INFORMATION: a, t, c, g, unknown or other
<220> FEATURE:
<221> NAME/KEY: modified_base
<222> LOCATION: (550)..(550)
<223> OTHER INFORMATION: a, t, c, g, unknown or other
<220> FEATURE:
<221> NAME/KEY: modified_base
<222> LOCATION: (552)..(552)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (561)..(561)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (569)..(571)
<223> OTHER INFORMATION: a, t, c, g, unknown or other
<220> FEATURE:
<221> NAME/KEY: modified_base
<222> LOCATION: (586)..(586)
<223> OTHER INFORMATION: a, t, c, g, unknown or other
<220> FEATURE:
<221> NAME/KEY: modified_base
<222> LOCATION: (589)..(591)
<223> OTHER INFORMATION: a, t, c, g, unknown or other
<220> FEATURE:
<221> NAME/KEY: modified_base
<222> LOCATION: (608)..(608)
<223> OTHER INFORMATION: a, t, c, g, unknown or other
<220> FEATURE:
<221> NAME/KEY: modified_base
<222> LOCATION: (612)..(612)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (686)..(688)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (733)..(733)
<223> OTHER INFORMATION: a, t, c, g, unknown or other
<220> FEATURE:
<221> NAME/KEY: modified_base
<222> LOCATION: (736)..(736)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (750)..(750)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (754)..(754)
<223> OTHER INFORMATION: a, t, c, g, unknown or other
<220> FEATURE:
<221> NAME/KEY: modified_base
<222> LOCATION: (757)..(757)
<223> OTHER INFORMATION: a, t, c, g, unknown or other
<220> FEATURE:
<221> NAME/KEY: modified_base
<222> LOCATION: (761)..(763)
<223> OTHER INFORMATION: a, t, c, g, unknown or other
<220> FEATURE:
<221> NAME/KEY: modified_base
<222> LOCATION: (767)..(767)
<223> OTHER INFORMATION: a, t, c, g, unknown or other
<220> FEATURE:
<221> NAME/KEY: modified_base
<222> LOCATION: (780)..(780)
<223> OTHER INFORMATION: a, t, c, g, unknown or other
<220> FEATURE:
<221> NAME/KEY: modified_base
<222> LOCATION: (786)..(788)
<223> OTHER INFORMATION: a, t, c, g, unknown or other

<400> SEQUENCE: 45
ggnnnntntc ntgtggcttt tntggccctt ttttgtgnta aagncacaca nggccnactc 60
atanattnca antcatgnng tcnggaannt gtnctnaata tctgtagagt gtgccaccca 120

-continued

```
tctcaaacat ganttacatt tgcangnatn cncnccctnac tgtgtaaatn tnnctgctgn    180

accagtgaac aaagtgctga gtcangagcn angcaantca tnntgnccan tannacggga    240

cacnngctgc atcctcggtc ctcanccccct cangctgcnc tggnctcnan nttccgccct    300

ctccannnng ctcagggacc ggnancgtcc ttctccattc ncgaatttgc atggctctta    360

gaaaggtagg aggcaacgat gnntgtcatc antgaacgga ntgcacctca aantttgcca    420

tgtgnttggn agaacaattt ctnnttangt nnanntcnca tgtgcanctt naggatanca    480

ccatttantg atcaatactg gttaacatta agtggtacnt atcgctttaa aaatcaggga    540

ntcgnncaan anatcangac ntncacagnn nagttaacat cacagnccnn nttcgggact    600

tgtgggtnaa angtgganaa tcctcacctc ttggccatng tttgactttg ggattgggaa    660

ttcaacnaga gctctgccaa nggcannntt gggagaatcn gggtnttctc ccacaattgg    720

ggggntggcc aangtntngg nggncntaan angnttntcc nnnaaanggg cccacttgtn    780

cggcannntt ttg                                                        793
```

<210> SEQ ID NO 46
<211> LENGTH: 774
<212> TYPE: DNA
<213> ORGANISM: Homo sapiens
<220> FEATURE:
<221> NAME/KEY: modified_base
<222> LOCATION: (3)..(10)
<223> OTHER INFORMATION: a, t, c, g, unknown or other
<220> FEATURE:
<221> NAME/KEY: modified_base
<222> LOCATION: (28)..(28)
<223> OTHER INFORMATION: a, t, c, g, unknown or other
<220> FEATURE:
<221> NAME/KEY: modified_base
<222> LOCATION: (499)..(499)
<223> OTHER INFORMATION: a, t, c, g, unknown or other
<220> FEATURE:
<221> NAME/KEY: modified_base
<222> LOCATION: (594)..(594)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (675)..(675)
<223> OTHER INFORMATION: a, t, c, g, unknown or other
<220> FEATURE:
<221> NAME/KEY: modified_base
<222> LOCATION: (683)..(683)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (691)..(693)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (714)..(714)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base

```
<222> LOCATION: (730)..(730)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (765)..(765)
<223> OTHER INFORMATION: a, t, c, g, unknown or other
<220> FEATURE:
<221> NAME/KEY: modified_base
<222> LOCATION: (769)..(770)
<223> OTHER INFORMATION: a, t, c, g, unknown or other
<220> FEATURE:
<221> NAME/KEY: modified_base
<222> LOCATION: (774)..(774)
<223> OTHER INFORMATION: a, t, c, g, unknown or other

<400> SEQUENCE: 46

ggnnnnnnnn tgtggccttt ttttgccntt ttttttttc ataaaaccat gtttattcaa     60

aaaaatctat tcacgaaagt ctggaaagcg taataaatat ctgtacagtg gccacccatc    120

tcaaacatga attacaaagc aggaacataa aaatgatgtg taaacataac tgctgagcca    180

gtgaacaaag tgctgagtca ggagcgaggc agagaagcgt gctcagtaga acggcacaga    240

tgctgcagcc tccgtcctca gcccctcaag ctgcgctgga gtccaccttc cgccctctcc    300

acaccgctca gggaccggca gcgtccttct ccattctcga atttgcatga cgcttagaaa    360

ggtaggaggc agcaaaacgt gtcagaaatg aacggagtgc aaatcaaact ttgccatgtg    420

cttgagagaa tcagtaaagc gttaggtaaa aatcccaagt gcagctttag gataacacca    480

tttaatgaac aatactggnt aacattaagt actattaacg ctttaaaatt caaacaatct    540

tccaaacatc aatacataca cagttagttt aaaatcacaa gcaaatcggg cctntagggt    600

aaaagtggaa atccccaact ccttgcccaa ggtttgacnt tgggatggga ttcaacaaaa    660

gctctcccac tgganattgg ganaatcang nnnttccccc acatnggggg ggtngcaagg    720

gaaaggnggn ccctntaggg gggggcaaca aagggggcca ctggnggtnn gtcn          774


<210> SEQ ID NO 47
<211> LENGTH: 2415
<212> TYPE: DNA
<213> ORGANISM: Homo sapiens

<400> SEQUENCE: 47

aattcctcga gcactgttgg cctactggag tgcgagatcc gctgctgctg aggagaggag     60

cgtcaacagc agcaccatgg tagctcaaca gaagaacctt gaaggctatg tgggatttgc    120

caatctccca aatcaagtat acagaaaatc ggtgaagaga ggttttgaat tcacgcttat    180

ggtagtgggt gaatctggat tgggaaagtc gacattaatc aactcattat tcctcacaga    240

tttgtattct ccagagtatc caggtccttc tcatagaatt aaaaagactg tacaggtgga    300

acaatccaaa gttttaatca aagaaggtgg tgttcagttg ctgctcacaa tagttgatac    360

cccaggattt ggagatgcag tggataatag taattgctgg cagcctgtta tcgactacat    420

tgatagtaaa tttgaggact acctaaatgc agaatcacga gtgaacagac gtcagatgct    480

tgataacagg gtgcagtgtt gtttatactt cattgctcct tcaggacatg gacttaaacc    540

attggatatt gagtttatga agcgtttgca tgaaaaagtg aatatcatcc cacttattgc    600

caaagcagac acactcacac cagaggaatg ccaacagttt aaaaaacaga taatgaaaga    660

aatccaagaa cataaaatta aaatatacga atttccagaa acagatgatg aagaagaaaa    720
```

-continued

```
taaacttgtt aaaaagataa aggaccgttt acctcttgct gtggtaggta gtaatactat    780

cattgaagtt aatggcaaaa gggtcagagg aaggcagtat ccttggggtg ttgctgaagt    840

tgaaaatggt gaacattgtg attttacaat cctaagaaat atgttgataa gaacacacat    900

gcaggacttg aaagatgtta ctaataatgt ccactatgag aactacagaa gcagaaaact    960

tgcagctgtg acttataatg gagttgataa caacaagaat aaagggcagc tgactaagag   1020

ccctctggca caaatggaag aagaaagaag ggagcatgta gctaaaatga agaagatgga   1080

gatggagatg gagcaggtgt ttgagatgaa ggtcaaagaa aaagttcaaa aactgaagga   1140

ctctgaagct gagctccagc ggcgccatga gcaaatgaaa aagaatttgg aagcacagca   1200

caaagaattg gaggaaaaac gtcgtcagtt cgaggatgag aaagcaaact gggaagctca   1260

acaacgtatt ttagaacaac agaactcttc aagaaccttg gaaaagaaca agaagaaagg   1320

gaagatcttt taaactctct attgaccacc agttaacgta ttagttgcca atatgccagc   1380

ttggacatca gtgtttgttg gatccgtttg accaatttgc accagtttta tccataatga   1440

tggatttaac agcatgacaa aaattatttt ttttttgtt cttgatggag attaagatgc   1500

cttgaattgt ctagggtgtt ctgtacttag aaagtaagag ctctaagtac ctttcctaca   1560

ttttcttttt ttattaaaca gatatcttca gtttaatgca agagaacatt ttactgttgt   1620

acaatcatgt tctggtggtt tgattgttta caggatattc caaaataaaa ggactctgga   1680

agattttcat tgaggataaa ttgccataat atgatgcaaa ctgtgcttct ctatgataat   1740

tacaatacaa aggttccatt cagtgcagca tatacaataa tgtaatttag tctaacacag   1800

ttgaccctat tttttgacac ttccattgtt taaaaataca catggaaaaa aaaaaaccct   1860

atatgcttac tgtgcaccta gagctttttt ataacaacgt ctttttgttt gtttgttttg   1920

gattctttaa atatatatta ttctcattta gtgccctctt tagccagaat ctcattactg   1980

cttcattttt gtaataacat ttaatttaga tattttccat atattggcac tgctaaaata   2040

gaatatagca tctttcatat ggtaggaacc aacaaggaaa ctttccttta actccctttt   2100

tacactttat ggtaagtagc agggggggaa atgcatttat agatcatttc taggcaaaat   2160

tgtgaagcta atgaccaacc tgtttctacc tatatgcagt ctctttattt tactagaaat   2220

gggaatcatg gcctcttgaa gagaaaaaag tcaccattct gcatttagct gtattcatat   2280

attgcatttc tgtatttttt gtttgtattg taaaaaaattc acataataaa cgatgttgtg   2340

atgtaaaaaa aaaaaaaaaa aaaaaaaaaa aggccacatg tgctcgagct gcaggtcgcg   2400

gccgctagac tagtc                                                    2415
```

```
<210> SEQ ID NO 48
<211> LENGTH: 2362
<212> TYPE: DNA
<213> ORGANISM: Homo sapiens

<400> SEQUENCE: 48

gaattcctcg agcactgttg gcctactggg gtggctggcg gaaacgggaa cgtgcagccg     60

cgggtgcagg agtcctgggg catggcgggg gcggggcagg gggaggcgcg cacagaacag    120

gctggggcat ccctcgccct ggctctttga gcccggacca gacagagatg tgataatgga    180

tcatcatgtt tctaccatca agcctcgaag aatccaaaac caaaatgtca ttcaccgctt    240

ggaacgccgg cggatcagtt caggcaaggc aggtacccac tggcaccaag tccgagtgtt    300

ccatcagaat gtcttcccca acttcacagt tgtcaacgtt gaaaagcctc cttgtttctt    360

gcgtaaattc tcacctgatg gacgctactt tattgctttt tcttcagacc agacatctct    420
```

-continued

```
tgaaatctat gagtaccagg gctgccaggc agcagaggac ctactgcagg gatacgaagg    480
agaaatcctg tccaatggca atgaccagcg gtcagtgaat atccggggcc ggctctttga    540
acgctttttt gtcctgctgc acattaccaa tgttgcggcc aatggtgagc acctgaaccg    600
ggagtgtagt ctcttcactg atgactgccg ctgtgtcatc gtgggctcag ctgcctacct    660
cccagatgag cctcaccctc catttttgga ggtatatcgg aacagtgaat cagtgacccc    720
caacccacgg tcccctctag aagactattc cctccatatc attgaccttc acaccggccg    780
cttatgtgat acacgcacgt tcaagtgtga caaggtggtc ttgtcacaca accaagggct    840
gtacttgtac aaaaacatcc tggccatctt gtctgtgcaa caacagacca tccatgtctt    900
ccaggtgact cctgaaggca ctttcattga tgtgcggacc attggccgct tttgctatga    960
ggatgacctg ctcactgtgt cagctgtttt ccctgaggta cagcgggaca gtcagacagg   1020
catggccaat ccctttaggg atcctttcat caattccctc aaacaccggt tgctggtata   1080
tttgtggcgc cgggcagaac aggatggtag tgcaatggcc aagaggcgct tcttccagta   1140
ttttgaccaa ctgcggcagc tgcgaatgtg gaaaatgcag cttctggatg aaaaccacct   1200
gtttatcaag tacactagtg aggatgtagt aacactgcga gtcacagatc catcacaggc   1260
atctttcttt gtggtgtaca atatggtgac gacagaggtg attgctgtgt ttgagaatac   1320
atcagatgag cttttggagc tctttgagaa cttctgtgac ctttttcgta atgctaccct   1380
gcacagtgaa gttcagtttc cctgctcagc ttctagcaac aattttgcaa ggcagatcca   1440
gcgccggttc aaagacacta ttataaatgc caagtatgga gggcacacag aggcagtacg   1500
ccggctgctg ggtcagctcc ccatcagtgc tcagtcttac agcggtagcc cctatctgga   1560
tttgtctctc ttcagttatg atgacaagtg ggtatctgtc atggagcggc ccaagacttg   1620
tggagatcac ccaatcaggt tctatgcccg ggactcgggc ctgctcaagt ttgagatcca   1680
ggcggggtta ctgggccgcc ccatcaacca cacagtgcga cgccttgttg ccttcacctt   1740
tcaccctttt gagcctttcg ctatttctgt gcagaggact aatgctgagt atgttgtcaa   1800
cttccatatg cgacactgct gcacgtaggt gcctcaccag agccagatta tctggtcttc   1860
caagactttg ccacccactt atctcagtgg actccaaagc aaaagctccc gactactagc   1920
tctgttagtt ccagcctgct atacctcaga tgggagagag ccagagagat gagtgagggt   1980
ggctcaacct aatggaattt ttaaattgta tacaatactg ctactgattg ttataatatc   2040
ctcttgcgtt ttccctgtgg gaatgcccag cattaattaa gtccatttca tttttgcttt   2100
actttgcatt tgattgctgt gaagatgaaa gcattagact tttatcccct tcatgtcact   2160
tcttcggcat tatggtttgc atctgaaagc agttaaatct tgtttactga tgagaatgac   2220
atacatcctt tccatttagc tcataagcac ggctatcttt ttaagagaaa aataaagcca   2280
tggtattttc atacttaaaa aaaaaaaaaa aaaaaaaagg ccacatgtgc tcgagctgca   2340
ggtcgcggcc gctagactag tc                                            2362
```

<210> SEQ ID NO 49
<211> LENGTH: 1865
<212> TYPE: DNA
<213> ORGANISM: Homo sapiens

<400> SEQUENCE: 49

```
aattcctcga gcactgttgg cctactggtt ttgagctttt tgtgtataca caatcccaaa     60
ctggaagaaa ttttaaaaaa aggaatcctg ctgtgaaagg tatatattac tctagatttt    120
```

-continued

```
tcttactgta aatattgtaa gattgtaata ctgtcgatat tttattaacc aacaaatgtt    180
aatctatgtg aaatcagact tattttaaat gtgcttctta tttactgtgt gtggtccctg    240
ttgctgacag tattaagtta tattctgatg taagattaac tttattaaag aatgtaaaca    300
ttaatgtttc cttatgggaa aacaaataaa gtataaagaa gacaattctt ttcattgaaa    360
tatactgtgt atttacactt gctagaccca gcaccactta taaatttagt acactgttca    420
gaattttagt taacacagct gacatggttg tgctctgttt gaaagtctaa gaataggtat    480
tgttggaata tacagtttgt atttgtctgc tgtgaatcat aatcttgaaa tttctaatca    540
agtttgtaaa atttttatag tgaaacattt taatgacaat ttaaaaattt atcttctcta    600
aagaatggtc aaaacaatat cctttcagaa atagaattgt tctttaatat ctttccaaaa    660
tgactttggt taaatggacc agatgtatat tagttaaaat ttaggactaa gttgttgata    720
ttctttgagt ttacaagtta atccttattg gagatgtgcc aatatacagt tagaatatca    780
ttaatttgca ctgtttgggg accccattta agaatgctga attttgccaa ctaagaagta    840
agcaaatgca atttaaaaag taaatttgag cattctgtat taaatatgtg cagttattat    900
cacatgaaga aacgcagtgt gtcgggctgt aatattacca tatttgctgt catgttctcc    960
catctcagtg ctgggaaatc accatgtgga aaccaagcaa acgtgttgtg catcagccgg   1020
cttgagtttg ttcaatatca aagctgaaaa ctagcgaggt ctgctgtact gcttattgaa   1080
gtattgtgat tattttaggc attgattctt acaaaatata tactgtaaca gtatactttg   1140
tacagattta aattttattt gaaaaaatga aataaagtag gcaaaagaat aaagatgttt   1200
atttttcatg tgactgtata atcagatcag tcttttgttt cagtgctttt tgggggaagg   1260
ggtctggttg cgatcttgga tttttttttt ttttgatagg tggaaacttt ttaggactca   1320
gtagcaggta tacttatgct tatgaattgg ctgcaagcat taagtgtgct ctcatactag   1380
agaactctat cttctatttt attttaaggt aggtttgctt atttttaaaa atgttatgtg   1440
aatggcctcc ctatcctggc atactgggtc atttaaaaaa ttctctggtg gtatgacagt   1500
gaacctagcc atcatgttga agagaaggga aacctttttcc caaagatcat gctccattct   1560
catggaaggt tttttgtttt ctgtcagtta caataaaaaa aatgtaatta tcatggatac   1620
atactagtta tacatactta tggggtacat gtaacatttt gaaacaagcg tacaatgtac   1680
tgattaaatc aggatgattg gggtatccat cacctgaagt atgtataatt tcttcgtttt   1740
aggaacattc taattccact cttagttatt tgaaatatat aataaattat ttttaatagt   1800
taaaaaaaaa aaaaaaaaaa aaggccacat gtgctcgagc tgcaggtcgc ggccgctaga   1860
ctagt                                                               1865
```

<210> SEQ ID NO 50
<211> LENGTH: 3457
<212> TYPE: DNA
<213> ORGANISM: Homo sapiens

<400> SEQUENCE: 50

```
gcactgttgg cctactggga gctgaggccc gcgtcgatcc tgggttggag gaggtggcgg     60
ccgctgaggc tgcggcgtga agacggcggg catggtgggg cgggagaaag agctctctat    120
acactttgtt cccgggagct gtcggctggt ggaggaggaa gttaacatcc ctaataggag    180
ggttctggtt actggtgcca ctgggcttct tggcagagct gtacacaaag aatttcagca    240
gaataattgg catgcagttg gctgtggttt cagaagagca agaccaaaat ttgaacaggt    300
taatctgttg gattctaatg cagttcatca catcattcat gattttcagc cccatgttat    360
```

-continued

```
agtacattgt gcagcagaga gaagaccaga tgttgtagaa aatcagccag atgctgcctc    420
tcaacttaat gtggatgctt ctgggaattt agcaaaggaa gcagctgctg ttggagcatt    480
tctcatctac attagctcag attatgtatt tgatggaaca aatccacctt acagagagga    540
agacatacca gctcccctaa atttgtatgg caaaacaaaa ttagatggag aaaaggctgt    600
cctggagaac aatctaggag ctgctgtttt gaggattcct attctgtatg ggaagttga     660
aaagctcgaa gaaagtgctg tgactgttat gtttgataaa gtgcagttca gcaacaagtc    720
agcaaacatg gatcactggc agcagaggtt ccccacacat gtcaaagatg tggccactgt    780
gtgccggcag ctagcagaga agagaatgct ggtaagaagg attcctgagt cctgtcttag    840
cgaaggtccg ctttgtcttt tccatgcttg aactttcaca gctgtacttg gagtgttact    900
gagtgaaagc caaaagtgct tttttaaaac taggagacca aacaaaagta gtttacatat    960
acactgtatt catgaagaat aaaaatatta tgctcttctg tttgaattta tttcttatgt   1020
actatagatc ccatcatttc ttttattgca aagtgttagg aaacttcaaa ataatcatct   1080
aaggtctttt aagaagatac tctttggggg ctgggcgtga tggctcacac ctgtaatccc   1140
agcacatttg aaaaagttgg tattaaatat aatatccata caaagaaaga tgagactgat   1200
ttagtttaga atattaatag gatgaccaca gtttttttaat atatgagaat tatattttgt   1260
aatatataac atgacaatat ttaagaaagt ttagctcaac ttgaaaaatg gttctattaa   1320
gtttttgttg tagcttggga taattaaaaa tactcattaa attgtactgt tttcataaaa   1380
atttgtaatg ctttttttata ttcccactaa ttaagtaaaa ttggagcctt tttttgattt   1440
taaaaattct taaggtttaa attctagaaa ttgctctttt aagtgttttg ctaagagtat   1500
tggtaggaat ttgattttag atatcttgtg gagacctttc cagaaaaaga gggttgcctt   1560
ttagttcctg gaccttattt taagtaagct ttttggtcaa acctattcta ctcagctcaa   1620
aaagttgaaa ctattgaatt tattgtgtca tcgttcttag gatccatcaa ttaagggaac   1680
ctttcactgg tctggcaatg aacagatgac taagtatgaa atggcatgtg caattgcaga   1740
tgccttcaac ctccccagca gtcacttaag acctgtaagt acatggctgt aaaaaccttt   1800
aggtccattg ctatggtata tattattgct gtgttgggta acttcatttc tcagtactaa   1860
tcaaagtgaa ctttgcttgt atgctggctg ttcatagtgc tacttttctc taaattatca   1920
tctgtagaga agatcatgag tattgaagtt tgtagaaaat gtattattgt cttgatcatg   1980
acaggcattt ggtttatttt tccagggatg atcaaatcag atttcttaca ctaagagcaa   2040
aaataagtag caaatataaa acctcaaaat gggcaggcac aatggctcat gcctgtaatc   2100
ccaacacttt gggaggctga cgcaggagga tcccttgagc ccaggaattt gagactagcc   2160
tgggcaatgg agggagatct catctctgtt taaaaatata tacatattta aaaaaaggtc   2220
agggggaaca aagccctcaa aatatagcct ttcacttact tttgattttt ttgtgtttat   2280
ctttctttaa agattactga cagccctgtc ctaggagcac aacgtccgag aaatgctcag   2340
cttgactgct ccaaattgga gaccttgggc attggccaac gaacaccatt tcgaattgga   2400
atcaaagaat cactttggcc tttcctcatt gacaagagat ggagacaaac ggtctttcat   2460
tagtttattt gtgttgggtt cttttttttt ttaaatgaaa agtatagtat gtggcacttt   2520
ttaaagaaca aaggaaatag ttttgtatga gtactttaat tgtgactctt aggatctttc   2580
aggtaaatga tgctcttgca ctagtgaaat tgtctaaaga aactaaaggg cagtcatgcc   2640
ctgtttgcag taatttttct ttttatcatt ttgtttgtcc tggctaaact tggagtttga   2700
```

-continued

```
gtatagtaaa ttatgatcct taaatatttg agagtcagga tgaagcagat ctgctgtaga   2760
cttttcagat gaaattgttc attctcgtaa cctccatatt ttcaggattt ttgaagctgt   2820
tgaccttttc atgttgatta ttttaaattg tgtgaaatag tataaaaatc attggtgttc   2880
attatttgct ttgcctgagc tcagatcaaa atgtttgaag aaaggaactt tatttttgca   2940
agttacgtac agtttttatg cttgagatat ttcaacatgt tatgtatatt ggaacttcta   3000
cagcttgatg cctcctgctt ttatagcagt ttatggggag cacttgaaag agcgtgtgta   3060
catgtatttt ttttctaggc aaacattgaa tgcaaacgtg tatttttttta atataaatat  3120
ataactgtcc ttttcatccc atgttgccgc taagtgatat ttcatatgtg tggttatact   3180
cataataatg ggccttgtaa gtcttttcac cattcatgaa taataataaa tatgtactgc   3240
tggcatgtaa tgcttagttt tcttgtattt acttcttttt ttaaatgtaa ggaccaaact   3300
tctaaactaa ttgttctttt gttgctttaa tttttaaaaa ttacattctt ctgatgtaac   3360
atgtgataca tacaaaagaa tatagtttaa tatgtattga aataaaacac aataaaatta   3420
acacttaaaa aaaaaaaaaa aaaggccaca tgtgctc                            3457
```

<210> SEQ ID NO 51
<211> LENGTH: 2158
<212> TYPE: DNA
<213> ORGANISM: Homo sapiens

<400> SEQUENCE: 51

```
cactgttggc ctactggata tttcatttag tgatgtatta ttgttattag ttgcattaaa     60
acaagccaag atggattagg tagacctcca cgttgtactt ccagtttcgt catgttatgg    120
tcttgggggt gcaggaattc ccaggtttcc ttgaggtgaa atctgaaagc tgagaaatat    180
agcacagctc acaaggaaga agtggataaa acagtgtcct cagagcagcc agggaatcct    240
aacccctgac gatcttcagt gaggcatttg gtactccaac ctgttgtgcc ttagccctga    300
gccccagtct gtgaggtgca tatggtccta gctaataggt cagtgggaaa agggagaaat    360
aataaacgag gctgtgtgta aacttacgtg taggaaacag gttaagctgt tctgccctgt    420
tgcatgcaga gagtagtctg aatgctattg ccacagtggt tttatttttta ttgtgtgatg   480
taaccatatg ccaatttttt tctttgacta ttgactcact attttataat gcatccttct    540
ggcaataatg aaataaaaat tagtaaacag aagtaactgt ttaatgaaaa tgaagtattt    600
gtatttctat ttatcaagaa agaaaagacg aacctgtggc atgcagagag tagtctgaat    660
gctattgcca cagtggtttt atttttattg tgtgatgtaa ccatatgcca atttttttct    720
ttgactattg actcactatt ttataatgca tccttctggc aataatgaaa taaaaattag    780
taaacagaag taactgttta atgaaaatga agtatttgta tttctattta tcaagaaaga    840
aaagacgaac ctgtggccga gcacgggggc tcacgcctgc ctcggcctcc caaaatgctg    900
agattacagg tgtgagccac cacgcccggc cttctctgta ttttcttgaa gtttgctgag    960
cttccttaaa accctgagtt ctctgcaaga agaaggatga tgacttatgg tgcctctcac   1020
tggtgaggtc caccttttct gcaattttga gcacagtcca aggccttgga aaagctttgt   1080
ttcttgagtc tctcaaataa gaacaacaac attagctttt ctgggagggc caatggctgt   1140
gctgtgatgg ggcatggatg ctttctcaga ggtactttcc ccctaagctt taggcacgtc   1200
tgaccatttc ttctgctttg gtccagtgct ttcctcatga tttagactct ggatgaaggt   1260
gtttttgaag taggtttact tgctgctgtc atcctgtgtc acctcactct ctgtggcctg   1320
gaagtgcagg gtttcaggcc tggctgtggg cggccattat atgacaaagg gttcagcgtc   1380
```

-continued

```
ccctgcatct ggtatgatgc cctctctggt tttaccacct ttagtcatca ttttacttgg   1440

ggtgtggaca tatttgttcc aggagcttcc ccaccctcta caacttattg gagggataaa   1500

ttgtcctaat gttttcttct ggtgttttta accatgaaat cttagacctg gagtagattt   1560

ggttaccaaa tagcttaagg agagaggaca taatatttga tttatgtaag atccaggaaa   1620

tgaggaaagg cacggtgcca tgagctgtgc ttccagccag accttattaa ctttcacaat   1680

tctttatgca aaagagacaa cttccagatg ttgctaatgg aggtatctca tgacctagag   1740

acaaaaccag gagcagcttc cttctatttc tccaaatcca aaaacgattg ctagggagtt   1800

agaccatggc ccagctctgc tttgagaaag ggaattttgc ttttgagatg attgaagtgc   1860

tttaaattcc tcagctgaga aatgagagat gtacagataa tgagacacac ggaggctttg   1920

ccgcatcaga cttcatgagc ttggagaaca tgcaggtgct cttctgacct cttagctgtt   1980

tgtcaggttt ctatgaccag gcaggtgtta ccagcactaa tgtttaggga ttcagctata   2040

ttttagcttc atttttatga tcctttttttt ttccagcctg ggcaacaaga gcgaaactgt   2100

ctcaaaaaaa aaaaaaaaaa aggccacatg tgctcgagct gcaggtcgcg gccgctag     2158
```

```
<210> SEQ ID NO 52
<211> LENGTH: 2142
<212> TYPE: DNA
<213> ORGANISM: Homo sapiens

<400> SEQUENCE: 52

gcactgttgg cctactggat taaaattaga aaagttgtgc ctttctcaag atgtgcacac     60

agtcagttgc aaaaccaaat ttgggattga tctcctgatt cctggtctga tatgttatcc    120

attactccat gaacagaaag atagaggtca tttctatgca gagaaaaaca aatgagctgt    180

gtcattgcag aaatgttctg catggtttgc tgccatctgt cttaaagctc aatctggact    240

cctaggaatt gggactgctg agctgcattt agatggacca tgtggacagg gcacagaaaa    300

tcctttattt ggagggcttg gttatttccc tatatggaaa ataaaggata caaaatattt    360

atgacaagat taagagccta gagctataga atttttgaga tctgacatcc tgttttgtaa    420

gattctggcc ctacatgtct ttttgttaga cttgctgtat tttatgtttg ttaaaacaca    480

gttggagaac aacagtaaac attgcttttg gaagaagaaa attataaagc agacagggca    540

ctggaatgga agtcactata ttctaacccc aactgtgata tattatgtgc ttttggatgc    600

tgcacactct gggggctgca gtttccttat tggataaaat caatgttgga aactaagatc    660

tcttgaagct ccctgaagat ttgctcagtc aacttcacat ggctttttga aatttaatac    720

ctttaaccag aaatgctctc ccaggttacc ttaagtcctc ttgtccaata tccgtgtggt    780

agcccctgta agcatttggg tttgtgatcc ctgatatcca gttccctttc agctttgtca    840

ttcaatgatg ctacaacaga aggattcagt gttagtagct ttgtggagca aagttttcaa    900

agtattgatt tattctgttg aaattgtgaa aacaaaggcc ttaaagctgt atctgtgcaa    960

caaaaatcta atataaactc agaattcttc tctaggcata ttgtttgttg tggtaatgat   1020

atagttgaaa acttttggaa aaataattta agactagaaa ttaggaattc ttcaggttaa   1080

agaaacatat gtcattgaat gtaattaagg ttatatgaag attatcagaa aaattgcacc   1140

aaaatgtgat caataatagc tttttcttgg ttgattgtct ctaagcatcc tttccaaatt   1200

atgtcaatac tgttctgcaa agtttggaga aaaactaaaa gatgtatacc aagaaatcca   1260

tgctggtaca ttgtaattta acctcctatt tttcctgaaa agtcactctt tagactaaaa   1320
```

-continued

```
aaagttcatc attgtgaggc atcactacag ttttataatt tttttcactg agtctttctc   1380

aatttaatat taaagggctt ttaagattta tcctccatgt gaaatttggg gctttatatt   1440

ctataggcct ttcttgaaaa tccaaatttc atatgaaaaa ctagaaaact gatgttggga   1500

attatttgtg tgaattcagt gaagtgtacc agttgacagc aagtcattct gggtgatata   1560

atcgttctca tcctcaatca gctgacataa aacaattctt tggagtccaa ttgaactcct   1620

tcaccagaga tggctgttga acttttaata gtttctgaaa ataaaataat caagcattta   1680

tttctcagga gcttaatata aatttcttct gttttatttt atctaggcat ttttattgaa   1740

ttgtacttga tttgattttc tgactcttct atgagaatgg ctttttactt gtaagtttca   1800

ctcaaattga cattttgata gtataacaca ttaatgaaat tcctagaaca gaggctatgt   1860

tctttgaaaa aaaatattga cagagtacac taaagggaca ttttaaagtg catttgattt   1920

cttttgcagc ttgataacat atttggtgat gtttggtagc tcccaaagct atactttcca   1980

gtaacatgtc cagatgagat ttgacaatgt tgcaatacat ctttccatat ctagatttat   2040

gtatgcaaat taagttcttg gcagtctatg aaaaccacaa aactcttatc tcccagccta   2100

acaaaaaaaa aaaaaaaaag gccacatgtg ctcgagctgc ag                      2142
```

<210> SEQ ID NO 53
<211> LENGTH: 846
<212> TYPE: DNA
<213> ORGANISM: Homo sapiens
<220> FEATURE:
<221> NAME/KEY: modified_base
<222> LOCATION: (3)..(5)
<223> OTHER INFORMATION: a, t, c, g, unknown or other
<220> FEATURE:
<221> NAME/KEY: modified_base
<222> LOCATION: (7)..(10)
<223> OTHER INFORMATION: a, t, c, g, unknown or other
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (14)..(15)
<223> OTHER INFORMATION: a, t, c, g, unknown or other
<220> FEATURE:
<221> NAME/KEY: modified_base
<222> LOCATION: (17)..(18)
<223> OTHER INFORMATION: a, t, c, g, unknown or other
<220> FEATURE:
<221> NAME/KEY: modified_base
<222> LOCATION: (22)..(25)
<223> OTHER INFORMATION: a, t, c, g, unknown or other
<220> FEATURE:
<221> NAME/KEY: modified_base
<222> LOCATION: (33)..(33)
<223> OTHER INFORMATION: a, t, c, g, unknown or other
<220> FEATURE:
<221> NAME/KEY: modified_base
<222> LOCATION: (48)..(48)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (762)..(762)
<223> OTHER INFORMATION: a, t, c, g, unknown or other
<220> FEATURE:
<221> NAME/KEY: modified_base
<222> LOCATION: (808)..(808)
<223> OTHER INFORMATION: a, t, c, g, unknown or other
<220> FEATURE:
<221> NAME/KEY: modified_base
<222> LOCATION: (820)..(820)
<223> OTHER INFORMATION: a, t, c, g, unknown or other
<220> FEATURE:
<221> NAME/KEY: modified_base
<222> LOCATION: (828)..(828)
<223> OTHER INFORMATION: a, t, c, g, unknown or other
<220> FEATURE:
<221> NAME/KEY: modified_base
<222> LOCATION: (845)..(846)
<223> OTHER INFORMATION: a, t, c, g, unknown or other

<400> SEQUENCE: 53
ggnnngnnnn gngnngnntt tnnnngggcc cgnatcctcg agcactgntg gcctactggg 60
agtagctcag ctcctattcc tgggaagcct ggaacgggga cttttgaaaa taactgcagc 120
ggcattcggg ttagggtccg tgctctccgc ctgcgccagg acagggtgaa gtggtcgggg 180
cgagcagagg gtgcgaaggt gcgggtgctg gtgcctcgca gcaggaggga gccccggctg 240
cgccgcgcga ctccctcttt ggccctcgga gcgcagcacc cggcggacaa gcggcgggac 300
gccaggacgc ggcgagcaag atctctcgtg gaagaggaag accaacacat gaaattgtcc 360
cttggaggca gcgaaatggg cctctcatcc catttgcagt cttccaaggc aggacctaca 420
cgcatcttta ccaagcaata cccacagttc tgtggtgtta cagggctttg accagcttcg 480
acttgaagga ttgctttgtg atgtgaccct gatgccaggt gacacagatg atgctttccc 540
tgtgcataga gtcatgatgg catctgctag tgattacttc aaggctatgt tcacagaatg 600
aaagaacaag atttaatgtg cattaaactt catggtgtga gcaaagtcgg tctaaggaaa 660
attattgatt tcatttatac tgcaaagctt tctcctaata tggacaacct tcaagacacc 720
tggaanctgc caatttccta cagattctgc cagttttgga cntctgtaaa gtgttcccaa 780
aaccggggtc actttaacaa ctgtgttnaa tttggccggn ttgcaaanac tacaaatcta 840 accgnn 846

<210> SEQ ID NO 54
<211> LENGTH: 836
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, t, c, g, unknown or other
<220> FEATURE:
<221> NAME/KEY: modified_base
<222> LOCATION: (6)..(9)
<223> OTHER INFORMATION: a, t, c, g, unknown or other
<220> FEATURE:
<221> NAME/KEY: modified_base
<222> LOCATION: (24)..(24)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (615)..(615)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (720)..(720)
<223> OTHER INFORMATION: a, t, c, g, unknown or other
<220> FEATURE:
<221> NAME/KEY: modified_base
<222> LOCATION: (734)..(734)

<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other
<220> FEATURE:
<221> NAME/KEY: modified_base
<222> LOCATION: (798)..(798)
<223> OTHER INFORMATION: a, t, c, g, unknown or other
<220> FEATURE:
<221> NAME/KEY: modified_base
<222> LOCATION: (803)..(803)
<223> OTHER INFORMATION: a, t, c, g, unknown or other
<220> FEATURE:
<221> NAME/KEY: modified_base
<222> LOCATION: (806)..(806)
<223> OTHER INFORMATION: a, t, c, g, unknown or other
<220> FEATURE:
<221> NAME/KEY: modified_base
<222> LOCATION: (816)..(816)
<223> OTHER INFORMATION: a, t, c, g, unknown or other
<220> FEATURE:
<221> NAME/KEY: modified_base
<222> LOCATION: (836)..(836)
<223> OTHER INFORMATION: a, t, c, g, unknown or other

<400> SEQUENCE: 54
ggntgnnnnt gggctttttt tggnctttga cattaaaagt ttttattggn cacaaaaaga 60
taaaacatgg aagttgaatt tactgagcaa aagcagctct ccaggtgaag ctgctatact 120
ttgtgctaaa taaccttatg aactgagtat acagaataca tataatatgc aagttacctc 180
aacagcaaag gagaaggagt agaatacagt ttttgaagat aaaatctggt caagtgacaa 240
attttgttgc tcaaaatttc tagcccttat ccacctaaat tctgtatggt tctacatata 300
tgcattcagt atgtgcatac tgaattccca ttttaatgga agctgctttt tggaagaatt 360
ctttttaatt tcacatttct ttgatgtgcc actcaatttt taaaaaaatt atatttgaca 420
tatgtgcatg tgtgtatgtg tatgtatgta tacacacttt aaaaacacca aacccttgtt 480
tataagtaga gggttcatgc tgctttttaa attaatatta gtgaatttaa gctacttctc 540
ctgtgtgtct aggaaacttt gtgttctcaa tgcacccaca cagtcaagtg ggttgacaga 600
tatgtcaaaa atacnttatg aaaagaggga ggtagctcat gcgagttggc aaccttttgt 660
gtaatggttc ctgttcaagc angctgcctc cctttgacat cctacagtca aagatgaaan 720
gggaaacttt tacntgaagc ctantggagc acaagttgta canttacaat aatccacctt 780
caacttggct tatggggntt acnaangtaa ggatgncaaa taccttacac caatan 836

<210> SEQ ID NO 55
<211> LENGTH: 3415
<212> TYPE: DNA
<213> ORGANISM: Homo sapiens

<400> SEQUENCE: 55
gaattcctcg agcactgttg gcctactggt tcggcttcca gactcagagg gagttattgc 60
agcaccagga gctccatgtc cctagcggca aacttcccag agaaagtgac atggaacact 120
ctccaagtgc aactgaagac agcttacagc cagccacaga cttattgacc agaagcgaac 180
ttccccagag ccaaaaggcc atgcagacta aagatgcgag ctctgacaca gagctggaca 240
agtgtgagaa aaagactcag ctctttctca cgaaccagag accagagata cagcctacaa 300
caaataaaca aagcttttct tacacaaaaa taaagtctga gccctctagc ccaagacttg 360

-continued

```
cctcatctcc agttcagcct aatattgggc cttctttccc tgtgggccct ttcctatctc    420
agttttcttt cccccaagat atcaccatgg tccctcaagc ttcagagatc ttagctaaga    480
tgtctgaact ggtgcatcgg cgactgaggc atggcagtag tagctaccct cccgtcattt    540
acagcccttt gatgcccaag ggggctactt gttttgagtg taacataaca ttcaataatt    600
tggataatta tctagtgcac aaaaagcatt attgcagcag ccgatggcag cagatggcta    660
agtccccaga gttccctagt gtgtcagaaa agatgcctga agctttgagt cccaacactg    720
gccaaacctc cataaacctt ctcaacccag ctgctcattc tgctgatcct gagaatccac    780
ttcttcaaac atcttgcatc aattcttcca ctgtcttaga tttaattggg ccaaatggga    840
agggccatga caaggacttt tccactcaaa ctaagaagct ctccacctcc agtaacaatg    900
atgacaaaat taatggaaaa cctgttgatg tgaaaaatcc cagtgtcccc ttagtggatg    960
gggaaagtga cccaaataag actacctgtg aagcttgcaa cattaccttc agccggcacg   1020
aaacatacat ggtccacaaa cagtattact gtgctacacg ccacgaccct ccactgaaga   1080
ggtctgcttc caacaaagtg cctgccatgc agagaaccat gcgcacacgc aagcgcagaa   1140
agatgtatga gatgtgccta cctgagcagg aacaaaggcc tccactggtt cagcagagat   1200
ttcttgacgt agccaacctc aataatcctt gtacctccac tcaagaaccc acagaagggc   1260
taggagagtg ctaccaccca agatgtgata tctttccagg aattgtctct aaacacttgg   1320
aaacttctct gacgatcaac aagtgtgttc cagtttccaa atgtgatact actcattcca   1380
gtgtttcctg cctagagatg gacgtgccca tagatctcag caaaaagtgt ttatctcagt   1440
ctgagcggac gaccacgtct cccaaaaggc tgctggacta tcacgagtgc actgtgtgca   1500
agatcagttt caataaggta gaaaactatc tggcccacaa gcagaatttc tgcccggtta   1560
ctgcacatca gcgtaatgac ctgggtcaac tggacggcaa agtgtttccg aatccagaaa   1620
gcgaacgaaa cagccctgat gtcagctacg aaagaagcat aataaaatgt gagaaaaatg   1680
ggaatttgaa gcagccttcc cccaatggaa acttattttc atcccaccta gcaaccctgc   1740
aaggcttgaa ggtctttagt gaagctgctc agctcattgc tacaaaagaa gaaaacagac   1800
atttgtttct tccacaatgc ctttaccctg gagcaataaa gaaagcaaaa ggagccgacc   1860
agctttctcc atattatgga atcaagccaa gtgattatat ttctggttct cttgtcatcc   1920
ataacactga catcgagcaa agcagaaatg cagaaaatga atctcctaaa ggccaggctt   1980
cctcaaatgg gtgtgctgcg ctgaagaaag attctctgcc attgttgccc aaaaatcgag   2040
gaatggtaat agtgaatggt ggactgaaac aagatgagag acctgctgcc aacccacagc   2100
aagagaacat ttcccagaat cctcagcacg aagacgacca caaatctccc tcgtggatct   2160
ctgagaaccc attagctgcc aatgagaatg tctcaccagg agttccctca gcagaggaac   2220
agttgtctag tatagcaaaa ggtgtgaatg gttccagcca ggctccaacc agtgggaaat   2280
attgccggct atgtgatatc cagttcaaca acctttcaaa ctttataact cacaagaagt   2340
tttattgctc atcacatgca gcagaacatg tcaaatgaac taactaaaca tcagtcacct   2400
ttggtatcag tgtttagtat gttgttctaa ccagtccaga aaaaaaaata agctgtttga   2460
attacatctg ggcaatcagg agataattca ttatggctga gttgaagact taaggtgtaa   2520
tttcattaca gtccattagt aaagtgtatt attggtgcca ttttcaaaaa aattaattta   2580
ttttaccagc agtattcata gctgtggtta tgttattttt tatttaaaaa ctttatatta   2640
aagtcatttg taatgttatt gtatagttat tgtgtagcac atatggtttg cactgtatag   2700
```

-continued

```
tagcttttaa agaaaatagt cacaatacag aaaagcattt tagaaatagc ttcaaaagca   2760
cttgtgtatc ttgatttttt cttatatgct gttgcagata tatgtatatg ctaaaatata   2820
acttgcaaag atgttctaaa tacacatgct ataagttcgc cttaagattt caattcttgg   2880
ataatcaggc tctgtttgca ctttatattt tagcagatac agtctcttag tcactaggct   2940
ttgcatttgt atgtagctgt atgtttccgt ccattttctt aatcctgaac ctgtatgtta   3000
aatgaagatg gcaatttttt tcttgtatag tacttgtatt ttctttcgct gatgcagctc   3060
tgtctcaatt tttaaacctt tgctgttaaa tgcaatactt tataaagaat gaacaaaatt   3120
actggaagca gtattgtaag taatgaggta gtattaatca gttttatctt ttgaaaggca   3180
cagtctaaat cgaaacccta aactcaatgc tgcaagtatg aatttaattc atatataaga   3240
tctatttaaa tataagagta gcaatactgc acctggtgat cacaaagata atgttctact   3300
tctgatagaa ataatttctc aacaaatgtt gttactatgc atgtatatgg atggaataaa   3360
attccagatt gttggaaaaa aaaaaaaaaa aaggccacat gtgctcgagc tgcag        3415
```

<210> SEQ ID NO 56
<211> LENGTH: 1829
<212> TYPE: DNA
<213> ORGANISM: Homo sapiens

<400> SEQUENCE: 56

```
gaattcctcg agcactgttg gcctactggg gcgcagggcg tgtacagcgc cgccgcgctc     60
ttctcgctca cggtcagcct ggacgacagg aactcctcgc gctacgtcat ccgcattgac    120
caggatgggc tcaccctgcc agagaggacc ctgtacctcg ctcaggatga ggacagtgag    180
aagatcctgg cagcatacag ggtgttcatg gagcgagtgc tcagcctcct gggtgcagac    240
gctgtggaac agaaggccca agagatcctg caagtggagc agcagctggc caacatcact    300
gtgtcagagt atgacgacct acggcgagat gtcagctcca tgtacaacaa ggtgacgctg    360
gggcagctgc agaagatcac cccccacttg cggtggaagt ggctgctaga ccagatcttc    420
caggaggact tctcagagga agaggaggtg gtgctgctgg cgacagacta catgcagcag    480
gtgtcgcagc tcatccgctc cacaccccac cgggtcctgc acaactacct ggtgtggcgc    540
gtggtggtgg tcctgagtga acacctgtcc ccgccattcc gtgaggcact gcacgagctg    600
gactggatgg acgccgagac cagggctgct gctcgggcca agctccagta catgatggtg    660
atggtcggct acccggactt cctgctgaaa cccgatgctg tggacaagga gtatgagttt    720
gaggtccatg agaagaccta cttcaagaac atcttgaaca gcatccgctt cagcatccag    780
ctctcagtta agaagattcg gcaggaggtg gacaagtcca cgtggctgct ccccccacag    840
gcgctcaatg cctactatct acccaacaag aaccagatgg tgttccccgc gggcatcctg    900
cagcccaccc tgtacgaccc tgacttccca cagtctctca actacggggg catcggcacc    960
atcattggac atgagctgac ccacggctac gacgactggg ggggccagta tgaccgctca   1020
gggaacctgc tgcactggtg gacggaggcc tcctacagcc gcttcctgcg aaaggctgag   1080
tgcatcgtcc gtctctatga caacttcact gtctacaacc agcgggtgaa cgggaaacac   1140
acgcttgggg agaacatcgc agatatgggc ggcctcaagc tggcctacca cgcctatcag   1200
aagtgggtgc gggagcacgg cccagagcgc ccacttcccc ggctcaagta cacacatgac   1260
cagctcttct tcattgcctt tgcccagaac tggtgcatca agcggcggtc gcagtccatc   1320
tacctgcagg tgctgactga caagcatgcc cctgagcact acagggtgct gggcagtgtg   1380
tcccagtttg aggagtttgg ccgggctttc cactgtccca aggactcacc catgaaccct   1440
```

```
gcccacaagt gttccgtgtg gtgagcctgg ctgcccgccc gcacgccccc actgcccccg   1500

cacgaatcac ctcctgctgg ctaccggggc aggcatgcac ccggtgccag ccccgctctg   1560

ggcaccacct gccttccagc ccctccagga cccggtccgc ctgctgcccc tcacttcagg   1620

aggggcctgg agcagggtga ggctggactt tggggggctg tgagggaaat atactggggt   1680

ccccagattc tgctctaagg gggccagacc ctctgccagg ctggattgta cgggccccac   1740

cttcgctgtg ttcttgctgc aaagtctggt caataaatca ctgcactgtt aaaaaaaaaa   1800

aaaaaaggcc acatgtgctc gagctgcag                                     1829


<210> SEQ ID NO 57
<211> LENGTH: 778
<212> TYPE: DNA
<213> ORGANISM: Homo sapiens
<220> FEATURE:
<221> NAME/KEY: modified_base
<222> LOCATION: (5)..(6)
<223> OTHER INFORMATION: a, t, c, g, unknown or other
<220> FEATURE:
<221> NAME/KEY: modified_base
<222> LOCATION: (10)..(10)
<223> OTHER INFORMATION: a, t, c, g, unknown or other
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (17)..(17)
<223> OTHER INFORMATION: a, t, c, g, unknown or other
<220> FEATURE:
<221> NAME/KEY: modified_base
<222> LOCATION: (26)..(26)
<223> OTHER INFORMATION: a, t, c, g, unknown or other
<220> FEATURE:
<221> NAME/KEY: modified_base
<222> LOCATION: (38)..(38)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (52)..(53)
<223> OTHER INFORMATION: a, t, c, g, unknown or other
<220> FEATURE:
<221> NAME/KEY: modified_base
<222> LOCATION: (56)..(56)
<223> OTHER INFORMATION: a, t, c, g, unknown or other
<220> FEATURE:
<221> NAME/KEY: modified_base
<222> LOCATION: (60)..(61)
<223> OTHER INFORMATION: a, t, c, g, unknown or other
<220> FEATURE:
<221> NAME/KEY: modified_base
<222> LOCATION: (63)..(63)
<223> OTHER INFORMATION: a, t, c, g, unknown or other
<220> FEATURE:
<221> NAME/KEY: modified_base
<222> LOCATION: (67)..(67)
<223> OTHER INFORMATION: a, t, c, g, unknown or other
<220> FEATURE:
<221> NAME/KEY: modified_base
<222> LOCATION: (71)..(72)
<223> OTHER INFORMATION: a, t, c, g, unknown or other
<220> FEATURE:
<221> NAME/KEY: modified_base
<222> LOCATION: (77)..(78)
<223> OTHER INFORMATION: a, t, c, g, unknown or other
<220> FEATURE:
<221> NAME/KEY: modified_base
<222> LOCATION: (87)..(88)
```

<223> OTHER INFORMATION: a, t, c, g, unknown or other
<220> FEATURE:
<221> NAME/KEY: modified_base
<222> LOCATION: (90)..(90)
<223> OTHER INFORMATION: a, t, c, g, unknown or other
<220> FEATURE:
<221> NAME/KEY: modified_base
<222> LOCATION: (93)..(94)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (111)..(111)
<223> OTHER INFORMATION: a, t, c, g, unknown or other
<220> FEATURE:
<221> NAME/KEY: modified_base
<222> LOCATION: (114)..(114)
<223> OTHER INFORMATION: a, t, c, g, unknown or other
<220> FEATURE:
<221> NAME/KEY: modified_base
<222> LOCATION: (121)..(121)
<223> OTHER INFORMATION: a, t, c, g, unknown or other
<220> FEATURE:
<221> NAME/KEY: modified_base
<222> LOCATION: (125)..(125)
<223> OTHER INFORMATION: a, t, c, g, unknown or other
<220> FEATURE:
<221> NAME/KEY: modified_base
<222> LOCATION: (130)..(131)
<223> OTHER INFORMATION: a, t, c, g, unknown or other
<220> FEATURE:
<221> NAME/KEY: modified_base
<222> LOCATION: (138)..(138)
<223> OTHER INFORMATION: a, t, c, g, unknown or other
<220> FEATURE:
<221> NAME/KEY: modified_base
<222> LOCATION: (140)..(141)
<223> OTHER INFORMATION: a, t, c, g, unknown or other
<220> FEATURE:
<221> NAME/KEY: modified_base
<222> LOCATION: (144)..(144)
<223> OTHER INFORMATION: a, t, c, g, unknown or other
<220> FEATURE:
<221> NAME/KEY: modified_base
<222> LOCATION: (147)..(147)
<223> OTHER INFORMATION: a, t, c, g, unknown or other
<220> FEATURE:
<221> NAME/KEY: modified_base
<222> LOCATION: (150)..(150)
<223> OTHER INFORMATION: a, t, c, g, unknown or other
<220> FEATURE:
<221> NAME/KEY: modified_base
<222> LOCATION: (155)..(155)
<223> OTHER INFORMATION: a, t, c, g, unknown or other
<220> FEATURE:
<221> NAME/KEY: modified_base
<222> LOCATION: (158)..(158)
<223> OTHER INFORMATION: a, t, c, g, unknown or other
<220> FEATURE:
<221> NAME/KEY: modified_base
<222> LOCATION: (161)..(161)
<223> OTHER INFORMATION: a, t, c, g, unknown or other
<220> FEATURE:
<221> NAME/KEY: modified_base
<222> LOCATION: (166)..(166)
<223> OTHER INFORMATION: a, t, c, g, unknown or other
<220> FEATURE:
<221> NAME/KEY: modified_base
<222> LOCATION: (174)..(174)
<223> OTHER INFORMATION: a, t, c, g, unknown or other
<220> FEATURE:
<221> NAME/KEY: modified_base
<222> LOCATION: (178)..(178)
<223> OTHER INFORMATION: a, t, c, g, unknown or other
<220> FEATURE:
<221> NAME/KEY: modified_base -continued
<222> LOCATION: (183)..(183)
<223> OTHER INFORMATION: a, t, c, g, unknown or other
<220> FEATURE:
<221> NAME/KEY: modified_base
<222> LOCATION: (187)..(187)
<223> OTHER INFORMATION: a, t, c, g, unknown or other
<220> FEATURE:
<221> NAME/KEY: modified_base
<222> LOCATION: (191)..(191)
<223> OTHER INFORMATION: a, t, c, g, unknown or other
<220> FEATURE:
<221> NAME/KEY: modified_base
<222> LOCATION: (197)..(197)
<223> OTHER INFORMATION: a, t, c, g, unknown or other
<220> FEATURE:
<221> NAME/KEY: modified_base
<222> LOCATION: (199)..(200)
<223> OTHER INFORMATION: a, t, c, g, unknown or other
<220> FEATURE:
<221> NAME/KEY: modified_base
<222> LOCATION: (202)..(203)
<223> OTHER INFORMATION: a, t, c, g, unknown or other
<220> FEATURE:
<221> NAME/KEY: modified_base
<222> LOCATION: (205)..(206)
<223> OTHER INFORMATION: a, t, c, g, unknown or other
<220> FEATURE:
<221> NAME/KEY: modified_base
<222> LOCATION: (208)..(208)
<223> OTHER INFORMATION: a, t, c, g, unknown or other
<220> FEATURE:
<221> NAME/KEY: modified_base
<222> LOCATION: (211)..(211)
<223> OTHER INFORMATION: a, t, c, g, unknown or other
<220> FEATURE:
<221> NAME/KEY: modified_base
<222> LOCATION: (213)..(213)
<223> OTHER INFORMATION: a, t, c, g, unknown or other
<220> FEATURE:
<221> NAME/KEY: modified_base
<222> LOCATION: (222)..(222)
<223> OTHER INFORMATION: a, t, c, g, unknown or other
<220> FEATURE:
<221> NAME/KEY: modified_base
<222> LOCATION: (225)..(227)
<223> OTHER INFORMATION: a, t, c, g, unknown or other
<220> FEATURE:
<221> NAME/KEY: modified_base
<222> LOCATION: (232)..(232)
<223> OTHER INFORMATION: a, t, c, g, unknown or other
<220> FEATURE:
<221> NAME/KEY: modified_base
<222> LOCATION: (234)..(234)
<223> OTHER INFORMATION: a, t, c, g, unknown or other
<220> FEATURE:
<221> NAME/KEY: modified_base
<222> LOCATION: (242)..(242)
<223> OTHER INFORMATION: a, t, c, g, unknown or other
<220> FEATURE:
<221> NAME/KEY: modified_base
<222> LOCATION: (256)..(256)
<223> OTHER INFORMATION: a, t, c, g, unknown or other
<220> FEATURE:
<221> NAME/KEY: modified_base
<222> LOCATION: (270)..(270)
<223> OTHER INFORMATION: a, t, c, g, unknown or other
<220> FEATURE:
<221> NAME/KEY: modified_base
<222> LOCATION: (280)..(280)
<223> OTHER INFORMATION: a, t, c, g, unknown or other
<220> FEATURE:
<221> NAME/KEY: modified_base
<222> LOCATION: (282)..(282)
<223> OTHER INFORMATION: a, t, c, g, unknown or other
<220> FEATURE:
<221> NAME/KEY: modified_base
<222> LOCATION: (293)..(293)
<223> OTHER INFORMATION: a, t, c, g, unknown or other
<220> FEATURE:

<221> NAME/KEY: modified_base
<222> LOCATION: (306)..(307)
<223> OTHER INFORMATION: a, t, c, g, unknown or other
<220> FEATURE:
<221> NAME/KEY: modified_base
<222> LOCATION: (310)..(310)
<223> OTHER INFORMATION: a, t, c, g, unknown or other
<220> FEATURE:
<221> NAME/KEY: modified_base
<222> LOCATION: (312)..(312)
<223> OTHER INFORMATION: a, t, c, g, unknown or other
<220> FEATURE:
<221> NAME/KEY: modified_base
<222> LOCATION: (318)..(318)
<223> OTHER INFORMATION: a, t, c, g, unknown or other
<220> FEATURE:
<221> NAME/KEY: modified_base
<222> LOCATION: (327)..(327)
<223> OTHER INFORMATION: a, t, c, g, unknown or other
<220> FEATURE:
<221> NAME/KEY: modified_base
<222> LOCATION: (338)..(339)
<223> OTHER INFORMATION: a, t, c, g, unknown or other
<220> FEATURE:
<221> NAME/KEY: modified_base
<222> LOCATION: (344)..(344)
<223> OTHER INFORMATION: a, t, c, g, unknown or other
<220> FEATURE:
<221> NAME/KEY: modified_base
<222> LOCATION: (347)..(347)
<223> OTHER INFORMATION: a, t, c, g, unknown or other
<220> FEATURE:
<221> NAME/KEY: modified_base
<222> LOCATION: (358)..(359)
<223> OTHER INFORMATION: a, t, c, g, unknown or other
<220> FEATURE:
<221> NAME/KEY: modified_base
<222> LOCATION: (367)..(367)
<223> OTHER INFORMATION: a, t, c, g, unknown or other
<220> FEATURE:
<221> NAME/KEY: modified_base
<222> LOCATION: (372)..(373)
<223> OTHER INFORMATION: a, t, c, g, unknown or other
<220> FEATURE:
<221> NAME/KEY: modified_base
<222> LOCATION: (387)..(387)
<223> OTHER INFORMATION: a, t, c, g, unknown or other
<220> FEATURE:
<221> NAME/KEY: modified_base
<222> LOCATION: (390)..(390)
<223> OTHER INFORMATION: a, t, c, g, unknown or other
<220> FEATURE:
<221> NAME/KEY: modified_base
<222> LOCATION: (394)..(396)
<223> OTHER INFORMATION: a, t, c, g, unknown or other
<220> FEATURE:
<221> NAME/KEY: modified_base
<222> LOCATION: (400)..(400)
<223> OTHER INFORMATION: a, t, c, g, unknown or other
<220> FEATURE:
<221> NAME/KEY: modified_base
<222> LOCATION: (404)..(404)
<223> OTHER INFORMATION: a, t, c, g, unknown or other
<220> FEATURE:
<221> NAME/KEY: modified_base
<222> LOCATION: (411)..(411)
<223> OTHER INFORMATION: a, t, c, g, unknown or other
<220> FEATURE:
<221> NAME/KEY: modified_base
<222> LOCATION: (414)..(414)
<223> OTHER INFORMATION: a, t, c, g, unknown or other
<220> FEATURE:
<221> NAME/KEY: modified_base
<222> LOCATION: (416)..(418)
<223> OTHER INFORMATION: a, t, c, g, unknown or other
<220> FEATURE:
<221> NAME/KEY: modified_base
<222> LOCATION: (428)..(428)
<223> OTHER INFORMATION: a, t, c, g, unknown or other -continued
<220> FEATURE:
<221> NAME/KEY: modified_base
<222> LOCATION: (439)..(440)
<223> OTHER INFORMATION: a, t, c, g, unknown or other
<220> FEATURE:
<221> NAME/KEY: modified_base
<222> LOCATION: (447)..(447)
<223> OTHER INFORMATION: a, t, c, g, unknown or other
<220> FEATURE:
<221> NAME/KEY: modified_base
<222> LOCATION: (452)..(452)
<223> OTHER INFORMATION: a, t, c, g, unknown or other
<220> FEATURE:
<221> NAME/KEY: modified_base
<222> LOCATION: (454)..(455)
<223> OTHER INFORMATION: a, t, c, g, unknown or other
<220> FEATURE:
<221> NAME/KEY: modified_base
<222> LOCATION: (465)..(465)
<223> OTHER INFORMATION: a, t, c, g, unknown or other
<220> FEATURE:
<221> NAME/KEY: modified_base
<222> LOCATION: (468)..(469)
<223> OTHER INFORMATION: a, t, c, g, unknown or other
<220> FEATURE:
<221> NAME/KEY: modified_base
<222> LOCATION: (476)..(476)
<223> OTHER INFORMATION: a, t, c, g, unknown or other
<220> FEATURE:
<221> NAME/KEY: modified_base
<222> LOCATION: (480)..(481)
<223> OTHER INFORMATION: a, t, c, g, unknown or other
<220> FEATURE:
<221> NAME/KEY: modified_base
<222> LOCATION: (486)..(487)
<223> OTHER INFORMATION: a, t, c, g, unknown or other
<220> FEATURE:
<221> NAME/KEY: modified_base
<222> LOCATION: (489)..(490)
<223> OTHER INFORMATION: a, t, c, g, unknown or other
<220> FEATURE:
<221> NAME/KEY: modified_base
<222> LOCATION: (494)..(495)
<223> OTHER INFORMATION: a, t, c, g, unknown or other
<220> FEATURE:
<221> NAME/KEY: modified_base
<222> LOCATION: (498)..(498)
<223> OTHER INFORMATION: a, t, c, g, unknown or other
<220> FEATURE:
<221> NAME/KEY: modified_base
<222> LOCATION: (502)..(503)
<223> OTHER INFORMATION: a, t, c, g, unknown or other
<220> FEATURE:
<221> NAME/KEY: modified_base
<222> LOCATION: (512)..(512)
<223> OTHER INFORMATION: a, t, c, g, unknown or other
<220> FEATURE:
<221> NAME/KEY: modified_base
<222> LOCATION: (516)..(517)
<223> OTHER INFORMATION: a, t, c, g, unknown or other
<220> FEATURE:
<221> NAME/KEY: modified_base
<222> LOCATION: (533)..(534)
<223> OTHER INFORMATION: a, t, c, g, unknown or other
<220> FEATURE:
<221> NAME/KEY: modified_base
<222> LOCATION: (537)..(537)
<223> OTHER INFORMATION: a, t, c, g, unknown or other
<220> FEATURE:
<221> NAME/KEY: modified_base
<222> LOCATION: (541)..(542)
<223> OTHER INFORMATION: a, t, c, g, unknown or other
<220> FEATURE:
<221> NAME/KEY: modified_base
<222> LOCATION: (544)..(545)
<223> OTHER INFORMATION: a, t, c, g, unknown or other
<220> FEATURE:
<221> NAME/KEY: modified_base
<222> LOCATION: (547)..(547)

<223> OTHER INFORMATION: a, t, c, g, unknown or other
<220> FEATURE:
<221> NAME/KEY: modified_base
<222> LOCATION: (552)..(552)
<223> OTHER INFORMATION: a, t, c, g, unknown or other
<220> FEATURE:
<221> NAME/KEY: modified_base
<222> LOCATION: (557)..(559)
<223> OTHER INFORMATION: a, t, c, g, unknown or other
<220> FEATURE:
<221> NAME/KEY: modified_base
<222> LOCATION: (565)..(565)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other
<220> FEATURE:
<221> NAME/KEY: modified_base
<222> LOCATION: (570)..(570)
<223> OTHER INFORMATION: a, t, c, g, unknown or other
<220> FEATURE:
<221> NAME/KEY: modified_base
<222> LOCATION: (576)..(576)
<223> OTHER INFORMATION: a, t, c, g, unknown or other
<220> FEATURE:
<221> NAME/KEY: modified_base
<222> LOCATION: (583)..(583)
<223> OTHER INFORMATION: a, t, c, g, unknown or other
<220> FEATURE:
<221> NAME/KEY: modified_base
<222> LOCATION: (587)..(591)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (596)..(597)
<223> OTHER INFORMATION: a, t, c, g, unknown or other
<220> FEATURE:
<221> NAME/KEY: modified_base
<222> LOCATION: (609)..(609)
<223> OTHER INFORMATION: a, t, c, g, unknown or other
<220> FEATURE:
<221> NAME/KEY: modified_base
<222> LOCATION: (611)..(612)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (620)..(620)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (626)..(626)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (638)..(638)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (647)..(647)
<223> OTHER INFORMATION: a, t, c, g, unknown or other
<220> FEATURE:
<221> NAME/KEY: modified_base
<222> LOCATION: (650)..(650)
<223> OTHER INFORMATION: a, t, c, g, unknown or other
<220> FEATURE:
<221> NAME/KEY: modified_base
<222> LOCATION: (660)..(660)
<223> OTHER INFORMATION: a, t, c, g, unknown or other
<220> FEATURE:
<221> NAME/KEY: modified_base
<222> LOCATION: (674)..(675)
<223> OTHER INFORMATION: a, t, c, g, unknown or other
<220> FEATURE:
<221> NAME/KEY: modified_base
<222> LOCATION: (681)..(682)
<223> OTHER INFORMATION: a, t, c, g, unknown or other
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (693)..(694)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (717)..(717)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (736)..(737)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (757)..(757)
<223> OTHER INFORMATION: a, t, c, g, unknown or other
<220> FEATURE:
<221> NAME/KEY: modified_base
<222> LOCATION: (759)..(760)
<223> OTHER INFORMATION: a, t, c, g, unknown or other
<220> FEATURE:
<221> NAME/KEY: modified_base
<222> LOCATION: (764)..(764)
<223> OTHER INFORMATION: a, t, c, g, unknown or other
<220> FEATURE:
<221> NAME/KEY: modified_base
<222> LOCATION: (776)..(776)
<223> OTHER INFORMATION: a, t, c, g, unknown or other

<400> SEQUENCE: 57
cctgnnagan antaccnggc acacanaaac acccaaanaa aattttaacn cnnaanattn 60
ncncccnccg nnggggnntt aaaaaannan ctnnccccc cccanaaaca ncancaaaac 120
ncacnaacan nacacatnan naancanccn caaanccnaa naaaanccaa cacnaaanaa 180
ccncaanaca nccaaancnn tnncnnanca nanaacccac anacnnncaa ancncccaaa 240
cnaacacaac caaacnaaac aacaactaan acaacaccan cnataaacca aanatacaaa 300

-continued

```
acaccnntcn cnacaaancc acacganaac acccaaanna cacnaanaac actcaaanna    360

aacaaancac annccaccaa aaaaacntan tacnnnaaan acancaaatc nacnannnca    420

acatcacnat cactcaccnn aaaacanaac ancnntcacc aacanaannc acaaanacan    480

ncctannann accnnacnac cnnaccccac anacannaac aacccacaaa tannccnaca    540

nnanncntca cnacaannnc aacgnantcn caaaanaccc ccncaannnn nanaannaca    600

ccacaacana nnaaaacnan aacnantaac anaaaaanac naaaaanaan accccaatcn    660

caccacaaaa cacnncacaa nncccccana atnncaccct caccncacaa acaaacnacc    720

accacaaaac aaanannaan aaaaaaanca aaaccancnn aatnacaaac aaaacncg      778
```

<210> SEQ ID NO 58
<211> LENGTH: 753
<212> TYPE: DNA
<213> ORGANISM: Homo sapiens
<220> FEATURE:
<221> NAME/KEY: modified_base
<222> LOCATION: (76)..(76)
<223> OTHER INFORMATION: a, t, c, g, unknown or other
<220> FEATURE:
<221> NAME/KEY: modified_base
<222> LOCATION: (343)..(343)
<223> OTHER INFORMATION: a, t, c, g, unknown or other
<220> FEATURE:
<221> NAME/KEY: modified_base
<222> LOCATION: (489)..(489)
<223> OTHER INFORMATION: a, t, c, g, unknown or other
<220> FEATURE:
<221> NAME/KEY: modified_base
<222> LOCATION: (547)..(547)
<223> OTHER INFORMATION: a, t, c, g, unknown or other
<220> FEATURE:
<221> NAME/KEY: modified_base
<222> LOCATION: (596)..(596)
<223> OTHER INFORMATION: a, t, c, g, unknown or other
<220> FEATURE:
<221> NAME/KEY: modified_base
<222> LOCATION: (601)..(601)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (647)..(647)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (706)..(706)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (711)..(711)
<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other
<220> FEATURE:
<221> NAME/KEY: modified_base
<222> LOCATION: (718)..(718)
<223> OTHER INFORMATION: a, t, c, g, unknown or other
<220> FEATURE:
<221> NAME/KEY: modified_base
<222> LOCATION: (720)..(720)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other

<400> SEQUENCE: 58

```
cctttcaggc aagcagtggt ctctagctgt taaaacattt ccttttgga tcacaatagc     60

ttctaaaact gccttngtag taaaggccat cagagaggta atactaaact gtgcatttgc    120

caaataagaa tatgaattgt ataaaagctc atattccaat cctagatcaa atggcaaaag    180

ttctacaaag ttggtttcca tgtttgtata aaagctccga ctgattttat gtattttgct    240

atgaaattac ctttgggtct tataatcagt atacctctac tcaggaatgt gcaaatgatt    300

ttatacagca cgacgctagt accgctctgt atgacagtaa ggnttttttt ttttcttctt    360

ttctaaatgg aaagaaaata tccctagtca gaaataaact gacaaattta cattctcctc    420

tcttaaaaaa gtaaataaaa taacattatt caaaacgtga attagctata gacatacaat    480

acaattacnt agatccatat caatacagca cattcaatct ggccaaaaat taatgattac    540

caagccngta tggatgctgc aatttcaaga gagatgtatg taccatggtt agagcntttg    600

naatgcacta tcctacagca gtctggttgg tnaattcang nactttntga gccangggaa    660

aaaaaagtaa cctggttggt tgaaggcttg ganaatcaag ggtganacnt ntnattcngn    720

tnggcngctt tgggccccat taaaaaggcc ggg                                 753
```

<210> SEQ ID NO 59
<211> LENGTH: 766
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (15)..(15)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (25)..(25)
<223> OTHER INFORMATION: a, t, c, g, unknown or other
<220> FEATURE:
<221> NAME/KEY: modified_base
<222> LOCATION: (28)..(28)
<223> OTHER INFORMATION: a, t, c, g, unknown or other
<220> FEATURE:
<221> NAME/KEY: modified_base
<222> LOCATION: (32)..(33)

<223> OTHER INFORMATION: a, t, c, g, unknown or other
<220> FEATURE:
<221> NAME/KEY: modified_base
<222> LOCATION: (42)..(43)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (59)..(59)
<223> OTHER INFORMATION: a, t, c, g, unknown or other
<220> FEATURE:
<221> NAME/KEY: modified_base
<222> LOCATION: (71)..(71)
<223> OTHER INFORMATION: a, t, c, g, unknown or other
<220> FEATURE:
<221> NAME/KEY: modified_base
<222> LOCATION: (84)..(86)
<223> OTHER INFORMATION: a, t, c, g, unknown or other
<220> FEATURE:
<221> NAME/KEY: modified_base
<222> LOCATION: (95)..(95)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (117)..(117)
<223> OTHER INFORMATION: a, t, c, g, unknown or other
<220> FEATURE:
<221> NAME/KEY: modified_base
<222> LOCATION: (149)..(149)
<223> OTHER INFORMATION: a, t, c, g, unknown or other
<220> FEATURE:
<221> NAME/KEY: modified_base
<222> LOCATION: (162)..(162)
<223> OTHER INFORMATION: a, t, c, g, unknown or other
<220> FEATURE:
<221> NAME/KEY: modified_base
<222> LOCATION: (166)..(166)
<223> OTHER INFORMATION: a, t, c, g, unknown or other
<220> FEATURE:
<221> NAME/KEY: modified_base
<222> LOCATION: (175)..(176)
<223> OTHER INFORMATION: a, t, c, g, unknown or other
<220> FEATURE:
<221> NAME/KEY: modified_base
<222> LOCATION: (184)..(184)
<223> OTHER INFORMATION: a, t, c, g, unknown or other
<220> FEATURE:
<221> NAME/KEY: modified_base
<222> LOCATION: (189)..(189)
<223> OTHER INFORMATION: a, t, c, g, unknown or other
<220> FEATURE:
<221> NAME/KEY: modified_base
<222> LOCATION: (200)..(200)
<223> OTHER INFORMATION: a, t, c, g, unknown or other
<220> FEATURE:
<221> NAME/KEY: modified_base
<222> LOCATION: (218)..(218)
<223> OTHER INFORMATION: a, t, c, g, unknown or other
<220> FEATURE:
<221> NAME/KEY: modified_base
<222> LOCATION: (221)..(221)
<223> OTHER INFORMATION: a, t, c, g, unknown or other
<220> FEATURE:
<221> NAME/KEY: modified_base
<222> LOCATION: (232)..(232)
<223> OTHER INFORMATION: a, t, c, g, unknown or other
<220> FEATURE:
<221> NAME/KEY: modified_base
<222> LOCATION: (242)..(242)
<223> OTHER INFORMATION: a, t, c, g, unknown or other
<220> FEATURE:
<221> NAME/KEY: modified_base
<222> LOCATION: (259)..(259)
<223> OTHER INFORMATION: a, t, c, g, unknown or other
<220> FEATURE:
<221> NAME/KEY: modified_base
<222> LOCATION: (275)..(275)
<223> OTHER INFORMATION: a, t, c, g, unknown or other
<220> FEATURE:
<221> NAME/KEY: modified_base
<222> LOCATION: (286)..(286)
<223> OTHER INFORMATION: a, t, c, g, unknown or other
<220> FEATURE:
<221> NAME/KEY: modified_base
<222> LOCATION: (293)..(293)
<223> OTHER INFORMATION: a, t, c, g, unknown or other
<220> FEATURE:
<221> NAME/KEY: modified_base
<222> LOCATION: (310)..(310)
<223> OTHER INFORMATION: a, t, c, g, unknown or other
<220> FEATURE:
<221> NAME/KEY: modified_base
<222> LOCATION: (313)..(313)
<223> OTHER INFORMATION: a, t, c, g, unknown or other
<220> FEATURE:
<221> NAME/KEY: modified_base
<222> LOCATION: (315)..(315)
<223> OTHER INFORMATION: a, t, c, g, unknown or other
<220> FEATURE:
<221> NAME/KEY: modified_base
<222> LOCATION: (319)..(320)
<223> OTHER INFORMATION: a, t, c, g, unknown or other
<220> FEATURE:
<221> NAME/KEY: modified_base
<222> LOCATION: (330)..(330)
<223> OTHER INFORMATION: a, t, c, g, unknown or other
<220> FEATURE:
<221> NAME/KEY: modified_base
<222> LOCATION: (338)..(338)
<223> OTHER INFORMATION: a, t, c, g, unknown or other
<220> FEATURE:
<221> NAME/KEY: modified_base
<222> LOCATION: (362)..(362)
<223> OTHER INFORMATION: a, t, c, g, unknown or other
<220> FEATURE:
<221> NAME/KEY: modified_base
<222> LOCATION: (373)..(373)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (394)..(394)
<223> OTHER INFORMATION: a, t, c, g, unknown or other
<220> FEATURE:
<221> NAME/KEY: modified_base
<222> LOCATION: (401)..(402)
<223> OTHER INFORMATION: a, t, c, g, unknown or other
<220> FEATURE:
<221> NAME/KEY: modified_base
<222> LOCATION: (405)..(405)
<223> OTHER INFORMATION: a, t, c, g, unknown or other
<220> FEATURE:
<221> NAME/KEY: modified_base
<222> LOCATION: (409)..(409)
<223> OTHER INFORMATION: a, t, c, g, unknown or other
<220> FEATURE:
<221> NAME/KEY: modified_base
<222> LOCATION: (412)..(412)
<223> OTHER INFORMATION: a, t, c, g, unknown or other
<220> FEATURE:
<221> NAME/KEY: modified_base
<222> LOCATION: (418)..(419)
<223> OTHER INFORMATION: a, t, c, g, unknown or other
<220> FEATURE:
<221> NAME/KEY: modified_base
<222> LOCATION: (425)..(425)
<223> OTHER INFORMATION: a, t, c, g, unknown or other
<220> FEATURE:

<221> NAME/KEY: modified_base
<222> LOCATION: (427)..(428)
<223> OTHER INFORMATION: a, t, c, g, unknown or other
<220> FEATURE:
<221> NAME/KEY: modified_base
<222> LOCATION: (430)..(430)
<223> OTHER INFORMATION: a, t, c, g, unknown or other
<220> FEATURE:
<221> NAME/KEY: modified_base
<222> LOCATION: (435)..(436)
<223> OTHER INFORMATION: a, t, c, g, unknown or other
<220> FEATURE:
<221> NAME/KEY: modified_base
<222> LOCATION: (445)..(445)
<223> OTHER INFORMATION: a, t, c, g, unknown or other
<220> FEATURE:
<221> NAME/KEY: modified_base
<222> LOCATION: (448)..(449)
<223> OTHER INFORMATION: a, t, c, g, unknown or other
<220> FEATURE:
<221> NAME/KEY: modified_base
<222> LOCATION: (453)..(453)
<223> OTHER INFORMATION: a, t, c, g, unknown or other
<220> FEATURE:
<221> NAME/KEY: modified_base
<222> LOCATION: (462)..(464)
<223> OTHER INFORMATION: a, t, c, g, unknown or other
<220> FEATURE:
<221> NAME/KEY: modified_base
<222> LOCATION: (472)..(472)
<223> OTHER INFORMATION: a, t, c, g, unknown or other
<220> FEATURE:
<221> NAME/KEY: modified_base
<222> LOCATION: (478)..(478)
<223> OTHER INFORMATION: a, t, c, g, unknown or other
<220> FEATURE:
<221> NAME/KEY: modified_base
<222> LOCATION: (481)..(481)
<223> OTHER INFORMATION: a, t, c, g, unknown or other
<220> FEATURE:
<221> NAME/KEY: modified_base
<222> LOCATION: (484)..(484)
<223> OTHER INFORMATION: a, t, c, g, unknown or other
<220> FEATURE:
<221> NAME/KEY: modified_base
<222> LOCATION: (492)..(492)
<223> OTHER INFORMATION: a, t, c, g, unknown or other
<220> FEATURE:
<221> NAME/KEY: modified_base
<222> LOCATION: (497)..(498)
<223> OTHER INFORMATION: a, t, c, g, unknown or other
<220> FEATURE:
<221> NAME/KEY: modified_base
<222> LOCATION: (501)..(501)
<223> OTHER INFORMATION: a, t, c, g, unknown or other
<220> FEATURE:
<221> NAME/KEY: modified_base
<222> LOCATION: (509)..(509)
<223> OTHER INFORMATION: a, t, c, g, unknown or other
<220> FEATURE:
<221> NAME/KEY: modified_base
<222> LOCATION: (511)..(511)
<223> OTHER INFORMATION: a, t, c, g, unknown or other
<220> FEATURE:
<221> NAME/KEY: modified_base
<222> LOCATION: (519)..(520)
<223> OTHER INFORMATION: a, t, c, g, unknown or other
<220> FEATURE:
<221> NAME/KEY: modified_base
<222> LOCATION: (524)..(525)
<223> OTHER INFORMATION: a, t, c, g, unknown or other
<220> FEATURE:
<221> NAME/KEY: modified_base
<222> LOCATION: (528)..(528)
<223> OTHER INFORMATION: a, t, c, g, unknown or other
<220> FEATURE:
<221> NAME/KEY: modified_base
<222> LOCATION: (532)..(532)
<223> OTHER INFORMATION: a, t, c, g, unknown or other
<220> FEATURE:
<221> NAME/KEY: modified_base
<222> LOCATION: (535)..(535)
<223> OTHER INFORMATION: a, t, c, g, unknown or other
<220> FEATURE:
<221> NAME/KEY: modified_base
<222> LOCATION: (537)..(538)
<223> OTHER INFORMATION: a, t, c, g, unknown or other
<220> FEATURE:
<221> NAME/KEY: modified_base
<222> LOCATION: (540)..(540)
<223> OTHER INFORMATION: a, t, c, g, unknown or other
<220> FEATURE:
<221> NAME/KEY: modified_base
<222> LOCATION: (542)..(546)
<223> OTHER INFORMATION: a, t, c, g, unknown or other
<220> FEATURE:
<221> NAME/KEY: modified_base
<222> LOCATION: (550)..(553)
<223> OTHER INFORMATION: a, t, c, g, unknown or other
<220> FEATURE:
<221> NAME/KEY: modified_base
<222> LOCATION: (556)..(556)
<223> OTHER INFORMATION: a, t, c, g, unknown or other
<220> FEATURE:
<221> NAME/KEY: modified_base
<222> LOCATION: (568)..(569)
<223> OTHER INFORMATION: a, t, c, g, unknown or other
<220> FEATURE:
<221> NAME/KEY: modified_base
<222> LOCATION: (572)..(572)
<223> OTHER INFORMATION: a, t, c, g, unknown or other
<220> FEATURE:
<221> NAME/KEY: modified_base
<222> LOCATION: (574)..(575)
<223> OTHER INFORMATION: a, t, c, g, unknown or other
<220> FEATURE:
<221> NAME/KEY: modified_base
<222> LOCATION: (577)..(577)
<223> OTHER INFORMATION: a, t, c, g, unknown or other
<220> FEATURE:
<221> NAME/KEY: modified_base
<222> LOCATION: (581)..(582)
<223> OTHER INFORMATION: a, t, c, g, unknown or other
<220> FEATURE:
<221> NAME/KEY: modified_base
<222> LOCATION: (599)..(599)
<223> OTHER INFORMATION: a, t, c, g, unknown or other
<220> FEATURE:
<221> NAME/KEY: modified_base
<222> LOCATION: (602)..(602)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (611)..(611)
<223> OTHER INFORMATION: a, t, c, g, unknown or other
<220> FEATURE:
<221> NAME/KEY: modified_base
<222> LOCATION: (621)..(621)
<223> OTHER INFORMATION: a, t, c, g, unknown or other
<220> FEATURE:
<221> NAME/KEY: modified_base
<222> LOCATION: (623)..(623)
<223> OTHER INFORMATION: a, t, c, g, unknown or other
<220> FEATURE:
<221> NAME/KEY: modified_base
<222> LOCATION: (625)..(625)
<223> OTHER INFORMATION: a, t, c, g, unknown or other
<220> FEATURE:
<221> NAME/KEY: modified_base
<222> LOCATION: (628)..(628)
<223> OTHER INFORMATION: a, t, c, g, unknown or other
<220> FEATURE:
<221> NAME/KEY: modified_base
<222> LOCATION: (631)..(631)

<223> OTHER INFORMATION: a, t, c, g, unknown or other
<220> FEATURE:
<221> NAME/KEY: modified_base
<222> LOCATION: (635)..(637)
<223> OTHER INFORMATION: a, t, c, g, unknown or other
<220> FEATURE:
<221> NAME/KEY: modified_base
<222> LOCATION: (639)..(640)
<223> OTHER INFORMATION: a, t, c, g, unknown or other
<220> FEATURE:
<221> NAME/KEY: modified_base
<222> LOCATION: (659)..(660)
<223> OTHER INFORMATION: a, t, c, g, unknown or other
<220> FEATURE:
<221> NAME/KEY: modified_base
<222> LOCATION: (664)..(664)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (668)..(669)
<223> OTHER INFORMATION: a, t, c, g, unknown or other
<220> FEATURE:
<221> NAME/KEY: modified_base
<222> LOCATION: (687)..(688)
<223> OTHER INFORMATION: a, t, c, g, unknown or other
<220> FEATURE:
<221> NAME/KEY: modified_base
<222> LOCATION: (694)..(694)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (707)..(707)
<223> OTHER INFORMATION: a, t, c, g, unknown or other
<220> FEATURE:
<221> NAME/KEY: modified_base
<222> LOCATION: (711)..(712)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (730)..(731)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other
<220> FEATURE:
<221> NAME/KEY: modified_base
<222> LOCATION: (742)..(742)
<223> OTHER INFORMATION: a, t, c, g, unknown or other
<220> FEATURE:
<221> NAME/KEY: modified_base
<222> LOCATION: (749)..(750)
<223> OTHER INFORMATION: a, t, c, g, unknown or other
<220> FEATURE:
<221> NAME/KEY: modified_base
<222> LOCATION: (754)..(755)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other

<400> SEQUENCE: 59

```
gaacaganac acaanaggca aanancanca cnngaaaaat tnnttccaan acacagacnc     60

caaagaaaca ngggggggata agcnnnaagg gcctntatga ccccnccacc ccacacngag   120

caccaccccg aaggggctgg aagccaggng aaccacccaa angggngcct gcagnnctgc   180

ccanctacng cccctcctcn gggaccacac agggacgncg naacagccaa cnccacacat   240

cngccaaaaa agagcaagnc atcaaggcaa gcagncacga ctcaaanactc ccnagctgca   300

gaaaaccaan ggngncagnn ggaacagggn aacacacnaa aaaagccaca caaaaaagga   360

anagacaggc aangaccaac caaagaaagg cncnaaggca nncgnaacna cngggaanna   420

caggngnnan aaacnngcca agcanggnnc acnaaaagga cnnncacaga gngaaaangg   480

nggnacccaa ancccnngg nagaacagna nccaccagnn aacnnagnca cnaancnngn   540

gnnnnngacn nnnggngcaa caaaaaannc ananngngac nnggaccaaa ggaaacaanc   600

gnaangcaag naaacaaaaa ncnanccngg ncccnnnann ggcaaccagg gaaagaaann   660

aaanananne cacaaaaggg aaaaaannaa aaanagaaaa aaaananccc nncaccccaa   720

aaaaaaanan naanaggggn gnaaaacann ccannacnaa aaaaac                   766
```

<210> SEQ ID NO 60
<211> LENGTH: 750
<212> TYPE: DNA
<213> ORGANISM: Homo sapiens
<220> FEATURE:
<221> NAME/KEY: modified_base
<222> LOCATION: (42)..(42)
<223> OTHER INFORMATION: a, t, c, g, unknown or other
<220> FEATURE:
<221> NAME/KEY: modified_base
<222> LOCATION: (44)..(45)
<223> OTHER INFORMATION: a, t, c, g, unknown or other
<220> FEATURE:
<221> NAME/KEY: modified_base
<222> LOCATION: (77)..(78)
<223> OTHER INFORMATION: a, t, c, g, unknown or other
<220> FEATURE:
<221> NAME/KEY: modified_base
<222> LOCATION: (103)..(103)
<223> OTHER INFORMATION: a, t, c, g, unknown or other
<220> FEATURE:
<221> NAME/KEY: modified_base
<222> LOCATION: (408)..(408)
<223> OTHER INFORMATION: a, t, c, g, unknown or other
<220> FEATURE:
<221> NAME/KEY: modified_base
<222> LOCATION: (479)..(479)
<223> OTHER INFORMATION: a, t, c, g, unknown or other
<220> FEATURE:
<221> NAME/KEY: modified_base
<222> LOCATION: (522)..(522)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (559)..(559)
<223> OTHER INFORMATION: a, t, c, g, unknown or other
<220> FEATURE:
<221> NAME/KEY: modified_base
<222> LOCATION: (568)..(568)
<223> OTHER INFORMATION: a, t, c, g, unknown or other
<220> FEATURE:
<221> NAME/KEY: modified_base
<222> LOCATION: (578)..(578)
<223> OTHER INFORMATION: a, t, c, g, unknown or other
<220> FEATURE:
<221> NAME/KEY: modified_base
<222> LOCATION: (583)..(583)

<223> OTHER INFORMATION: a, t, c, g, unknown or other
<220> FEATURE:
<221> NAME/KEY: modified_base
<222> LOCATION: (592)..(592)
<223> OTHER INFORMATION: a, t, c, g, unknown or other
<220> FEATURE:
<221> NAME/KEY: modified_base
<222> LOCATION: (628)..(628)
<223> OTHER INFORMATION: a, t, c, g, unknown or other
<220> FEATURE:
<221> NAME/KEY: modified_base
<222> LOCATION: (631)..(631)
<223> OTHER INFORMATION: a, t, c, g, unknown or other
<220> FEATURE:
<221> NAME/KEY: modified_base
<222> LOCATION: (638)..(638)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (658)..(658)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (673)..(673)
<223> OTHER INFORMATION: a, t, c, g, unknown or other
<220> FEATURE:
<221> NAME/KEY: modified_base
<222> LOCATION: (680)..(680)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (692)..(692)
<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (700)..(701)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (716)..(717)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (725)..(726)
<223> OTHER INFORMATION: a, t, c, g, unknown or other
<220> FEATURE:
<221> NAME/KEY: modified_base
<222> LOCATION: (729)..(730)
<223> OTHER INFORMATION: a, t, c, g, unknown or other
<220> FEATURE:
<221> NAME/KEY: modified_base
<222> LOCATION: (732)..(732)
<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (737)..(737)
<223> OTHER INFORMATION: a, t, c, g, unknown or other
<220> FEATURE:
<221> NAME/KEY: modified_base
<222> LOCATION: (748)..(749)
<223> OTHER INFORMATION: a, t, c, g, unknown or other

<400> SEQUENCE: 60
aaggaattgt tacagaaaat gcaaatatca gtatttgaaa antnntttcc attacacaga 60
ctccaaagaa acaaggnnga taagcgccgt ggtcctctat ganccccatca ccccacactg 120 agcaccaccc cgaaggggct ggaagccagg tgatccaccc aaatgtgtgc ctgcagtttc 180
tgcccagcta ctgcccctcc tctgggatca cacagggatg tcgtaacagc caactccaca 240
catctgccaa aaaagagcaa gtcatcaagg cgagcagtct cgactcaaga ctccctagct 300
gcagaaaacc aatgttgtca gttgtaacag gttaatatat tatttatgcc acacaaaaaa 360
ggaatagtac aggcaatgat cttccaaaga aagctttaag gcatctgnaa cttctgggaa 420
tttcaggggt tttatcttgc cagcaagctc tactaaagta cttcacagag tgagaaggng 480
gctccaagtc cctttggtga agttggtgcc acctgcttcc tntggcacca agctggggtg 540
gggagctttg gggcttnang aagtcttntg ggacttgncc aanggaacaa gngtctggca 600
tggaaacatt acccttcctt ggtcctgntc nggcaccngg gaagtaancg tagcttgnct 660
ttaaggngaa acnttcatan tnaaaagggn cntttnttcn naanaaaana aacctnnang 720
gnggnnaann tntnccnttt ccaaaaannc 750

<210> SEQ ID NO 61
<211> LENGTH: 756
<212> TYPE: DNA
<213> ORGANISM: Homo sapiens
<220> FEATURE:
<221> NAME/KEY: modified_base
<222> LOCATION: (7)..(7)
<223> OTHER INFORMATION: a, t, c, g, unknown or other
<220> FEATURE:
<221> NAME/KEY: modified_base
<222> LOCATION: (18)..(18)
<223> OTHER INFORMATION: a, t, c, g, unknown or other
<220> FEATURE:
<221> NAME/KEY: modified_base
<222> LOCATION: (47)..(47)
<223> OTHER INFORMATION: a, t, c, g, unknown or other
<220> FEATURE:
<221> NAME/KEY: modified_base
<222> LOCATION: (619)..(619)
<223> OTHER INFORMATION: a, t, c, g, unknown or other
<220> FEATURE:
<221> NAME/KEY: modified_base
<222> LOCATION: (676)..(676)
<223> OTHER INFORMATION: a, t, c, g, unknown or other
<220> FEATURE:
<221> NAME/KEY: modified_base
<222> LOCATION: (694)..(694)

-continued

<223> OTHER INFORMATION: a, t, c, g, unknown or other
<220> FEATURE:
<221> NAME/KEY: modified_base
<222> LOCATION: (734)..(734)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other

<400> SEQUENCE: 61
gttttgnaaa aatagccncg aaacggtgtt tttaaagttg aggtctngaa gacctggctc 60
ggtttctggg aaggtgggtc ttttgtgatg tggtccccgg gcggtgcact tgggagccat 120
ggcggggcca ggacctctgg cagcgcaggg atggagcccg caggtgatga gcttgggagg 180
tgagttgtgg aggctgcgct cacatcaatg cccagtgccc tccccgaggg gcctggttct 240
ctctccacag gggcggggga agcacacagg ggacagggag gggtgctggg ttctctctcc 300
tcgggacagg gagcgcagcc aggttctctc tcctcgggac agggtggtgc ccgttgcgtg 360
cattccccag ctgcagccac gagaaacaat ttggagcgga acccgggctc tgacctcccc 420
tcatcctcag ccttccccca gggatgggcc gtgagatgaa tgtggtcacc ggcccaatcc 480
aagggtctat ggccaaaccg cagacccgga ggaagcaggc caggccatct ggggagccgg 540
cttcccttct cttctccctg ctccacaaag ctgtctcatc cagaagccag gcccgcctgt 600
gagcaagggg aggctgcang tgttccttca cctgaagcgt gtgaaagcca acaggcccca 660
ccctggtctc agccgnagcc ccttccagac tcanggggcc aaaccacttt tcacagccat 720
tgtaaccaaa cgtntggcca cactttgntc gactca 756

<210> SEQ ID NO 62
<211> LENGTH: 799
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (25)..(25)
<223> OTHER INFORMATION: a, t, c, g, unknown or other
<220> FEATURE:
<221> NAME/KEY: modified_base
<222> LOCATION: (28)..(28)
<223> OTHER INFORMATION: a, t, c, g, unknown or other
<220> FEATURE:
<221> NAME/KEY: modified_base
<222> LOCATION: (34)..(34)
<223> OTHER INFORMATION: a, t, c, g, unknown or other
<220> FEATURE:
<221> NAME/KEY: modified_base
<222> LOCATION: (37)..(37)
<223> OTHER INFORMATION: a, t, c, g, unknown or other
<220> FEATURE:
<221> NAME/KEY: modified_base
<222> LOCATION: (50)..(50)
<223> OTHER INFORMATION: a, t, c, g, unknown or other
<220> FEATURE:
<221> NAME/KEY: modified_base
<222> LOCATION: (54)..(54)
<223> OTHER INFORMATION: a, t, c, g, unknown or other
<220> FEATURE:
<221> NAME/KEY: modified_base
<222> LOCATION: (63)..(63)
<223> OTHER INFORMATION: a, t, c, g, unknown or other -continued
<220> FEATURE:
<221> NAME/KEY: modified_base
<222> LOCATION: (70)..(72)
<223> OTHER INFORMATION: a, t, c, g, unknown or other
<220> FEATURE:
<221> NAME/KEY: modified_base
<222> LOCATION: (75)..(75)
<223> OTHER INFORMATION: a, t, c, g, unknown or other
<220> FEATURE:
<221> NAME/KEY: modified_base
<222> LOCATION: (78)..(78)
<223> OTHER INFORMATION: a, t, c, g, unknown or other
<220> FEATURE:
<221> NAME/KEY: modified_base
<222> LOCATION: (84)..(84)
<223> OTHER INFORMATION: a, t, c, g, unknown or other
<220> FEATURE:
<221> NAME/KEY: modified_base
<222> LOCATION: (87)..(87)
<223> OTHER INFORMATION: a, t, c, g, unknown or other
<220> FEATURE:
<221> NAME/KEY: modified_base
<222> LOCATION: (94)..(95)
<223> OTHER INFORMATION: a, t, c, g, unknown or other
<220> FEATURE:
<221> NAME/KEY: modified_base
<222> LOCATION: (98)..(98)
<223> OTHER INFORMATION: a, t, c, g, unknown or other
<220> FEATURE:
<221> NAME/KEY: modified_base
<222> LOCATION: (100)..(102)
<223> OTHER INFORMATION: a, t, c, g, unknown or other
<220> FEATURE:
<221> NAME/KEY: modified_base
<222> LOCATION: (107)..(107)
<223> OTHER INFORMATION: a, t, c, g, unknown or other
<220> FEATURE:
<221> NAME/KEY: modified_base
<222> LOCATION: (114)..(114)
<223> OTHER INFORMATION: a, t, c, g, unknown or other
<220> FEATURE:
<221> NAME/KEY: modified_base
<222> LOCATION: (122)..(122)
<223> OTHER INFORMATION: a, t, c, g, unknown or other
<220> FEATURE:
<221> NAME/KEY: modified_base
<222> LOCATION: (124)..(124)
<223> OTHER INFORMATION: a, t, c, g, unknown or other
<220> FEATURE:
<221> NAME/KEY: modified_base
<222> LOCATION: (127)..(127)
<223> OTHER INFORMATION: a, t, c, g, unknown or other
<220> FEATURE:
<221> NAME/KEY: modified_base
<222> LOCATION: (129)..(130)
<223> OTHER INFORMATION: a, t, c, g, unknown or other
<220> FEATURE:
<221> NAME/KEY: modified_base
<222> LOCATION: (138)..(139)
<223> OTHER INFORMATION: a, t, c, g, unknown or other
<220> FEATURE:
<221> NAME/KEY: modified_base
<222> LOCATION: (143)..(143)
<223> OTHER INFORMATION: a, t, c, g, unknown or other
<220> FEATURE:
<221> NAME/KEY: modified_base
<222> LOCATION: (145)..(145)
<223> OTHER INFORMATION: a, t, c, g, unknown or other
<220> FEATURE:
<221> NAME/KEY: modified_base
<222> LOCATION: (148)..(148)
<223> OTHER INFORMATION: a, t, c, g, unknown or other
<220> FEATURE:
<221> NAME/KEY: modified_base
<222> LOCATION: (151)..(151)
<223> OTHER INFORMATION: a, t, c, g, unknown or other
<220> FEATURE:
<221> NAME/KEY: modified_base
<222> LOCATION: (153)..(155)

-continued

<223> OTHER INFORMATION: a, t, c, g, unknown or other
<220> FEATURE:
<221> NAME/KEY: modified_base
<222> LOCATION: (159)..(159)
<223> OTHER INFORMATION: a, t, c, g, unknown or other
<220> FEATURE:
<221> NAME/KEY: modified_base
<222> LOCATION: (163)..(163)
<223> OTHER INFORMATION: a, t, c, g, unknown or other
<220> FEATURE:
<221> NAME/KEY: modified_base
<222> LOCATION: (166)..(167)
<223> OTHER INFORMATION: a, t, c, g, unknown or other
<220> FEATURE:
<221> NAME/KEY: modified_base
<222> LOCATION: (170)..(171)
<223> OTHER INFORMATION: a, t, c, g, unknown or other
<220> FEATURE:
<221> NAME/KEY: modified_base
<222> LOCATION: (173)..(173)
<223> OTHER INFORMATION: a, t, c, g, unknown or other
<220> FEATURE:
<221> NAME/KEY: modified_base
<222> LOCATION: (175)..(175)
<223> OTHER INFORMATION: a, t, c, g, unknown or other
<220> FEATURE:
<221> NAME/KEY: modified_base
<222> LOCATION: (177)..(177)
<223> OTHER INFORMATION: a, t, c, g, unknown or other
<220> FEATURE:
<221> NAME/KEY: modified_base
<222> LOCATION: (183)..(184)
<223> OTHER INFORMATION: a, t, c, g, unknown or other
<220> FEATURE:
<221> NAME/KEY: modified_base
<222> LOCATION: (188)..(189)
<223> OTHER INFORMATION: a, t, c, g, unknown or other
<220> FEATURE:
<221> NAME/KEY: modified_base
<222> LOCATION: (191)..(191)
<223> OTHER INFORMATION: a, t, c, g, unknown or other
<220> FEATURE:
<221> NAME/KEY: modified_base
<222> LOCATION: (199)..(199)
<223> OTHER INFORMATION: a, t, c, g, unknown or other
<220> FEATURE:
<221> NAME/KEY: modified_base
<222> LOCATION: (206)..(206)
<223> OTHER INFORMATION: a, t, c, g, unknown or other
<220> FEATURE:
<221> NAME/KEY: modified_base
<222> LOCATION: (208)..(209)
<223> OTHER INFORMATION: a, t, c, g, unknown or other
<220> FEATURE:
<221> NAME/KEY: modified_base
<222> LOCATION: (211)..(212)
<223> OTHER INFORMATION: a, t, c, g, unknown or other
<220> FEATURE:
<221> NAME/KEY: modified_base
<222> LOCATION: (222)..(222)
<223> OTHER INFORMATION: a, t, c, g, unknown or other
<220> FEATURE:
<221> NAME/KEY: modified_base
<222> LOCATION: (224)..(226)
<223> OTHER INFORMATION: a, t, c, g, unknown or other
<220> FEATURE:
<221> NAME/KEY: modified_base
<222> LOCATION: (231)..(231)
<223> OTHER INFORMATION: a, t, c, g, unknown or other
<220> FEATURE:
<221> NAME/KEY: modified_base
<222> LOCATION: (233)..(234)
<223> OTHER INFORMATION: a, t, c, g, unknown or other
<220> FEATURE:
<221> NAME/KEY: modified_base
<222> LOCATION: (239)..(239)
<223> OTHER INFORMATION: a, t, c, g, unknown or other
<220> FEATURE:
<221> NAME/KEY: modified_base -continued
<222> LOCATION: (243)..(243)
<223> OTHER INFORMATION: a, t, c, g, unknown or other
<220> FEATURE:
<221> NAME/KEY: modified_base
<222> LOCATION: (247)..(247)
<223> OTHER INFORMATION: a, t, c, g, unknown or other
<220> FEATURE:
<221> NAME/KEY: modified_base
<222> LOCATION: (250)..(250)
<223> OTHER INFORMATION: a, t, c, g, unknown or other
<220> FEATURE:
<221> NAME/KEY: modified_base
<222> LOCATION: (254)..(254)
<223> OTHER INFORMATION: a, t, c, g, unknown or other
<220> FEATURE:
<221> NAME/KEY: modified_base
<222> LOCATION: (262)..(262)
<223> OTHER INFORMATION: a, t, c, g, unknown or other
<220> FEATURE:
<221> NAME/KEY: modified_base
<222> LOCATION: (265)..(266)
<223> OTHER INFORMATION: a, t, c, g, unknown or other
<220> FEATURE:
<221> NAME/KEY: modified_base
<222> LOCATION: (272)..(272)
<223> OTHER INFORMATION: a, t, c, g, unknown or other
<220> FEATURE:
<221> NAME/KEY: modified_base
<222> LOCATION: (281)..(281)
<223> OTHER INFORMATION: a, t, c, g, unknown or other
<220> FEATURE:
<221> NAME/KEY: modified_base
<222> LOCATION: (288)..(289)
<223> OTHER INFORMATION: a, t, c, g, unknown or other
<220> FEATURE:
<221> NAME/KEY: modified_base
<222> LOCATION: (299)..(299)
<223> OTHER INFORMATION: a, t, c, g, unknown or other
<220> FEATURE:
<221> NAME/KEY: modified_base
<222> LOCATION: (305)..(305)
<223> OTHER INFORMATION: a, t, c, g, unknown or other
<220> FEATURE:
<221> NAME/KEY: modified_base
<222> LOCATION: (307)..(307)
<223> OTHER INFORMATION: a, t, c, g, unknown or other
<220> FEATURE:
<221> NAME/KEY: modified_base
<222> LOCATION: (311)..(313)
<223> OTHER INFORMATION: a, t, c, g, unknown or other
<220> FEATURE:
<221> NAME/KEY: modified_base
<222> LOCATION: (320)..(320)
<223> OTHER INFORMATION: a, t, c, g, unknown or other
<220> FEATURE:
<221> NAME/KEY: modified_base
<222> LOCATION: (326)..(326)
<223> OTHER INFORMATION: a, t, c, g, unknown or other
<220> FEATURE:
<221> NAME/KEY: modified_base
<222> LOCATION: (328)..(328)
<223> OTHER INFORMATION: a, t, c, g, unknown or other
<220> FEATURE:
<221> NAME/KEY: modified_base
<222> LOCATION: (332)..(333)
<223> OTHER INFORMATION: a, t, c, g, unknown or other
<220> FEATURE:
<221> NAME/KEY: modified_base
<222> LOCATION: (342)..(342)
<223> OTHER INFORMATION: a, t, c, g, unknown or other
<220> FEATURE:
<221> NAME/KEY: modified_base
<222> LOCATION: (348)..(350)
<223> OTHER INFORMATION: a, t, c, g, unknown or other
<220> FEATURE:
<221> NAME/KEY: modified_base
<222> LOCATION: (355)..(357)
<223> OTHER INFORMATION: a, t, c, g, unknown or other
<220> FEATURE:

-continued

<221> NAME/KEY: modified_base
<222> LOCATION: (369)..(369)
<223> OTHER INFORMATION: a, t, c, g, unknown or other
<220> FEATURE:
<221> NAME/KEY: modified_base
<222> LOCATION: (376)..(376)
<223> OTHER INFORMATION: a, t, c, g, unknown or other
<220> FEATURE:
<221> NAME/KEY: modified_base
<222> LOCATION: (378)..(378)
<223> OTHER INFORMATION: a, t, c, g, unknown or other
<220> FEATURE:
<221> NAME/KEY: modified_base
<222> LOCATION: (380)..(380)
<223> OTHER INFORMATION: a, t, c, g, unknown or other
<220> FEATURE:
<221> NAME/KEY: modified_base
<222> LOCATION: (382)..(382)
<223> OTHER INFORMATION: a, t, c, g, unknown or other
<220> FEATURE:
<221> NAME/KEY: modified_base
<222> LOCATION: (386)..(389)
<223> OTHER INFORMATION: a, t, c, g, unknown or other
<220> FEATURE:
<221> NAME/KEY: modified_base
<222> LOCATION: (391)..(391)
<223> OTHER INFORMATION: a, t, c, g, unknown or other
<220> FEATURE:
<221> NAME/KEY: modified_base
<222> LOCATION: (394)..(395)
<223> OTHER INFORMATION: a, t, c, g, unknown or other
<220> FEATURE:
<221> NAME/KEY: modified_base
<222> LOCATION: (397)..(397)
<223> OTHER INFORMATION: a, t, c, g, unknown or other
<220> FEATURE:
<221> NAME/KEY: modified_base
<222> LOCATION: (400)..(400)
<223> OTHER INFORMATION: a, t, c, g, unknown or other
<220> FEATURE:
<221> NAME/KEY: modified_base
<222> LOCATION: (404)..(405)
<223> OTHER INFORMATION: a, t, c, g, unknown or other
<220> FEATURE:
<221> NAME/KEY: modified_base
<222> LOCATION: (411)..(411)
<223> OTHER INFORMATION: a, t, c, g, unknown or other
<220> FEATURE:
<221> NAME/KEY: modified_base
<222> LOCATION: (414)..(416)
<223> OTHER INFORMATION: a, t, c, g, unknown or other
<220> FEATURE:
<221> NAME/KEY: modified_base
<222> LOCATION: (419)..(419)
<223> OTHER INFORMATION: a, t, c, g, unknown or other
<220> FEATURE:
<221> NAME/KEY: modified_base
<222> LOCATION: (423)..(423)
<223> OTHER INFORMATION: a, t, c, g, unknown or other
<220> FEATURE:
<221> NAME/KEY: modified_base
<222> LOCATION: (427)..(427)
<223> OTHER INFORMATION: a, t, c, g, unknown or other
<220> FEATURE:
<221> NAME/KEY: modified_base
<222> LOCATION: (432)..(433)
<223> OTHER INFORMATION: a, t, c, g, unknown or other
<220> FEATURE:
<221> NAME/KEY: modified_base
<222> LOCATION: (446)..(446)
<223> OTHER INFORMATION: a, t, c, g, unknown or other
<220> FEATURE:
<221> NAME/KEY: modified_base
<222> LOCATION: (450)..(450)
<223> OTHER INFORMATION: a, t, c, g, unknown or other
<220> FEATURE:
<221> NAME/KEY: modified_base
<222> LOCATION: (455)..(455)
<223> OTHER INFORMATION: a, t, c, g, unknown or other
<220> FEATURE:
<221> NAME/KEY: modified_base
<222> LOCATION: (461)..(461)
<223> OTHER INFORMATION: a, t, c, g, unknown or other
<220> FEATURE:
<221> NAME/KEY: modified_base
<222> LOCATION: (465)..(465)
<223> OTHER INFORMATION: a, t, c, g, unknown or other
<220> FEATURE:
<221> NAME/KEY: modified_base
<222> LOCATION: (477)..(477)
<223> OTHER INFORMATION: a, t, c, g, unknown or other
<220> FEATURE:
<221> NAME/KEY: modified_base
<222> LOCATION: (487)..(487)
<223> OTHER INFORMATION: a, t, c, g, unknown or other
<220> FEATURE:
<221> NAME/KEY: modified_base
<222> LOCATION: (492)..(494)
<223> OTHER INFORMATION: a, t, c, g, unknown or other
<220> FEATURE:
<221> NAME/KEY: modified_base
<222> LOCATION: (496)..(496)
<223> OTHER INFORMATION: a, t, c, g, unknown or other
<220> FEATURE:
<221> NAME/KEY: modified_base
<222> LOCATION: (498)..(498)
<223> OTHER INFORMATION: a, t, c, g, unknown or other
<220> FEATURE:
<221> NAME/KEY: modified_base
<222> LOCATION: (505)..(505)
<223> OTHER INFORMATION: a, t, c, g, unknown or other
<220> FEATURE:
<221> NAME/KEY: modified_base
<222> LOCATION: (507)..(507)
<223> OTHER INFORMATION: a, t, c, g, unknown or other
<220> FEATURE:
<221> NAME/KEY: modified_base
<222> LOCATION: (509)..(509)
<223> OTHER INFORMATION: a, t, c, g, unknown or other
<220> FEATURE:
<221> NAME/KEY: modified_base
<222> LOCATION: (522)..(525)
<223> OTHER INFORMATION: a, t, c, g, unknown or other
<220> FEATURE:
<221> NAME/KEY: modified_base
<222> LOCATION: (528)..(528)
<223> OTHER INFORMATION: a, t, c, g, unknown or other
<220> FEATURE:
<221> NAME/KEY: modified_base
<222> LOCATION: (530)..(530)
<223> OTHER INFORMATION: a, t, c, g, unknown or other
<220> FEATURE:
<221> NAME/KEY: modified_base
<222> LOCATION: (535)..(535)
<223> OTHER INFORMATION: a, t, c, g, unknown or other
<220> FEATURE:
<221> NAME/KEY: modified_base
<222> LOCATION: (540)..(542)
<223> OTHER INFORMATION: a, t, c, g, unknown or other
<220> FEATURE:
<221> NAME/KEY: modified_base
<222> LOCATION: (544)..(546)
<223> OTHER INFORMATION: a, t, c, g, unknown or other
<220> FEATURE:
<221> NAME/KEY: modified_base
<222> LOCATION: (550)..(550)
<223> OTHER INFORMATION: a, t, c, g, unknown or other
<220> FEATURE:
<221> NAME/KEY: modified_base
<222> LOCATION: (558)..(558)
<223> OTHER INFORMATION: a, t, c, g, unknown or other
<220> FEATURE:
<221> NAME/KEY: modified_base
<222> LOCATION: (564)..(564)
<223> OTHER INFORMATION: a, t, c, g, unknown or other
<220> FEATURE:
<221> NAME/KEY: modified_base
<222> LOCATION: (568)..(568)

<223> OTHER INFORMATION: a, t, c, g, unknown or other
<220> FEATURE:
<221> NAME/KEY: modified_base
<222> LOCATION: (574)..(574)
<223> OTHER INFORMATION: a, t, c, g, unknown or other
<220> FEATURE:
<221> NAME/KEY: modified_base
<222> LOCATION: (580)..(580)
<223> OTHER INFORMATION: a, t, c, g, unknown or other
<220> FEATURE:
<221> NAME/KEY: modified_base
<222> LOCATION: (582)..(582)
<223> OTHER INFORMATION: a, t, c, g, unknown or other
<220> FEATURE:
<221> NAME/KEY: modified_base
<222> LOCATION: (584)..(585)
<223> OTHER INFORMATION: a, t, c, g, unknown or other
<220> FEATURE:
<221> NAME/KEY: modified_base
<222> LOCATION: (589)..(590)
<223> OTHER INFORMATION: a, t, c, g, unknown or other
<220> FEATURE:
<221> NAME/KEY: modified_base
<222> LOCATION: (592)..(592)
<223> OTHER INFORMATION: a, t, c, g, unknown or other
<220> FEATURE:
<221> NAME/KEY: modified_base
<222> LOCATION: (595)..(597)
<223> OTHER INFORMATION: a, t, c, g, unknown or other
<220> FEATURE:
<221> NAME/KEY: modified_base
<222> LOCATION: (604)..(604)
<223> OTHER INFORMATION: a, t, c, g, unknown or other
<220> FEATURE:
<221> NAME/KEY: modified_base
<222> LOCATION: (609)..(609)
<223> OTHER INFORMATION: a, t, c, g, unknown or other
<220> FEATURE:
<221> NAME/KEY: modified_base
<222> LOCATION: (612)..(612)
<223> OTHER INFORMATION: a, t, c, g, unknown or other
<220> FEATURE:
<221> NAME/KEY: modified_base
<222> LOCATION: (617)..(617)
<223> OTHER INFORMATION: a, t, c, g, unknown or other
<220> FEATURE:
<221> NAME/KEY: modified_base
<222> LOCATION: (622)..(623)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (637)..(637)
<223> OTHER INFORMATION: a, t, c, g, unknown or other
<220> FEATURE:
<221> NAME/KEY: modified_base
<222> LOCATION: (642)..(642)
<223> OTHER INFORMATION: a, t, c, g, unknown or other
<220> FEATURE:
<221> NAME/KEY: modified_base
<222> LOCATION: (653)..(653)
<223> OTHER INFORMATION: a, t, c, g, unknown or other
<220> FEATURE:
<221> NAME/KEY: modified_base
<222> LOCATION: (656)..(657)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (670)..(671)
<223> OTHER INFORMATION: a, t, c, g, unknown or other
<220> FEATURE:
<221> NAME/KEY: modified_base -continued
<222> LOCATION: (673)..(673)
<223> OTHER INFORMATION: a, t, c, g, unknown or other
<220> FEATURE:
<221> NAME/KEY: modified_base
<222> LOCATION: (680)..(680)
<223> OTHER INFORMATION: a, t, c, g, unknown or other
<220> FEATURE:
<221> NAME/KEY: modified_base
<222> LOCATION: (684)..(684)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (692)..(692)
<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (698)..(700)
<223> OTHER INFORMATION: a, t, c, g, unknown or other
<220> FEATURE:
<221> NAME/KEY: modified_base
<222> LOCATION: (710)..(711)
<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (746)..(747)
<223> OTHER INFORMATION: a, t, c, g, unknown or other
<220> FEATURE:
<221> NAME/KEY: modified_base
<222> LOCATION: (760)..(761)
<223> OTHER INFORMATION: a, t, c, g, unknown or other
<220> FEATURE:
<221> NAME/KEY: modified_base
<222> LOCATION: (768)..(771)
<223> OTHER INFORMATION: a, t, c, g, unknown or other
<220> FEATURE:
<221> NAME/KEY: modified_base
<222> LOCATION: (777)..(777)
<223> OTHER INFORMATION: a, t, c, g, unknown or other
<220> FEATURE:
<221> NAME/KEY: modified_base
<222> LOCATION: (788)..(788)
<223> OTHER INFORMATION: a, t, c, g, unknown or other
<220> FEATURE:
<221> NAME/KEY: modified_base
<222> LOCATION: (791)..(791)
<223> OTHER INFORMATION: a, t, c, g, unknown or other

<400> SEQUENCE: 62
ctttggcaaa aagacccgna aanancanaa tatnaanaaa tttttcaaan acanaatttt 60
tcnaaaaacn nnggnaancc ttanaanggg gatnnccnan nnaaacnagg aaanccccat 120
ananatnann tacccaanna aananaanac ncnnntaant acngannaan nanananaaa 180

```
aannaaanna nccaaaaana aacctnanna nncacaacaa angnnnacaa nannaaaana    240

tanccanaan cacnaaaaca anaannacaa anaaaacaca nataaaanna aaaacaaanc    300

ataanantaa nnnacacaan acagananaa annaaaaaag anaaaagnnn actcnnnaac    360

aacaaaaana aaacgnanan tnacannnna ncanncnaan accnnccaaa naannnaana    420

canaaanaac annactatca cacgcncaan actanataca nacancccaa cacaaantaa    480

tcaaaanacc tnnncnanaa actcntnana caaaaaaaaa cnnnnatngn tacanaacan    540

nnannngacn aaaccacnaa cacncaanaa aacncaaacn anannaaann tnatnnnaac    600

aaanaacana gnaatcnacc anngaacata anaacanaaa cnacaaaaca aanaanntaa    660

caacaaanan nanaaccacn tacnaaaaan cncaanannn aacacataan nantcaaacc    720

aacaaaanac ctacacanaa tacnanncaa aagaataccn naaacacnnn nataaanata    780

acatacanac ngaaacccg                                                 799
```

```
<210> SEQ ID NO 63
<211> LENGTH: 796
<212> TYPE: DNA
<213> ORGANISM: Homo sapiens
<220> FEATURE:
<221> NAME/KEY: modified_base
<222> LOCATION: (584)..(584)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (751)..(751)
<223> OTHER INFORMATION: a, t, c, g, unknown or other
<220> FEATURE:
<221> NAME/KEY: modified_base
<222> LOCATION: (772)..(772)
<223> OTHER INFORMATION: a, t, c, g, unknown or other
<220> FEATURE:
<221> NAME/KEY: modified_base
<222> LOCATION: (784)..(784)
<223> OTHER INFORMATION: a, t, c, g, unknown or other
<220> FEATURE:
<221> NAME/KEY: modified_base
<222> LOCATION: (786)..(786)
<223> OTHER INFORMATION: a, t, c, g, unknown or other
<220> FEATURE:
<221> NAME/KEY: modified_base
<222> LOCATION: (791)..(791)
<223> OTHER INFORMATION: a, t, c, g, unknown or other

<400> SEQUENCE: 63
```

```
gcctgttggc ctactggagc aaaagaagaa gaagaaggag gtgaaggtga agaaggagag     60

gaaaccaaag aagctgaaga ggaggagaag aaagttgaag gtgctgggga ggaacaagca    120

gctaagaaga aagattgaac ccccatttcc ttaattattt caggaataat tctcccgaaa    180

tcaggtcaac cccatcacca accaaccaac cagttgagtt ccagattcta tgtgaattaa    240

aaagtcaata tatgtataat tctgagatga cttaggttgg acattcaatg ttgtgctatg    300

aatttcctct ttatgcagag tatctgtttg cttgcagagt ggctttctgg cttgctgcca    360

gcctgtgcat ggtccacgct tatgagttca ggatctacgg caatgtgaat cattcagatg    420

tttacaataa aaaacaccac atgagtaaat gaattcacta atgttaatgt taaacttcat    480

ggaaaaatag tcctttgaac cttcggtggt tagcaattaa agaccctgag ttatgtgcaa    540
```

```
taaatagtaa ataaagttat cccgaatgat gtatttttg ctgnggttgg tacttaatta    600

aaatacctta aagatggcac caatataaag tatatccagt ggctattgcc tncaattttt   660

aaaaagttga aattttaaca attccaatac tttttttctt cttcaattgg aaattctgag   720

ggatncagta tgcatgattc ctggggaaat ntttcccaca aaaatttact gntattaaca   780

tgantnaatg ngaaag                                                   796
```

<210> SEQ ID NO 64
<211> LENGTH: 821
<212> TYPE: DNA
<213> ORGANISM: Homo sapiens
<220> FEATURE:
<221> NAME/KEY: modified_base
<222> LOCATION: (13)..(13)
<223> OTHER INFORMATION: a, t, c, g, unknown or other
<220> FEATURE:
<221> NAME/KEY: modified_base
<222> LOCATION: (110)..(110)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (731)..(731)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other
<220> FEATURE:
<221> NAME/KEY: modified_base
<222> LOCATION: (772)..(772)
<223> OTHER INFORMATION: a, t, c, g, unknown or other
<220> FEATURE:
<221> NAME/KEY: modified_base
<222> LOCATION: (789)..(789)
<223> OTHER INFORMATION: a, t, c, g, unknown or other
<220> FEATURE:
<221> NAME/KEY: modified_base
<222> LOCATION: (795)..(797)
<223> OTHER INFORMATION: a, t, c, g, unknown or other
<220> FEATURE:
<221> NAME/KEY: modified_base
<222> LOCATION: (800)..(800)
<223> OTHER INFORMATION: a, t, c, g, unknown or other
<220> FEATURE:
<221> NAME/KEY: modified_base
<222> LOCATION: (811)..(813)
<223> OTHER INFORMATION: a, t, c, g, unknown or other
<220> FEATURE:
<221> NAME/KEY: modified_base
<222> LOCATION: (817)..(817)
<223> OTHER INFORMATION: a, t, c, g, unknown or other

<400> SEQUENCE: 64

```
tttttctta ggnttttac tattttatta tggcacacag gatagaggat ggtacagttt     60

tcttacttca accaagtaat tctcaaagca tccagctatt tccatttggn taaagttact   120

ttttgcacat agcttgcatc tgtttgagac ttaccatgta catcaaccca ggtctagtaa   180

gcagaaatgt gaaaagtttt gtttctgagg agacgcctca tctttacaga agccaataca   240

ctgagagcct tcatagttcc aatccattac catcatggca aggaagcact ttacctattc   300

gcatagcaac atatatttaa ctagaaatag gtggtacaaa gggattaagt aactttaaat   360
```

-continued

```
ggagaccact ttggtttcag gttaaattaa taacttatag agatcgctaa aaaacaaata    420

ttgaatgaaa ttagctgcaa agcaattgtt tcagaacaaa ggcagaatag cagatagtaa    480

tatcatctat atttattcca catcaaatgc aagagcgttc ttaactttac gacagaaagg    540

atacatgggg ccgtgtattt gatgcaatgt ccaaccagtc aagctatcat tgaaatccaa    600

atatttccag tagagacatg cagagcaatg tcaatgtaac atacaagcnt attaccttcc    660

cccttaagtg actcataatt tcattacttg gggctgnagc ttttaaaagg ttaaaaatgt    720

gtaccattaa ntgggattac tttgagggac cagaattncg cttaacaacc cncttaatca    780

tgacctcang gattnnngcn acatgttttc nnnggantgg g                       821
```

```
<210> SEQ ID NO 65
<211> LENGTH: 738
<212> TYPE: DNA
<213> ORGANISM: Homo sapiens
<220> FEATURE:
<221> NAME/KEY: modified_base
<222> LOCATION: (59)..(59)
<223> OTHER INFORMATION: a, t, c, g, unknown or other
<220> FEATURE:
<221> NAME/KEY: modified_base
<222> LOCATION: (76)..(76)
<223> OTHER INFORMATION: a, t, c, g, unknown or other
<220> FEATURE:
<221> NAME/KEY: modified_base
<222> LOCATION: (89)..(89)
<223> OTHER INFORMATION: a, t, c, g, unknown or other
<220> FEATURE:
<221> NAME/KEY: modified_base
<222> LOCATION: (91)..(91)
<223> OTHER INFORMATION: a, t, c, g, unknown or other
<220> FEATURE:
<221> NAME/KEY: modified_base
<222> LOCATION: (484)..(484)
<223> OTHER INFORMATION: a, t, c, g, unknown or other
<220> FEATURE:
<221> NAME/KEY: modified_base
<222> LOCATION: (535)..(535)
<223> OTHER INFORMATION: a, t, c, g, unknown or other
<220> FEATURE:
<221> NAME/KEY: modified_base
<222> LOCATION: (537)..(537)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (720)..(721)
<223> OTHER INFORMATION: a, t, c, g, unknown or other

<400> SEQUENCE: 65

ctgtcagtca cattatccca tttcctaggt ctgtctcttt ttctttgca gtttaattnt     60

tagtaaataa gagggnttta agtctcaang ntttggtcag agataaactc agacactgcc    120

tcgatatcac gaagttctca tttataccaa ctcttatctt cacgccaccg tgaattctca    180

tcggcataag gaggaaaaga gatggcacca aaggggaaaa aaatctggtg gtgtaatttg    240

gcatcttcat taagcaagcc atgagcagct tgtgaaatgc ttcatttatg gggccgccag    300

ctgggagaga gaggcgttct cacaatgcct tgaaaatggg aactttgcat cctttaaatt    360

tttccaaact gacttagttt gtttaccttg aatttctggg atggggcaaa tgtgaccttc    420

atgctatagg gcccacgttt ccagatttgg tatggaaaga aggaagaaag tctgaccctc    480

ttgnttttaa gataggcaaa aggaagatga gatagtccat ggttcaccac ccaangncct    540

tctgggcact ggctgggctg acgctgggcc tggttccagc tatgcctacc tttctcttgc    600
```

```
cataccacac cgttgcttta tgagcattct tttggtaagg ncaagatcaa gataaccttt    660

ttcctttgaa taataggacc agcacctttc ccagtgggcc tttaatggca tctgaatgtn    720

naaagggaaa ccaccctt                                                  738


<210> SEQ ID NO 66
<211> LENGTH: 745
<212> TYPE: DNA
<213> ORGANISM: Homo sapiens
<220> FEATURE:
<221> NAME/KEY: modified_base
<222> LOCATION: (81)..(81)
<223> OTHER INFORMATION: a, t, c, g, unknown or other
<220> FEATURE:
<221> NAME/KEY: modified_base
<222> LOCATION: (84)..(84)
<223> OTHER INFORMATION: a, t, c, g, unknown or other
<220> FEATURE:
<221> NAME/KEY: modified_base
<222> LOCATION: (97)..(98)
<223> OTHER INFORMATION: a, t, c, g, unknown or other
<220> FEATURE:
<221> NAME/KEY: modified_base
<222> LOCATION: (332)..(332)
<223> OTHER INFORMATION: a, t, c, g, unknown or other
<220> FEATURE:
<221> NAME/KEY: modified_base
<222> LOCATION: (616)..(616)
<223> OTHER INFORMATION: a, t, c, g, unknown or other
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other

<400> SEQUENCE: 66

tctacgcata ggcatgtgcg tactgggcca taatgcaaaa cttgtcatct tttgctctag     60

attacagttg cagaagttga nggncactat tctaggnnat acctggttga ttattcctgg    120

ggcagacata cagatattga aactgcttta cagcagtgta tgatgatttt aacagtatca    180

tatgcctcat aatgttcact tttgctttca actatcctac aattttcatt aacttttcag    240

aaataccttg caaattgttt ttcatcttgt gctatcaaaa aaatgttctg ccagttgcat    300

tgagtcctta gtatctgtct agaggtgcag anatctccat agcaactcca cagatgagga    360

gggtgggctc ttaccttccc tggccagccc cagaggactc gtaatggcag agctgaggtc    420

acttacctgg ggatggttca tggcttagaa cacaataggt tttcaataaa cattagcttc    480

ttgaacaaat gcatatgtgg aatggcttta ccatttgcaa aaattagggt gtcaatgtgc    540

cagttaatat tacacattca cctatcgatc caccccacac tgcaatgaga acaggggtaa    600

aatatatgca gactgnaccc ttccactgat aggaaaaaat cancacgatc ataactctgc    660

cttgggattt ctgcatgcta ctacagcttn ccaggaangn ccaaagcttt actttgaatt    720

aacgctgaac ttggtttaat tgggg                                          745


<210> SEQ ID NO 67
```

<211> LENGTH: 739
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (71)..(72)
<223> OTHER INFORMATION: a, t, c, g, unknown or other
<220> FEATURE:
<221> NAME/KEY: modified_base
<222> LOCATION: (87)..(87)
<223> OTHER INFORMATION: a, t, c, g, unknown or other
<220> FEATURE:
<221> NAME/KEY: modified_base
<222> LOCATION: (116)..(116)
<223> OTHER INFORMATION: a, t, c, g, unknown or other
<220> FEATURE:
<221> NAME/KEY: modified_base
<222> LOCATION: (355)..(355)
<223> OTHER INFORMATION: a, t, c, g, unknown or other
<220> FEATURE:
<221> NAME/KEY: modified_base
<222> LOCATION: (623)..(623)
<223> OTHER INFORMATION: a, t, c, g, unknown or other
<220> FEATURE:
<221> NAME/KEY: modified_base
<222> LOCATION: (632)..(632)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (638)..(638)
<223> OTHER INFORMATION: a, t, c, g, unknown or other
<220> FEATURE:
<221> NAME/KEY: modified_base
<222> LOCATION: (654)..(654)
<223> OTHER INFORMATION: a, t, c, g, unknown or other
<220> FEATURE:
<221> NAME/KEY: modified_base
<222> LOCATION: (679)..(679)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (687)..(687)
<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base
<222> LOCATION: (730)..(730)
<223> OTHER INFORMATION: a, t, c, g, unknown or other

```
<400> SEQUENCE: 67

tnaaaccccc ctgctgttaa gacttgacat tcaatatttt ttgatcacat tctttttttat     60

agcttagcta nnggcaacat ttgtggncat ataaattgca aaagaagctt tctcgngtac    120

atacattttt aaaagcttga aattgatgtg aacttttaaa aacacgtagg atctgtatta    180

cattctacat ctcaaaacaa atttaattaa agtgaatatc attccagtat atacaatatg    240

cctaagaccc agaattggca cactgattta ctagttgaaa atataacagt attcaccaaa    300

cttcaatgta tactttttgg agagaatgaa attacagtat ttcttaattt actgnaatgt    360

catctttgta attatgaatt aacaattcaa tgagaggaga cttggttgat taaattaatg    420

ctggtcctac acattatatc taaaggatct tcgtatatga ctactatctt cttggattat    480

tttaacaggt aaaatatcaa agtggccatt aaaaacagag ttgacttttc accattgctg    540

gttttctggt gagacatgtg gaaaggaagg acaggtggac ttttcaacta actagctctc    600

tgatttttaa taagatcctc aantcttttg gnctnagnta cctatctgtc caanggtaag    660

catatgctta atcactaana cnggtanatc ctgccnttaa naaccttatn aaccaaatnc    720

tggaccntan ggtacaaaa                                                 739


<210> SEQ ID NO 68
<211> LENGTH: 747
<212> TYPE: DNA
<213> ORGANISM: Homo sapiens
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (54)..(54)
<223> OTHER INFORMATION: a, t, c, g, unknown or other
<220> FEATURE:
<221> NAME/KEY: modified_base
<222> LOCATION: (69)..(69)
<223> OTHER INFORMATION: a, t, c, g, unknown or other
<220> FEATURE:
<221> NAME/KEY: modified_base
<222> LOCATION: (81)..(81)
<223> OTHER INFORMATION: a, t, c, g, unknown or other
<220> FEATURE:
<221> NAME/KEY: modified_base
<222> LOCATION: (95)..(95)
<223> OTHER INFORMATION: a, t, c, g, unknown or other
<220> FEATURE:
<221> NAME/KEY: modified_base
<222> LOCATION: (111)..(112)
<223> OTHER INFORMATION: a, t, c, g, unknown or other
<220> FEATURE:
<221> NAME/KEY: modified_base
<222> LOCATION: (444)..(444)
<223> OTHER INFORMATION: a, t, c, g, unknown or other
<220> FEATURE:
<221> NAME/KEY: modified_base
<222> LOCATION: (501)..(501)
<223> OTHER INFORMATION: a, t, c, g, unknown or other
<220> FEATURE:
<221> NAME/KEY: modified_base
<222> LOCATION: (508)..(508)
<223> OTHER INFORMATION: a, t, c, g, unknown or other
<220> FEATURE:
<221> NAME/KEY: modified_base
<222> LOCATION: (538)..(538)
<223> OTHER INFORMATION: a, t, c, g, unknown or other
<220> FEATURE:
<221> NAME/KEY: modified_base
<222> LOCATION: (541)..(541)
<223> OTHER INFORMATION: a, t, c, g, unknown or other
<220> FEATURE:
```

<221> NAME/KEY: modified_base
<222> LOCATION: (545)..(545)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (622)..(622)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (654)..(654)
<223> OTHER INFORMATION: a, t, c, g, unknown or other
<220> FEATURE:
<221> NAME/KEY: modified_base
<222> LOCATION: (661)..(661)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (685)..(685)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other
<220> FEATURE:
<221> NAME/KEY: modified_base
<222> LOCATION: (716)..(716)
<223> OTHER INFORMATION: a, t, c, g, unknown or other
<220> FEATURE:
<221> NAME/KEY: modified_base
<222> LOCATION: (718)..(718)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (732)..(732)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (737)..(737)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other

<400> SEQUENCE: 68

```
aaaacctcca gnaatatttt cacactacct tctattttaa agttcacact tttnattcca     60
gagcagggna tggtcaggcc ngggtgggct ccccnccctc tccccttggc nntggtaacc    120
actggcccca gggactcagc ctgctttcct atccatcccc tcagtagctg tcaccatgca    180
ggttacccct tctgtttctt ctaccactaa ctccatgtct gactgcaagt gaaaggaaca    240
gaagcccaaa cctttgggtt ttaaggagtt tattgctaat ctgtaaaaca gaaagagaca    300
ggagataagc atgacaaaat atagggaaga aatgactttt gcctaaactt ccaattgtgt    360
acaattgaag cctctgcttt atagctctta gcacacctct caaataagaa ggcaagtact    420
gggaaagctc tgaacctgtg gcanaaccac tgatagctgt ggagctattc aaggagtctg    480
ggaatcaagg ggattatcaa nacattgnta gaataaatta atcttactgg atatatanca    540
naaantttc aagcatatgt aaatgctact aataccaaat aattacacct tgttttcttt    600
aaaccggaac tcttaaanat gnctctacaa aantttttga atnggaangg ctgnatgctc    660
naaaaacttn aaaacactac tgganaaaaa aggtctcngg aaggngatga aanccntnac    720
attggaacnt tnatnantta aatnggg                                        747
```

<210> SEQ ID NO 69
<211> LENGTH: 726
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (13)..(13)
<223> OTHER INFORMATION: a, t, c, g, unknown or other
<220> FEATURE:
<221> NAME/KEY: modified_base
<222> LOCATION: (596)..(596)
<223> OTHER INFORMATION: a, t, c, g, unknown or other
<220> FEATURE:
<221> NAME/KEY: modified_base
<222> LOCATION: (640)..(640)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other

<400> SEQUENCE: 69

```
tntctgtccc agnctgttga tcttaaaact agttgattta aagagttttt ttgcacatca     60
tttcaattat atttgtgaac ttagaaaggt aacttacaat ctaaccagcc atcatatcat    120
atcctatcag gctagatatc tcaatagtag actgaataca aagctaattt tttttacatg    180
tcaatattgg cacaaactgg aatgaaagaa tagtttgatt cagacctgct ccactatgtg    240
ttgctaaaac acatgctatg agcactccag gaaacactat attttttcca aaaaatatgt    300
gattatatat gttaaagtat agataacatt tcacacttgg atacatatgt gcatttactg    360
tatttcttgg taagcatatt tttgggggaa agtgctgctg atatgataca agtagacaaa    420
```

-continued

```
atttaaatga aattttgcac attctatgga aaatggtttc tggtaaactg agaaggatat    480

taaaataagt ggcttttttc tgggctacca ttattggttg atttctcttt gcaagtgtat    540

agaacctgtc atacattcat gataaggagc actgaaaaat tactcattca aatttnccct    600

gggcacgtaa ggcaaaatat tggccggttg ggatttcaan ggcaagtgac gacgcaattt    660

ccttccagtc agacccccca gncccccttg ctgggacatg gggangcana aagtcccttg    720

accatc                                                               726
```

```
<210> SEQ ID NO 70
<211> LENGTH: 854
<212> TYPE: DNA
<213> ORGANISM: Homo sapiens
<220> FEATURE:
<221> NAME/KEY: modified_base
<222> LOCATION: (19)..(19)
<223> OTHER INFORMATION: a, t, c, g, unknown or other
<220> FEATURE:
<221> NAME/KEY: modified_base
<222> LOCATION: (30)..(30)
<223> OTHER INFORMATION: a, t, c, g, unknown or other
<220> FEATURE:
<221> NAME/KEY: modified_base
<222> LOCATION: (35)..(36)
<223> OTHER INFORMATION: a, t, c, g, unknown or other
<220> FEATURE:
<221> NAME/KEY: modified_base
<222> LOCATION: (39)..(39)
<223> OTHER INFORMATION: a, t, c, g, unknown or other
<220> FEATURE:
<221> NAME/KEY: modified_base
<222> LOCATION: (44)..(44)
<223> OTHER INFORMATION: a, t, c, g, unknown or other
<220> FEATURE:
<221> NAME/KEY: modified_base
<222> LOCATION: (56)..(56)
<223> OTHER INFORMATION: a, t, c, g, unknown or other
<220> FEATURE:
<221> NAME/KEY: modified_base
<222> LOCATION: (58)..(58)
<223> OTHER INFORMATION: a, t, c, g, unknown or other
<220> FEATURE:
<221> NAME/KEY: modified_base
<222> LOCATION: (60)..(60)
<223> OTHER INFORMATION: a, t, c, g, unknown or other
<220> FEATURE:
<221> NAME/KEY: modified_base
<222> LOCATION: (63)..(63)
<223> OTHER INFORMATION: a, t, c, g, unknown or other
<220> FEATURE:
<221> NAME/KEY: modified_base
<222> LOCATION: (67)..(67)
<223> OTHER INFORMATION: a, t, c, g, unknown or other
<220> FEATURE:
<221> NAME/KEY: modified_base
<222> LOCATION: (81)..(82)
<223> OTHER INFORMATION: a, t, c, g, unknown or other
<220> FEATURE:
<221> NAME/KEY: modified_base
<222> LOCATION: (86)..(86)
<223> OTHER INFORMATION: a, t, c, g, unknown or other
<220> FEATURE:
<221> NAME/KEY: modified_base
<222> LOCATION: (90)..(90)
<223> OTHER INFORMATION: a, t, c, g, unknown or other
<220> FEATURE:
<221> NAME/KEY: modified_base
<222> LOCATION: (93)..(94)
<223> OTHER INFORMATION: a, t, c, g, unknown or other
<220> FEATURE:
<221> NAME/KEY: modified_base
<222> LOCATION: (96)..(97)
<223> OTHER INFORMATION: a, t, c, g, unknown or other
<220> FEATURE:
<221> NAME/KEY: modified_base
```

<222> LOCATION: (99)..(99)
<223> OTHER INFORMATION: a, t, c, g, unknown or other
<220> FEATURE:
<221> NAME/KEY: modified_base
<222> LOCATION: (103)..(103)
<223> OTHER INFORMATION: a, t, c, g, unknown or other
<220> FEATURE:
<221> NAME/KEY: modified_base
<222> LOCATION: (105)..(105)
<223> OTHER INFORMATION: a, t, c, g, unknown or other
<220> FEATURE:
<221> NAME/KEY: modified_base
<222> LOCATION: (108)..(109)
<223> OTHER INFORMATION: a, t, c, g, unknown or other
<220> FEATURE:
<221> NAME/KEY: modified_base
<222> LOCATION: (114)..(115)
<223> OTHER INFORMATION: a, t, c, g, unknown or other
<220> FEATURE:
<221> NAME/KEY: modified_base
<222> LOCATION: (119)..(119)
<223> OTHER INFORMATION: a, t, c, g, unknown or other
<220> FEATURE:
<221> NAME/KEY: modified_base
<222> LOCATION: (122)..(123)
<223> OTHER INFORMATION: a, t, c, g, unknown or other
<220> FEATURE:
<221> NAME/KEY: modified_base
<222> LOCATION: (127)..(127)
<223> OTHER INFORMATION: a, t, c, g, unknown or other
<220> FEATURE:
<221> NAME/KEY: modified_base
<222> LOCATION: (134)..(134)
<223> OTHER INFORMATION: a, t, c, g, unknown or other
<220> FEATURE:
<221> NAME/KEY: modified_base
<222> LOCATION: (159)..(159)
<223> OTHER INFORMATION: a, t, c, g, unknown or other
<220> FEATURE:
<221> NAME/KEY: modified_base
<222> LOCATION: (162)..(162)
<223> OTHER INFORMATION: a, t, c, g, unknown or other
<220> FEATURE:
<221> NAME/KEY: modified_base
<222> LOCATION: (164)..(164)
<223> OTHER INFORMATION: a, t, c, g, unknown or other
<220> FEATURE:
<221> NAME/KEY: modified_base
<222> LOCATION: (172)..(172)
<223> OTHER INFORMATION: a, t, c, g, unknown or other
<220> FEATURE:
<221> NAME/KEY: modified_base
<222> LOCATION: (179)..(179)
<223> OTHER INFORMATION: a, t, c, g, unknown or other
<220> FEATURE:
<221> NAME/KEY: modified_base
<222> LOCATION: (181)..(181)
<223> OTHER INFORMATION: a, t, c, g, unknown or other
<220> FEATURE:
<221> NAME/KEY: modified_base
<222> LOCATION: (185)..(186)
<223> OTHER INFORMATION: a, t, c, g, unknown or other
<220> FEATURE:
<221> NAME/KEY: modified_base
<222> LOCATION: (188)..(188)
<223> OTHER INFORMATION: a, t, c, g, unknown or other
<220> FEATURE:
<221> NAME/KEY: modified_base
<222> LOCATION: (196)..(196)
<223> OTHER INFORMATION: a, t, c, g, unknown or other
<220> FEATURE:
<221> NAME/KEY: modified_base
<222> LOCATION: (198)..(199)
<223> OTHER INFORMATION: a, t, c, g, unknown or other
<220> FEATURE:
<221> NAME/KEY: modified_base
<222> LOCATION: (207)..(208)
<223> OTHER INFORMATION: a, t, c, g, unknown or other
<220> FEATURE:

-continued

<221> NAME/KEY: modified_base
<222> LOCATION: (210)..(211)
<223> OTHER INFORMATION: a, t, c, g, unknown or other
<220> FEATURE:
<221> NAME/KEY: modified_base
<222> LOCATION: (217)..(217)
<223> OTHER INFORMATION: a, t, c, g, unknown or other
<220> FEATURE:
<221> NAME/KEY: modified_base
<222> LOCATION: (222)..(222)
<223> OTHER INFORMATION: a, t, c, g, unknown or other
<220> FEATURE:
<221> NAME/KEY: modified_base
<222> LOCATION: (227)..(227)
<223> OTHER INFORMATION: a, t, c, g, unknown or other
<220> FEATURE:
<221> NAME/KEY: modified_base
<222> LOCATION: (229)..(229)
<223> OTHER INFORMATION: a, t, c, g, unknown or other
<220> FEATURE:
<221> NAME/KEY: modified_base
<222> LOCATION: (235)..(235)
<223> OTHER INFORMATION: a, t, c, g, unknown or other
<220> FEATURE:
<221> NAME/KEY: modified_base
<222> LOCATION: (253)..(253)
<223> OTHER INFORMATION: a, t, c, g, unknown or other
<220> FEATURE:
<221> NAME/KEY: modified_base
<222> LOCATION: (259)..(259)
<223> OTHER INFORMATION: a, t, c, g, unknown or other
<220> FEATURE:
<221> NAME/KEY: modified_base
<222> LOCATION: (273)..(274)
<223> OTHER INFORMATION: a, t, c, g, unknown or other
<220> FEATURE:
<221> NAME/KEY: modified_base
<222> LOCATION: (280)..(280)
<223> OTHER INFORMATION: a, t, c, g, unknown or other
<220> FEATURE:
<221> NAME/KEY: modified_base
<222> LOCATION: (287)..(288)
<223> OTHER INFORMATION: a, t, c, g, unknown or other
<220> FEATURE:
<221> NAME/KEY: modified_base
<222> LOCATION: (298)..(298)
<223> OTHER INFORMATION: a, t, c, g, unknown or other
<220> FEATURE:
<221> NAME/KEY: modified_base
<222> LOCATION: (300)..(300)
<223> OTHER INFORMATION: a, t, c, g, unknown or other
<220> FEATURE:
<221> NAME/KEY: modified_base
<222> LOCATION: (302)..(304)
<223> OTHER INFORMATION: a, t, c, g, unknown or other
<220> FEATURE:
<221> NAME/KEY: modified_base
<222> LOCATION: (306)..(306)
<223> OTHER INFORMATION: a, t, c, g, unknown or other
<220> FEATURE:
<221> NAME/KEY: modified_base
<222> LOCATION: (308)..(308)
<223> OTHER INFORMATION: a, t, c, g, unknown or other
<220> FEATURE:
<221> NAME/KEY: modified_base
<222> LOCATION: (313)..(313)
<223> OTHER INFORMATION: a, t, c, g, unknown or other
<220> FEATURE:
<221> NAME/KEY: modified_base
<222> LOCATION: (317)..(317)
<223> OTHER INFORMATION: a, t, c, g, unknown or other
<220> FEATURE:
<221> NAME/KEY: modified_base
<222> LOCATION: (319)..(319)
<223> OTHER INFORMATION: a, t, c, g, unknown or other
<220> FEATURE:
<221> NAME/KEY: modified_base
<222> LOCATION: (325)..(327)
<223> OTHER INFORMATION: a, t, c, g, unknown or other
<220> FEATURE:
<221> NAME/KEY: modified_base
<222> LOCATION: (331)..(331)
<223> OTHER INFORMATION: a, t, c, g, unknown or other
<220> FEATURE:
<221> NAME/KEY: modified_base
<222> LOCATION: (333)..(333)
<223> OTHER INFORMATION: a, t, c, g, unknown or other
<220> FEATURE:
<221> NAME/KEY: modified_base
<222> LOCATION: (347)..(348)
<223> OTHER INFORMATION: a, t, c, g, unknown or other
<220> FEATURE:
<221> NAME/KEY: modified_base
<222> LOCATION: (353)..(353)
<223> OTHER INFORMATION: a, t, c, g, unknown or other
<220> FEATURE:
<221> NAME/KEY: modified_base
<222> LOCATION: (364)..(365)
<223> OTHER INFORMATION: a, t, c, g, unknown or other
<220> FEATURE:
<221> NAME/KEY: modified_base
<222> LOCATION: (387)..(387)
<223> OTHER INFORMATION: a, t, c, g, unknown or other
<220> FEATURE:
<221> NAME/KEY: modified_base
<222> LOCATION: (393)..(393)
<223> OTHER INFORMATION: a, t, c, g, unknown or other
<220> FEATURE:
<221> NAME/KEY: modified_base
<222> LOCATION: (396)..(396)
<223> OTHER INFORMATION: a, t, c, g, unknown or other
<220> FEATURE:
<221> NAME/KEY: modified_base
<222> LOCATION: (401)..(401)
<223> OTHER INFORMATION: a, t, c, g, unknown or other
<220> FEATURE:
<221> NAME/KEY: modified_base
<222> LOCATION: (407)..(407)
<223> OTHER INFORMATION: a, t, c, g, unknown or other
<220> FEATURE:
<221> NAME/KEY: modified_base
<222> LOCATION: (412)..(412)
<223> OTHER INFORMATION: a, t, c, g, unknown or other
<220> FEATURE:
<221> NAME/KEY: modified_base
<222> LOCATION: (414)..(414)
<223> OTHER INFORMATION: a, t, c, g, unknown or other
<220> FEATURE:
<221> NAME/KEY: modified_base
<222> LOCATION: (416)..(416)
<223> OTHER INFORMATION: a, t, c, g, unknown or other
<220> FEATURE:
<221> NAME/KEY: modified_base
<222> LOCATION: (422)..(422)
<223> OTHER INFORMATION: a, t, c, g, unknown or other
<220> FEATURE:
<221> NAME/KEY: modified_base
<222> LOCATION: (424)..(425)
<223> OTHER INFORMATION: a, t, c, g, unknown or other
<220> FEATURE:
<221> NAME/KEY: modified_base
<222> LOCATION: (436)..(436)
<223> OTHER INFORMATION: a, t, c, g, unknown or other
<220> FEATURE:
<221> NAME/KEY: modified_base
<222> LOCATION: (444)..(445)
<223> OTHER INFORMATION: a, t, c, g, unknown or other
<220> FEATURE:
<221> NAME/KEY: modified_base
<222> LOCATION: (453)..(454)
<223> OTHER INFORMATION: a, t, c, g, unknown or other
<220> FEATURE:
<221> NAME/KEY: modified_base
<222> LOCATION: (457)..(457)
<223> OTHER INFORMATION: a, t, c, g, unknown or other
<220> FEATURE:
<221> NAME/KEY: modified_base
<222> LOCATION: (465)..(465)

<223> OTHER INFORMATION: a, t, c, g, unknown or other
<220> FEATURE:
<221> NAME/KEY: modified_base
<222> LOCATION: (479)..(479)
<223> OTHER INFORMATION: a, t, c, g, unknown or other
<220> FEATURE:
<221> NAME/KEY: modified_base
<222> LOCATION: (482)..(483)
<223> OTHER INFORMATION: a, t, c, g, unknown or other
<220> FEATURE:
<221> NAME/KEY: modified_base
<222> LOCATION: (485)..(485)
<223> OTHER INFORMATION: a, t, c, g, unknown or other
<220> FEATURE:
<221> NAME/KEY: modified_base
<222> LOCATION: (488)..(488)
<223> OTHER INFORMATION: a, t, c, g, unknown or other
<220> FEATURE:
<221> NAME/KEY: modified_base
<222> LOCATION: (497)..(497)
<223> OTHER INFORMATION: a, t, c, g, unknown or other
<220> FEATURE:
<221> NAME/KEY: modified_base
<222> LOCATION: (499)..(499)
<223> OTHER INFORMATION: a, t, c, g, unknown or other
<220> FEATURE:
<221> NAME/KEY: modified_base
<222> LOCATION: (505)..(507)
<223> OTHER INFORMATION: a, t, c, g, unknown or other
<220> FEATURE:
<221> NAME/KEY: modified_base
<222> LOCATION: (513)..(514)
<223> OTHER INFORMATION: a, t, c, g, unknown or other
<220> FEATURE:
<221> NAME/KEY: modified_base
<222> LOCATION: (521)..(521)
<223> OTHER INFORMATION: a, t, c, g, unknown or other
<220> FEATURE:
<221> NAME/KEY: modified_base
<222> LOCATION: (524)..(524)
<223> OTHER INFORMATION: a, t, c, g, unknown or other
<220> FEATURE:
<221> NAME/KEY: modified_base
<222> LOCATION: (529)..(529)
<223> OTHER INFORMATION: a, t, c, g, unknown or other
<220> FEATURE:
<221> NAME/KEY: modified_base
<222> LOCATION: (536)..(536)
<223> OTHER INFORMATION: a, t, c, g, unknown or other
<220> FEATURE:
<221> NAME/KEY: modified_base
<222> LOCATION: (544)..(544)
<223> OTHER INFORMATION: a, t, c, g, unknown or other
<220> FEATURE:
<221> NAME/KEY: modified_base
<222> LOCATION: (547)..(547)
<223> OTHER INFORMATION: a, t, c, g, unknown or other
<220> FEATURE:
<221> NAME/KEY: modified_base
<222> LOCATION: (552)..(552)
<223> OTHER INFORMATION: a, t, c, g, unknown or other
<220> FEATURE:
<221> NAME/KEY: modified_base
<222> LOCATION: (554)..(554)
<223> OTHER INFORMATION: a, t, c, g, unknown or other
<220> FEATURE:
<221> NAME/KEY: modified_base
<222> LOCATION: (557)..(557)
<223> OTHER INFORMATION: a, t, c, g, unknown or other
<220> FEATURE:
<221> NAME/KEY: modified_base
<222> LOCATION: (562)..(562)
<223> OTHER INFORMATION: a, t, c, g, unknown or other
<220> FEATURE:
<221> NAME/KEY: modified_base
<222> LOCATION: (565)..(565)
<223> OTHER INFORMATION: a, t, c, g, unknown or other
<220> FEATURE:
<221> NAME/KEY: modified_base
<222> LOCATION: (574)..(574)
<223> OTHER INFORMATION: a, t, c, g, unknown or other
<220> FEATURE:
<221> NAME/KEY: modified_base
<222> LOCATION: (580)..(580)
<223> OTHER INFORMATION: a, t, c, g, unknown or other
<220> FEATURE:
<221> NAME/KEY: modified_base
<222> LOCATION: (582)..(585)
<223> OTHER INFORMATION: a, t, c, g, unknown or other
<220> FEATURE:
<221> NAME/KEY: modified_base
<222> LOCATION: (588)..(588)
<223> OTHER INFORMATION: a, t, c, g, unknown or other
<220> FEATURE:
<221> NAME/KEY: modified_base
<222> LOCATION: (591)..(591)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (601)..(601)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (613)..(613)
<223> OTHER INFORMATION: a, t, c, g, unknown or other
<220> FEATURE:
<221> NAME/KEY: modified_base
<222> LOCATION: (616)..(616)
<223> OTHER INFORMATION: a, t, c, g, unknown or other
<220> FEATURE:
<221> NAME/KEY: modified_base
<222> LOCATION: (620)..(621)
<223> OTHER INFORMATION: a, t, c, g, unknown or other
<220> FEATURE:
<221> NAME/KEY: modified_base
<222> LOCATION: (627)..(627)
<223> OTHER INFORMATION: a, t, c, g, unknown or other
<220> FEATURE:
<221> NAME/KEY: modified_base
<222> LOCATION: (629)..(630)
<223> OTHER INFORMATION: a, t, c, g, unknown or other
<220> FEATURE:
<221> NAME/KEY: modified_base
<222> LOCATION: (634)..(634)
<223> OTHER INFORMATION: a, t, c, g, unknown or other
<220> FEATURE:
<221> NAME/KEY: modified_base
<222> LOCATION: (641)..(641)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (651)..(651)
<223> OTHER INFORMATION: a, t, c, g, unknown or other
<220> FEATURE:
<221> NAME/KEY: modified_base
<222> LOCATION: (655)..(655)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (676)..(676)
<223> OTHER INFORMATION: a, t, c, g, unknown or other
<220> FEATURE:

-continued

<221> NAME/KEY: modified_base
<222> LOCATION: (686)..(686)
<223> OTHER INFORMATION: a, t, c, g, unknown or other
<220> FEATURE:
<221> NAME/KEY: modified_base
<222> LOCATION: (690)..(691)
<223> OTHER INFORMATION: a, t, c, g, unknown or other
<220> FEATURE:
<221> NAME/KEY: modified_base
<222> LOCATION: (694)..(695)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (708)..(708)
<223> OTHER INFORMATION: a, t, c, g, unknown or other
<220> FEATURE:
<221> NAME/KEY: modified_base
<222> LOCATION: (710)..(711)
<223> OTHER INFORMATION: a, t, c, g, unknown or other
<220> FEATURE:
<221> NAME/KEY: modified_base
<222> LOCATION: (718)..(719)
<223> OTHER INFORMATION: a, t, c, g, unknown or other
<220> FEATURE:
<221> NAME/KEY: modified_base
<222> LOCATION: (725)..(726)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (733)..(733)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (748)..(749)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (755)..(755)
<223> OTHER INFORMATION: a, t, c, g, unknown or other
<220> FEATURE:
<221> NAME/KEY: modified_base
<222> LOCATION: (760)..(760)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other
<220> FEATURE:
<221> NAME/KEY: modified_base
<222> LOCATION: (768)..(768)
<223> OTHER INFORMATION: a, t, c, g, unknown or other
<220> FEATURE:
<221> NAME/KEY: modified_base
<222> LOCATION: (771)..(772)
<223> OTHER INFORMATION: a, t, c, g, unknown or other
<220> FEATURE:
<221> NAME/KEY: modified_base
<222> LOCATION: (775)..(775)
<223> OTHER INFORMATION: a, t, c, g, unknown or other
<220> FEATURE:
<221> NAME/KEY: modified_base
<222> LOCATION: (777)..(777)
<223> OTHER INFORMATION: a, t, c, g, unknown or other
<220> FEATURE:
<221> NAME/KEY: modified_base
<222> LOCATION: (783)..(783)
<223> OTHER INFORMATION: a, t, c, g, unknown or other
<220> FEATURE:
<221> NAME/KEY: modified_base
<222> LOCATION: (793)..(793)
<223> OTHER INFORMATION: a, t, c, g, unknown or other
<220> FEATURE:
<221> NAME/KEY: modified_base
<222> LOCATION: (799)..(799)
<223> OTHER INFORMATION: a, t, c, g, unknown or other
<220> FEATURE:
<221> NAME/KEY: modified_base
<222> LOCATION: (802)..(802)
<223> OTHER INFORMATION: a, t, c, g, unknown or other
<220> FEATURE:
<221> NAME/KEY: modified_base
<222> LOCATION: (806)..(806)
<223> OTHER INFORMATION: a, t, c, g, unknown or other
<220> FEATURE:
<221> NAME/KEY: modified_base
<222> LOCATION: (809)..(809)
<223> OTHER INFORMATION: a, t, c, g, unknown or other
<220> FEATURE:
<221> NAME/KEY: modified_base
<222> LOCATION: (816)..(816)
<223> OTHER INFORMATION: a, t, c, g, unknown or other
<220> FEATURE:
<221> NAME/KEY: modified_base
<222> LOCATION: (822)..(822)
<223> OTHER INFORMATION: a, t, c, g, unknown or other
<220> FEATURE:
<221> NAME/KEY: modified_base
<222> LOCATION: (825)..(826)
<223> OTHER INFORMATION: a, t, c, g, unknown or other
<220> FEATURE:
<221> NAME/KEY: modified_base
<222> LOCATION: (833)..(833)
<223> OTHER INFORMATION: a, t, c, g, unknown or other
<220> FEATURE:
<221> NAME/KEY: modified_base
<222> LOCATION: (835)..(835)
<223> OTHER INFORMATION: a, t, c, g, unknown or other
<220> FEATURE:
<221> NAME/KEY: modified_base
<222> LOCATION: (838)..(838)
<223> OTHER INFORMATION: a, t, c, g, unknown or other
<220> FEATURE:
<221> NAME/KEY: modified_base
<222> LOCATION: (844)..(844)
<223> OTHER INFORMATION: a, t, c, g, unknown or other
<220> FEATURE:
<221> NAME/KEY: modified_base
<222> LOCATION: (849)..(849)
<223> OTHER INFORMATION: a, t, c, g, unknown or other
<220> FEATURE:
<221> NAME/KEY: modified_base
<222> LOCATION: (852)..(852)
<223> OTHER INFORMATION: a, t, c, g, unknown or other
<220> FEATURE:
<221> NAME/KEY: modified_base
<222> LOCATION: (854)..(854)
<223> OTHER INFORMATION: a, t, c, g, unknown or other

<400> SEQUENCE: 70
acccccctca aattttggna aaacaacccn caggnnccna aaanaaggga acaaananan 60
canacanaaa atttttaaaa nntcancaan ggnncnncnt atncnagnng ggcnnttana 120
annccanaaa accncccccc aaacacaaca caacaaaanc cnanaaaacc anaccaaanc 180
naaannancc atacantnnc aaaaaannan nttaacnata anataananc accancaccc 240
caaaacaaac canaaaacna aacccaaccc acnnaacaan caaaaannaa aaaatcanan 300
cnnnancnac aanacancna acaannncac nanaacaaaa aaaaccnnca acnaacacca 360

-continued

```
accnnacacc ccaaaccaca acaaaantaa cancanccca nactccnaaa anancnccac    420

cntnnacaaa caaaanaaac aaannacaac aanntanaca acacnacaca acacacaanc    480

annanaanaa aacccancnc aaaannnaca acnnacaaac naanccacna aaaaanacca    540

ccanacncac cnanaanacc cnaanaacaa acancaaacn cnnnntcnaa nanccaaacc    600

nacancaaaa canacnaaan ncaaaanann aaanaacaac nacacnacaa naacnacaca    660

tcacaatacc anacanacaa ccacanatan ncanncnaca caacaacnan nccaaacnna    720

acacnnccnc aancaacnca cacacctnnc cnaanaaaan aanaccanac nnaancnaaa    780

tanaatacaa ccncacacnc anaacnacnt aaccancaca cnacnnacac canananaanat    840

cacncccanc ancn                                                      854
```

<210> SEQ ID NO 71
<211> LENGTH: 728
<212> TYPE: DNA
<213> ORGANISM: Homo sapiens
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (687)..(687)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (712)..(712)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other

<400> SEQUENCE: 71

```
atgttgccct actgggctgg cggcagtgac aggaggcgcg aacccgcagc gcttaccgcg     60

cggcgccgca ccatggagcc cgccgtgtcg ctggccgtgt gcgcgctgct cttcctgctg    120

tgggtgcgcc tgaaggggct ggagttcgct tatcttcgat atctactact acgtgcgcgc    180

ctgggtggtg ttcaagctca gcagcgctcc gcgcctgcac gagcagcgcg tgcgggacat    240

ccagaagcag gtgcgggaat ggaaggagca gggtagcaag accttcatgt gcacggggcg    300

ccctggctgg ctcactgtct cactacgtgt cgggaagtac aagaagacac acaaaaacat    360

catgatcaac ctgatggaca ttctggaagt ggacaccaag aaacagattg tccgtgtgga    420

gcccttggtg accatgggcc aggtgactgc cctgctgacc tccattggct ggactctccc    480

cgtgttgcct gagcttgatg acctacagtg gggggcttga tcatgggcac aggcatcgaa    540

gtcatcatcc cacaagtacg gcctgttcca acacatctgc actgcttacg agctggtcct    600

gctgatggca gctttgtgcg atgcacttcg tccgaaaact canacctggt ctatgccgta    660

ccctggtcct tgtgggacct ggggttnctg gtgggccgtt ganatccgga tnatccctgc    720

caagaaan                                                             728
```

<210> SEQ ID NO 72
<211> LENGTH: 740
<212> TYPE: DNA
<213> ORGANISM: Homo sapiens
<220> FEATURE:
<221> NAME/KEY: modified_base

```
<222> LOCATION: (8)..(8)
<223> OTHER INFORMATION: a, t, c, g, unknown or other
<220> FEATURE:
<221> NAME/KEY: modified_base
<222> LOCATION: (18)..(18)
<223> OTHER INFORMATION: a, t, c, g, unknown or other
<220> FEATURE:
<221> NAME/KEY: modified_base
<222> LOCATION: (29)..(29)
<223> OTHER INFORMATION: a, t, c, g, unknown or other
<220> FEATURE:
<221> NAME/KEY: modified_base
<222> LOCATION: (573)..(573)
<223> OTHER INFORMATION: a, t, c, g, unknown or other
<220> FEATURE:
<221> NAME/KEY: modified_base
<222> LOCATION: (598)..(598)
<223> OTHER INFORMATION: a, t, c, g, unknown or other
<220> FEATURE:
<221> NAME/KEY: modified_base
<222> LOCATION: (602)..(602)
<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (682)..(682)
<223> OTHER INFORMATION: a, t, c, g, unknown or other
<220> FEATURE:
<221> NAME/KEY: modified_base
<222> LOCATION: (724)..(724)
<223> OTHER INFORMATION: a, t, c, g, unknown or other

<400> SEQUENCE: 72

aattgcantc cctttttnca ggccctttna tttaaacaga agcagcggcc ccacagccac     60

ggggacatgt cttccagaca gtagacacag tgcctgtggc tgtaagagcc tgacagggaa    120

gattcatgcc tttctccttg gcccccatga ccaaagaaga aaataaaaat cacacaccat    180

acactgccac acccatctcc acccctccct ttcagtaata tccaagtatt catccttctg    240

gccaaagaaa ctggctacaa ttctgattct aaagaaaacc ttcatgcagc caagaaactc    300

agggctctgg aggggagagc cttactctga tactttccac atgcactgcc cactggcatc    360

aagtttaact ccatccaaaa ccatcacatg gatggccagg gacaggactg gctacaaaaa    420

aaagccatga actcagctca ccatgctaag aagactgcct ctttccaggc aagattttac    480

tggagcaaca taaccggagg gtgtgattcc aaaatacctt cctttccaag ccccgggttg    540

tggataaggc tggattttgg gtatatgact aanggcgaca gaagctgctg gcatcttntg    600

gncaccgtcc caatggctta aggttggang cttcactggc aaacaatggc actggttaac    660

tagcttcggg taaccattta tntacagcaa gtagaatcat cagttttgac tgggcaagga    720

agcncatggg tcttccttta                                                740


<210> SEQ ID NO 73
<211> LENGTH: 761
<212> TYPE: DNA
<213> ORGANISM: Homo sapiens
<220> FEATURE:
<221> NAME/KEY: modified_base
<222> LOCATION: (121)..(121)
<223> OTHER INFORMATION: a, t, c, g, unknown or other
<220> FEATURE:
<221> NAME/KEY: modified_base
<222> LOCATION: (722)..(723)
<223> OTHER INFORMATION: a, t, c, g, unknown or other
<220> FEATURE:
<221> NAME/KEY: modified_base
<222> LOCATION: (732)..(732)
```

<223> OTHER INFORMATION: a, t, c, g, unknown or other
<220> FEATURE:
<221> NAME/KEY: modified_base
<222> LOCATION: (753)..(753)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other

<400> SEQUENCE: 73

```
cactgttggc ctactggaac ttgtaacaca gaattgaact gatactagtt tccttgcctt     60

aaattaatta tatgtcatcc caagggtctc tgttaattct gctttgccaa gcaataatga    120

natctgggtt tggcattaga agtatttcat aattttggtt ttttatttag gtttcctcca    180

catctgtaaa gtgattgatt aaattagagg aggcgtgtag aataaatccc aatcccattg    240

caactggcag agctttataa atctttataa attcagttac aacaaaggag aggatcctac    300

accattagag ccatgccatc aggtgtttgc aagtgacagc tgtagtgtgt tgcctcaaat    360

aataccaagt tataaataat accaagtaat tatcaactca ctcccaaatt taataagata    420

tcaaagtcca aaaggttact taggagtagt cttccgtggg ggaagataaa tttattaaag    480

agtcatgtac tgatcttttt cttgggattt tttttccttt cccagaaaaa aaaattattt    540

tggtgactga tcaattgtaa acaattttct tccttactta caaatcatcc gtcagaaaaa    600

taaaagtgga cttcctttct aagcattaca attagcctgg gcaagaagtg ttatgattgg    660

cttattcttt aagccggctt actttttggg atttgggtga aatggctttt gaaaagaaag    720

tnnatggata gnattaataa ctactttgga tangcttntg c                        761
```

<210> SEQ ID NO 74
<211> LENGTH: 783
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (8)..(13)
<223> OTHER INFORMATION: a, t, c, g, unknown or other
<220> FEATURE:
<221> NAME/KEY: modified_base
<222> LOCATION: (599)..(599)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (694)..(694)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:
<221> NAME/KEY: modified_base
<222> LOCATION: (715)..(715)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (757)..(758)
<223> OTHER INFORMATION: a, t, c, g, unknown or other
<220> FEATURE:
<221> NAME/KEY: modified_base
<222> LOCATION: (761)..(762)
<223> OTHER INFORMATION: a, t, c, g, unknown or other
<220> FEATURE:
<221> NAME/KEY: modified_base
<222> LOCATION: (772)..(772)
<223> OTHER INFORMATION: a, t, c, g, unknown or other
<220> FEATURE:
<221> NAME/KEY: modified_base
<222> LOCATION: (779)..(779)
<223> OTHER INFORMATION: a, t, c, g, unknown or other

<400> SEQUENCE: 74
gngnnggnnn nnntttgtgg cctttttttt ttttttttct tttcaatcat agtcactctg 60
gtgaatccaa gcataaacag acaaatccaa ctacaactca acagggtgca gatggggagg 120
gcagggcaac atctatgtat atgttcagct gctccagcag aacagacagc atggcttcca 180
gctgggactg ggggaaaaga accatttcca agggggtgtg ttccccttg tcgggtgtgg 240 agggctgata ctatgcatgt ggagctgagc agcgggctgg gctgtctggg aggttggcag 300
ctacaagcta gggtgcaagt gggggacagc gggactgtgg gcctgccctg ggtgccttgc 360
ccttccatcc tggtgccgca ctgacaacca agacgcccag cctgctgctg tgggctcagc 420
acaggaaggg gccaggcctt ctcaggggaa agggctctct tcatgtcaac aaggcagaaa 480
cacctagggt cacagctgaa cagtgccctg gctcacatct gtgacgggag gaggagacag 540
ggaaccgaat cagatcatga gattcgtggt gagggtccag ttggatgaat ggaactgana 600
gtgaaaagct ggggtcccac tcttgggcct gggactttgc cttccttaat ttaacctcag 660
tatggagtan gnaccttctg naaccaacca gggncattac tggnaaaggg tggtnaagct 720
gggaaattng gacattgnga cctttnataa ggggttnngc nntgattggc tnttacggna 780
aaa 783

<210> SEQ ID NO 75
<211> LENGTH: 761
<212> TYPE: DNA
<213> ORGANISM: Homo sapiens
<220> FEATURE:
<221> NAME/KEY: modified_base
<222> LOCATION: (688)..(688)
<223> OTHER INFORMATION: a, t, c, g, unknown or other
<220> FEATURE:
<221> NAME/KEY: modified_base
<222> LOCATION: (706)..(706)
<223> OTHER INFORMATION: a, t, c, g, unknown or other

<400> SEQUENCE: 75

-continued

```
cctcggcact gttggcctac tggatgaata aaacactctt tggtggtgac tgaggcatca     60

ttagaaggcc cagacgattt ccactattca cagcatttcc ttttctcaga aggactcttt    120

atatttccat gtaaatctag atctttggag caattaagat ggaattacaa tttctaggga    180

gcattttaag gaaaatgttt tggctttttc ataattttat gtcttacagt atggaattat    240

aatacgaaaa tctttatatg agttttggct tcttggtatt tgtacttatt caggggaaaa    300

agtctttcga ttacttatgc ctctatagag cttaatttct tgagaaattc aacagtcatt    360

ttcaccagca taattttatc ttaaggaata actaatagga aaagtcagct taattattta    420

aggccctagt ttctacatat aatatattcg atagaaatga aaatctgccg tggaattaac    480

taataagtag taacaataaa cttcatattt agaatgcaaa gtctataaag aataatttta    540

catgatcctc aatatcaact ccagtttaaa aagtggtatt tttaaaacat ttgaaaccaa    600

gtctggttaa tttcaatcag aagatgcaaa tccatacttt tgatctatgg ttgattttgc    660

taataaatatt tggaaggaga atgcctanca aggaccaaac cattanattt aaaaatcaaa   720

ccgattcttc atacgctcat agtcccatat gggaatttgg g                        761
```

<210> SEQ ID NO 76
<211> LENGTH: 788
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (8)..(13)
<223> OTHER INFORMATION: a, t, c, g, unknown or other
<220> FEATURE:
<221> NAME/KEY: modified_base
<222> LOCATION: (17)..(17)
<223> OTHER INFORMATION: a, t, c, g, unknown or other
<220> FEATURE:
<221> NAME/KEY: modified_base
<222> LOCATION: (376)..(376)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (731)..(731)
<223> OTHER INFORMATION: a, t, c, g, unknown or other
<220> FEATURE:
<221> NAME/KEY: modified_base
<222> LOCATION: (760)..(760)
<223> OTHER INFORMATION: a, t, c, g, unknown or other
<220> FEATURE:
<221> NAME/KEY: modified_base
<222> LOCATION: (788)..(788)
<223> OTHER INFORMATION: a, t, c, g, unknown or other

<400> SEQUENCE: 76

```
gngnntgnnn nnntttnggg cctttttttt tttttttgag tctgaaaatt ccatttatta     60

aaacacatac attgtccatg tgggatgaaa atgtgcacat cacattcagg ttttcctgct    120

ttaacatttc tgtagttctc tctttgaaac acacactcca cagatcttat ataggaaaaa    180
```

-continued

```
tgtgaacaac ttttgggctg caaaacatta atgcatacat aacaattcat cattgccaag    240
agcagctaga agcaaatatt aaggaagaaa gacaaagaag tataaaaatt cctaaagaca    300
gcatgcttta ttttctcaaa attccatatg tgactatgag cgtatggaga aatcgtttga    360
tttttaaatt tattgntttg tccttggtag gcaatctcct tcaaatatta ttagcaaaat    420
caaacataga tcaaagtatg tatttgcatc ttctgattga aattaaacag tacttggttt    480
caaatgtttt aaaaataaca ctttttaaac tggagttgat attgaggatc atgtaaaatt    540
attctttata gactttgcat tctaaatatg aagtttattg gtactactta ttagttaatt    600
ccacggcaga ttttcatttc tatcgaatat attatatgta gaaactangg ccttaaataa    660
ttaagctgac ttttcctatt aggtattcct taagataaaa ttatgctggn gaaaatgact    720
gtgaatttct naagaaatta actctataga aggcataagn aatcgaaaga ctttttccct    780
gaataagn                                                              788
```

```
<210> SEQ ID NO 77
<211> LENGTH: 738
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other
<220> FEATURE:
<221> NAME/KEY: modified_base
<222> LOCATION: (597)..(597)
<223> OTHER INFORMATION: a, t, c, g, unknown or other
<220> FEATURE:
<221> NAME/KEY: modified_base
<222> LOCATION: (604)..(604)
<223> OTHER INFORMATION: a, t, c, g, unknown or other
<220> FEATURE:
<221> NAME/KEY: modified_base
<222> LOCATION: (640)..(640)
<223> OTHER INFORMATION: a, t, c, g, unknown or other
<220> FEATURE:
<221> NAME/KEY: modified_base
<222> LOCATION: (650)..(650)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other

<400> SEQUENCE: 77

ctactggnat gaaaaggatg agcaaggaga aatgccccaa aggagactga cccggcgcgg     60
tgctggcggg agcgctcaag ggcagcggat ttgttgttgt tgctgttttc ctttgtgggt    120
gtttggtgct tgatttccag aaactctcca gcgacttgga cttcttcttt ttttttttt     180
ctttttagat agaagtgact gtgtggttgg tctctgaggt atttgggga ctctgtattt     240
gctcgtttac gtgttggaaa aaccaagtgg ctttggggtt tcgccctatc ccactccctc    300
tctttcctgc tccattggtt ccttaagaaa tgctatattt tgtgagtgca agctggcttg    360
```

-continued

```
gggagccctc tcttgtgtaa atgtccccca tgtttctgaa aagtgctgta agtttaagtc    420

ccctcacccc cagcactgcc caaacagggg ccaagtgcgc cccaattcca agaatgaagg    480

cagagcgaca acagtgcgga caccccggct gctagcccac ggtgaacccg gcggggttgc    540

ccaccagttg cgaaagcccc ctttctnaag gagcacgcgg acctcggtgg agatctncaa    600

tgangcttaa aggaacccaa ggcctcggcc gggttggggn ttggcctcan tgcattggac    660

ccctggtntt ttccctgaag gctggctcgc gtggccggcn cgggtggtgg gccttccggt    720

tcttgcccna ggaccaat                                                  738
```

<210> SEQ ID NO 78
<211> LENGTH: 785
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (6)..(11)
<223> OTHER INFORMATION: a, t, c, g, unknown or other
<220> FEATURE:
<221> NAME/KEY: modified_base
<222> LOCATION: (40)..(40)
<223> OTHER INFORMATION: a, t, c, g, unknown or other
<220> FEATURE:
<221> NAME/KEY: modified_base
<222> LOCATION: (90)..(90)
<223> OTHER INFORMATION: a, t, c, g, unknown or other
<220> FEATURE:
<221> NAME/KEY: modified_base
<222> LOCATION: (110)..(110)
<223> OTHER INFORMATION: a, t, c, g, unknown or other
<220> FEATURE:
<221> NAME/KEY: modified_base
<222> LOCATION: (115)..(115)
<223> OTHER INFORMATION: a, t, c, g, unknown or other
<220> FEATURE:
<221> NAME/KEY: modified_base
<222> LOCATION: (132)..(132)
<223> OTHER INFORMATION: a, t, c, g, unknown or other
<220> FEATURE:
<221> NAME/KEY: modified_base
<222> LOCATION: (134)..(134)
<223> OTHER INFORMATION: a, t, c, g, unknown or other
<220> FEATURE:
<221> NAME/KEY: modified_base
<222> LOCATION: (154)..(154)
<223> OTHER INFORMATION: a, t, c, g, unknown or other
<220> FEATURE:
<221> NAME/KEY: modified_base
<222> LOCATION: (208)..(208)
<223> OTHER INFORMATION: a, t, c, g, unknown or other
<220> FEATURE:
<221> NAME/KEY: modified_base
<222> LOCATION: (215)..(215)
<223> OTHER INFORMATION: a, t, c, g, unknown or other
<220> FEATURE:
<221> NAME/KEY: modified_base
<222> LOCATION: (217)..(217)
<223> OTHER INFORMATION: a, t, c, g, unknown or other
<220> FEATURE:
<221> NAME/KEY: modified_base
<222> LOCATION: (235)..(235)
<223> OTHER INFORMATION: a, t, c, g, unknown or other
<220> FEATURE:
<221> NAME/KEY: modified_base
<222> LOCATION: (239)..(239)
<223> OTHER INFORMATION: a, t, c, g, unknown or other
<220> FEATURE:
<221> NAME/KEY: modified_base
<222> LOCATION: (291)..(291)
<223> OTHER INFORMATION: a, t, c, g, unknown or other
<220> FEATURE:
<221> NAME/KEY: modified_base
<222> LOCATION: (296)..(296)
<223> OTHER INFORMATION: a, t, c, g, unknown or other
<220> FEATURE:
<221> NAME/KEY: modified_base
<222> LOCATION: (305)..(305)
<223> OTHER INFORMATION: a, t, c, g, unknown or other
<220> FEATURE:
<221> NAME/KEY: modified_base
<222> LOCATION: (320)..(320)
<223> OTHER INFORMATION: a, t, c, g, unknown or other
<220> FEATURE:
<221> NAME/KEY: modified_base
<222> LOCATION: (336)..(336)
<223> OTHER INFORMATION: a, t, c, g, unknown or other
<220> FEATURE:
<221> NAME/KEY: modified_base
<222> LOCATION: (345)..(345)
<223> OTHER INFORMATION: a, t, c, g, unknown or other
<220> FEATURE:
<221> NAME/KEY: modified_base
<222> LOCATION: (370)..(370)
<223> OTHER INFORMATION: a, t, c, g, unknown or other
<220> FEATURE:
<221> NAME/KEY: modified_base
<222> LOCATION: (376)..(377)
<223> OTHER INFORMATION: a, t, c, g, unknown or other
<220> FEATURE:
<221> NAME/KEY: modified_base
<222> LOCATION: (380)..(380)
<223> OTHER INFORMATION: a, t, c, g, unknown or other
<220> FEATURE:
<221> NAME/KEY: modified_base
<222> LOCATION: (392)..(392)
<223> OTHER INFORMATION: a, t, c, g, unknown or other
<220> FEATURE:
<221> NAME/KEY: modified_base
<222> LOCATION: (406)..(406)
<223> OTHER INFORMATION: a, t, c, g, unknown or other
<220> FEATURE:
<221> NAME/KEY: modified_base
<222> LOCATION: (417)..(417)
<223> OTHER INFORMATION: a, t, c, g, unknown or other
<220> FEATURE:
<221> NAME/KEY: modified_base
<222> LOCATION: (458)..(458)
<223> OTHER INFORMATION: a, t, c, g, unknown or other
<220> FEATURE:
<221> NAME/KEY: modified_base
<222> LOCATION: (539)..(539)
<223> OTHER INFORMATION: a, t, c, g, unknown or other
<220> FEATURE:
<221> NAME/KEY: modified_base
<222> LOCATION: (543)..(543)
<223> OTHER INFORMATION: a, t, c, g, unknown or other
<220> FEATURE:
<221> NAME/KEY: modified_base
<222> LOCATION: (560)..(560)
<223> OTHER INFORMATION: a, t, c, g, unknown or other
<220> FEATURE:
<221> NAME/KEY: modified_base
<222> LOCATION: (579)..(579)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (639)..(639)
<223> OTHER INFORMATION: a, t, c, g, unknown or other
<220> FEATURE:
<221> NAME/KEY: modified_base
<222> LOCATION: (643)..(643)
<223> OTHER INFORMATION: a, t, c, g, unknown or other
<220> FEATURE:
<221> NAME/KEY: modified_base
<222> LOCATION: (647)..(647)

-continued

<223> OTHER INFORMATION: a, t, c, g, unknown or other
<220> FEATURE:
<221> NAME/KEY: modified_base
<222> LOCATION: (671)..(671)
<223> OTHER INFORMATION: a, t, c, g, unknown or other
<220> FEATURE:
<221> NAME/KEY: modified_base
<222> LOCATION: (687)..(688)
<223> OTHER INFORMATION: a, t, c, g, unknown or other
<220> FEATURE:
<221> NAME/KEY: modified_base
<222> LOCATION: (710)..(712)
<223> OTHER INFORMATION: a, t, c, g, unknown or other
<220> FEATURE:
<221> NAME/KEY: modified_base
<222> LOCATION: (714)..(714)
<223> OTHER INFORMATION: a, t, c, g, unknown or other
<220> FEATURE:
<221> NAME/KEY: modified_base
<222> LOCATION: (719)..(719)
<223> OTHER INFORMATION: a, t, c, g, unknown or other
<220> FEATURE:
<221> NAME/KEY: modified_base
<222> LOCATION: (723)..(723)
<223> OTHER INFORMATION: a, t, c, g, unknown or other
<220> FEATURE:
<221> NAME/KEY: modified_base
<222> LOCATION: (761)..(761)
<223> OTHER INFORMATION: a, t, c, g, unknown or other
<220> FEATURE:
<221> NAME/KEY: modified_base
<222> LOCATION: (765)..(767)
<223> OTHER INFORMATION: a, t, c, g, unknown or other
<220> FEATURE:
<221> NAME/KEY: modified_base
<222> LOCATION: (769)..(769)
<223> OTHER INFORMATION: a, t, c, g, unknown or other
<220> FEATURE:
<221> NAME/KEY: modified_base
<222> LOCATION: (780)..(780)
<223> OTHER INFORMATION: a, t, c, g, unknown or other
<220> FEATURE:
<221> NAME/KEY: modified_base
<222> LOCATION: (785)..(785)
<223> OTHER INFORMATION: a, t, c, g, unknown or other

<400> SEQUENCE: 78
gnntgnnnnn nttttgtggc ctttatttga atccctttn tttttcttt ttttttttt 60 ttttttttt tttttttag ggccagcgtn tgggctccat ttgatcaggn cagcntttat 120
tagtaggaag cngnaacatt tacaactggt cctngggcag gaaccgggag ggccaccacc 180
cgcggccgcc cacgcgagcc cagccttnag ggganaagc agcgcgtcca atgcnctgng 240
gacaaacccc aacccgcccg aggccctggg ctcctttaag cctcactgga natctncacc 300
gaggncccgc gtgctccctn aggaaagggg gctttngcaa ctggngggca accccgccgg 360
gctttaccgn gggctnncan ccggggtgtc cncactgttg tcgctntgcc ttcattnttg 420
gaattggggc gcacttggcc cctgtttggg cagtgctngg ggtgagggga ctaaactaca 480
gcacttttca aaaacatggg ggacatttac acaagagagg gctccccaag ccagcttgna 540
ctnacaaaat atagcatttn ttaaggaacc aatggagcng gaaagaaagg gantgggata 600
tgggcgaaac cccaaagccc ttgggttttt caacacgtna acnagcnaat tcagattccc 660
caaatcctta nagaccaacc cacagtnnct tttttttaaa aagaaaaaan nnanggaana 720
atncaaatcc cttggaaagt tttgggaatc aacccccaaa ncccnnnang gaaaaccggn 780 ccccn 785

<210> SEQ ID NO 79
<211> LENGTH: 774

-continued

<212> TYPE: DNA
<213> ORGANISM: Homo sapiens
<220> FEATURE:
<221> NAME/KEY: modified_base
<222> LOCATION: (1)..(3)
<223> OTHER INFORMATION: a, t, c, g, unknown or other
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (12)..(12)
<223> OTHER INFORMATION: a, t, c, g, unknown or other
<220> FEATURE:
<221> NAME/KEY: modified_base
<222> LOCATION: (15)..(16)
<223> OTHER INFORMATION: a, t, c, g, unknown or other
<220> FEATURE:
<221> NAME/KEY: modified_base
<222> LOCATION: (24)..(24)
<223> OTHER INFORMATION: a, t, c, g, unknown or other
<220> FEATURE:
<221> NAME/KEY: modified_base
<222> LOCATION: (607)..(607)
<223> OTHER INFORMATION: a, t, c, g, unknown or other
<220> FEATURE:
<221> NAME/KEY: modified_base
<222> LOCATION: (648)..(648)
<223> OTHER INFORMATION: a, t, c, g, unknown or other
<220> FEATURE:
<221> NAME/KEY: modified_base
<222> LOCATION: (675)..(675)
<223> OTHER INFORMATION: a, t, c, g, unknown or other
<220> FEATURE:
<221> NAME/KEY: modified_base
<222> LOCATION: (714)..(714)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other

<400> SEQUENCE: 79
nnngagggng gntgnnttcc tttntgaatc ctttgcctgt cggcctactg gcagataaag 60
ccttatgctg cccaccagcc cactaaatgt attaaatacc tgtctctatg tagcttatgt 120
aaaaactcaa tgttgactgt cccgtgtctg ctgcatttaa aagctcattg tgattctatc 180
atcttgctat gccaatgcct tatgttatgg tgtcatgtat ataggccatg gtacaaaagt 240
gactgtcaac tgcttactca acatctagtc agaaaaggtc tgaggcagtg caataacgct 300
tttagtcaaa ctggctcact gttggagtca tttacatctg tgtattcttt accgtaaata 360
ctgaaatagt attttttaac tgttttttca ggcttgtaat aaatatctgt gtcatatcta 420
catagtcaaa atacattgag taattcagtt taaaagtgtt gcctactaac aaactaaaga 480
gaaacatcta ctgattttcc atataattgc ttattttcat tgccaatgta gacctgcctg 540
gaatggtgtc tttcaccact atcatgtgta aaataaaggg aggctattgt ggtgaatttt 600
cacctgnctg acattagctc tttcactagc aaaaggatgt ccatcctnaa aagtgacctg 660
ctacccgagg tccantttca aaaggcatct taatttaatt ttgctccaaa attnaaaatg 720
ggtgnctcca aacttacctn tgtagacttt taaaggccag cattgggggg gaag 774

<210> SEQ ID NO 80
<211> LENGTH: 784
<212> TYPE: DNA

-continued

<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (10)..(11)
<223> OTHER INFORMATION: a, t, c, g, unknown or other
<220> FEATURE:
<221> NAME/KEY: modified_base
<222> LOCATION: (31)..(33)
<223> OTHER INFORMATION: a, t, c, g, unknown or other
<220> FEATURE:
<221> NAME/KEY: modified_base
<222> LOCATION: (40)..(40)
<223> OTHER INFORMATION: a, t, c, g, unknown or other
<220> FEATURE:
<221> NAME/KEY: modified_base
<222> LOCATION: (47)..(47)
<223> OTHER INFORMATION: a, t, c, g, unknown or other
<220> FEATURE:
<221> NAME/KEY: modified_base
<222> LOCATION: (513)..(513)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (637)..(637)
<223> OTHER INFORMATION: a, t, c, g, unknown or other
<220> FEATURE:
<221> NAME/KEY: modified_base
<222> LOCATION: (663)..(663)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (754)..(754)
<223> OTHER INFORMATION: a, t, c, g, unknown or other

<400> SEQUENCE: 80
gnagtggttn natttggtgg cctttttga nnncccttn ttttttnttt tcatttacac 60
atttattttc tatctcgctt attctaccag actgaaatgg agaacaatgc cagcaatttt 120
atagacattt tgacataaag taaacaagta ttttgatgtt gaacaattgt acagactact 180
acatgcatat aggtatgctg attggtgcag aaatattgag ttgatcaaca aaactattaa 240
tacgaaatca catttccttt ttatggagtt aaaatgcagc agatatggga acattgatac 300
aaacaccatt aaatggcaga aaaaggcatt gtagtaacga tgcaggatgg acagctgaac 360
aaacacgagt atgctaactc atatcctgtc tacaaaactg aaataagaac attttgtatg 420
caaatagaat gaaagaaagc atgttgaggc aggtgaatga gactagacaa caagacttaa 480

```
ccacttatgt ttaagcttct attgagagtt tgnattaaaa gtatttcaac atggtataaa    540

gaagaaatgc taatgctatt atgtgtgtgg ccaggatagg ataattcaat tgngaattca    600

taaataatga aatactgatg gggcttcttt ttcctgnagc attcagagca tcatagacta    660

gtntgnaaan ccttttaaac cctggaggtt atnaaaggca ataatgcttn atgcgactgt    720

cctagaaatc taataccntg tttacttaaa aatngggaaa tggttactta ccatttccat    780

agga                                                                  784
```

```
<210> SEQ ID NO 81
<211> LENGTH: 782
<212> TYPE: DNA
<213> ORGANISM: Homo sapiens
<220> FEATURE:
<221> NAME/KEY: modified_base
<222> LOCATION: (2)..(8)
<223> OTHER INFORMATION: a, t, c, g, unknown or other
<220> FEATURE:
<221> NAME/KEY: modified_base
<222> LOCATION: (10)..(10)
<223> OTHER INFORMATION: a, t, c, g, unknown or other
<220> FEATURE:
<221> NAME/KEY: modified_base
<222> LOCATION: (12)..(19)
<223> OTHER INFORMATION: a, t, c, g, unknown or other
<220> FEATURE:
<221> NAME/KEY: modified_base
<222> LOCATION: (25)..(27)
<223> OTHER INFORMATION: a, t, c, g, unknown or other
<220> FEATURE:
<221> NAME/KEY: modified_base
<222> LOCATION: (540)..(540)
<223> OTHER INFORMATION: a, t, c, g, unknown or other
<220> FEATURE:
<221> NAME/KEY: modified_base
<222> LOCATION: (615)..(615)
<223> OTHER INFORMATION: a, t, c, g, unknown or other
<220> FEATURE:
<221> NAME/KEY: modified_base
<222> LOCATION: (644)..(644)
<223> OTHER INFORMATION: a, t, c, g, unknown or other
<220> FEATURE:
<221> NAME/KEY: modified_base
<222> LOCATION: (654)..(654)
<223> OTHER INFORMATION: a, t, c, g, unknown or other
<220> FEATURE:
<221> NAME/KEY: modified_base
<222> LOCATION: (659)..(659)
<223> OTHER INFORMATION: a, t, c, g, unknown or other
<220> FEATURE:
<221> NAME/KEY: modified_base
<222> LOCATION: (711)..(711)
<223> OTHER INFORMATION: a, t, c, g, unknown or other
<220> FEATURE:
<221> NAME/KEY: modified_base
<222> LOCATION: (729)..(730)
<223> OTHER INFORMATION: a, t, c, g, unknown or other
<220> FEATURE:
<221> NAME/KEY: modified_base
<222> LOCATION: (739)..(739)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (778)..(778)
<223> OTHER INFORMATION: a, t, c, g, unknown or other
```

```
<400> SEQUENCE: 81

gnnnnnnntn gnnnnnnnnt tggannncct tgagcactgt tggcctactg gtttaatctc      60

attttctcct aaagttcttc tcttcaatat gatctgcaaa gggttgaaag tgctgtcctc     120

caaaccaggc gtaagaaagt ggttacagat aaagcaagta aatccattaa agaagaaatg     180

ggaagatctg ttgtgtgcct tatctgaccc agcattatcg ctggaggga agtgcttata      240

gggaaggaag agaagtttgg tcaattgatg cagtctcagt atgatgacag ctggtgactt     300

cctgagggtt attcatcaca cttcagcagg gtgatgtttt caaagcctgc gtgtgaccat     360

gtcactcctc tgttctccag cgctttcaaa ataaaactga aatccgtctc agagggccag     420

tctcagagta tcccctgcca gccccatcct tcactgctca gcagtcacct ccttccccct     480

cctcatcctt ttgaggtctc ttctgatcct tcaggggcca gcttctctcc gtcccatggn     540

tggttgccta tgctgatccc ctacatggat cttcggtcac cttcatcact cttacctggg     600

tagtctcttc ctggncttta tccaagtcaa cttcgcttct gcangaatgc ctgncttgna     660

accttaagtc cttctggtcc cctcttaaaa cactggctat tctcctggga ngcagtaatt     720

ccagtagtnn attgcatcnt ttgnaacncg ttttgattaa tgcccgtggt ttccctanaa     780

ct                                                                    782


<210> SEQ ID NO 82
<211> LENGTH: 788
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (9)..(11)
<223> OTHER INFORMATION: a, t, c, g, unknown or other
<220> FEATURE:
<221> NAME/KEY: modified_base
<222> LOCATION: (28)..(30)
<223> OTHER INFORMATION: a, t, c, g, unknown or other
<220> FEATURE:
<221> NAME/KEY: modified_base
<222> LOCATION: (44)..(44)
<223> OTHER INFORMATION: a, t, c, g, unknown or other
<220> FEATURE:
<221> NAME/KEY: modified_base
<222> LOCATION: (593)..(593)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (778)..(778)
<223> OTHER INFORMATION: a, t, c, g, unknown or other

<400> SEQUENCE: 82

gnnggggtnn nttggtggcc tttttgannn cctttctgac tgcntttcat taacttcctt      60

taaaacgctt ttcttttggg tcaaatgaca catctgacat ttctttggtt tcttgaaact     120

tctacaccca ccttccactt attagacaat tacctatagg gactctactg atactagtgg     180

gcttggggag gtccccaaat gctggtggga ccctgatccc ggcaggtgtc caggctcttg     240

acaccgtctc aagaaggaat tcaaggatga gtcaggcaac agtggaagta cagagattta     300
```

```
taacaacggg aaaagtacac actcaagaaa gggggagtgt aggcggactc aagagagcac    360

catgcctaag gggatttggg gctgctacct ttatgtgttt ctttagccaa ggggtggaat    420

acttatgaaa attcctggga aagggtggaa atttcttaga attgtgatgc catccatttt    480

tacaccaaac gtaggtattc tcggaattca tggtgctggt cacctaggac ctcgtgatat    540

gctcattaac atggtaagtc actcattaac atcccaagtc acaagtgact tangatgtta    600

acaaacacat cacgagggcc taagtgaatc ctagtcaaat tcagcaccat gttgggtcca    660

cttgggctta accagcttgg gccatgcccc gggttttnaa ggatctgatc aagccacaag    720

cctttaagca tttgaaactg ntatctggat ttttttttt taaaaacacg ttttggtntg    780

tgcaggct                                                              788
```

```
<210> SEQ ID NO 83
<211> LENGTH: 780
<212> TYPE: DNA
<213> ORGANISM: Homo sapiens
<220> FEATURE:
<221> NAME/KEY: modified_base
<222> LOCATION: (2)..(7)
<223> OTHER INFORMATION: a, t, c, g, unknown or other
<220> FEATURE:
<221> NAME/KEY: modified_base
<222> LOCATION: (10)..(19)
<223> OTHER INFORMATION: a, t, c, g, unknown or other
<220> FEATURE:
<221> NAME/KEY: modified_base
<222> LOCATION: (25)..(27)
<223> OTHER INFORMATION: a, t, c, g, unknown or other
<220> FEATURE:
<221> NAME/KEY: modified_base
<222> LOCATION: (33)..(33)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (659)..(659)
<223> OTHER INFORMATION: a, t, c, g, unknown or other
<220> FEATURE:
<221> NAME/KEY: modified_base
<222> LOCATION: (691)..(691)
<223> OTHER INFORMATION: a, t, c, g, unknown or other
<220> FEATURE:
<221> NAME/KEY: modified_base
<222> LOCATION: (747)..(747)
<223> OTHER INFORMATION: a, t, c, g, unknown or other
<220> FEATURE:
<221> NAME/KEY: modified_base
<222> LOCATION: (764)..(764)
<223> OTHER INFORMATION: a, t, c, g, unknown or other

<400> SEQUENCE: 83
```

```
gnnnnnnttn nnnnnnnnnt tggannncct tgngcactgt tggcctactg ggatcctgtt     60

tgacattttt atggctgtat ttgtaaactt aaacacacca gtgtctgttc ttgatgcagt    120

tgctatttag gatgagttaa gtgcctgggg agtccctcaa aaggttaaag ggattcccat    180

cattggaatc ttatcaccag ataggcaagt ttatgaccaa acaagagagt actggcttta    240

tcctctaacc tcatattttc tcccacttgg caagtccttt gtggcattta ttcatcagtc    300

agggtgtccg attggtccta gaacttccaa aggctgcttg tcatagaagc cattgcatct    360
```

-continued

```
ataaagcaac ggctcctgtt aaatggtatc tcctttctga ggctcctact aaaagtcatt    420

tgttacctaa acttatgtgc ttaacaggca atgcttctca gaccacaaag cagaaagaag    480

aagaaaagct cctgactaaa tcagggctgg gcttagacag agttgatctg tagaatatct    540

ttaaaggaga gatgtcaact ttctgcacta ttcccagcct ctgctcctcc tgctaccctc    600

ttcccttcct ctctccttca cttnacccac aatcttgaaa aacttncttt ctcttctgng    660

aacatcattg gccagatcca ttttcaatgg nctggattct tttaatttcc tttcaacttg    720

aaagaaactg gacattaggc actatgnggt gggtactgcc ctantggtca agtgcctctt    780
```

```
<210> SEQ ID NO 84
<211> LENGTH: 792
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (5)..(6)
<223> OTHER INFORMATION: a, t, c, g, unknown or other
<220> FEATURE:
<221> NAME/KEY: modified_base
<222> LOCATION: (8)..(12)
<223> OTHER INFORMATION: a, t, c, g, unknown or other
<220> FEATURE:
<221> NAME/KEY: modified_base
<222> LOCATION: (34)..(34)
<223> OTHER INFORMATION: a, t, c, g, unknown or other
<220> FEATURE:
<221> NAME/KEY: modified_base
<222> LOCATION: (207)..(207)
<223> OTHER INFORMATION: a, t, c, g, unknown or other
<220> FEATURE:
<221> NAME/KEY: modified_base
<222> LOCATION: (521)..(521)
<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (661)..(661)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (698)..(698)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (737)..(737)
<223> OTHER INFORMATION: a, t, c, g, unknown or other
<220> FEATURE:
<221> NAME/KEY: modified_base
<222> LOCATION: (784)..(784)
<223> OTHER INFORMATION: a, t, c, g, unknown or other

<400> SEQUENCE: 84

gnngnngnnn nnttggtggc cttttttttt tccntttttt ttttttttcc tttagtcttt     60
```

-continued

```
taatgttagc cttttaatat tttccaataa gtgctttcaa ctcagcaata tacatatcat    120

gctttcctca ttattattga tccatcaata aatatacaaa aaccagagga agggtgtgct    180

ctgaaaagtc aaagtaacaa taacagnggt cattgtacag cacaagaatg aacaatgggc    240

tattctttga aaactcaaaa caaatgattt acacaaagac atatctataa cataaaggtg    300

aatggaccat gttattctta ttcttaagta cattttgctt ttccagataa gtcaaatgtt    360

tcctctctcc tactcctctg atataacagt attgaatgaa tgttggctac aaaatcaatt    420

cttggtgttg ttatgaatct caatataaaa cttttggaaa ggttctgcta gaaaagccaa    480

ttctaccagg cttgaaatat ggattcgaag atgtcttttg nctcttttga tttttcactc    540

agagctaatt ttaagggaag tcttcaggag acacaaaaga tttacaattg caagaaaaat    600

tacatcttta gctcttaagg tgctttgcna aataattaaa tggtgggcct ttacttttat    660

naaganccag tttaaatgac ttaacccaag tcacctgnaa atcattggna aaaatggccg    720

ggtagncaaa ctgggcnttc caaagttccc cccttgaaat caagggagtg ggaatccatc    780

ttanttcctt aa                                                         792
```

```
<210> SEQ ID NO 85
<211> LENGTH: 787
<212> TYPE: DNA
<213> ORGANISM: Homo sapiens
<220> FEATURE:
<221> NAME/KEY: modified_base
<222> LOCATION: (2)..(2)
<223> OTHER INFORMATION: a, t, c, g, unknown or other
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (7)..(7)
<223> OTHER INFORMATION: a, t, c, g, unknown or other
<220> FEATURE:
<221> NAME/KEY: modified_base
<222> LOCATION: (12)..(13)
<223> OTHER INFORMATION: a, t, c, g, unknown or other
<220> FEATURE:
<221> NAME/KEY: modified_base
<222> LOCATION: (16)..(19)
<223> OTHER INFORMATION: a, t, c, g, unknown or other
<220> FEATURE:
<221> NAME/KEY: modified_base
<222> LOCATION: (23)..(23)
<223> OTHER INFORMATION: a, t, c, g, unknown or other
<220> FEATURE:
<221> NAME/KEY: modified_base
<222> LOCATION: (31)..(31)
<223> OTHER INFORMATION: a, t, c, g, unknown or other
<220> FEATURE:
<221> NAME/KEY: modified_base
<222> LOCATION: (574)..(574)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (660)..(660)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (750)..(750)
```

<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (755)..(755)
<223> OTHER INFORMATION: a, t, c, g, unknown or other
<220> FEATURE:
<221> NAME/KEY: modified_base
<222> LOCATION: (760)..(760)
<223> OTHER INFORMATION: a, t, c, g, unknown or other
<220> FEATURE:
<221> NAME/KEY: modified_base
<222> LOCATION: (763)..(763)
<223> OTHER INFORMATION: a, t, c, g, unknown or other
<220> FEATURE:
<221> NAME/KEY: modified_base
<222> LOCATION: (765)..(765)
<223> OTHER INFORMATION: a, t, c, g, unknown or other
<220> FEATURE:
<221> NAME/KEY: modified_base
<222> LOCATION: (771)..(771)
<223> OTHER INFORMATION: a, t, c, g, unknown or other
<220> FEATURE:
<221> NAME/KEY: modified_base
<222> LOCATION: (777)..(777)
<223> OTHER INFORMATION: a, t, c, g, unknown or other

<400> SEQUENCE: 85

```
gngnngnggg gnnttnnnnt tgnattcctt nagcactgtt ggcctactgg gaattacaca     60

tcctcttgtt cttaaaaaag caagtgtctt tcgtgttgga ggacaaaatc ccctaccatt    120

ttcacgttgt gctactaaga gatctcaaat attagtcttt gtccggaccc ttccatagta    180

caccttagcg ctgagactga gccagcttgg gggtcaggta ggtagaccct gttagggaca    240

gagcctagtg gtaaatccaa gagaaatgat cctatccaaa gctgattcac aaacccacgc    300

tcacctgaca gccgagggac acgagcatca ctctgctgga cggaccatta ggggccttgc    360

caaggtctac cttagagcaa acccagtacc tcagacagga aagtcgggct ttgaccacta    420

ccatatctgg tagcccattt tctaggcatt gtgaataggt aggtagctag tcacactttt    480

cagaccaatt caaactgtct atgcacaaaa ttccgtgggc ctagatggag ataatttttt    540

ttcttctcag ctttatgaag agaagggaaa ctgnctagga ttcagctgaa ccaccaggaa    600

cctggcaaca tcacgattta agctaagggt gggangctaa cgaagtctac tcctctttgn    660

aaatcaagga attggttaaa atgggattgg caatccttta aataaagatg aacttgggtt    720

caagnccaat gggaattatt ttgggttggn ancanaacan cangnacctt naaaatntta    780

agccaag                                                              787
```

<210> SEQ ID NO 86
<211> LENGTH: 789
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, unknown or other
<220> FEATURE:
<221> NAME/KEY: modified_base
<222> LOCATION: (5)..(5)
<223> OTHER INFORMATION: a, t, c, g, unknown or other
<220> FEATURE:
<221> NAME/KEY: modified_base
<222> LOCATION: (8)..(12)
<223> OTHER INFORMATION: a, t, c, g, unknown or other
<220> FEATURE:
<221> NAME/KEY: modified_base
<222> LOCATION: (32)..(32)
<223> OTHER INFORMATION: a, t, c, g, unknown or other
<220> FEATURE:
<221> NAME/KEY: modified_base
<222> LOCATION: (35)..(35)
<223> OTHER INFORMATION: a, t, c, g, unknown or other
<220> FEATURE:
<221> NAME/KEY: modified_base
<222> LOCATION: (46)..(46)
<223> OTHER INFORMATION: a, t, c, g, unknown or other
<220> FEATURE:
<221> NAME/KEY: modified_base
<222> LOCATION: (201)..(201)
<223> OTHER INFORMATION: a, t, c, g, unknown or other
<220> FEATURE:
<221> NAME/KEY: modified_base
<222> LOCATION: (595)..(595)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (657)..(657)
<223> OTHER INFORMATION: a, t, c, g, unknown or other
<220> FEATURE:
<221> NAME/KEY: modified_base
<222> LOCATION: (664)..(664)
<223> OTHER INFORMATION: a, t, c, g, unknown or other
<220> FEATURE:
<221> NAME/KEY: modified_base
<222> LOCATION: (666)..(666)
<223> OTHER INFORMATION: a, t, c, g, unknown or other
<220> FEATURE:
<221> NAME/KEY: modified_base
<222> LOCATION: (693)..(693)
<223> OTHER INFORMATION: a, t, c, g, unknown or other
<220> FEATURE:
<221> NAME/KEY: modified_base
<222> LOCATION: (695)..(695)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (710)..(710)
<223> OTHER INFORMATION: a, t, c, g, unknown or other
<220> FEATURE:
<221> NAME/KEY: modified_base
<222> LOCATION: (766)..(766)
<223> OTHER INFORMATION: a, t, c, g, unknown or other
<220> FEATURE:
<221> NAME/KEY: modified_base
<222> LOCATION: (783)..(783)
<223> OTHER INFORMATION: a, t, c, g, unknown or other

<400> SEQUENCE: 86
gnngnggnnn nnttggtggc cttttttttt tnccnttttt tttttntttt tttatgtata 60
aacaggtacc agttttgatt ttatttaatc atttcataca ttaacataca tgacacatca 120
aaatgagaaa tgcacagttt aaccgttcaa cagctggcct tacttcaaaa gaacactata 180
ttcatattaa acatttacag nctttccatc taactttaca catgtcctaa atcattttcc 240
agcacttctc acatagaagt ctagttttgc tctttaaaat caccatctgt atcacccccta 300 gtagacgcga gggtttcccc aattacatgc tgaagagagc cagccaccac cccacctaaa 360
gacatccaag cagctccaga gcctgcctcc gaggccaccc cttcgccacg gcagtctcga 420
ttccaagaac tgattatctg acactagtga accagcacta aaggctgtag gatgtgacta 480
catcacagtt ccagaaggaa gggggaccat ggccaagaga agccctaaat gacagaagct 540

```
cattaaaacc aagtccccca aaccttctga aacatcgtta gcaaggagct actgntttcc    600

tttcttaaac atggtttggg gcatgacaca ctntggaagt ggtgaactgg tacacanttg    660

gggngngggg acattaacat caaaaactac tgngngnaac ttgagaaagn ctgattaaag    720

attcaatggt ttctaaaact aactcaaatc ggtgaccaga cttttnccag tttattacaa    780

tgngggtgg                                                            789
```

<210> SEQ ID NO 87
<211> LENGTH: 766
<212> TYPE: DNA
<213> ORGANISM: Homo sapiens
<220> FEATURE:
<221> NAME/KEY: modified_base
<222> LOCATION: (8)..(8)
<223> OTHER INFORMATION: a, t, c, g, unknown or other
<220> FEATURE:
<221> NAME/KEY: modified_base
<222> LOCATION: (523)..(523)
<223> OTHER INFORMATION: a, t, c, g, unknown or other
<220> FEATURE:
<221> NAME/KEY: modified_base
<222> LOCATION: (615)..(615)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (757)..(757)
<223> OTHER INFORMATION: a, t, c, g, unknown or other

<400> SEQUENCE: 87

```
cactgttngc ctactggctt tttttcagcc caggggcccg gcgcacgaaa cctgtttggg     60

aggttatggg atgataaacc caatcctgaa gccctaagtg acagttcaga gcgtcttttc    120

tcctttggcg tcatcgcaga tgttcaattt gcagacttag aagatggctt taatttccaa    180

ggaaccaggc ggcgatacta cagacatagt cttcttcact tacagggtgc cattgaagac    240

tggaataatg aaagcagcat gccctgttgt gtccttcagc ttggagatat catcgatgga    300

tataatgcac agtataatgc atccaaaaag tccctagaac ttgttatgga catgttcaag    360

aggcttaaag ttccagttca tcatacatgg ggaaaccatg aattctataa cttcagtaga    420

gagtatttaa cacactctaa acttaacact aagtttctag aagatcagat tgtcatcatc    480

ctgagaccat gccttcagaa gattattatg cttatcattt tgnaccattc cctaaattcc    540

gggtcatttt acttgatgca tatgacttga gtgtcttggg ccgtggatca gtcttcttca    600

aaatacgagc agtgnatgaa gatattgagg gagcacaatc caaatacgga ctgaatagtc    660

ctcaaggact tctgagcccc agtttgtcca gttaatggag gattcaagcc aagaacagtt    720

aactgggtga atgaaggcta ccattctntg acccaancaa gaaaag                   766
```

<210> SEQ ID NO 88
<211> LENGTH: 785
<212> TYPE: DNA
<213> ORGANISM: Homo sapiens
<220> FEATURE:
<221> NAME/KEY: modified_base
<222> LOCATION: (4)..(5)
<223> OTHER INFORMATION: a, t, c, g, unknown or other
<220> FEATURE:
<221> NAME/KEY: modified_base
<222> LOCATION: (11)..(11)
<223> OTHER INFORMATION: a, t, c, g, unknown or other
<220> FEATURE:
<221> NAME/KEY: modified_base
<222> LOCATION: (14)..(14)
<223> OTHER INFORMATION: a, t, c, g, unknown or other
<220> FEATURE:
<221> NAME/KEY: modified_base
<222> LOCATION: (19)..(19)
<223> OTHER INFORMATION: a, t, c, g, unknown or other
<220> FEATURE:
<221> NAME/KEY: modified_base
<222> LOCATION: (503)..(503)
<223> OTHER INFORMATION: a, t, c, g, unknown or other
<220> FEATURE:
<221> NAME/KEY: modified_base
<222> LOCATION: (665)..(665)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other
<220> FEATURE:
<221> NAME/KEY: modified_base
<222> LOCATION: (752)..(752)
<223> OTHER INFORMATION: a, t, c, g, unknown or other
<220> FEATURE:
<221> NAME/KEY: modified_base
<222> LOCATION: (769)..(769)
<223> OTHER INFORMATION: a, t, c, g, unknown or other
<220> FEATURE:
<221> NAME/KEY: modified_base
<222> LOCATION: (785)..(785)
<223> OTHER INFORMATION: a, t, c, g, unknown or other

<400> SEQUENCE: 88
gaannccttt ngantttttnt actaaacaat gagacagagg atttttattt ttttgtttag 60
gagggacaaa cacaaagctc attttctatc aagttaaaat aaattagact aacaatggaa 120
ggctctttct ttcttgtaat tcataattct atctggaact ctgcctctcc ctttcaacat 180
cattttgtca ggatagacat gaactgtgcc aaaggcttgg ctgtctggag ctgtttcaat 240
aactccttct aggttgacgt ggtatacacc aaaaggatcc tcagagtagc caccatcatg 300
ggtgtgacca gcaaagaaac acaccacaca ctcatgagac caaatgactg ccagggcatc 360
tctgtagttc caggccaggc acacattgtc agaggcgtcc gggtaaatgg gaagatggct 420
cacaatcacc accttttctt ggtttgtgtc agagaatgtt agcacttcat tcaaccagtt 480
tagctggtct tggctgaatc ctncattaaa ctggacaaac tggggctcaa aaagtccttg 540
aggactattc aagttccgta tttggatggg ctcctcaata tcttcataca ctggtcggat 600
tttggagaaa actgatccac gcccaagaca cttaaagcat atgcatcaag taaaatgaac 660
ccggnattta gggaatggtc caaaatggat agccttaata aancttttga aagcattggg 720
cttaaggatg atgtncaatc tggacctttt anaaacttaa gggttaaant taaaaggggg 780 gtaan 785

<210> SEQ ID NO 89
<211> LENGTH: 717
<212> TYPE: DNA
<213> ORGANISM: Homo sapiens
<220> FEATURE:
<221> NAME/KEY: modified_base
<222> LOCATION: (689)..(689)
<223> OTHER INFORMATION: a, t, c, g, unknown or other
<220> FEATURE:
<221> NAME/KEY: modified_base
<222> LOCATION: (694)..(694)
<223> OTHER INFORMATION: a, t, c, g, unknown or other
<220> FEATURE:

<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:
<221> NAME/KEY: modified_base
<222> LOCATION: (707)..(707)
<223> OTHER INFORMATION: a, t, c, g, unknown or other
<220> FEATURE:
<221> NAME/KEY: modified_base
<222> LOCATION: (716)..(716)
<223> OTHER INFORMATION: a, t, c, g, unknown or other

<400> SEQUENCE: 89

```
gggcactgtt ggcctactgg tatagttcat gacctggact ttctgtactc ttggaagctg     60

ggctccttaa aggaggcctc tagtgaacac ctttatctcc atgtccctct tagagcccag    120

agagctgccc ataggcattt tccagaattc ctcatgtcac ctagttcaat ttccattaac    180

tcagatcagc cattgtgatt caccatttgt caggctctca ggtttaacaa aacctactat    240

caccatcatc cttcaacagc cacagtctga attgagccaa catttttttt tctttgagaa    300

agaagtggac tggggcacaa cttttagtct gaggggagct agtggaaatc tagacaatag    360

aagtcatcga tagcagcttt tcctcaaatg tgtgactcct caggggctaa actgctctta    420

gcttagaatt atgctttact agagatctag cagataagtg ggttaatcac taccatcctg    480

taactagtta tatagcttcc agacatgagg gagacatcaa acagggatgg aagcaacccc    540

aaggatatgc aagaagggca tgatgaaccc ccttcctctg gcaggagaac aaggccaacc    600

aagggacaga ctggaaagca cttagatggt taaggaggag aaaggggaac ctttgccagt    660

ccttggcttt tgccaagtca agccagttnt ccgntgcttg naanctntaa cgcagna       717
```

<210> SEQ ID NO 90
<211> LENGTH: 726
<212> TYPE: DNA
<213> ORGANISM: Homo sapiens
<220> FEATURE:
<221> NAME/KEY: modified_base
<222> LOCATION: (5)..(5)
<223> OTHER INFORMATION: a, t, c, g, unknown or other
<220> FEATURE:
<221> NAME/KEY: modified_base
<222> LOCATION: (610)..(610)
<223> OTHER INFORMATION: a, t, c, g, unknown or other
<220> FEATURE:
<221> NAME/KEY: modified_base
<222> LOCATION: (618)..(618)
<223> OTHER INFORMATION: a, t, c, g, unknown or other
<220> FEATURE:
<221> NAME/KEY: modified_base
<222> LOCATION: (635)..(635)
<223> OTHER INFORMATION: a, t, c, g, unknown or other
<220> FEATURE:
<221> NAME/KEY: modified_base
<222> LOCATION: (656)..(656)
<223> OTHER INFORMATION: a, t, c, g, unknown or other
<220> FEATURE:
<221> NAME/KEY: modified_base
<222> LOCATION: (658)..(658)
<223> OTHER INFORMATION: a, t, c, g, unknown or other
<220> FEATURE:
<221> NAME/KEY: modified_base
<222> LOCATION: (691)..(691)
<223> OTHER INFORMATION: a, t, c, g, unknown or other
<220> FEATURE:
<221> NAME/KEY: modified_base
<222> LOCATION: (701)..(701)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other

<400> SEQUENCE: 90

```
ttttnctttt tggtgtttct ctcttttatt taaaaacagt gcttcattac catgtgcaaa     60
ggctgaggca gtgctcctcc ttcgcttaga gtttataaaa gccagcaaca tgatcaataa    120
tttatacaca tggagagtaa tacaaaaaaa taaggaataa aagctaaaga tctaactact    180
ccgaccttca caattccagc tacttgataa taataagagt aacccaatga atactgtatg    240
gtctgaaagc tactatacaa tatgattctt aacgagaagg gaagggaatt agagactgtc    300
acaaagccct gggatgcttc tctggagtta gcagggaaac aggaccctgg gcaagcagct    360
cgggtgtcct aggaagtgat tctgggggag gacgggaggg gagagagaag gctaggtggt    420
cgattacaca agcatcccat gtaatgcccc catgccccaa aggtacctgt tttgccatgg    480
caatgggagg ggctggagga acagcatgtt gcatgtaggg atggtccggt ccctgccatg    540
gggagtgggg agaagaggag aggttctgtg gcattttgag ccttgcaaag atttggactg    600
aaaagctcan agactcangt aggtcaacct gtcanggaca agtacacttc aacggntntc    660
ttctcgcttt gcagccctac ttacgcgtgt nagccccaag nttgnttcaa cttttcacaa    720
gcagan                                                               726
```

<210> SEQ ID NO 91
<211> LENGTH: 722
<212> TYPE: DNA
<213> ORGANISM: Homo sapiens
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (684)..(684)
<223> OTHER INFORMATION: a, t, c, g, unknown or other

<400> SEQUENCE: 91

```
ggcactgcng gcctactggc ttcacaatat tctttatttc tctgtctctg tctctctctc     60
tcaagtcaga gtgtacaaca gtaagcaaag tttggcctct gttctcgcgt gaaatcaagt    120
taacatgctc cacctgttga tatgtttgta agagaaatct catgtatatg cacatatgca    180
gaatttctgc tctttgcttc tcaggaaatc tcttttctcc aatgtaggaa gaacacatta    240
aaatgaataa gtcatgttat ttttagaaaa cagaaaagca aataaatgtg tgaatagaat    300
atgcactgtt tctgtgcttg aaacattgaa cattgaatat tgattgaaag gccaccatga    360
actttgaaag accactgtgt tcagagaact gtgatagaaa ctaaaagagt ataaaaagat    420
gtgatacttt catttttgag aggtttacag tgggatgcag aaaaaaagaa acctgtaaat    480
gtgaatggca gtgtgtttgg ttagtgccta ctggctatat aaaattgctt ttggatgtgt    540
ttcatgattc cttataaaac gaagacttaa taagtttact tggcagctga tgggcaaagt    600
tttaaaaaaa atcaaatgag ttttttggtt tcctttaagc agttcctggc aatgctttct    660
tttttttat ttcaaacaga tganttttta aaacaatgat tgcatttaga accttcaaga    720
ag                                                                   722
```

<210> SEQ ID NO 92
<211> LENGTH: 724
<212> TYPE: DNA
<213> ORGANISM: Homo sapiens
<220> FEATURE:
<221> NAME/KEY: modified_base
<222> LOCATION: (696)..(696)
<223> OTHER INFORMATION: a, t, c, g, unknown or other

<400> SEQUENCE: 92

```
tttccctttt ttcggaactg taaggttctt aacttctcca atagtgcacg gctctgaaaa     60

gtacttttag aaagcagttc caacatttct tttcaggcag ttcttaagaa tgttggaatg    120

tgaacaacaa caaaaaaaag ttgcttcaac cacagcctgc actctgcatt tggcccgcaa    180

gcactgctga cgttgcagaa taaataccaa tgacaccaca agcaacttga aaaaattttt    240

tggactgaca aagctcacat tatgcaacac ttaattgagt atatttcttc acatagagag    300

aaacagcaca gtggtcacag ggtaaaatcc agtgaattga atatactggg cattttaatt    360

gcagaaaatt gtgcattcct gccatcattg tttataataa ctacatacac gtgctgcatt    420

aaaccagttc tgagtttaag acctaaatga accagactca gacacacaga ctgctttcct    480

actccctact gccatcatag actaaacaag tatcagtcat gaataaaaca tcaaggtgaa    540

atataaatat acacatcgcc cttctcaaaa gtatcatggc aaaggccctt acacataata    600

aaactgcttg gtgcatctct tatgggaaga cacagagtac agacagctgt gctagtcctg    660

gctcaagagt ccagccttta ttaacccaaa gcttanggcc taagcccctt tgacaccaag    720

gaag                                                                 724
```

<210> SEQ ID NO 93
<211> LENGTH: 758
<212> TYPE: DNA
<213> ORGANISM: Homo sapiens
<220> FEATURE:
<221> NAME/KEY: modified_base
<222> LOCATION: (522)..(522)
<223> OTHER INFORMATION: a, t, c, g, unknown or other
<220> FEATURE:
<221> NAME/KEY: modified_base
<222> LOCATION: (612)..(612)
<223> OTHER INFORMATION: a, t, c, g, unknown or other
<220> FEATURE:
<221> NAME/KEY: modified_base
<222> LOCATION: (646)..(646)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (670)..(670)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (688)..(688)
<223> OTHER INFORMATION: a, t, c, g, unknown or other
<220> FEATURE:
<221> NAME/KEY: modified_base
<222> LOCATION: (690)..(690)
<223> OTHER INFORMATION: a, t, c, g, unknown or other
<220> FEATURE:
<221> NAME/KEY: modified_base
<222> LOCATION: (724)..(724)
<223> OTHER INFORMATION: a, t, c, g, unknown or other
<220> FEATURE:
<221> NAME/KEY: modified_base
<222> LOCATION: (730)..(730)
<223> OTHER INFORMATION: a, t, c, g, unknown or other
<220> FEATURE:
<221> NAME/KEY: modified_base
<222> LOCATION: (739)..(739)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (758)..(758)
<223> OTHER INFORMATION: a, t, c, g, unknown or other

<400> SEQUENCE: 93

```
cactgttggc ctactggaat tattcagttg cggagacctg tttgagaaaa aaaactcttt     60

gtcttcttta atcaagtgtt gtattgtctg tggcactgtt ttaaatgaaa gacaattaaa    120

ttgctttgct gttttataca ttgttgtctt taatcactag tctaaactct atgtttttat    180

gaaagcatct ttaaattttt tttcttagct gttctttctt gtttgtggta taacctttct    240

gtaccatctt ttggttctgt ggaaatgccc ttaataacac ataggattag gactaaattt    300

tggagatggg taagtttgag caaagagtca gtcaacacag gggaggattt ttgaaatttt    360

atctctaaaa acagtttcc aattcagagt ttttaaaacc cttttaaaaa tatagttagt    420

tttcagtggt ttcttttact tttaagtgtt tttacacttg gaagtcagat atctaaaaat    480

agggaatggt cttttgctat tttaagatct ctactaaaat gnaatctgta gtgtttcttg    540

gttcagagca tatcttaaaa gatcagacag gggcatttgg ggccctcttc ccatccactg    600

ctttcactca anggaaaata agactcttgg tctgcaaatc tggctntggc anaaatgggc    660

tactggtttn cntggggacc ntttaagnan tatggtggaa gaccgttttc ctcagtggaa    720

accnggtccn aagctttcng gtaaanaagc ctatgacn                            758
```

<210> SEQ ID NO 94
<211> LENGTH: 758
<212> TYPE: DNA
<213> ORGANISM: Homo sapiens
<220> FEATURE:
<221> NAME/KEY: modified_base
<222> LOCATION: (539)..(539)
<223> OTHER INFORMATION: a, t, c, g, unknown or other
<220> FEATURE:
<221> NAME/KEY: modified_base
<222> LOCATION: (563)..(563)
<223> OTHER INFORMATION: a, t, c, g, unknown or other
<220> FEATURE:
<221> NAME/KEY: modified_base
<222> LOCATION: (567)..(567)
<223> OTHER INFORMATION: a, t, c, g, unknown or other
<220> FEATURE:
<221> NAME/KEY: modified_base
<222> LOCATION: (590)..(590)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (609)..(609)
<223> OTHER INFORMATION: a, t, c, g, unknown or other
<220> FEATURE:

-continued

<221> NAME/KEY: modified_base
<222> LOCATION: (616)..(616)
<223> OTHER INFORMATION: a, t, c, g, unknown or other
<220> FEATURE:
<221> NAME/KEY: modified_base
<222> LOCATION: (622)..(622)
<223> OTHER INFORMATION: a, t, c, g, unknown or other
<220> FEATURE:
<221> NAME/KEY: modified_base
<222> LOCATION: (625)..(625)
<223> OTHER INFORMATION: a, t, c, g, unknown or other
<220> FEATURE:
<221> NAME/KEY: modified_base
<222> LOCATION: (629)..(629)
<223> OTHER INFORMATION: a, t, c, g, unknown or other
<220> FEATURE:
<221> NAME/KEY: modified_base
<222> LOCATION: (644)..(644)
<223> OTHER INFORMATION: a, t, c, g, unknown or other
<220> FEATURE:
<221> NAME/KEY: modified_base
<222> LOCATION: (652)..(652)
<223> OTHER INFORMATION: a, t, c, g, unknown or other
<220> FEATURE:
<221> NAME/KEY: modified_base
<222> LOCATION: (655)..(656)
<223> OTHER INFORMATION: a, t, c, g, unknown or other
<220> FEATURE:
<221> NAME/KEY: modified_base
<222> LOCATION: (669)..(669)
<223> OTHER INFORMATION: a, t, c, g, unknown or other
<220> FEATURE:
<221> NAME/KEY: modified_base
<222> LOCATION: (675)..(676)
<223> OTHER INFORMATION: a, t, c, g, unknown or other
<220> FEATURE:
<221> NAME/KEY: modified_base
<222> LOCATION: (680)..(682)
<223> OTHER INFORMATION: a, t, c, g, unknown or other
<220> FEATURE:
<221> NAME/KEY: modified_base
<222> LOCATION: (687)..(687)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (705)..(708)
<223> OTHER INFORMATION: a, t, c, g, unknown or other
<220> FEATURE:
<221> NAME/KEY: modified_base
<222> LOCATION: (715)..(715)
<223> OTHER INFORMATION: a, t, c, g, unknown or other
<220> FEATURE:
<221> NAME/KEY: modified_base
<222> LOCATION: (722)..(722)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (727)..(727)
<223> OTHER INFORMATION: a, t, c, g, unknown or other
<220> FEATURE:
<221> NAME/KEY: modified_base
<222> LOCATION: (729)..(729)
<223> OTHER INFORMATION: a, t, c, g, unknown or other
<220> FEATURE:
<221> NAME/KEY: modified_base
<222> LOCATION: (733)..(734)
<223> OTHER INFORMATION: a, t, c, g, unknown or other
<220> FEATURE:
<221> NAME/KEY: modified_base
<222> LOCATION: (741)..(741)
<223> OTHER INFORMATION: a, t, c, g, unknown or other
<220> FEATURE:
<221> NAME/KEY: modified_base
<222> LOCATION: (744)..(744)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (748)..(748)
<223> OTHER INFORMATION: a, t, c, g, unknown or other
<220> FEATURE:
<221> NAME/KEY: modified_base
<222> LOCATION: (753)..(753)
<223> OTHER INFORMATION: a, t, c, g, unknown or other
<220> FEATURE:
<221> NAME/KEY: modified_base
<222> LOCATION: (756)..(757)
<223> OTHER INFORMATION: a, t, c, g, unknown or other

<400> SEQUENCE: 94

```
ttttttttta attttttgta gagatgggtc ttgaactctt gggcttaagc gatcctcccg     60

cctcagcctc ctgaagtgtt gggattacag gtgtgagcca catgccaggc ccgaaagttt    120

gtatataaca tacatgaaca tgtctcacca aaaccccaa gctccaaata ttcaaatgaa    180

aattgttcat aaatataaaa cataccctgg aactttgcta tcatattcaa tatcctgaag    240

ttttatttag ggtaaaactt tccatcctga attctgtcaa caaggtttag ttactttaaa    300

actctcatta aatagcagtc tcacctataa agcatatatt catataggtt aaaatattct    360

attgctagaa aacctatggc tcatgtttat ctactgataa agcccaaaag tcttgacttt    420

tcagagaatg gcttttaagt tcactgaggc ttcataacag atgctttttc atttcctatc    480

ataaagagag caggatttta ctatacaggt ggcatattac tggtcaatcc agctatggnt    540

acagcacttt agaccaaacc ggngcanttt tacaaaccac acattgtaan ggttttgaac    600

atttnggana caggtnctgg anatntaant tggtattacc cttntattcc anagnntttc    660

ccttttacna acttnncccn nngaagnagt cccttcncgn ttcannnnac ccttnatttt    720

anctngntnc aanntttgg naantncntt ttnccnnc                             758
```

<210> SEQ ID NO 95
<211> LENGTH: 747
<212> TYPE: DNA
<213> ORGANISM: Homo sapiens
<220> FEATURE:
<221> NAME/KEY: modified_base
<222> LOCATION: (1)..(1)
<223> OTHER INFORMATION: a, t, c, g, unknown or other
<220> FEATURE:
<221> NAME/KEY: modified_base
<222> LOCATION: (621)..(621)
<223> OTHER INFORMATION: a, t, c, g, unknown or other
<220> FEATURE:
<221> NAME/KEY: modified_base
<222> LOCATION: (668)..(668)
<223> OTHER INFORMATION: a, t, c, g, unknown or other
<220> FEATURE:
<221> NAME/KEY: modified_base
<222> LOCATION: (672)..(672)
<223> OTHER INFORMATION: a, t, c, g, unknown or other
<220> FEATURE:
<221> NAME/KEY: modified_base
<222> LOCATION: (686)..(686)
<223> OTHER INFORMATION: a, t, c, g, unknown or other
<220> FEATURE:

-continued

<221> NAME/KEY: modified_base
<222> LOCATION: (692)..(692)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (740)..(740)
<223> OTHER INFORMATION: a, t, c, g, unknown or other

<400> SEQUENCE: 95

```
ngagcactgt tggcctactg gtactagagg tgctaagtta gaacactagg cttttattga     60

ggcaggtttt aatattgata gatgcttttt gtttggtttg tttcttctgg gagagaatgg    120

aggacttaag tagaagtagc tactgataac agactttcta gtagcagttt ccactccacg    180

gttacctttt tagtttcata gtatcttttc acaaagtatt acaaataagc tagattctcc    240

cagtttggga atgcaagttt gctacatttt tagcctggca atatttgtgt aggtattgcc    300

ttattggaaa ttctggaaac ctgatactgc aacctgcaat gtaggatgtt tgtatggcat    360

ttaaaggtaa tggtgatgtt tattattcta tactttgcat tctgtgagag taattttcac    420

tctgtcttaa gtgtgagtaa gcctcttcta aaaatcttgt tcttgccaag aaatttataa    480

atcacatacg aagacgtctg ttgctaacag ttaactttat gaggtaacta tatccttcta    540

tttctctgga ctcattttta aaaaatatgc cgaatctgca tactggttaa ggtagtatat    600

aagtttatga gagaagtgga nagctttctt ccttgaaaag tcggtatttg gtgagatcca    660

tttgcctnac anaaaggtgt ccccantcca tncccattgn cagataataa atattttgag    720

aaaagngcct aaacagctgn aatctta                                        747
```

<210> SEQ ID NO 96
<211> LENGTH: 768
<212> TYPE: DNA
<213> ORGANISM: Homo sapiens
<220> FEATURE:
<221> NAME/KEY: modified_base
<222> LOCATION: (3)..(3)
<223> OTHER INFORMATION: a, t, c, g, unknown or other
<220> FEATURE:
<221> NAME/KEY: modified_base
<222> LOCATION: (658)..(658)
<223> OTHER INFORMATION: a, t, c, g, unknown or other
<220> FEATURE:
<221> NAME/KEY: modified_base
<222> LOCATION: (678)..(678)
<223> OTHER INFORMATION: a, t, c, g, unknown or other
<220> FEATURE:
<221> NAME/KEY: modified_base
<222> LOCATION: (726)..(726)
<223> OTHER INFORMATION: a, t, c, g, unknown or other
<220> FEATURE:
<221> NAME/KEY: modified_base
<222> LOCATION: (728)..(728)
<223> OTHER INFORMATION: a, t, c, g, unknown or other

<400> SEQUENCE: 96

```
ttnttttct tttttaaaaa cccagtagtt ttatttcaaa gtataaattt caggcttgct     60

ggacaaaacc ccactacagg taacacttat acagacacca ctctactata catttaaaaa    120

agaaaaacac acacacgcac gcacacacac acacaaacct tcaaaaccct aataaaaata    180

gggccacttg ctggagccca gtttgtatta gacattagga aggtcttact tacattgtct    240
```

```
tattatttac actttcaatt gcaataaaga aaaattagga tgcaagtttc ttacaaagga    300

tttttatatt taattttaaa atggctgata aaatactaaa gccagaatcc ccaaaaggtg    360

tttgattgcc cagttacctt atttacaaaa caaaacaaaa caaaaacaga caaaaacaaa    420

gacctcaaaa aaataataaa gacggcattt aaatatgggt acttagctga ctctacaaat    480

aaaaaacaaa gaaaagttta ttttaacatg gtaaattatt gaaaatgaga aaacaaaaca    540

tgtgtttgca ttatcctatt cctccccatt ggctggctca aggggatgaa tgagtttcaa    600

ggaattagga caagtctggc acactaacaa acgcttcatg agaattgctg atttttgngt    660

gtccaaaagt taaaaatnat aataattaaa aaaatagggc atttgccagt aaaaatagta    720

agggangnag gaatcacaca tcgggtttag aggtatttga tattgcaa                 768
```

```
<210> SEQ ID NO 97
<211> LENGTH: 750
<212> TYPE: DNA
<213> ORGANISM: Homo sapiens
<220> FEATURE:
<221> NAME/KEY: modified_base
<222> LOCATION: (600)..(600)
<223> OTHER INFORMATION: a, t, c, g, unknown or other
<220> FEATURE:
<221> NAME/KEY: modified_base
<222> LOCATION: (605)..(605)
<223> OTHER INFORMATION: a, t, c, g, unknown or other
<220> FEATURE:
<221> NAME/KEY: modified_base
<222> LOCATION: (627)..(627)
<223> OTHER INFORMATION: a, t, c, g, unknown or other
<220> FEATURE:
<221> NAME/KEY: modified_base
<222> LOCATION: (669)..(669)
<223> OTHER INFORMATION: a, t, c, g, unknown or other
<220> FEATURE:
<221> NAME/KEY: modified_base
<222> LOCATION: (679)..(679)
<223> OTHER INFORMATION: a, t, c, g, unknown or other
<220> FEATURE:
<221> NAME/KEY: modified_base
<222> LOCATION: (684)..(684)
<223> OTHER INFORMATION: a, t, c, g, unknown or other
<220> FEATURE:
<221> NAME/KEY: modified_base
<222> LOCATION: (748)..(749)
<223> OTHER INFORMATION: a, t, c, g, unknown or other

<400> SEQUENCE: 97

cgagcactgt tggcctactg gatcgtataa aatcttatgt ggaagccaaa cattaaactg     60

gtaaaaatca tttcaggttg agggtgtatg ttggtgggta cgaagtggtt tcagagcttc    120

cctctcagtt ttcccagtgt tccccaaaga ctcctaggac acctcggggg agctcagggg    180

acccaatgca gcacaactag aggccccagc ctccacactg cctggtgggg gggtctagac    240

tgaatcgtga aatcacccta tctatgggct gtgtgtccag ttgttggggt gaggtctggg    300

gagtggggga tgcaagtggt ggagggaatg aaaggaggga gggaaacttc cagtgcctca    360

tcattcaccc tccccataga tggcacctgg gctccccggg gctgggtcag gctctgagtg    420

acagccattg aagagaagcc agcctccagg aaatttctcc agcatgactg ggcatcctct    480

ctcctagcca aatatatcag agctttgagg aaaatgggct tctggccagg ccacactcgt    540

ccttaggaag agctggttca tctgaggaat ctttttgtag acaggtgctg gtccttgaan    600

ggtangtccg ctgagcttgc gccatanaat gcctacacca ctggcatcct ttagtcctgc    660

tgaagggang gactaactnc tggnaatttt cgtttggtga tcaataaagg ttggtggatt    720
```

```
ggcaagtgcc acctggataa ttctacanna                                    750


<210> SEQ ID NO 98
<211> LENGTH: 760
<212> TYPE: DNA
<213> ORGANISM: Homo sapiens
<220> FEATURE:
<221> NAME/KEY: modified_base
<222> LOCATION: (9)..(9)
<223> OTHER INFORMATION: a, t, c, g, unknown or other
<220> FEATURE:
<221> NAME/KEY: modified_base
<222> LOCATION: (575)..(575)
<223> OTHER INFORMATION: a, t, c, g, unknown or other
<220> FEATURE:
<221> NAME/KEY: modified_base
<222> LOCATION: (591)..(591)
<223> OTHER INFORMATION: a, t, c, g, unknown or other
<220> FEATURE:
<221> NAME/KEY: modified_base
<222> LOCATION: (602)..(602)
<223> OTHER INFORMATION: a, t, c, g, unknown or other
<220> FEATURE:
<221> NAME/KEY: modified_base
<222> LOCATION: (624)..(624)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (667)..(667)
<223> OTHER INFORMATION: a, t, c, g, unknown or other
<220> FEATURE:
<221> NAME/KEY: modified_base
<222> LOCATION: (686)..(686)
<223> OTHER INFORMATION: a, t, c, g, unknown or other
<220> FEATURE:
<221> NAME/KEY: modified_base
<222> LOCATION: (716)..(716)
<223> OTHER INFORMATION: a, t, c, g, unknown or other

<400> SEQUENCE: 98

tttttttttnt ttgtgagggg gaccgagttt tgctctttcc acccaggctg gagtacaatg      60

gtgcaatctt ggctcactgc aacctccgcc tgtcaggttc aagtgattct cctgcctcag     120

cctcccgagt agctgagatt acaggcacac aacaccgtgc ccagctaact tctatatttt     180

tagtagaaac ggggtttcac catgttggcc aggttggtct ctaacttctg acctcaagtg     240

atccaccccc cttcagcctc tcaaagtgct aggattacag gcgtgagcca tcgcgcccag     300

cctgtaataa ttcttaaaaa caatcaacat tataaaaaat aaaaattgta gggtaccatg     360

aaaccaagct gattgttctt cccaggggag gaggaagggc cagagaggat ttggaaggta     420

ttatccagca caggttaggt ttgatcagtc agtggatgct gctgggttgg aaactggatt     480

ttccatctac cagtgcacac tcagccctca gtattcttag agcacatgag gaaaaaaaat     540

cactattaag ctttaatttc cagagccctt actgngtgct ttgtgcaatg nactttattc     600

tnacaacaac ccagagatgt aagnattttt agcccatttg acagatgang aaattgatgc     660

cagaaangat aagaaacttg cttaanggta catagatggg gaaggcaagc ttgcangggt     720

agaaaccaag cccgttggtg aatcctaata ataatgggcc                         760


<210> SEQ ID NO 99
<211> LENGTH: 781
<212> TYPE: DNA
<213> ORGANISM: Homo sapiens
<220> FEATURE:
<221> NAME/KEY: modified_base
```

<222> LOCATION: (543)..(543)
<223> OTHER INFORMATION: a, t, c, g, unknown or other
<220> FEATURE:
<221> NAME/KEY: modified_base
<222> LOCATION: (650)..(660)
<223> OTHER INFORMATION: a, t, c, g, unknown or other
<220> FEATURE:
<221> NAME/KEY: modified_base
<222> LOCATION: (697)..(697)
<223> OTHER INFORMATION: a, t, c, g, unknown or other
<220> FEATURE:
<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (733)..(733)
<223> OTHER INFORMATION: a, t, c, g, unknown or other
<220> FEATURE:
<221> NAME/KEY: modified_base
<222> LOCATION: (738)..(738)
<223> OTHER INFORMATION: a, t, c, g, unknown or other
<220> FEATURE:
<221> NAME/KEY: modified_base
<222> LOCATION: (753)..(753)
<223> OTHER INFORMATION: a, t, c, g, unknown or other
<220> FEATURE:
<221> NAME/KEY: modified_base
<222> LOCATION: (781)..(781)
<223> OTHER INFORMATION: a, t, c, g, unknown or other

<400> SEQUENCE: 99
cactgttggc ctactggatt aatttactcg cagttgctgc tgctcaggaa gagagacaag 60
gaatatttta acagaatcaa ggcatagaag aatcaccatt ttatttgagc ctctaatcag 120
agtcagacca gtagagaaat taaataagat tagaaaactc tgtactgaaa gctgctgatg 180
cttcaaaaat gaaaacaaga tctcacaact ctccctgtta gttgaaaata tatcaatttg 240
ctctgaaagg attcagctgc ctagtgttgc cattactaac ataaacatat ggctcatatt 300
tccatccaga gaaattaatg ctaaattggt gcctcgctaa catcagatac actgtattat 360
gcttaaatat attcagtaaa atgtggaaag gggtattaac aacgacaaca aaaagatgga 420 ttttttttt ctcacaatca cagttgctaa tccagtggga gatgtttgag agagttttgt 480
tcaacatcac agtgagagtg cctagggaaa tcagaaaatt acaatggatt cccctttgat 540
tgnaataagt gttgattttc tccatgagtt ggttatcctg tctagtgatt tgatggtgaa 600
cttttctaaa taaatagccc tttcccttcg gtgtcggtaa aaaaaaaaan nnnnnnnnnn 660
aaaaaaaaag gccacatgtg ctcgaactgc aggtcgnggn ccgttagact agtctaagag 720
aaaaaccttc canacttncc ctgaacctga acnttaaaag gatgccattg gtggtggtaa 780 n 781

<210> SEQ ID NO 100
<211> LENGTH: 776
<212> TYPE: DNA
<213> ORGANISM: Homo sapiens
<220> FEATURE:
<221> NAME/KEY: modified_base
<222> LOCATION: (302)..(302)
<223> OTHER INFORMATION: a, t, c, g, unknown or other
<220> FEATURE:
<221> NAME/KEY: modified_base
<222> LOCATION: (458)..(458)
<223> OTHER INFORMATION: a, t, c, g, unknown or other
<220> FEATURE:
<221> NAME/KEY: modified_base
<222> LOCATION: (558)..(558)
<223> OTHER INFORMATION: a, t, c, g, unknown or other
<220> FEATURE:

<221> NAME/KEY: modified_base
<222> LOCATION: (700)..(700)
<223> OTHER INFORMATION: a, t, c, g, unknown or other
<220> FEATURE:
<221> NAME/KEY: modified_base
<222> LOCATION: (704)..(704)
<223> OTHER INFORMATION: a, t, c, g, unknown or other
<220> FEATURE:
<221> NAME/KEY: modified_base
<222> LOCATION: (725)..(725)
<223> OTHER INFORMATION: a, t, c, g, unknown or other
<220> FEATURE:
<221> NAME/KEY: modified_base
<222> LOCATION: (742)..(742)
<223> OTHER INFORMATION: a, t, c, g, unknown or other
<220> FEATURE:
<221> NAME/KEY: modified_base
<222> LOCATION: (746)..(746)
<223> OTHER INFORMATION: a, t, c, g, unknown or other
<220> FEATURE:
<221> NAME/KEY: modified_base
<222> LOCATION: (773)..(773)
<223> OTHER INFORMATION: a, t, c, g, unknown or other

<400> SEQUENCE: 100

```
tttttttttt tttaccgaca ccggagggga aagggctatt tatttagaaa agttcaccat     60

caaatcacta gacaggataa acaactcatg gagaaaatca acacttatta caatcaaagg    120

ggaatccatt gtaattttct gatttcccta ggcactctca ctgtgatgtt gaacaaaact    180

ctctcaaaca tctcccactg gattagcaac tgtgattgtg agaaaaaaaa aatccatctt    240

tttgttgtcg ttgttaatac ccctttccac attttactga atatatttaa gcataataca    300

gngtatctga tgttagcgag gcaccaattt agcattaatt tctctggatg gaaatatgag    360

ccatatgttt atgttagtaa tggcaacact aggcagctga atcctttcag agcaaattga    420

tatattttca actaacaggg agagttgtga gatcttgntt tcatttttga agcatcagca    480

gctttcagta cagagttttc taatcttatt taatttctct actggtctga ctctgattag    540

aggctcaaat aaaatggnga ttcttctatg ccttgattct ggtaaaatat tccttggctc    600

tcttcctgag cagcagcaac tgcgagtaaa ttaatccagt aggccaacag gctcgaggaa    660

ttccgcagct tttaaagcag aagtacactt ccgtcaaggn ctanaagtaa aggcaccatc    720

cctgnggagc cagtctttgg anttgnacca ccaccggatc cgggaccgga aanaat        776
```

<210> SEQ ID NO 101
<211> LENGTH: 740
<212> TYPE: DNA
<213> ORGANISM: Homo sapiens
<220> FEATURE:
<221> NAME/KEY: modified_base
<222> LOCATION: (6)..(6)
<223> OTHER INFORMATION: a, t, c, g, unknown or other
<220> FEATURE:
<221> NAME/KEY: modified_base
<222> LOCATION: (16)..(16)
<223> OTHER INFORMATION: a, t, c, g, unknown or other
<220> FEATURE:
<221> NAME/KEY: modified_base
<222> LOCATION: (106)..(106)
<223> OTHER INFORMATION: a, t, c, g, unknown or other
<220> FEATURE:
<221> NAME/KEY: modified_base
<222> LOCATION: (594)..(594)
<223> OTHER INFORMATION: a, t, c, g, unknown or other
<220> FEATURE:
<221> NAME/KEY: modified_base
<222> LOCATION: (633)..(633)
<223> OTHER INFORMATION: a, t, c, g, unknown or other
<220> FEATURE:
<221> NAME/KEY: modified_base
<222> LOCATION: (681)..(681)
<223> OTHER INFORMATION: a, t, c, g, unknown or other
<220> FEATURE:
<221> NAME/KEY: modified_base
<222> LOCATION: (696)..(696)
<223> OTHER INFORMATION: a, t, c, g, unknown or other
<220> FEATURE:
<221> NAME/KEY: modified_base
<222> LOCATION: (713)..(713)
<223> OTHER INFORMATION: a, t, c, g, unknown or other

<400> SEQUENCE: 101

```
actgtnggcc tactgncaga tgaactaggt cagatccctt ggaaagattg aatatagaat      60

tttaatggca tcaaatagtt ctgtccttcc atattagaca attatntttc aaccgaagtc     120

acattttgga gaagactcta taccagaatc ttagtaagag ctttttattc tctgtgtagt     180

agtaggatag ctttttgggg gtgttttcct ggtttttcca aattgctaca attttaacaa     240

ttatgatcat gaatagcaaa aagaaagaaa acatcactca gaagtgaaga aaagcgcttg     300

gtcagacaca aaagcccagt cacaaaggtt aaaataacca tcattttgtg agccttttta     360

caatgcacta gacaccgtga ggtgtgcatc atctccatcc ctcacagcag cactgaaggg     420

tagatgatat tattcccagc atcctattgc tatccagagg gaaaggaggc ttagccaacg     480

ggctgcaaac attccaattc cttttcctga gatggacgca tgaactctct tggcccaaag     540

gcattaaata ttccggccat gtaacccgat gccccttctt ggaattcaga gctnccctgc     600

aacctgctgg gtatcatttg gcttctatca cangctggca acggtgagaa gtacacatgg     660

gtcacgctca tgtaaatatt ncagaccata tggcangtgg gatttctcac tgnaaatgaa     720

cacattggct ttggtctata                                                 740
```

<210> SEQ ID NO 102
<211> LENGTH: 742
<212> TYPE: DNA
<213> ORGANISM: Homo sapiens
<220> FEATURE:
<221> NAME/KEY: modified_base
<222> LOCATION: (68)..(68)
<223> OTHER INFORMATION: a, t, c, g, unknown or other
<220> FEATURE:
<221> NAME/KEY: modified_base
<222> LOCATION: (484)..(484)
<223> OTHER INFORMATION: a, t, c, g, unknown or other
<220> FEATURE:
<221> NAME/KEY: modified_base
<222> LOCATION: (500)..(500)
<223> OTHER INFORMATION: a, t, c, g, unknown or other
<220> FEATURE:
<221> NAME/KEY: modified_base
<222> LOCATION: (649)..(649)
<223> OTHER INFORMATION: a, t, c, g, unknown or other
<220> FEATURE:
<221> NAME/KEY: modified_base
<222> LOCATION: (669)..(669)
<223> OTHER INFORMATION: a, t, c, g, unknown or other
<220> FEATURE:
<221> NAME/KEY: modified_base
<222> LOCATION: (691)..(691)
<223> OTHER INFORMATION: a, t, c, g, unknown or other
<220> FEATURE:
<221> NAME/KEY: modified_base
<222> LOCATION: (705)..(705)
<223> OTHER INFORMATION: a, t, c, g, unknown or other
<220> FEATURE:
<221> NAME/KEY: modified_base
<222> LOCATION: (735)..(735)
<223> OTHER INFORMATION: a, t, c, g, unknown or other

<400> SEQUENCE: 102

-continued

```
ttttcttttt ctttggaggt caccatttct gagctggaaa gttaggactc attggatgat      60

catgaatnca taagaaggta gaaatcggtg aagggcccac tattaaccta tcatttagaa     120

atgattttca tgggtcattt attaagagcc catggaaaga gttctgcaaa gatccctgaa     180

agaaatgcag ctcttgccca gtcatcacct tttacggttg agaaagttga agctcagaga     240

aattataaac tccaccaagt tttgtacagg ttagtagcag agtctaaagt ctgctgtttt     300

acccttattt tggtgttcct ttaacacgta ttattgtaca tctactgtcc taggaactga     360

gcaaattaca tttgttgttt accccaaact ttgatattag gaaagaaaaa aacatgtatc     420

ttaaaacaac gaaaggaaga tctgtttcct ttttcatctt ttgtgcattt gccctctttc     480

tagnttctta agtttaatgn ttctttttta gtaacctata ggacattgca ctaggcctga     540

aggagaaaga cattttgggc tgcagtgaca agaaagtgat agtttaatgc aagggttccc     600

caaaatggta tgagaagctt ctattttaca ttttattttc attggtggnt ttttggtttt     660

aaagatggng aagtggggca aaaagtggaa ntttccactg gaagngaatt ttgggctttt     720

ttactgggat tcaangggaa ga                                              742
```

<210> SEQ ID NO 103
<211> LENGTH: 734
<212> TYPE: DNA
<213> ORGANISM: Homo sapiens
<220> FEATURE:
<221> NAME/KEY: modified_base
<222> LOCATION: (6)..(6)
<223> OTHER INFORMATION: a, t, c, g, unknown or other
<220> FEATURE:
<221> NAME/KEY: modified_base
<222> LOCATION: (15)..(15)
<223> OTHER INFORMATION: a, t, c, g, unknown or other

<400> SEQUENCE: 103

```
ctgtcngcct actgntccac aacagaaaat agactgaatt taaaaaaatt gatgattatg      60

aaaaatttgg tgatttccag aaatatgagt ttactcgttt aaaatagatg actcagtata     120

gaatttcatg tgataatgtt tttcattagt attcatgatc tgatcctaga aatatttttc     180

tcgtgttttt tttttttcca aacaatttat tttagattgc aactagtaga taattgcttt     240

atgttttagg gaaaagaatc gcttaattat tgtaatccct caaacacaat attggaactt     300

ttaccatgac catttctaat gccagcccca caatatagct gaatcttgcc atcaagctta     360

ctatctaagg aatctcagtc ttcttttcta gtttatgaac tacggtaatt gaaaaaaggg     420

atttccaaaa gataattgta ttgattaatc caatttctgg gttgagcata aggttgtaaa     480

ttggagatca ttcatataaa ttgaatacaa agggagaatt ttttttaagt cttttttga     540

catattaaat gatttatgct gaactcctaa aagctttcca gccccacaga gcttcaatag     600

atgtctaatg gagcctgaat gccagctcta tttttggtgc ttatccagta ggtgggaaac     660

ctttaacagt aggatgagtc tttggttccg ttccatggaa aagctcatgg gctaacattt     720

atgacttcta atgt                                                       734
```

<210> SEQ ID NO 104
<211> LENGTH: 738
<212> TYPE: DNA
<213> ORGANISM: Homo sapiens
<220> FEATURE:
<221> NAME/KEY: modified_base
<222> LOCATION: (587)..(587)
<223> OTHER INFORMATION: a, t, c, g, unknown or other
<220> FEATURE:
<221> NAME/KEY: modified_base
<222> LOCATION: (600)..(600)
<223> OTHER INFORMATION: a, t, c, g, unknown or other
<220> FEATURE:
<221> NAME/KEY: modified_base
<222> LOCATION: (620)..(620)
<223> OTHER INFORMATION: a, t, c, g, unknown or other
<220> FEATURE:
<221> NAME/KEY: modified_base
<222> LOCATION: (628)..(628)
<223> OTHER INFORMATION: a, t, c, g, unknown or other
<220> FEATURE:
<221> NAME/KEY: modified_base
<222> LOCATION: (653)..(653)
<223> OTHER INFORMATION: a, t, c, g, unknown or other
<220> FEATURE:
<221> NAME/KEY: modified_base
<222> LOCATION: (703)..(703)
<223> OTHER INFORMATION: a, t, c, g, unknown or other
<220> FEATURE:
<221> NAME/KEY: modified_base
<222> LOCATION: (706)..(706)
<223> OTHER INFORMATION: a, t, c, g, unknown or other
<220> FEATURE:
<221> NAME/KEY: modified_base
<222> LOCATION: (709)..(709)
<223> OTHER INFORMATION: a, t, c, g, unknown or other
<220> FEATURE:
<221> NAME/KEY: modified_base
<222> LOCATION: (712)..(712)
<223> OTHER INFORMATION: a, t, c, g, unknown or other
<220> FEATURE:
<221> NAME/KEY: modified_base
<222> LOCATION: (721)..(721)
<223> OTHER INFORMATION: a, t, c, g, unknown or other

<400> SEQUENCE: 104
ccttttaaga ggtggggtct tgctatatca ccatggctgc agcgatcctg gactcaaggg 60
agtggctggg actaaaggcg tgcaccaccg cacctggctt taaattctcc cttttcctgc 120
tttgtgtgag tgagataagc agtatgcatg agaagatctt agagtaagaa agtcaaagaa 180
gacgacagtg atttgagctg cttcattgtt tggccccaaa gccaggcaga cctcatagtt 240
ctagcagcca ggatcctggt gttaatcagt gtcaataact taattttagt gttttgctct 300
tttcctgagt cagcagttag tttccatgat ttttacctga attctttggt tatcgggtct 360
ttaatctgcg ttgaggattt agtgtgttgg gagagtctgc tgcttgtgcc aaggcttcct 420
gctgctccag gccagtttag cagtgtgacc actgctcacc atcagctgac ggagcttcag 480
tccctgtgct ccagccttgt tccccggaca cctgctaagg ccaacagcta gatattcagc 540
acctgtctga ccagataccg ttcctacaga ggcatctgct actttgnatg cacaagcttn 600
cacatgttgc tataatctgn tccaatgncc tactccttgg tggtgatttt ctncaattct 660
caatggccag cctttcattg gcccaatgca actggccctg atntgncang tncaacaggg 720
nttttcagat actagaag 738

<210> SEQ ID NO 105
<211> LENGTH: 27
<212> TYPE: RNA
<213> ORGANISM: Artificial Sequence
<220> FEATURE:
<223> OTHER INFORMATION: Description of Artificial Sequence: Synthetic RNA sequence

<400> SEQUENCE: 105
agcaucgagu cggccuuggc cuacugg 27

<210> SEQ ID NO 106
<211> LENGTH: 42

-continued

```
<212> TYPE: DNA
<213> ORGANISM: Artificial Sequence
<220> FEATURE:
<223> OTHER INFORMATION: Description of Artificial Sequence: Adapter-primer

<400> SEQUENCE: 106

gcggctgaag acggcctatg tggccttttt tttttttttt tt                          42


<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 107

agcatcgagt cggccttgtt g                                                 21


<210> SEQ ID NO 108
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 108

gcgctgaaga cggcctatgt                                                   20
```

NUCLEIC ACID SEQUENCES HAVING CHARACTERISTICS OF ENHANCED EXPRESSION IN HUMAN NEUROBLASTOMA WITH FAVORABLE PROGNOSIS BASED ON COMPARISON BETWEEN HUMAN NEUROBLASTOMA WITH FAVORABLE PROGNOSIS AND HUMAN NEUROBLASTOMA WITH UNFAVORABLE PROGNOSIS

This Application is a Rule 1.53(b) Divisional Patent Application of U.S. patent application Ser. No. 10/220,891 filed on and having a 35 U.S.C. §371(c) date of Mar. 7, 2003 now U.S. Pat. No. 7,087,383, which is a National Phase of International Application No. PCT/JP01/01631 filed Mar. 2, 2001 which designated the U.S. and was not published under PCT Article 21(2) in English, and which was issued as U.S. Pat. No. 7,087,383, and this divisional application claims, via the aforesaid U.S. Application and the aforesaid International Application, the foreign priority benefit of and claims the priority from Japanese Application No. 2000-159195, filed Mar. 7, 2000, and from Japanese Application No. 2000-140387, filed Mar. 12, 2000, the complete disclosures of all the prior applications, including any and all sequence listings (as well as paper copy, disc copy and/or diskette copy), are incorporated herein by reference.

TECHNICAL FIELD

This invention relates to nucleic acids derived from genes expressed in human neuroblastomas. More specifically, the invention relates to nucleic acids and their fragments derived from the genes whose expression is enhanced in human neuroblastoma with favorable prognosis based on comparison between human neuroblastoma with favorable prognosis and human neuroblastoma with unfavorable prognosis as well as to their utility in the diagnosis of prognosis for human neuroblastomas.

BACKGROUND ART

Individual tumors exhibit distinct characteristic natures, and their biological properties are not necessarily identical even though the basic principle of oncogenesis is the same. Rapid advances in the understanding of cancer from a molecular biological and molecular genetic perspective in recent years have opened the way to an explanation of oncogenesis and tumor cell biology on the genetic level.

Neuroblastomas

Neuroblastoma is a pediatric cancer occurring in sympathetic gangliocytes and adrenal medullary cells which originate from cells of the peripheral sympathetic nervous system. Of these sympathetic nervous system cells, neural crest cells in the initial stage of development migrate to the abdomen, differentiating and maturing at sites where sympathetic ganglia are formed. Some of these cells migrate further to the adrenal bodies, penetrating through the adrenal cortex which is already in the process of formation, and reaching the medulla and forming medullary substance there. The neural crest cells also serve as a source of other peripheral nerve cells, differentiating into dorsal root ganglia (sensory nerves), skin pigment cells, thyroid C cells, some pulmonary cells, intestinal gangliocytes, and the like.

Prognosis for Neuroblastoma

Neuroblastoma is characterized by a varied clinical profile (Nakagawara, Shinkeigashu no Hassei to Sono Bunshi Kiko

[Neuroblastoma Development and Molecular Mechanism], Shoni Naika 30, 143, 1998). For example, neuroblastomas occurring at less than one year of age have very favorable prognosis, with the majority undergoing differentiation and cell death, and spontaneous regression. Currently, most neuroblastomas discovered by a positive result in the commonly performed mass screening of 6-month-old infant urine are of the type which tend to undergo this spontaneous regression. On the other hand, neuroblastomas occurring at age 1 or higher are highly malignant and lead to death of the infant in the majority of cases. It is also hypothesized that a somatic mutation occurs in highly malignant neuroblastomas in infants older than one year of age, which are of monoclonal nature, whereas in naturally regressing neuroblastomas, the genetic mutation remains at only a germline mutation. See Knudson A G, et al.: Regression of neuroblastoma IV-S: A genetic hypothesis, N. Engl. J. Med. 302, 1254 (1980)).

Tumor Markers which Allow the Diagnosis of Prognosis for Neuroblastoma

With recent advances in molecular biology research, it has become clear that expression of the high affinity nerve growth factor (NGF) receptor TrkA is closely connected with control of differentiation and cell death. See Nakagawara A., The NGF story and neuroblastoma, Med. Pediatr. Oncol., 31, 113 (1998). Trk is a membrane-spanning receptor, existing as the three main types, Trk-A, -B and -C. These Trk family receptors play an important role in specific nerve cell differentiation and survival in the central nervous and peripheral nervous systems. See Nakagawara, et al., Shinkeigasaiboushu ni Okeru Neurotrophin Juyoutai no Hatsugen to Yogo [Expression of Neurotrophin Receptors and Prognosis in Neuroblastoma], Shoni Geka (Pediatric Surgery), 29:425-432, 1997. The survival and differentiation of tumor cells is controlled by signals from Trk tyrosine kinase and Ret tyrosine kinase. In particular, the role of TrkA receptor is most significant, with TrkA expression being notably high in neuroblastomas with favorable prognosis, and its signals exerting a powerful control over survival and differentiation of tumor cells, and cell death (apoptosis). In neuroblastomas with unfavorable prognosis, on the other hand, TrkA expression is significantly suppressed, while tumor development is aided by a mechanism in which survival is promoted by signals from TrkB and Ret.

It has become clear that amplification of the neural oncogene N-myc has become clearly associated with the prognosis of neuroblastoma. See Nakagawara, Noushinkeishuyo no Tadankai Hatsugan [Multistage Oncogenesis of Cerebral and Neural Tumors], Molecular Medicine, 364, 366(1999). This gene, first cloned in neuroblastoma, is ordinarily only present in a single copy per haploid set in normal cells and neuroblastomas with favorable prognosis, whereas it has been found to be amplified several dozen times in neuroblastomas with unfavorable prognosis. Thus, amplification of N-myc is closely linked to tumor progression.

Up till the present time, however, no oncogene other than N-myc is known to be expressed in neuroblastomas, and absolutely no genetic information other than that of N-myc has been known in relation to favorable or unfavorable prognosis.

DISCLOSURE OF THE INVENTION

This invention has been accomplished in light of the circumstances described above, and its object is to identify the information of genes which are expressed in neuroblastomas, to further identify the information of the genes which is related to favorable or unfavorable prognosis, and to allow the diagnosis for favorable or unfavorable prognosis of neuroblastoma based on that genetic information.

In the course of conducting diligent research in line with the aforementioned object, the present inventors have examined the prognoses of neuroblastomas and have succeeded in constructing cDNA libraries from clinical tissues with favorable prognosis and unfavorable prognosis. Approximately 2400 clones were respectively obtained from these two types of cDNA libraries and were classified according to the prognosis of neuroblastoma (whether favorable or unfavorable).

The present inventors further determined the partial or whole sequences of these cloned genes, and upon performing a homology search, selected suitable genes.

Moreover, upon comparing the classified gene groups as described above against the selected genes, the present inventors found that the expression of a considerable number of the genes is enhanced only in clinical tissues of neuroblastoma with favorable prognosis.

Based on such knowledge, the present inventors have succeeded in providing genetic information (nucleic acid sequence information etc.) for the detection and cloning of the genes only expressed in human neuroblastomas with favorable prognosis. Furthermore, based on the aforementioned nucleic acid sequence information it has been made possible to carry out the method for detection of prognosis and to design tumor markers which can be used therefor, and this invention has thereupon been completed.

Specifically, this invention provides the nucleic acids and nucleic acid fragments described under 1. to 8. below. The invention further provides uses for those nucleic acids and nucleic acid fragments as described under 9 to 11. below.

1. A nucleic acid derived from a gene expressed in human neuroblastoma, the nucleic acid comprising a sequence selected from the group consisting of the nucleic acid sequences set forth in SEQ ID NO:1 to NO:104 in the Sequence Listing, or its complementary nucleic acid.

2. The nucleic acid according to 1. above, characterized in that the nucleic acid is DNA.

3. A nucleic acid derived from a gene whose expression is enhanced in human neuroblastoma with favorable prognosis based on comparison between human neuroblastoma with favorable prognosis and human neuroblastoma with unfavorable prognosis, the nucleic acid comprising a sequence selected from the group consisting of the nucleic acid sequences set forth in SEQ ID NO:1 to NO:104 in the Sequence Listing, or its complementary nucleic acid.

4. The nucleic acid according to 3. above, characterized in that the nucleic acid is DNA.

5. A fragment of the nucleic acid according to any one of 1. to 4. above.

6. An isolated nucleic acid which can hybridize to the nucleic acid according to any one of 1. to 4. above under stringent conditions.

7. The isolated nucleic acid according to 6. above, characterized in that the nucleic acid is DNA.

8. A PCR primer comprising the nucleic acid according to 7. above.

9. A method of diagnosing the prognosis of human neuroblastoma, the method comprising detecting the nucleic acid according to 3. above from clinical tissue of human neuroblastoma.

10. A diagnosis kit for the prognosis of human neuroblastoma, containing a pair of PCR primers according to 8. above.

Accordingly, preferred as the nucleic acid described above is nucleic acid derived from a gene whose expression is enhanced only in human neuroblastoma with favorable prognosis, upon comparison between human neuroblastoma with favorable prognosis and human neuroblastoma with unfavorable prognosis, as information relating to the sequence of said nucleic acid will allow the diagnosis for prognosis of human neuroblastoma.

BEST MODE FOR CARRYING OUT THE INVENTION

Figure 1:
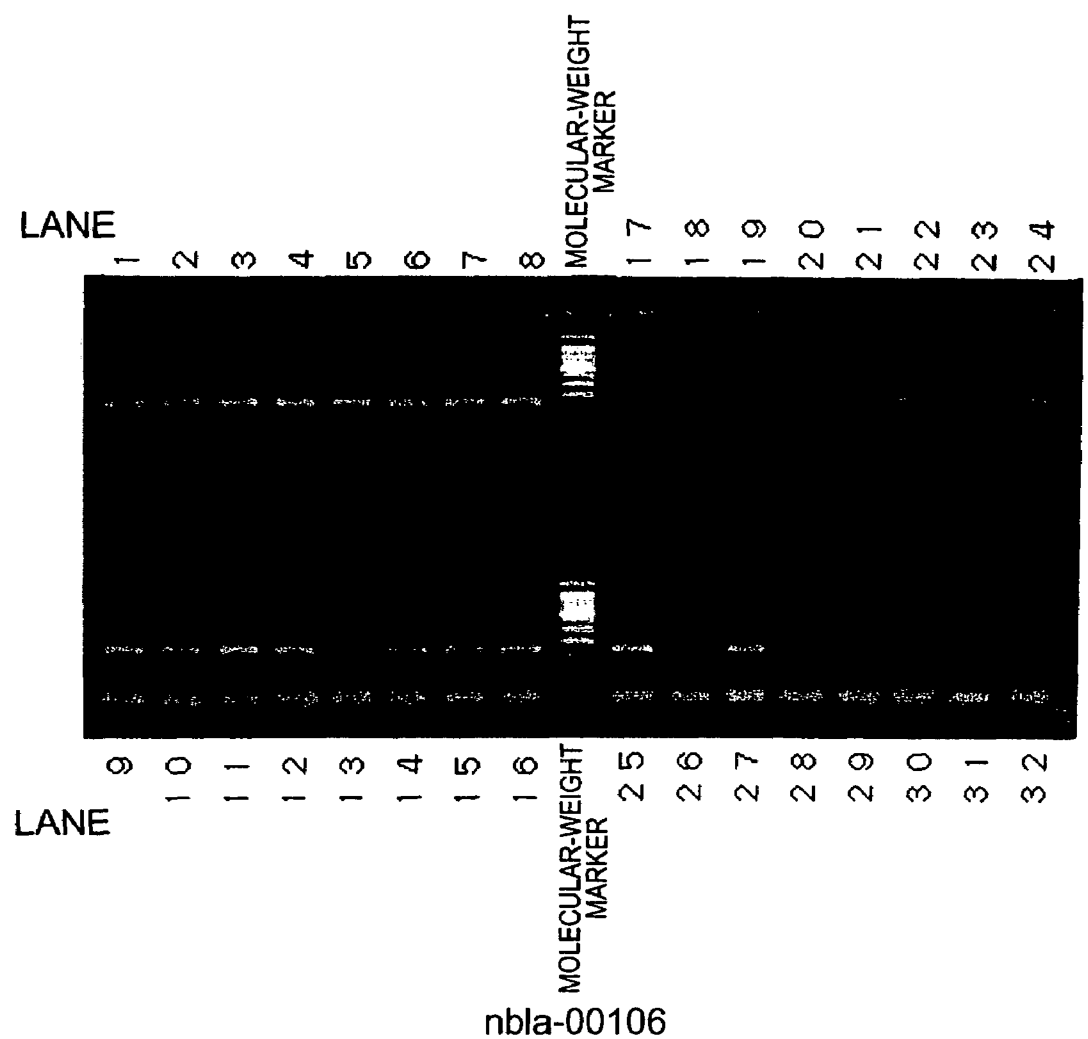
FIG. 1 is an illustration corresponding to an electrophoregram showing an example of a gene whose expression was found enhanced in human neuroblastomas with favorable prognosis (the result from nucleic acid sequence nbla-00106), as a result of examining the level of gene expression in human neuroblastomas with favorable prognosis and with unfavorable prognosis by semi-quantitative PCR. In the figure, Lanes 1-16 are clinical tissue specimens of human neuroblastomas with favorable prognosis. On the other hand, Lanes 17-32 are clinical tissue specimens of human neuroblastomas with unfavorable prognosis.

The nucleic acids derived from the genes expressed in human neuroblastomas according to this invention (hereinafter referred to as "genes of the invention") and their related nucleic acid fragments (hereinafter referred to respectively as “nucleic acids of the invention” and “nucleic acid fragments of the invention”, or where distinction between the nucleic acids and their fragments is not particularly necessary in description, they will be collectively referred to as “nucleic acids of the invention”) will now be explained in greater detail, with reference to preferred embodiments of the invention.

The nucleic acids of the invention are derived from the genes of the invention as mentioned above, and they either constitute the genes or are obtained from the genes by in vivo or in vitro procedures. The term “nucleic acids” as used throughout the present specification refers to, for example, DNA or RNA, or polynucleotides derived therefrom which are active as DNA or RNA, and preferably they are DNA or RNA. Particularly preferred nucleic acids either have sequences identical to the human cDNA sequences disclosed in the present specification or have sequences complementary thereto.

The term “hybridize under stringent conditions” as used in the present specification means that two nucleic acids (or fragments) hybridize to each other under the hybridization conditions described by Sambrook, J. et al. in “Expression of cloned genes in *E. coli*”, Molecular Cloning: A Laboratory Manual (1989), Cold Spring Harbor Laboratory Press, New York, USA, 9.47-9.62 and 11.45-11.61.

More specifically, the “stringent conditions” refers to hybridization at approximately 45° C., 6.0×SSC, followed by washing at 50° C., 2.0×SSC. The stringency may be selected by choosing a salt concentration in the washing step from approximately 2.0×SSC, 50° C. as low stringency to approximately 0.2×SSC, 50° C. as high stringency. Also, the temperature in the washing step may be increased from room temperature, or approximately 22° C. as low stringency conditions, to approximately 65° C. as high stringency conditions.

The term “isolated nucleic acid” as used throughout the present specification refers to a nucleic acid or a polynucleotide containing substantially no cellular substances or culture medium, if prepared by recombinant DNA techniques, or containing substantially no precursor chemical substances or other chemical substances, if prepared by chemical synthesis.

The term “favorable prognosis” as used throughout the present specification refers to a condition of human neuroblastoma in which the tumor is localized or has become a regressing or benign sympathetic ganglion neoplasm, and is judged by a physician to have low malignancy based on N-myc or other tumor markers (TrkA, chromosomal aberration, etc.). According to a preferred embodiment of the invention, a favorable prognosis is a case of stage 1 or 2, with an onset age of less than one year and survival without recurrence for 5 or more years after surgery, and with no amplification of N-myc in the clinical tissue; however, there is no limitation to such specific cases. The term “unfavorable prognosis” as used throughout the present specification refers to a condition of human neuroblastoma in which progression of the tumor has been observed, and it is judged by a physician to have high malignancy based on N-myc or other tumor markers. According to a preferred embodiment of the invention, an unfavorable prognosis is a case of stage 4, with an onset age of greater than one year, death within 3 years after surgery and amplification of N-myc in the clinical tissue; however, there is no limitation to such specific cases.

Neuroblastoma is a tumor consisting of actual nerve cells, of which only two types of tumor are known in humans, and analysis of the genes expressed therein is expected to provide very useful knowledge for understanding the biology of nerve cells. Specifically, it is extremely difficult, and practically impossible, to obtain site-specific homogeneous tissue from the brain or peripheral nerves. On the other hand, a neuroblastoma consists of an almost homogeneous nerve cell population (though tumorized) derived from peripheral sympathetic nerve cells, and thus offers a high possibility of obtaining homogeneous expression of neuro-related genes. Furthermore, since neuroblastoma is a type of cancer, it will characteristically have many important genes expressed in the immature stage of neurogenesis.

Clinically and biologically, neuroblastoma can be neatly classified into favorable prognosis and unfavorable prognosis types. Cancer cells from neuroblastoma with favorable prognosis are characterized by having a very slow rate of proliferation, with spontaneous regression beginning at some point. Findings to date have confirmed that nerve cell differentiation and apoptosis (nerve cell death) occur in the spontaneous regression, and that the differentiation which occurs in the maturation stages of normal nerve cells and programmed cell death are phenomena very closely resembling each other. Consequently, it is highly probable that the analysis of genes expressed in such tumors will lead to obtaining important genetic information relating to nerve cell differentiation and apoptosis.

Neuroblastomas with unfavorable prognosis are tumors consisting of cancer cells which continue to exhibit definitely malignant proliferation. The probability is very high, therefore, that they have a large number of important genes connected with nerve cell proliferation or genes expressed in undifferentiated nerve cells. In other words, it is highly probable that these will allow the obtainment of genetic information completely different from the profile of genes expressed in neuroblastomas with favorable prognosis.

It is commonly reported that nerve cells contain more expressed gene types than cells derived from other organs. Neuroblastoma cell lines are derived from clinical tissues with unfavorable prognosis, and it is believed that the gene expression profile in the case of tumor development and progression is substantially altered from that of normal nerve cells.

Neuroblastoma is characteristically a pediatric tumor, and because of the very low possibility of effects by acquired factors, it is expected that analysis of the mechanism of cancerization will also yield embryological information with high probability. More surprisingly, the nucleic acids of the invention include nucleic acids of genes whose expression is enhanced only in specific cell cycle phases, and this further suggests the very strong possibility of obtaining genetic information highly useful for the analysis of cancerization mechanisms and related to development and differentiation.

The nucleic acids of the invention, having the various characteristics mentioned above and derived from the genes which can yield useful genetic information, are obtained from human neuroblastoma clinical tissues and have any of the nucleic acid sequences set forth in SEQ ID NO:1 to NO:104 in the Sequence Listing, or a portion thereof.

As a result of comparing levels of expression of the genes according to this invention in clinical tissues from human neuroblastomas with favorable prognosis and with unfavorable prognosis, a highly significant difference was found in the genes corresponding to the nucleic acid sequences set forth I SEQ ID NO:1 to NO:104 in the Sequence Listing. That is, expression of these genes was enhanced in human neuroblastomas with favorable prognosis. Thus, in addition to providing the useful genetic information described above, the nucleic acid sequences set forth in SEQ ID NO:1 to NO:104 can also be utilized as data for tumor markers to diagnose favorable or unfavorable prognosis of neuroblastoma, by detecting the nucleic acid having any of these nucleic acid sequences.

Specifically, this invention will make it possible to obtain various gene information on or relating to human neuroblastoma through the following means.

(1) Probes for Hybridization

According to one embodiment of this invention, the nucleic acids of the invention or their fragments may be used as probes for hybridization in order to detect genes expressed in human neuroblastoma. The nucleic acids of the invention or their fragments may also be used as probes for hybridization in order to determine gene expression in various tumors and normal tissues, to identify the distribution of the gene expression.

When the nucleic acids of this invention or their fragments are used as probes for hybridization, there are no particular limitations on the actual method of hybridization. As preferred methods there may be mentioned, for example, Northern hybridization, Southern hybridization, colony hybridization, dot hybridization, fluorescence in situ hybridization (FISH), in situ hybridization (ISH), DNA chip methods, and microarray methods.

As one application example of the hybridization, the nucleic acid of this invention or its fragment may be used as a probe for Northern hybridization to measure the length of mRNA or to quantitatively detect gene expression in a sample to be examined.

As another application example, the nucleic acid of the invention or its fragment may be used as a probe for Southern hybridization to detect the presence or absence of the DNA sequence in genomic DNA of a sample to be examined.

As still another application example, the nucleic acid of the invention or its fragment may be used as a probe for fluorescence in situ hybridization (FISH) to identify the location of the gene on a chromosome.

As yet another application example, the nucleic acid of the invention or its fragment may be used as a probe for in situ hybridization to identify the tissue distribution of gene expression.

When the nucleic acid of the invention or its fragment is used as a probe for hybridization, a nucleic acid residue length of at least 40 is necessary; and among the nucleic acids and their fragments of the invention, the one with 40 or more contiguous residues or its fragment is preferably used. More preferably, the one with 60 or more residues is used.

Nucleic acid probe techniques for the types of hybridization mentioned above are well known to one skilled in the art, and for example, conditions suitable for hybridization between a nucleic acid probe of various lengths according to the invention and target polynucleotide may be readily determined. For example, Sambrook et al. described in "Molecular Cloning: A Laboratory Manual, loc. cit. may be followed for such manipulations which are well known to one skilled in the art.

A probe according to this invention is preferably labeled in an easily detectable fashion. The detectable label may be an element or compound, of any type which can be detected either visually or using devices. As commonly used detectable labels there may be mentioned radioactive isotopes, avidin or biotin, and fluorescent substances (FITC, rhodamine, and the like). The radioactive isotopes include $^{32}P$, $^{14}C$, $^{125}I$, $^{3}H$ and $^{35}S$. Biotin-labeled probes are detected after hybridization using labeling means such as avidin/streptavidin, fluorescent labels, enzymes, gold colloidal complexes or the like. A probe according to the invention may also be labeled by binding with a protein. Radioactive or fluorescent histone single-stranded DNA binding protein may be used for this purpose.

(2) Primers for Use in PCR

In addition to hybridization for the detection of target genes (e.g., the genes according to this invention), any nucleic acid sequence included in the nucleic acid of the invention or its fragment may be used as a primer in a polymerase chain reaction (PCR). For example, mRNA may be extracted from a sample to be examined, and the gene expression may be semi-quantitatively measured by RT-PCR. This may be carried out by a method well known to one skilled in the art. See, for example, Sambrook et al. described in "Molecular Cloning: A Laboratory Manual," loc. cit. and Idenshibyo Nyumon [Introduction to Genetic Diseases] (Takahisa, S.: Nankodo Publishing).

When the nucleic acid of this invention or its fragment is used as a PCR primer, a nucleic acid residue length of 10 to 60 is necessary; and among the nucleic acids of the invention and their fragments, the one with 10 to 60 contiguous residues or its fragment is preferably used. More preferably, the one with 15 to 30 residues is used. In most cases, a primer sequence with a GC content of 40-60% is preferred. Also, there is preferably no difference in the Tm values of the two primers used for amplification. Preferably there is no annealing at the 3' ends of the primers and no secondary structure is formed in the primers.

(3) Gene Screening

A nucleic acid of the invention or its fragment may also be used to detect the expression distribution of a target gene which is expressed in various tissues or cells. This may be accomplished, for example, by using the nucleic acid of the invention or its fragment as a probe for hybridization or as a primer for PCR, as described above.

Expression distribution of a target gene can also be detected using a DNA chip, microarray or the like. That is, the nucleic acid of the invention or its fragment may be directly attached to the chip or array. For this purpose, methods for spotting such a nucleic acid (DNA) onto plates using a high precision dispenser are known (see, for example, U.S. Pat. No. 5,807,522). mRNA extracted from cells of a tissue specimen may be labeled there with a fluorescent substance or the like, hybridized, and an analysis may be made of the type of tissue cells with high expression of the gene. The DNA attached to the chip or array may be the reaction product of PCR using the nucleic acid of the invention or its fragment as the primer. Alternatively, nucleic acid fragments of the invention may be directly synthesized on a substrate to prepare a DNA chip or array (see, for example, U.S. Pat. No. 5,424,186).

(4) Gene Cloning

The nucleic acid of this invention or its fragment may be used for cloning a gene which is expressed in human neuroblastoma. For example, by using the nucleic acid of the invention or its fragment as a probe for northern hybridization or southern hybridization, or as a primer for PCR, cloning of a gene containing the nucleic acid of the invention or its fragment is possible. As the genes subjected to such cloning there may be mentioned genes with differing levels of expression particularly between neuroblastoma with favorable prognosis and neuroblastoma with unfavorable prognosis, genes whose forms of expression differ in other tissues or cancer cells, genes whose expression is cell cycle phase-dependent, genes induced upon neurodifferentiation and genes whose expression is regulated by oncogenes or tumor suppressor genes. The cloning may be carried out according to ordinary gene recombination techniques, by incorporating the nucleic acid of the invention or its fragment into an appropriate plasmid or bacteriophage to construct an expression vector, introducing this into host cells for transformation (or transduction), and culturing the transformants. The individual manipulations for this procedure are described in detail by Sambrook et al. in "Molecular Cloning: A Laboratory Manual," loc. cit., as well as in other well-known literature.

(5) Methods of Diagnosing Tumor Prognosis and Tumor Markers to be used Therefor

As mentioned above, the genes related to the nucleic acids of this invention have their expression enhanced in human neuroblastomas with favorable prognosis. The nucleic acid (DNA) of the invention or its fragment may therefore be used as a probe for hybridization, or as a primer for PCR to allow the identification of prognosis. Specifically, this may be accomplished by examining whether the expression of the gene is enhanced in a clinical tissue containing sample taken from a subject. The methods of detecting the gene include Northern blotting hybridization, in situ hybridization and RT-PCR, as mentioned above among others.

When hybridization is employed, prognosis may be diagnosed as favorable if the amount of nucleic acid hybridizing to the probe is increased in the sample. When RT-PCR is employed, mRNA is extracted from the sample and reverse transcribed into DNA, amplification is performed using the aforementioned primer, and the gene expression is semi-quantitatively measured. The prognosis may be diagnosed as favorable if the gene expression is then found to be enhanced. For the purpose of such specific diagnosis it is preferred to utilize a diagnosis kit containing a pair of such primers as essential components. In addition to the primer components, the diagnosis kit also include known components such as PCR buffer, detergent solution and enzymes.

(6) Antisense Oligonucleotides

According to another embodiment of this invention there are provided antisense oligonucleotides to the nucleic acids of the invention. The antisense oligonucleotides are capable of hybridizing to the nucleic acids of the invention, and include antisense DNAS and antisense RNAS. Antisense DNA inhibits transcription of mRNA from DNA, while antisense RNA inhibits translation of mRNA. Native types of such antisense oligonucleotides may be synthesized using an automated synthesizer or by PCR using the nucleic acid of the invention as templates. The antisense oligonucleotides also encompass antisense oligonucleotide derivatives having improved binding affinity for the target DNA or mRNA, tissue selectivity, cell permeability, nuclease resistance and intracellular stability. Such derivatives may be synthesized using antisense technology known in the art.

Antisense oligonucleotides having sequences complementary to the sequences near the translation initiation codon of the mRNA, those of the ribosome-binding site, and those of the capping site or the splicing site are capable of inhibiting synthesis of the RNA and therefore will exhibit a particularly notable inhibitory effect on gene expression. This invention therefore encompasses such antisense oligonucleotides.

(7) Gene Therapy

According to a further embodiment of this invention, there are provided nucleic acid sequences encoding the therapeutic genes to be used in gene therapy. Thus, the nucleic acid of the invention can be transferred into a vector for use in gene transportation, whereby the transgene (i.e., the gene of the invention) can be expressed by an arbitrary expression promoter and can be used for the gene therapy of cancers, for example.

1. Vectors

The transferable viral vectors may be prepared from DNA viruses or RNA viruses. They may be any viral vector of an MOMLV vector, a herpes virus vector, an Adenovirus vector, an AAV vector, a HIV vector, a Seidai virus vector and the like. One or more proteins among the constituent protein group of a viral vector are substituted by the constituent proteins of a different species of virus, or alternatively a part of the nucleic acid sequence constituting genetic information is substituted by the nucleic acid sequence of a different species of virus to form a viral vector of the pseudo-type which can also be used in this invention. For example, there is mentioned a pseudo-type viral vector wherein the Env protein (an envelop protein of HIV) is substituted by the VSV-G protein (an envelop protein of vesicular stomatitis virus or VSV) (Naldini L., et al., Science 272, 263-267, 1996). Further, virues having a host spectrum other than human is usable as the viral vector insofar as they are efficacious. As for the vectors other than those of viral origin, there may be used complexes of calcium phosphate and nucleic acid, ribosomes, cation-lipid complexes, Seidai virus liposomes, polymer carriers having polycation as the main chain and others. In addition, methods such as electroporation and gene guns may be used as a gene transfer system.

2. Expression Promoters

As for the expression cassettes to be used for the therapeutic gene, any cassettes without any particular limitations may be used insofar as they can cause genes to express in the target cells. One skilled in the art can readily select such expression cassettes. Preferably, they are expression cassettes capable of gene expression in the cells derived from an animal, more preferably, expression cassettes capable of gene expression in the cells derived from a mammal, and most preferably expression cassettes capable of gene expression in the cells derived from a human. The gene promoters that can be used as expression cassettes include: for example, virus-derived promoters from an Adenovirus, a cytomegalovirus, a human immunodeficiency virus, a simian virus 40, a Rous sarcoma virus, a herpes simplex virus, a murine leukemia virus, a sinbis virus, a hepatitis type A virus, a hepatitis type B virus, a hepatitis type C virus, a papilloma virus, a human T cell leukemia virus, an influenza virus, a Japanese encephalitis virus, a JC virus, parbovirus B19, a poliovirus, and the like; mammal-derived promoters such as albumin, SRα, a heat shock protein, and an elongation factor; chimera type promoters such as a CAG promoter; and the promoters whose expression can be induced by tetracyclines, steroids and the like.

The gene group discovered by this invention as being expressed in human neuroblastomas with favorable prognosis will now be explained in greater detail by way of the examples; however, the technical scope of the invention will not be restricted to those example.

EXAMPLES

Production Example 1

Construction of cDNA Library From Human Neuroblastoma

1. Obtaining Samples

Human neuroblastoma clinical tissue specimens were quasi-aseptically frozen immediately after surgical extraction and then preserved at −80° C.

2. Selecting Samples with Favorable Prognosis

Prognosis of the samples obtained in 1. above was carried out based on the following criteria.

| Favorable prognosis | Unfavorable prognosis |
|---|---|
| Stage 1 or 2 | Stage 4 |
| Age of onset: <1 | Age of onset: ≧1 |
| Survival for ≧5 years after surgery without recurrence | Death within 3 years after surgery |
| No amplification of N-myc | Amplification of N-myc |

Amplification of N-myc in the aforementioned two sample types was confirmed in the following manner.

The clinical tissue specimen obtained in 1. above was thinly sliced with a scalpel and then thoroughly homogenized after addition of 5 ml of TEN buffer (50 mM Tris-HCl (pH=8.0)/1 mM EDTA/100 mM NaCl). Upon adding 750 μl of SDS (10%) and 125 μl of proteinase K (20 mg/ml) to the mixture, it was gently stirred and allowed to stand at 50° C. for 8 hours. This was followed by phenol/chloroform treatment and finally ethanol precipitation to obtain purified genomic DNA. A 5 μg portion of the obtained genomic DNA was completely digested with the restriction endonuclease EcoRI (NEB Inc.), and an N-myc probe was used to determine amplification of N-myc by Southern hybridization.

3. Preparation of mRNA from Clinical Tissue of Human Neuroblastoma with Favorable Prognosis A 2-3 g portion of the clinical tissue samples of human neuroblastoma judged to have favorable prognosis in 2. above was treated using a Total RNA Extraction Kit (QIAGEN Inc.) and the total RNA was extracted. The extracted total RNA was purified using an oligo dT cellulose column (Collaborative Research, Inc.) to obtain a pool of mRNA with a polyA structure.

4. Dephosphorylation of mRNA

A 100-200 μg portion of the mRNA pool prepared in 3. above was dissolved in 67.3 μl of distilled sterile water containing 0.1% diethyl pyrocarbonate (DEPC), and then 20 μl of 5XBAP buffer (Tris-HCl (500 mM, pH=7.0)/mercaptoethanol (50 mM)), 2.7 μl of RNasin (40 unit/μl: Promega Inc.) and 10 μl of BAP (0.25 unit/μl, bacteria-derived alkali phosphatase: Takara Shuzo Co. Ltd.) were added. The mixture was reacted at 37° C. for 1 hour to effect dephosphorylation of the 5' end of the mRNA. This was followed by phenol/chloroform treatment two times, and finally ethanol precipitation to obtain a purified dephosphorylated mRNA pool.

5. Decapping of Dephosphorylated mRNA

The total amount of the dephosphorylated mRNA pool prepared in 4. above was dissolved in 75.3 μl of distilled sterile water containing 0.1% DEPC, and then 20 μl of 5X TAP buffer (sodium acetate (250 mM, pH=5.5)/mercaptoethanol (50 mM), EDTA (5 mM, pH=8.0)), 2.7 μl of RNasin (40 unit/μl) and 2 μl of TAP (tobacco acid pyrophosphatase: 20 unit/μl) were added. The mixture was reacted at 37° C. for 1 hour to effect decapping treatment of the 5' end of the dephosphorylated mRNA. The dephosphorylated mRNA of incomplete length with no capped structure remained without decapping, and with the 5' end dephosphorylated. This was followed by phenol/chloroform treatment and ethanol precipitation to obtain a purified decapped mRNA pool.

6. Preparation of Oligo-Capped mRNA

The total amount of the decapped mRNA pool prepared in 5. above was dissolved in 11 μl of distilled sterile water containing 0.1% DEPC, and then 4 μl of 5'-oligo RNA (5'-AGCAUCGAGUCGGCCUUGGCCUACUGG-3': 100 ng/μl), 10 μl of 10× ligation buffer (Tris-HCl (500 mM, pH=7.0)/mercaptoethanol (100 mM)), 10 μl of magnesium chloride (50 mM), 2.5 μl of ATP (24 mM), 2.5 μl of RNasin (40 unit/μl), 10 μl of T4 RNA ligase (25 unit/μl: Takara Shuzo Co. Ltd.) and 50 μl of polyethylene glycol (50% w/v, PEG8000: Sigma Corporation) were added. The mixture was reacted at 20° C. for 3 hours for ligation of the 5'-oligo RNA to the 5' end of the decapped mRNA. The dephosphorylated mRNA of incomplete length with no capped structure resulted in no ligation to the 5'-oligo RNA. This was followed by phenol/chloroform treatment and ethanol precipitation to obtain a purified oligo-capped mRNA pool.

7. Removal of DNA from Oligo-Capped mRNA

The oligo-capped mRNA pool prepared in 6. above was dissolved in 70.3 μl of distilled sterile water containing 0.1% DEPC, and then 4 μl of Tris-HCl (1 M, pH=7.0), 5.0 μl of DTT (0.1 M), 16 μl of magnesium chloride (50 mM), 2.7 μl of RNasin (40 unit/μl) and 2 μl of DNaseI (5 unit/μl: Takara Shuzo Co. Ltd.) were added. The mixture was reacted at 37° C. for 10 minutes to dissolve the excess DNA. This was followed by phenol/chloroform treatment and ethanol precipitation and column purification (S-400HR: Pharmacia Biotech Inc.), to obtain a purified DNA(−) oligo-capped mRNA pool.

8. Preparation of 1st Strand cDNA

The DNA(−) oligo-capped mRNA pool prepared in 7. above was reverse transcribed using SuperScript II (kit by Life Tech Oriental, Inc.) to obtain a pool of 1st strand cDNA. The pool of DNA(−) oligo-capped mRNA was dissolved in 21 μl of sterile distilled water, and then 10 μl of 10× First Strand buffer (kit accessory), 8 μl of DNTP mix (5 mM, kit accessory), 6 μl of DTT (0.1 M, kit accessory), 2.5 μl of oligo-dT adapter primer (5 pmol/μl, 5'-GCGGCTGAAGACGGCCTATGTGGCC TTTTTTTTTTTTTTTTT-3'), 2.0 μl of RNasin (40 unit/μl) and 2 μl of SuperScript II RTase (kit accessory) were added. The mixture was reacted at 42° C. for 3 hours to effect reverse transcription. This was followed by phenol/chloroform treatment, alkali treatment and neutralization treatment to dissolve all the RNA and purification was carried out by ethanol precipitation.

9. Preparation of 2nd Strand cDNA

The 1st strand cDNA pool prepared in 8. above was subjected to PCR amplification using Gene Amp (kit by Perkin Elmer Inc.). The pool of 1st strand cDNA was dissolved in 52.4 μl of sterile distilled water, and then 30 μl of 3.3× Reaction buffer (kit accessory), 8 μl of DNTP mix (2.5 mM, kit accessory), 4.4 μl of magnesium acetate (25 mM, kit accessory), 1.6 μl of Primer F (10 pmol/μl, 5'-AGCATCGAGTCGGCCTTGTTG-3'), 1.6 μl of Primer R (10 pmol/μl, 5'-GCGCTGAAGACGGCCTATGT-3') and 2 μl of rTth (kit accessory) were added. A 100 μl portion of mineral oil was gently added to the mixture and overlayed thereon. After denaturing the reaction solution at 94° C. for 5 minutes, a cycle of 94° C. for 1 minute, 52° C. for 1 minute and 72° C. for 10 minutes was repeated 12 times, and then the solution was allowed to stand at 72° C. for 10 minutes to complete the PCR reaction. This was followed by phenol/chloroform treatment and ethanol precipitation to obtain a 2nd strand cDNA pool.

10. SfiI Treatment of 2nd Strand cDNA

The 2nd strand cDNA pool prepared in 9. above was dissolved in 87 μl of sterile distilled water, and then 10XNEB buffer (NEB Inc.), 100XBSA (bovine serum albumin available from NEB Inc.) and 2 μl of SfiI (restriction endonuclease, 20 unit/μl, NEB Inc.) were added. The mixture was reacted overnight at 50° C. to effect SfiI restriction endonuclease treatment. This was followed by phenol/chloroform treatment and ethanol precipitation to obtain a pool of cDNA which had been SfiI-treated at both ends.

11. Size Fractionation of SfiI-treated cDNA

The SfiI-treated cDNA pool prepared in 10. above was electrophoresed on 1% agarose gel and a fraction with >2 kb was purified using Geneclean II (Bio101 Inc.). The purified cDNA pool was dissolved in 100 μl of sterile distilled water and allowed to stand at 37° C. for 6 hours. This was followed by phenol/chloroform treatment and ethanol precipitation to obtain a long-chain cDNA pool.

12. cDNA Library

The long-chain cDNA pool prepared in 11. above was ligated into the cloning vector pME18S-FL3 (provided by Prof. Sumio Kanno of the Institute of Medical Science, Tokyo University) using a DNA Ligation Kit ver.1 (kit by Takara Shuzo Co. Ltd.). The long-chain cDNA pool was dissolved in 8 μl of sterile distilled water, and then 1 μl of pME18S-FL3 pretreated with restriction endonuclease DraIII, 80 μl of Solution A (kit accessory) and 10 μl of Solution B (kit accessory) were added and reaction was conducted at 16° C. for 3 hours. This was followed by phenol/chloroform treatment and ethanol precipitation for purification to obtain a cDNA library.

Example 2

Transformation into *E. coli*

1. Cloning

The cDNA library prepared in Example 1, 12. above was used for transformation into *E. coli* (TOP-10: Invitrogen Corporation). The cDNA library was dissolved in 10 μl of sterile distilled water and mixed with TOP-10. The mixture was then incubated on ice for 30 minutes, at 40° C. for 1 minute and on ice for 5 minutes. After adding 500 μl of SOB medium, shake culturing was performed at 37° C. for 60 minutes. Appropriate amounts thereof were seeded onto ampicillin-containing agar media and culturing was continued at 37° C. for a day and a night to obtain *E. coli* clones.

2. Preservation of *E. coli* Clones (Preparation of Glycerol Stock)

The *E. coli* clones on agar media obtained in 1. above were collected with toothpick and suspended in 120 μl of LB medium prepared in a 96-well plate. The 96-well plate was then allowed to stand overnight at 37° C. for culturing of the *E. coli*. A 72 μl portion of 60% glycerol solution was then added and preserved at −20° C. (glycerol stock)

Example 3

Nucleic Acid Sequence Determination

1. Preparation of Plasmid

The 10 μl of glycerol stock prepared in Example 2, 2. above was transferred to a 15 ml centrifugation tube, and then 3 ml of LB medium and 50 μg/ml of ampicillin were added and shaking was carried out overnight at 37° C. for culturing of the *E. coli*. A QIAprep Spin Miniprep Kit (QIAGEN Inc.) was then used to extract and purify a plasmid DNA from the *E. coli*.

2. Analysis of Both End Sequences

Both end sequences of the plasmid DNA prepared in 1. above were determined using a DNA Sequencing Kit (kit by ABI). There were combined 600 ng of plasmid DNA, 8 μl of premix (kit accessory) and 3.2 pmol of primers, and sterile distilled water was added to a total of 20 μl. After denaturing the mixture at 96° C. for 2 minutes, a cycle of 96° C. for 10 seconds, 50° C. for 5 seconds and 60° C. for 4 minutes was repeated 25 times for reaction. The product was then purified by ethanol precipitation. Sequence determination was carried out by polyacrylamide gel electrophoresis under denaturing conditions, using ABI377 (ABI).

Example 4

Homology Search of Database

An internet nucleic acid sequence homology search was conducted for the nucleic acid sequence data obtained from the both end-sequence analysis in Example 3. The search was conducted using the BLAST database of the NCBI (National Center of Biotechnology Information, http://www.ncbi.nblm.nih.gov/BLAST).

Example 5

Comparison of Gene Expression Levels in Human Neuroblastomas with Favorable Prognosis and Unfavorable Prognosis by Semi-Quantitative PCR PCR primers were synthesized from the nucleic acid sequences of portions of the gene group obtained in Example 4, and the expression levels in the clinical tissues of human neuroblastomas with favorable prognosis and unfavorable prognosis were comparatively quantitated. mRNA was extracted from the human neuroblastoma clinical tissues by the method described in Examples 1-3, and rTaq (Takara Shuzo Co. Ltd.) was used for PCR reaction. Specifically, 5 μl of sterile distilled water, 2 μl of mRNA, 1 μl of 10XrTaq buffer, 1 μl of 2 mM dNTPs, 0.5 μl each of the synthesized primer set and 0.5 μl of rTaq were combined. After denaturing the mixture at 95° C. for 2 minutes, a cycle of 95° C. for 15 seconds, 55° C. for 15 seconds and 72° C. for 20 seconds was repeated 35 times, and then the mixture was allowed to stand at 72° C. for 6 minutes for PCR reaction. The reaction solution was subjected to 1% agarose gel electrophoresis. Consequently, when the PCR primers based on the nucleic acid sequences set forth in SEQ ID NO:1 to NO:104 in the Sequence Listing were used in amplification, the genes whose expression was enhanced only in neuroblastomas with favorable prognosis were identified. Tables 1 and 2 show the information on the nucleic acid sequences set forth in SEQ ID NO:1 to NO:104, including the results of the homology search shown in Example 4 (73 nucleic acid sequences among 104 nucleic acid sequences had no homology).

Figure 2:
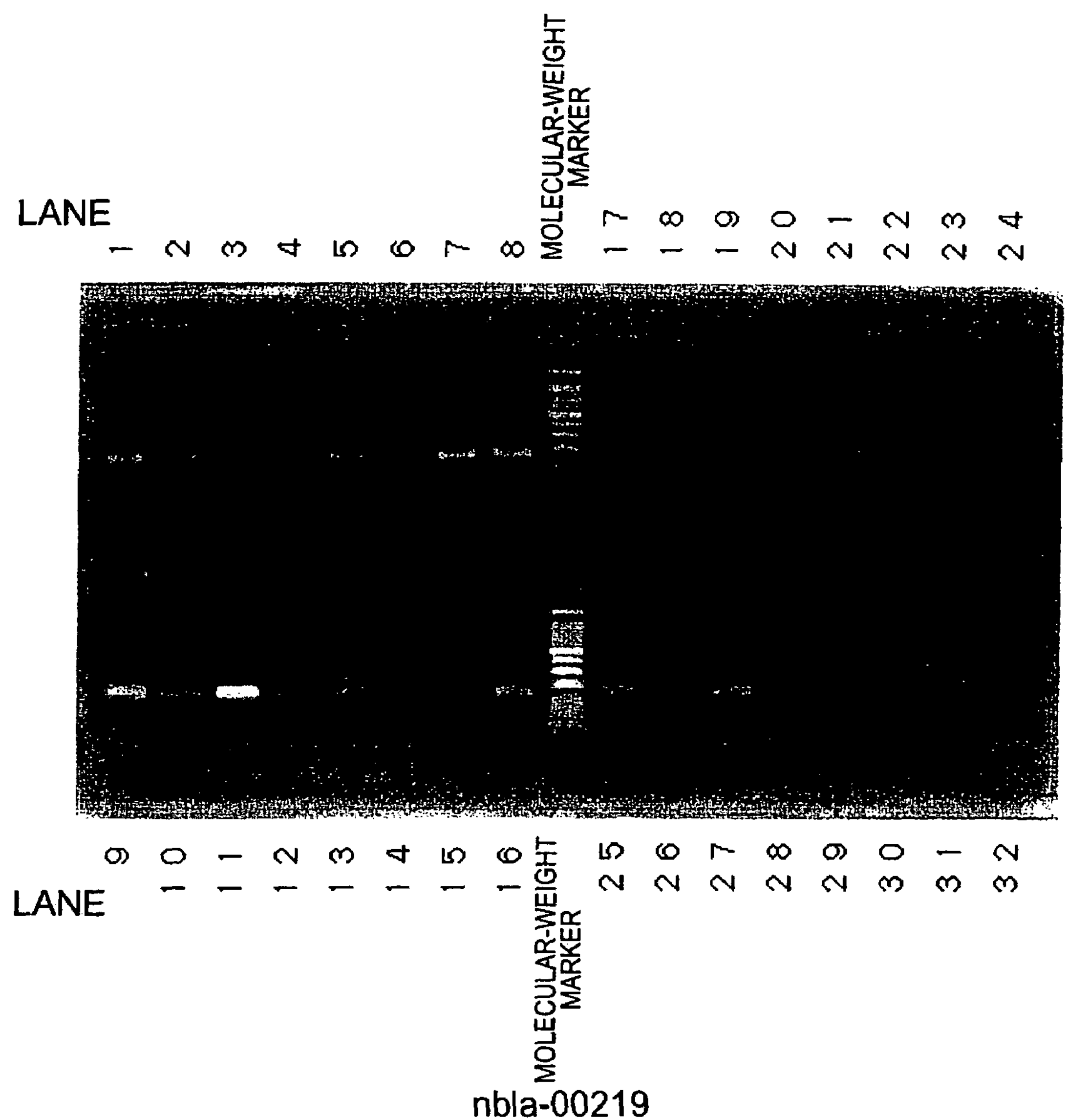
FIG. 2 is an illustration corresponding to an electrophoregram showing another example of a gene whose expression was found enhanced in human neuroblastomas with favorable prognosis (the result from nucleic acid sequence nbla-00219), as a result of examining the level of gene expression in human neuroblastomas with favorable prognosis and with unfavorable prognosis by semi-quantitative PCR. In the figure, Lanes 1-16 are clinical tissue specimens of human neuroblastomas with favorable prognosis. On the other hand, Lanes 17-32 are clinical tissue specimens of human neuroblastomas with unfavorable prognosis.
Figure 3:
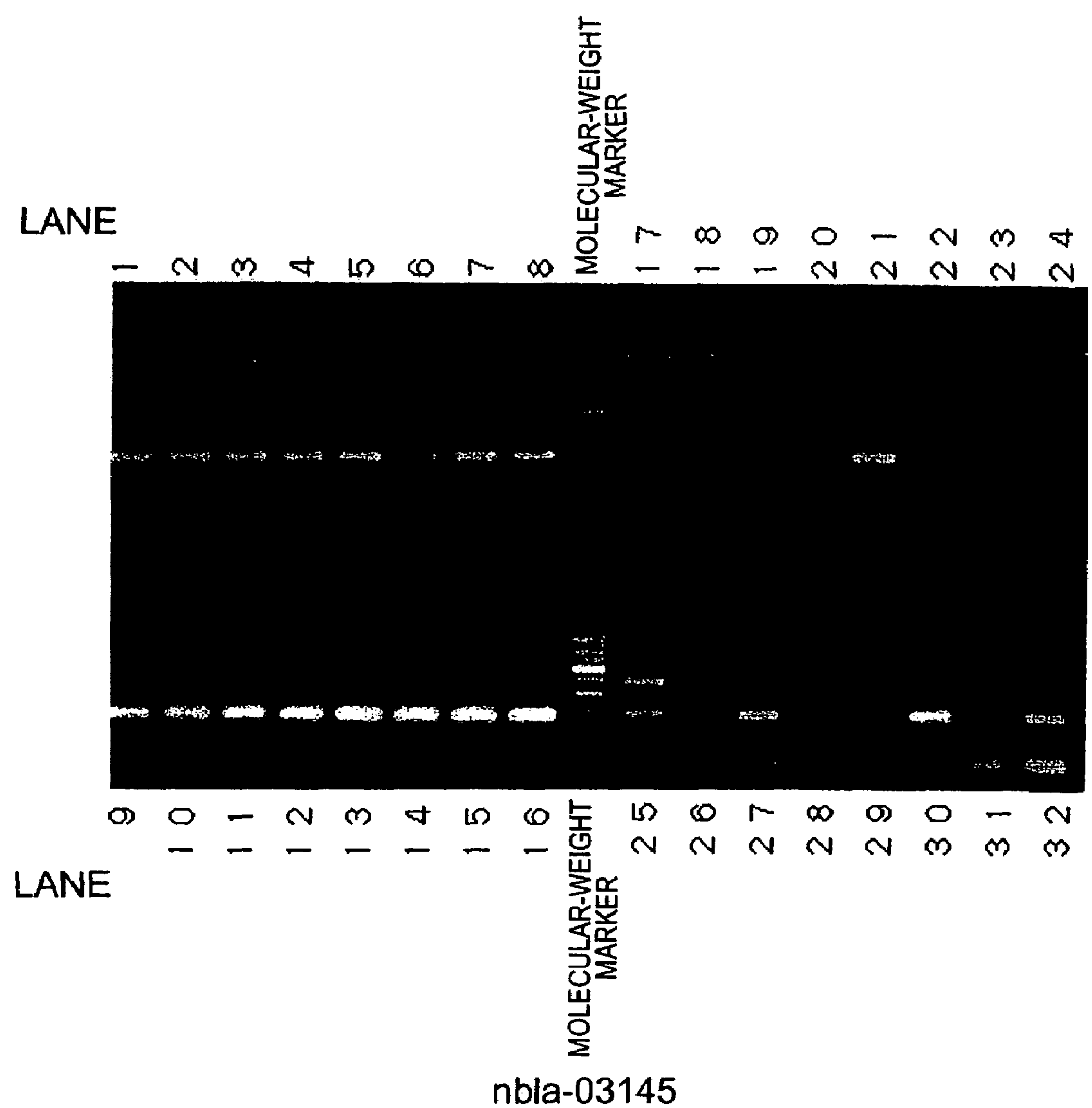
FIG. 3 is an illustration corresponding to an electrophoregram showing still another example of a gene whose expression was found enhanced in human neuroblastoma with favorable prognosis (the result from nucleic acid sequence nbla-03145), as a result of examining the level of gene expression in human neuroblastomas with favorable prognosis and with unfavorable prognosis by semi-quantitative PCR. In the figure, Lanes 1-16 are clinical tissue specimens of human neuroblastomas with favorable prognosis. On the other hand, Lanes 17-32 are clinical tissue specimens of human neuroblastomas with unfavorable prognosis.

Examples of the measurements of gene expression levels in human neuroblastomas with favorable prognosis and unfavorable prognosis by semi-quantitative PCR (Nucleic acid sequences nbla-00106, nbla-00219 and nbla-03145) are shown in FIGS. 1-3.

TABLE 1

Nucleic acid sequences whose expression is enhanced in neuroblastomas with favorable prognosis

| SEQ ID | CLONE NAME | CELL CYCLE PHASE SPECIFICITY | HOMOLOGY (ACCESSION No.) |
|---|---|---|---|
| 1 | nbla-00002 | | KIAA0327(AB002325) |
| 2 | nbla-00012 | S PHASE | — |
| 3 | nbla-00052 | | — |
| 4 | nbla-00067 | | — |
| 5 | nbla-00078 | S PHASE | KIAA0322(AB002320) |
| 6 | nbla-00086-f | | GTPaseRAB68(AF166492) |
| 7 | nbla-00086-r | | — |
| 8 | nbla-00100 | G2/M PHASE | KIAA0632(AB014532) |
| 9 | nbla-00106 | | — |
| 10 | nbla-00113 | | KIAA0874(AB020681) |
| 11 | nbla-00118 | | — |
| 12 | nbla-00126 | | MAB21L1(NM_005584) |
| 13 | nbla-00137 | | — |
| 14 | nbla-00150 | G2/M PHASE | SART-3(AB020880) |
| 15 | nbla-00158 | | — |
| 16 | nbla-00172 | G2/M PHASE | — |
| 17 | nbla-00177 | S PHASE | — |
| 18 | nbla-00204 | | — |
| 19 | nbla-00219 | | KIAA0367(AB002365) |
| 20 | nbla-00235 | G2/M PHASE | — |
| 21 | nbla-00237 | | — |
| 22 | nbla-00271 | | KIAA0886(AB020693) |
| 23 | nbla-00343 | | KIAA1145(AB032971) |
| 24 | nbla-00371 | S PHASE | — |
| 25 | nbla-00375 | | — |
| 26 | nbla-00418 | | — |
| 27 | nbla-00433 | | — |
| 28 | nbla-00437 | S PHASE AND G2/M PHASE | — |
| 29 | nbla-00490 | G2/M PHASE | T1-227H(D50525) |
| 30 | nbla-00538-f | | DKFZp566D1146(AL080222) |
| 31 | nbla-00538-r | | DKFZp566D1146(AL080222) |
| 32 | nbla-00613 | | — |
| 33 | nbla-00650 | | — |
| 34 | nbla-00652 | S PHASE AND G2/M PHASE | FLJ10739 fis(AK001601) |
| 35 | nbla-00660 | G2/M PHASE | — |
| 36 | nbla-00693 | | DKFZp434G0827(AL122107) |
| 37 | nbla-00697 | G1 PHASE AND S PHASE | — |
| 38 | nbla-00715 | | — |
| 39 | nbla-00744 | | — |
| 40 | nbla-00761 | S PHASE | KIAA0751(AB018294) |
| 41 | nbla-00830-f | | — |
| 42 | nbla-00830-r | | — |
| 43 | nbla-00831-f | | KIAA0868(AB020675) |
| 44 | nbla-00831-r | | KIAA0868(AB020675) |
| 45 | nbla-00832-f | | — |
| 46 | nbla-00832-r | | (AF140710) |
| 47 | nbla-02942 | | (NM_001788) |
| 48 | nbla-02975 | G1 PHASE | FLJ10103 fis(AK000965) |
| 49 | nbla-02981 | | — |
| 50 | nbla-02999 | G2/M PHASE | (AF182814) |
| 51 | nbla-03010 | G1 PHASE | — |
| 52 | nbla-03103 | G1 PHASE | — |
| 53 | nbla-03107-f | | KIAA1309(AB037730) |
| 54 | nbla-03107-r | | KIAA1309(AB037730) |

TABLE 2

Nucleic acid sequences whose expression is enhanced in neuroblastomas with favorable prognosis

| | | | |
|---|---|---|---|
| 55 | nbla-03139 | S PHASE AND M PHASE | FOG2(NM_012082) |
| 56 | nbla-03145 | G1 PHASE | XCE(Y16187) |
| 57 | nbla-03199-f | S PHASE | — |
| 58 | nbla-03199-r | S PHASE | — |
| 59 | nbla-03212-f | S PHASE | — |
| 60 | nbla-03212-r | S PHASE | — |
| 61 | nbla-03219-f | | — |
| 62 | nbla-03219-r | | — |
| 63 | nbla-03301-f | S PHASE | NF-L(X05608) |
| 64 | nbla-03301-r | S PHASE | — |
| 65 | nbla-03461-f | | — |
| 66 | nbla-03461-r | | — |
| 67 | nbla-03539-f | S PHASE | — |
| 68 | nbla-03539-r | S PHASE | — |
| 69 | nbla-03575-f | S PHASE AND G2/M PHASE | KIAA0517(AB011089) |
| 70 | nbla-03575-r | S PHASE AND G2/M PHASE | — |
| 71 | nbla-03646-f | | KIAA0018(D13643) |
| 72 | nbla-03646-r | | KIAA0018(D13643) |
| 73 | nbla-03684-f | | — |
| 74 | nbla-03755-r | S PHASE | — |
| 75 | nbla-03759-f | | — |
| 76 | nbla-03759-r | | — |
| 77 | nbla-03761-f | | — |
| 78 | nbla-03761-r | | — |
| 79 | nbla-03771-f | | — |
| 80 | nbla-03771-r | | — |
| 81 | nbla-03777-f | | — |
| 82 | nbla-03777-r | | — |
| 83 | nbla-03779-f | | — |
| 84 | nbla-03779-r | | — |
| 85 | nbla-03781-f | | — |
| 86 | nbla-03781-r | | DKFZp434C035(AL137633) |
| 87 | nbla-03831-f | | — |
| 88 | nbla-03831-r | | — |
| 89 | nbla-03851-f | | — |
| 90 | nbla-03851-r | | — |
| 91 | nbla-03862-f | | — |
| 92 | nbla-03862-r | | — |
| 93 | nbla-03898-f | | — |
| 94 | nbla-03898-r | | — |
| 95 | nbla-03911-f | | — |
| 96 | nbla-03911-r | | — |
| 97 | nbla-03914-f | | — |
| 98 | nbla-03914-r | | — |
| 99 | nbla-04021-f | | — |
| 100 | nbla-04021-r | | — |
| 101 | nbla-04055-f | | — |
| 102 | nbla-04055-r | | — |
| 103 | nbla-04061-f | | — |
| 104 | nbla-04061-r | | — |

Example 6

MEASUREMENT of Cell Cycle Phase-dependent Gene Expression Levels by Semi-quantitative PCR PCR primers were synthesized from the nucleic acid sequences of portions of the gene group obtained in Example 4, and HeLa cells were used for comparative quantitation of cell cycle phase-dependent gene expression levels. The HeLa cells used were treated in each of the following manners.

(1) Untreated (2) Treated with 400 μM of mimosine for 18 hours, with 65% of the cells arrested in the G1 phase.

(3) Treated with 2 mM thymidine for 20 hours, with 100% of the cells arrested in the S phase.

Figure 4:
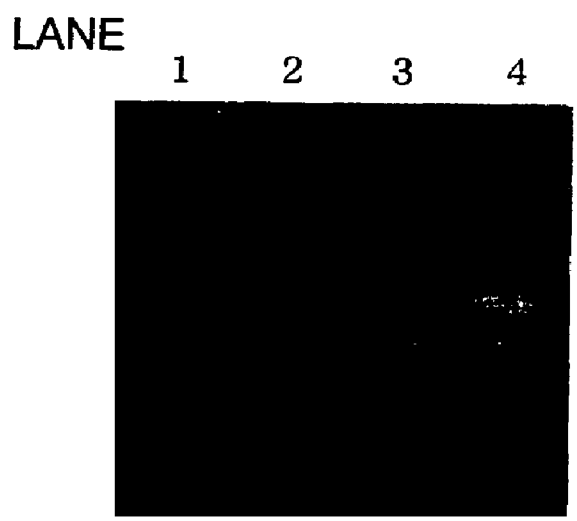
FIG. 4 is an illustration corresponding to an electrophoregram showing an example of a gene whose expression was noted (the result from nucleic acid sequence nbla-00100), as a result of examining the level of cell cycle phase-specific gene expression by semi-quantitative PCR. In the figure, Lane 1 represents untreated HeLa cells (60-70% confluent). Lane 2 represents HeLa cells treated with 400 μM of mimosine for 18 hours, with 65% arrested in the G1 phase. Lane 3 represents HeLa cells treated with 2 mM thymidine for 20 hours, with 100% arrested in the S phase. Lane 4 represents HeLa cells treated with 0.6 μg/ml of nocodazole for 18 hours, with 85% arrested in the G2/M phase.

(4) Treated with 0.6 μg/ml of nocodazole, with 85% of the cells arrested in the G2/M phase.

mRNA was extracted from the aforementioned 4 types of HeLa cells by the method described in Examples 1-3, and rTaq (Takara Shuzo Co. Ltd.) was used for PCR reaction. Specifically, 5 μl of sterile distilled water, 2 μl of mRNA, 1 μl of 10XrTaq buffer, 1 μl of 2 mM dNTPs, 0.5 μl each of the synthesized primer set and 0.5 μl of rTaq were combined. After denaturing the mixture at 95° C. for 2 minutes, a cycle of 95° C. for 15 seconds, 55° C. for 15 seconds and 72° C. for 20 seconds was repeated 35 times, and then the mixture was allowed to stand at 72° C. for 6 minutes for PCR reaction. The reaction solution was subjected to 1% agarose gel electrophoresis. Consequently, when the PCR primers based on the nucleic acid sequences set forth in SEQ ID NO:1 to NO:104 in the Sequence Listing were used in amplification, it was found that the gene expression was specific for cell cycle phase in 31 nucleic acid sequences. An example of the electrophoresis results (Nucleic acid sequence nbla-00100) is shown in FIG. 4. Also, Tables 1 and 2 have displayed a tabulation of the cell cycle phase specificities and individual nucleic acid sequences that were discovered in the manner presented herein.

INDUSTRIAL APPLICABILITY

The nucleic acids of this invention provide information relating to the genes expressed in neuroblastoma.

The nucleic acids of the invention or their fragments may be used as probes or primers for various types of hybridization or PCR, and permit detection of the expression of the aforementioned genes in other tissues and cells, as well as analysis of their structure and functions. Production of the human proteins encoded by the genes through genetic engineering is also possible.

The nucleic acids of the invention are those derived from a gene whose expression is enhanced in human neuroblastoma with favorable prognosis based on comparison between human neuroblastoma with favorable prognosis and human neuroblastoma with unfavorable prognosis, and therefore allow the diagnosis for prognosis of neuroblastoma based on this genetic information from these nucleic acids. Unlike the N-myc gene which is a factor for unfavorable prognosis, these genes are considered factors for favorable prognosis, similar to the TrkA gene, and therefore can serve as markers (tumor markers) for neuroblastoma malignancy and sensitivity to anti-cancer agents.

The invention claimed is:

1. An isolated nucleic acid derived from a gene expressed in human neuroblastoma, the isolated nucleic acid comprising the sequence as set forth in SEQ ID NO:36 in the Sequence Listing, or a fully complementary nucleic acid thereof.

2. The isolated nucleic acid according to claim 1, wherein the nucleic acid is DNA.

3. A method of diagnosing the prognosis of human neuroblastoma, said method comprising extracting a neuroblastoma specimen from a subject; detecting at least one nucleic acid in the specimen, the nucleic acid comprising the sequence as set forth in SEQ ID NO:36 in the Sequence Listing or a fully complementary nucleic acid thereof; and diagnosing the prognosis of the human neuroblastoma as favorable if said nucleic acid is detected.

* * * * *